United States Patent
Bourne et al.

(10) Patent No.: US 11,753,443 B2
(45) Date of Patent: *Sep. 12, 2023

(54) CONJUGATED HEPCIDIN MIMETICS

(71) Applicant: Protagonist Therapeutics, Inc., Newark, CA (US)

(72) Inventors: Gregory Thomas Bourne, Brisbane (AU); Ashok Bhandari, Pleasanton, CA (US); Brian Troy Frederick, Ben Lomand, CA (US); Jie Zhang, Salisbury (AU); Adam Stephenson, Chapel Hill (AU); Mark Leslie Smythe, Bardon (AU); Roopa Taranath, Cupertino, CA (US); David Liu, Newark, CA (US)

(73) Assignee: Protagonist Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/964,708

(22) PCT Filed: Feb. 8, 2019

(86) PCT No.: PCT/US2019/017192
§ 371 (c)(1),
(2) Date: Jul. 24, 2020

(87) PCT Pub. No.: WO2019/157268
PCT Pub. Date: Aug. 15, 2019

(65) Prior Publication Data
US 2020/0361992 A1    Nov. 19, 2020

Related U.S. Application Data

(60) Provisional application No. 62/749,450, filed on Oct. 23, 2018, provisional application No. 62/717,390, filed on Aug. 10, 2018, provisional application No. 62/627,952, filed on Feb. 8, 2018, provisional application No. 62/627,948, filed on Feb. 8, 2018.

(51) Int. Cl.
*C07K 7/08* (2006.01)
*A61K 38/00* (2006.01)
*A61K 9/00* (2006.01)

(52) U.S. Cl.
CPC .............. *C07K 7/08* (2013.01); *A61K 9/0053* (2013.01); *A61K 38/00* (2013.01)

(58) Field of Classification Search
CPC .................................. C07K 7/08; A61K 38/00
See application file for complete search history.

(56) References Cited

U.S. PATENT DOCUMENTS

| 4,684,620 | A | 8/1987 | Hruby et al. |
|---|---|---|---|
| 4,724,229 | A | 2/1988 | Ali |
| 5,192,746 | A | 3/1993 | Lobl et al. |
| 5,293,050 | A | 3/1994 | Chapple-Sokol et al. |
| 5,354,707 | A | 10/1994 | Chapple-Sokol et al. |
| 5,494,897 | A | 2/1996 | Shikawa et al. |
| 5,569,741 | A | 10/1996 | Coy et al. |
| 5,990,084 | A | 11/1999 | Richter et al. |
| 6,087,334 | A | 7/2000 | Beeley et al. |
| 6,235,711 | B1 | 5/2001 | Dutta |
| 6,818,617 | B1 | 11/2004 | Niewiarowski |
| 7,534,764 | B2 | 5/2009 | Ganz et al. |
| 7,589,170 | B1 | 9/2009 | Smythe et al. |
| 7,718,598 | B1 | 5/2010 | Smythe et al. |
| 7,745,391 | B2 | 6/2010 | Mintz et al. |
| 8,313,950 | B2 | 11/2012 | Rovin et al. |
| 8,435,941 | B2 | 5/2013 | Ganz et al. |
| 8,536,140 | B2 | 9/2013 | Clandinin et al. |
| 8,568,706 | B2 | 10/2013 | Grabstein et al. |
| 8,796,418 | B2 | 8/2014 | Walensky et al. |
| 8,946,150 | B2 | 2/2015 | Gallagher et al. |
| 8,999,935 | B2 | 4/2015 | Huang |
| 9,169,292 | B2 | 10/2015 | Gallagher et al. |
| 9,273,093 | B2 | 3/2016 | Bhandari et al. |
| 9,315,545 | B2 | 4/2016 | Merutka |
| 9,518,091 | B2 | 12/2016 | Bhandari et al. |
| 9,624,268 | B2 | 4/2017 | Bourne et al. |
| 9,714,270 | B2 | 7/2017 | Bhandari et al. |
| 9,809,623 | B2 | 11/2017 | Bhandari et al. |
| 9,822,157 | B2 | 11/2017 | Smythe et al. |
| 10,023,614 | B2 | 7/2018 | Bhandari et al. |
| 10,030,061 | B2 | 7/2018 | Smythe et al. |
| 10,035,824 | B2 | 7/2018 | Bhandari et al. |
| 10,059,744 | B2 | 8/2018 | Bhandari et al. |
| 10,196,424 | B2 | 2/2019 | Bourne et al. |
| 10,278,957 | B2 | 5/2019 | Anandan et al. |
| 10,301,371 | B2 | 5/2019 | Bhandari et al. |
| 10,407,468 | B2 | 9/2019 | Bhandari et al. |
| 10,442,846 | B2 | 10/2019 | Smythe et al. |
| 10,501,515 | B2 | 12/2019 | Smythe et al. |
| 10,626,146 | B2 | 4/2020 | Bhandari et al. |
| 10,729,676 | B2 | 8/2020 | Anandan et al. |
| 10,787,490 | B2 | 9/2020 | Bhandari et al. |

(Continued)

FOREIGN PATENT DOCUMENTS

| CA | 2015761 A1 | 11/1990 |
|---|---|---|
| CL | 2018000128 A1 | 6/2018 |

(Continued)

OTHER PUBLICATIONS

Cherry, et al., "Vedolizumab: an α4β7 integrin antagonist for ulcerative colitis and Crohn's disease." Ther Adv Chronic Dis. (2015); 6(5): 224-233.

(Continued)

*Primary Examiner* — Amber D Steele
(74) *Attorney, Agent, or Firm* — Cooley LLP

(57) ABSTRACT

The present invention provides hepcidin analogues with improved in vivo half lives, and related pharmaceutical compositions and methods of use thereof.

10 Claims, 5 Drawing Sheets

Specification includes a Sequence Listing.

(56) References Cited

U.S. PATENT DOCUMENTS

| | | |
|---|---|---|
| 10,941,183 B2 | 3/2021 | Bhandari et al. |
| 11,041,000 B2 | 6/2021 | Bhandari et al. |
| 11,111,272 B2 | 9/2021 | Bhandari et al. |
| 11,472,842 B2 | 10/2022 | Bourne et al. |
| 2003/0166138 A1 | 9/2003 | Kinsella et al. |
| 2003/0166514 A1 | 9/2003 | Jones et al. |
| 2004/0052785 A1 | 3/2004 | Goodman et al. |
| 2004/0123343 A1 | 6/2004 | La Rosa et al. |
| 2004/0152868 A1 | 8/2004 | Larsen et al. |
| 2004/0176293 A1 | 9/2004 | Peterson et al. |
| 2006/0166881 A1 | 7/2006 | Hotchkiss et al. |
| 2006/0183884 A1 | 8/2006 | Blaschuk et al. |
| 2007/0032417 A1 | 2/2007 | Baell |
| 2007/0166308 A1 | 7/2007 | Pullen et al. |
| 2007/0191272 A1 | 8/2007 | Stemmer et al. |
| 2007/0197430 A1 | 8/2007 | Baell et al. |
| 2008/0019913 A1 | 1/2008 | Polt et al. |
| 2008/0213277 A1 | 9/2008 | Sasu et al. |
| 2008/0260820 A1 | 10/2008 | Borrelly et al. |
| 2008/0300180 A1 | 12/2008 | Schambye et al. |
| 2009/0053819 A1 | 2/2009 | Seymour et al. |
| 2009/0170143 A1 | 7/2009 | Uttenthal et al. |
| 2009/0257952 A1 | 10/2009 | Cochran et al. |
| 2009/0325810 A1 | 12/2009 | Lapointe et al. |
| 2010/0151487 A1 | 6/2010 | Rovin et al. |
| 2010/0183617 A1 | 7/2010 | Herr et al. |
| 2010/0190710 A1 | 7/2010 | Chemtob et al. |
| 2010/0196441 A1 | 8/2010 | Sondermeijer et al. |
| 2010/0272731 A1 | 10/2010 | Presta et al. |
| 2010/0280098 A1 | 11/2010 | Juliano et al. |
| 2011/0059087 A1 | 3/2011 | Lewis et al. |
| 2011/0086024 A1 | 4/2011 | Arthos et al. |
| 2011/0118186 A1 | 5/2011 | Schteingart et al. |
| 2011/0142889 A1 | 6/2011 | Lee et al. |
| 2011/0212104 A1 | 9/2011 | Beaumont et al. |
| 2011/0282029 A1 | 11/2011 | Holmes et al. |
| 2012/0021975 A1 | 1/2012 | Hoffman et al. |
| 2012/0040894 A1 | 2/2012 | Ganz et al. |
| 2012/0071422 A1 | 3/2012 | Gallagher et al. |
| 2012/0115930 A1 | 5/2012 | Monia et al. |
| 2013/0029907 A1 | 1/2013 | Gallagher et al. |
| 2013/0137123 A1 | 5/2013 | Cucchiara et al. |
| 2013/0172272 A1 | 7/2013 | Gallagher et al. |
| 2013/0183755 A1 | 7/2013 | Gallagher et al. |
| 2013/0310303 A1 | 11/2013 | Eldar-Finkelman et al. |
| 2013/0338132 A1 | 12/2013 | Koshiba et al. |
| 2014/0005128 A1 | 1/2014 | Mo et al. |
| 2014/0193465 A1 | 7/2014 | Bhandari et al. |
| 2014/0286953 A1 | 9/2014 | Sasu et al. |
| 2014/0294901 A1 | 10/2014 | Bhandari et al. |
| 2014/0294902 A1 | 10/2014 | Bhandari et al. |
| 2014/0336110 A1 | 11/2014 | Ganz et al. |
| 2015/0056301 A1 | 2/2015 | Kawabe et al. |
| 2015/0118315 A1 | 4/2015 | Wilson |
| 2015/0157692 A1 | 6/2015 | Fu |
| 2015/0203555 A1 | 7/2015 | Gellman et al. |
| 2015/0284429 A1 | 10/2015 | Merutka |
| 2016/0031944 A1 | 2/2016 | Bhandari et al. |
| 2016/0039878 A1 | 2/2016 | Gallagher et al. |
| 2016/0145306 A1 | 5/2016 | Bourne et al. |
| 2016/0152664 A1 | 6/2016 | Bhandari et al. |
| 2016/0159862 A1 | 6/2016 | Bhandari et al. |
| 2016/0199437 A1 | 7/2016 | Wilson |
| 2016/0222076 A1 | 8/2016 | Smythe et al. |
| 2016/0228491 A1 | 8/2016 | Wilson |
| 2016/0368966 A1 | 12/2016 | Bhandari et al. |
| 2017/0051013 A1 | 2/2017 | Merutka |
| 2017/0313754 A1 | 11/2017 | Bourne et al. |
| 2017/0327541 A1 | 11/2017 | Bhandari et al. |
| 2017/0362292 A1 | 12/2017 | Ruchala et al. |
| 2018/0022778 A1 | 1/2018 | Bourne et al. |
| 2018/0079782 A1 | 3/2018 | Bhandari et al. |
| 2018/0079783 A1 | 3/2018 | Bhandari et al. |
| 2018/0086811 A1 | 3/2018 | Smythe et al. |
| 2018/0099995 A1 | 4/2018 | Bhandari et al. |
| 2018/0100004 A1 | 4/2018 | Smythe et al. |
| 2018/0105572 A1 | 4/2018 | Bhandari et al. |
| 2018/0148477 A1 | 5/2018 | Bhandari et al. |
| 2019/0002500 A1 | 1/2019 | Bhandari et al. |
| 2019/0002503 A1 | 1/2019 | Bourne et al. |
| 2019/0016756 A1 | 1/2019 | Bhandari et al. |
| 2019/0076400 A1 | 3/2019 | Anandan et al. |
| 2019/0185535 A1 | 6/2019 | Smythe et al. |
| 2019/0185536 A1 | 6/2019 | Smythe et al. |
| 2019/0231746 A1 | 8/2019 | Anandan et al. |
| 2019/0248870 A1 | 8/2019 | Bhandari et al. |
| 2019/0264197 A1 | 8/2019 | Barkan et al. |
| 2019/0270786 A1 | 9/2019 | Bhandari et al. |
| 2019/0300590 A1 | 10/2019 | Bhandari et al. |
| 2019/0337983 A1 | 11/2019 | Bhandari et al. |
| 2020/0017549 A1 | 1/2020 | Bhandari et al. |
| 2020/0017566 A1 | 1/2020 | Bourne et al. |
| 2020/0040037 A1 | 2/2020 | Bhandari et al. |
| 2020/0064357 A1 | 2/2020 | Cheng et al. |
| 2020/0207822 A1 | 7/2020 | Bhandari et al. |
| 2020/0239516 A1 | 7/2020 | Richelle et al. |
| 2020/0239523 A1 | 7/2020 | Bhandari et al. |
| 2021/0009638 A1 | 1/2021 | Bhandari et al. |
| 2021/0061872 A1 | 3/2021 | Liu et al. |
| 2021/0147483 A1 | 5/2021 | Bourne et al. |
| 2021/0261622 A1 | 8/2021 | Sun et al. |
| 2021/0363185 A1 | 11/2021 | Bhandari et al. |
| 2021/0371466 A1 | 12/2021 | Bhandari et al. |
| 2022/0041658 A1 | 2/2022 | Bhandari et al. |
| 2022/0251142 A1 | 8/2022 | Bhandari et al. |
| 2022/0348626 A1 | 11/2022 | Smythe et al. |
| 2022/0372099 A1 | 11/2022 | Liu et al. |

FOREIGN PATENT DOCUMENTS

| | | |
|---|---|---|
| CL | 2018003322 A1 | 1/2019 |
| CN | 101307085 A | 11/2008 |
| CN | 101358201 A | 2/2009 |
| DE | 10107707 A1 | 8/2002 |
| JP | 2010-517529 A | 5/2010 |
| JP | 2010-536364 A | 12/2010 |
| JP | 2011-231085 A | 11/2011 |
| JP | 2012-525124 A | 10/2012 |
| JP | 2016-521257 A | 7/2016 |
| JP | 2017-530090 A | 10/2017 |
| WO | WO 1992/017492 A1 | 10/1992 |
| WO | WO-9411018 A1 | 5/1994 |
| WO | WO-9617617 A1 | 6/1996 |
| WO | WO-1997007129 A1 | 2/1997 |
| WO | WO 1997/025351 A2 | 7/1997 |
| WO | WO 1998/008871 A1 | 3/1998 |
| WO | WO 2000/055184 A1 | 3/1998 |
| WO | WO-9833524 A1 | 8/1998 |
| WO | WO 1999/002194 A1 | 1/1999 |
| WO | WO 1999/026615 A1 | 6/1999 |
| WO | WO 2000/006243 A2 | 2/2000 |
| WO | WO 2000/009560 A1 | 2/2000 |
| WO | WO 2000/018789 A1 | 4/2000 |
| WO | WO 2000/018790 A1 | 4/2000 |
| WO | WO 2000/023474 A1 | 4/2000 |
| WO | WO 2000/055119 A1 | 9/2000 |
| WO | WO 2000/061580 A1 | 10/2000 |
| WO | WO 2001/068586 A2 | 9/2001 |
| WO | WO 2003/066678 A1 | 8/2003 |
| WO | WO 2004/011650 A2 | 2/2004 |
| WO | WO 2004/092405 A2 | 10/2004 |
| WO | WO 2006/032104 A1 | 3/2006 |
| WO | WO 2007/138291 A2 | 12/2007 |
| WO | WO 2008/097461 A2 | 8/2008 |
| WO | WO-2008101017 A2 | 8/2008 |
| WO | WO 2008/134659 A2 | 11/2008 |
| WO | WO 2008/140602 A2 | 11/2008 |
| WO | WO 2009/002947 A2 | 12/2008 |
| WO | WO 2009/027752 A2 | 3/2009 |
| WO | WO 2010/065815 A2 | 6/2010 |
| WO | WO 2010/116752 A1 | 10/2010 |
| WO | WO 2010/124874 A1 | 11/2010 |
| WO | WO 2011/091357 A1 | 7/2011 |
| WO | WO 2011/149942 A2 | 12/2011 |

(56) References Cited

FOREIGN PATENT DOCUMENTS

| | | | |
|---|---|---|---|
| WO | WO 2012/052205 A1 | 4/2012 | |
| WO | WO 2013/086143 A1 | 6/2013 | |
| WO | WO-2013172954 A1 | 11/2013 | |
| WO | WO 2014/059213 A1 | 4/2014 | |
| WO | WO 2014/127316 A2 | 8/2014 | |
| WO | WO 2014/145561 * | 9/2014 | ............ A61K 38/10 |
| WO | WO 2014/145561 A2 | 9/2014 | |
| WO | WO 2014/165448 A1 | 10/2014 | |
| WO | WO 2014/165449 A1 | 10/2014 | |
| WO | WO 2014/210056 A1 | 12/2014 | |
| WO | WO 2015/054500 A2 | 4/2015 | |
| WO | WO 2015/157283 A1 | 10/2015 | |
| WO | WO 2015/176035 A1 | 11/2015 | |
| WO | WO 2015/183963 A2 | 12/2015 | |
| WO | WO 2015/200916 * | 12/2015 | ............... C12Q 1/68 |
| WO | WO 2015/200916 A2 | 12/2015 | |
| WO | WO 2016/004093 A2 | 1/2016 | |
| WO | WO 2016/011208 A1 | 1/2016 | |
| WO | WO 2016/054411 A1 | 4/2016 | |
| WO | WO 2016/054445 A1 | 4/2016 | |
| WO | WO 2016/109363 A1 | 7/2016 | |
| WO | WO 2016/115168 A1 | 7/2016 | |
| WO | WO 2016/195663 A1 | 12/2016 | |
| WO | WO 2016/200364 A1 | 12/2016 | |
| WO | WO 2017/011820 A2 | 1/2017 | |
| WO | WO-2017068089 A2 | 4/2017 | |
| WO | WO 2017/117411 A1 | 7/2017 | |
| WO | WO-2017165676 A1 | 9/2017 | |
| WO | WO 2018/022937 A1 | 2/2018 | |
| WO | WO-2018022917 A1 | 2/2018 | |
| WO | WO-2018048944 A1 | 3/2018 | |
| WO | WO 2018/089693 A2 | 5/2018 | |
| WO | WO 2018/136646 A1 | 7/2018 | |
| WO | WO-2018128828 A1 | 7/2018 | |
| WO | WO-2019051494 A1 | 3/2019 | |
| WO | WO 2019/157268 A1 | 8/2019 | |
| WO | WO 2019/246273 A1 | 12/2019 | |
| WO | WO-2019246349 A1 | 12/2019 | |
| WO | WO 2020/014646 A1 | 1/2020 | |
| WO | WO-2020198682 A1 | 10/2020 | |
| WO | WO-2021007433 A1 | 1/2021 | |
| WO | WO-2021046246 A1 | 3/2021 | |
| WO | WO-2021142373 A1 | 7/2021 | |
| WO | WO-2021146441 A1 | 7/2021 | |
| WO | WO-2021146454 A1 | 7/2021 | |
| WO | WO-2021146458 A1 | 7/2021 | |
| WO | WO-2022026629 A1 | 2/2022 | |
| WO | WO-2022026631 A1 | 2/2022 | |
| WO | WO-2022026633 A1 | 2/2022 | |
| WO | WO-2022109328 A1 | 5/2022 | |
| WO | WO-2022212696 A1 | 10/2022 | |
| WO | WO-2022212698 A1 | 10/2022 | |
| WO | WO-2022212700 A2 | 10/2022 | |
| WO | WO-2022266060 A1 | 12/2022 | |
| WO | WO-2023288017 A2 | 1/2023 | |
| WO | WO-2023288019 A2 | 1/2023 | |
| WO | WO-2023288028 A2 | 1/2023 | |

OTHER PUBLICATIONS

European Application No. 17771175.1, Extended European Search Report dated Mar. 4, 2020, 11 pages.
European Application No. 17771175.1, Partial Supplementary European Search Report dated Nov. 25, 2019, 15 pages.
European Application No. EP 19750312.1, Partial Supplementary European Search Report dated Nov. 29, 2021, 13 pages.
Görmer, et al., "Efficient Microwave-Assisted Synthesis of Unsymmetrical Disulfides", J. Org. Chem. (Feb. 1, 2010); 75(5): 1811-1813.
PCT/US2017/023859, International Preliminary Report on Patentability, dated Sep. 25, 2018, 9 pages.
PCT/US2017/023859, International Search Report and Written Opinion, dated Jul. 26, 2017, 14 pages.
PCT/US2017/023859, Invitation to Pay Additional Fees, dated May 25, 2017, 3 pages.
PCT/US2019/041665, International Preliminary Report on Patentability, dated Jan. 12, 2021, 7 pages.
PCT/US2020/041409, International Preliminary Report on Patentability, dated Jan. 11, 2022, 8 pages.
PCT/US2020/041409, International Search Report and Written Opinion, dated Dec. 3, 2020, 17 pages.
PCT/US2020/041409, Invitation to pay additional search fees, dated Sep. 28, 2020, 2 pages.
U.S. Appl. No. 16/510,118, Office Action dated Mar. 18, 2021, 14 pages.
U.S. Appl. No. 15/467,810, Notice of Allowability dated Mar. 13, 2019, 8 pages.
U.S. Appl. No. 16/510,118, Notice of Allowance dated Sep. 13, 2021, 8 pages.
U.S. Appl. No. 17/061,336, Office Action dated Jan. 12, 2022, 17 pages.
U.S. Appl. No. 17/099,308, Office Action dated Jan. 3, 2022, 28 pages.
Hawe, et al., "Forced degradation of therapeutic proteins." J Pharm Sci. (Mar. 2012); 101(3): 895-913. Epub Nov. 14, 2011.
U.S. Appl. No. 14/714,198, filed May 15, 2015, Bhandari et al.
U.S. Appl. No. 14/775,469, filed Mar. 17, 2014, Smythe et al.
U.S. Appl. No. 14/800,627, filed Jul. 15, 2015, Bourne et al.
U.S. Appl. No. 14/872,975, filed Oct. 1, 2015, Bhandari et al.
U.S. Appl. No. 15/000,923, filed Jan. 19, 2016, Bhandari et al.
U.S. Appl. No. 15/046,325, filed Feb. 17, 2016, Bhandari et al.
U.S. Appl. No. 15/255,750, filed Sep. 2, 2016, Bhandari et al.
U.S. Appl. No. 15/258,540, filed Sep. 7, 2016, Bhandari et al.
U.S. Appl. No. 15/321,124, filed Dec. 21, 2016, Bourne et al.
U.S. Appl. No. 15/442,229, filed Feb. 24, 2017, Bourne et al.
U.S. Appl. No. 15/467,810, filed Mar. 23, 2017, Bhandari et al.
U.S. Appl. No. 15/486,684, filed Apr. 13, 2017, Bhandari et al.
U.S. Appl. No. 15/493,471, filed Apr. 21, 2017, Bhandari et al.
U.S. Appl. No. 15/514,983, filed Mar. 28, 2017, Bhandari et al.
U.S. Appl. No. 15/614,047, filed Jun. 5, 2017, Bhandari et al.
U.S. Appl. No. 15/698,407, filed Sep. 7, 2017, Bhandari, et al.
U.S. Appl. No. 15/720,333, filed Sep. 29, 2017, Smythe, et al.
U.S. Appl. No. 15/828,214, filed Nov. 30, 2017, Smythe, et al.
U.S. Appl. No. 15/831,087, filed Dec. 4, 2017, Bhandari et al.
U.S. Appl. No. 15/831,099, filed Dec. 4, 2017, Bhandari, et al.
U.S. Appl. No. 15/831,100, filed Dec. 4, 2017, Bhandari et al.
U.S. Appl. No. 15/831,120, filed Dec. 4, 2017, Bhandari et al.
U.S. Appl. No. 15/836,648, filed Dec. 8, 2017, Bhandari, et al.
U.S. Appl. No. 15/745,371, filed Jan. 16, 2018, Bhandari, et al.
U.S. Appl. No. 16/035,060, filed Jul. 13, 2018, Bhandari, et al.
U.S. Appl. No. 16/037,982, filed Jul. 17, 2018, Smythe, et al.
U.S. Appl. No. 16/039,813, filed Jul. 19, 2018, Bhandari, et al.
U.S. Appl. No. 16/113,072, filed Aug. 27, 2018, Bhandari, et al.
U.S. Appl. No. 16/128,352, filed Sep. 11, 2018, Anandan, et al.
U.S. Appl. No. 16/217,864, filed Dec. 12, 2018, Bourne, et al.
U.S. Appl. No. 16/282,908, filed Feb. 22, 2019, Bhandari, et al.
U.S. Appl. No. 16/282,920, filed Feb. 22, 2019, Bhandari, et al.
U.S. Appl. No. 16/319,958, filed Jan. 23, 2019, Bhandari, et al.
U.S. Appl. No. 16/348,293, filed May 8, 2019, Cheng, et al.
U.S. Appl. No. 16/376,565, filed Apr. 5, 2019, Bhandari, et al.
U.S. Appl. No. 16/382,783, filed Apr. 12, 2019, Bhandari, et al.
U.S. Appl. No. 16/417,075, filed May 20, 2019, Bhandari, et al.
U.S. Appl. No. 16/439,435, filed Jun. 12, 2019, Bourne, et al.
U.S. Appl. No. 16/478,733, filed Jul. 17, 2019, Bhandari, et al.
U.S. Appl. No. 16/510,118, filed Jul. 12, 2019, Bhandari, et al.
U.S. Appl. No. 16/553,486, filed Aug. 28, 2019, Smythe, et al.
U.S. Appl. No. 16/656,339, filed Oct. 17, 2019, Bhandari, et al.
U.S. Appl. No. 16/689,884, filed Nov. 20, 2019, Bhandari, et al.
U.S. Appl. No. 16/700,659, filed Dec. 2, 2019, Bhandari, et al.
U.S. Appl. No. 16/774,686, filed Jan. 28, 2020, Bhandari, et al.
U.S. Appl. No. 16/780,297, filed Feb. 3, 2020, Bhandari, et al.
U.S. Appl. No. 16/781,516, filed Feb. 4, 2020, Bhandari, et al.
U.S. Appl. No. 16/839,368, filed Apr. 3, 2020, Smythe, et al.
U.S. Appl. No. 16/856,521, filed Apr. 23, 2020, Bhandari, et al.
U.S. Appl. No. 16/931,046, filed Jul. 16, 2020, Bhandari, et al.
U.S. Appl. No. 16/940,989, filed Jul. 28, 2020, Bhandari, et al.

(56) References Cited

OTHER PUBLICATIONS

U.S. Appl. No. 16/964,708, filed Jul. 24, 2020, Bourne, et al.
U.S. Appl. No. 17/001,428, filed Aug. 24, 2020, Bhandari, et al.
U.S. Appl. No. 17/011,844, filed Sep. 3, 2020, Liu et al.
U.S. Appl. No. 17/061,336, filed Oct. 1, 2020, Bourne, et al.
Adams and Macmillan, "Investigation of peptide thioester formation via N→Se acyl transfer." Journal of Peptide Science (2013); 19 (2): 65-73.
Andreu, et al., "Formation of Disulfide Bonds in Synthetic Peptides and Proteins" Ch. 7 in Synthetic Peptides and Proteins. In: Pennington M.W., Dunn B.M. (eds) Peptide Synthesis Protocols. Methods in Molecular Biology (1994); 35: 91-169.
Ashby, et al., "Plasma hepcidin levels are elevated but responsive to erythropoietin therapy in renal disease." Kidney International (2009); 75 (9): 976-981.
Balasubramanian and Kuppuswamy, "RGD-containing Peptides Activate S6K1 through $\beta_3$ Integrin in Adult Cardiac Muscle Cells", J Biol Chem. (Oct. 24, 2003); 278(43): 42214-42224. Epub Aug. 9, 2003.
Boer, J., et al., "Design and Synthesis of Potent and Selective $\alpha_4\beta_7$ Integrin Antagonists." J. Med. Chem. (2001); 44 (16): 2586-2592.
Bowie, et al., "Deciphering the Message in Protein Sequences: Tolerance to Amino Acid Substitutions." Science (1990); 247: 1306-1310.
Brayden, D.J., and Mrsny, R.J., "Oral peptide delivery: prioritizing the leading technologies". Therapeutic Delivery (2011); 2(12): 1567-1573.
Chatterjee, J. et al., "N-Methylation of Peptides: a New Perspective in Medicinal Chemistry", Accounts of Chemical Research, 41(10): 1331-1342 (2008).
Clark, et al., "Understanding the Structure/Activity Relationships of the Iron Regulatory Peptide Hepcidin." Chem Biol. (Mar. 2011); 18(3): 336-343.
Clark, Richard J., et al. "Design, synthesis, and characterization of cyclic analogues of the iron regulatory peptide hormone hepcidin." Peptide Science (2013); 100.5: 519-526.
Database EPO Proteins [Online] Dec. 3, 2010 (Dec. 3, 2010), "Sequence from Patent WO2010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from U.S. Pat. No. 8,313,950.", XP002761650, retrieved from EBI accession No. USPOP:AGA36544 Database accession No. AGA36544, 1 page.
Davies, J.S., "The Cyclization of Peptides and Depsipeptides", J Pept Sci. (Aug. 2003); 9(8): 471-501.
De Mast, et al., "Increased serum hepcidin and alterations in blood iron parameters associated with asymptomatic P. falciparum and P. vivax malaria." Haematologica (2010); 95 (7): 1068-1074.
Definition of Isostere, Medical Definition and More from Merriam-Webster Dictionary, 3 pages, www.merriam-webster.com/medical/isostere accessed on Feb. 5, 2015.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing α-Helices in Short Oligopeptides through Binding by an Artificial Hydrophobic Cavity." Journal of the American Chemical Society (2010); 132.16: 5564-5565.
Dubree, Nathan J.P. et al., "Selective α4β7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)-Mediated Cell Adhesion Based on the Ile-Leu-Asp-Val Tetrapeptide", J. Peptide Sci. (2000); 6: 321-341.
European Application No. 14763104.8, Extended European Search Report dated Sep. 23, 2016, 10 pages.
European Application No. 14779463.0, Extended European Search Report dated Nov. 9, 2016, 9 pages.
European Application No. 14780207.8, Extended European Search Report dated Feb. 17, 2017, 9 pages.
European Application No. 14780207.8, Partial Supplementary European Search Report dated Nov. 16, 2016, 6 pages.
European Application No. 15792950.6, Extended European Search Report dated May 2, 2018, 10 pages.
European Application No. 15812513.8, Extended European Search Report dated Apr. 12, 2018, 11 pages.
European Application No. 15821351.2, Extended European Search Report dated Jan. 3, 2018, 6 pages.
European Application No. 15846131.9, Extended European Search Report dated Jan. 25, 2018, 8 pages.
European Application No. 15846983.3, Extended European Search Report dated Jun. 19, 2018, 10 pages.
European Application No. 15846983.3, Partial European Search Report dated Mar. 2, 2018, 11 pages.
European Application No. 16825301.1, Extended European Search Report dated Jan. 21, 2019, 6 pages.
European Application No. 18741939.5, Partial Supplementary European Search Report dated Aug. 26, 2020, 13 pages.
European Application No. 18741939.5, Extended European Search Report dated Nov. 27, 2020, 11 pages.
Ganz and Nemeth, "Hepcidin and iron homeostasis." Biochimica et Biophysica Acta (BBA)—Molecular Cell Research (Sep. 2012); 1823 (9): 1434-1443.
Gee et al. "Cyclic Peptides as Non-carboxyl-terminal Ligands of Syntrophin PDZ Domains," The Journal of Biological Chemistry, 273(34): 21980-21987 (1998).
Gentilucci, et al., "Chemical Modifications Designed to Improve Peptide Stability: Incorporation of Non-Natural Amino Acids, Pseudo-Peptide Bonds, and Cyclization". Curr Pharm Des. (2010); 16(28): 3185-3203.
Girelli, Domenico, et al. "Hepcidin in the diagnosis of iron disorders." Blood (2016); 127.23 : 2809-2813.
Haanstra, et al., "Antagonizing the a4B1 Integrin, but no a4B7, Inhibits Leukocytic Infiltration of the Central Nervous System in Rhesus Monkey Experimental Autoimmune Encephalomyelitis", Journal of Immunology, 90(5): 1961-1973 (2013).
Ilyin, Gennady, et al. "Comparative analysis of mouse hepcidin 1 and 2 genes: evidence for different patterns of expression and co-inducibility during iron overload 1." FEBS Letters (2003); 542.1-3 : 22-26.
Jackson, D.Y., "Alpha 4 integrin antagonists." Current Pharmaceutical Design, (8)14: 1229-1253 (2002).
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Jordan, John B., et al. "Hepcidin revisited, disulfide connectivity, dynamics, and structure." Journal of Biological Chemistry (2009); 284.36: 24155-24167.
Kelleman, A. et al., "Incorporation of thioether building blocks into an $\alpha_\nu\beta_3$-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, p. 9, 3 pages.
Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Krause, Alexander, et al. "LEAP-1, a novel highly disulfide-bonded human peptide, exhibits antimicrobial activity." FEBS Letters (2000); 480.2-3 : 147-150.
Kuchař, et al., "Human interleukin-23 receptor antagonists derived from an albumin-binding domain scaffold inhibit IL-23-dependent ex vivo expansion of IL-17-producing T-cells". Proteins (Jun. 2014); 82(6): 975-989. Epub Nov. 23, 2013.

(56) References Cited

OTHER PUBLICATIONS

Legge and Morieson, "On the prediction of partition coefficients and $R_F$ values of peptides." Aust. J. Biol. Sci. (1964); 17: 561-571.
Ley, Klaus, et al. "Integrin-based therapeutics: biological basis, clinical use and new drugs." Nature Reviews Drug Discovery (2016); 15.3: 173-183.
Li and Roller, "Cyclization Strategies in Peptide Derived Drug Design." Curr. Topics Med. Chem. (2002); 2: 325-341.
Liu, Shuang, "Radiolabeled Cyclic RGD Peptides as Integrin $\alpha_v\beta_3$-Targeted Radiotracers: Maximizing Binding Affinity via Bivalency." Bioconjugate Chem. (2009); 20 (12): 2199-2213.
Liu, Shuang, "Radiolabeled Multimeric Cyclic RGD Peptides as Integrin avB3 Targeted Radiotracers for Tumor Imaging", School of Health Science, Purdue University, Molecular Pharmaceutics (2006); 3(5): 472-487.
Madsen, Kjeld, et al. "Structure—activity and protraction relationship of long-acting glucagon-like peptide-1 derivatives: importance of fatty acid length, polarity, and bulkiness." Journal of Medicinal Chemistry (2007); 50.24: 6126-6132.
Hruby and Bonner, "Design of Novel Synthetic Peptides Inlcuding Cyclic Conformationally and Topgraphically Constrained Analogs". Methods in Molecular Biology, Ch. 11, vol. 35 Peptide Synthesis Protocols, Edited by M.W Pennington and B. M. Dunn Copyright, 1994 Humana Press Inc, Totowa, NJ, pp. 201-241, 40 pages.
Muñoz, Manuel, et al. "Disorders of iron metabolism. Part II: iron deficiency and iron overload." Journal of Clinical Pathology (2011); 64.4: 287-296.
Nemeth, Elizabeta, et al. "The N-terminus of hepcidin is essential for its interaction with ferroportin: structure-function study." Blood (2006); 107.1: 328-333.
Park, C.H., et al., "Hepcidin, a urinary antimicrobial peptide synthesized in the liver." J Biol Chem. (2001); 276(11): 7806-7810. Epub Dec. 11, 2000.
Parrow, et al., "Prospects for a hepcidin mimic to treat β-thalassemia and hemochromatosis." Expert Review of Hematology (2011); 4 (3): 233-235.
Pattarawarapan, "Selective Formation of Homo- and Heterobivalent Peptidomimetics." J. Med. Chem. (Aug. 2003); 46 (17): 3565-3567.
PCT/US2013/064439, International Preliminary Reporton Patentability, dated Apr. 14, 2015, 8 pages.
PCT/US2013/064439, International Search Report and Written Opinion, dated Jan. 24, 2014, 15 pages.
PCT/US2014/030352, International Preliminary Reporton Patentability, dated Sep. 15, 2015, 7 pages.
PCT/US2014/030352, International Search Report and Written Opinion, dated Nov. 28, 2014, 12 pages.
PCT/US2014/030352, Invitation to Pay Additional Fees, dated Sep. 10, 2014, 2 pages.
PCT/US2014/032391, International Preliminary Reporton Patentability, dated Oct. 6, 2015, 8 pages.
PCT/US2014/032391, International Search Report, dated Aug. 7, 2014, 5 pages.
PCT/US2014/032391, Written Opinion, dated Aug. 7, 2014, 7 pages.
PCT/US2014/032392, International Preliminary Reporton Patentability, dated Oct. 6, 2015, 10 pages.
PCT/US2014/032392, International Search Report and Written Opinion, dated Sep. 15, 2014, 15 pages.
PCT/US2015/031243, International Preliminary Reporton Patentability, dated Nov. 22, 2016, 8 pages.
PCT/US2015/031243, International Search Report and Written Opinion, dated Aug. 5, 2015, 14 pages.
PCT/US2015/038370, International Preliminary Reporton Patentability, dated Dec. 27, 2016, 4 pages.
PCT/US2015/038370, International Search Report and Written Opinion, dated Sep. 14, 2015, 5 pages.
PCT/US2015/040658, International Preliminary Reporton Patentability, dated Jan. 17, 2017, 5 pages.
PCT/US2015/040658, International Search Report and Written Opinion, dated Oct. 28, 2015, 12 pages.
PCT/US2015/053558, International Preliminary Reporton Patentability, dated Apr. 4, 2017, 9 pages.
PCT/US2015/053558, International Search Report and Written Opinion, dated Feb. 19, 2016, 16 pages.
PCT/US2015/053558, Invitation to Pay Additional Fees, dated Dec. 16, 2015, 3 pages.
PCT/US2015/053603, International Preliminary Reporton Patentability, dated Apr. 4, 2017, 8 pages.
PCT/US2015/053603, International Search Report and Written Opinion, dated Feb. 12, 2016, 13 pages.
PCT/US2015/053603, Invitation to Pay Additional Fees, dated Dec. 10, 2015, 3 pages.
PCT/US2016/042680, (2nd) International Search Report and Written Opinion, dated Apr. 17, 2017, 13 pages.
PCT/US2016/042680, International Search Report and Written Opinion, dated Jan. 13, 2017, 12 pages.
PCT/US2016/069255, International Search Report and Written Opinion dated Jun. 1, 2017, 11 pages.
PCT/US2016/069255, Invitation to Pay Additional Fees, dated Mar. 30, 2017, 2 pages.
PCT/US2016/069255, International Preliminary Reporton Patentability, dated Jul. 3, 2018, 7 pages.
PCT/US2017/044249, International Preliminary Reporton Patentability, dated Jan. 29, 2019, 9 pages.
PCT/US2017/044249, International Search Report and Written Opinion, dated Nov. 21, 2017, 14 pages.
PCT/US2017/044249, Invitation to Pay Additional Fees, dated Sep. 14, 2017, 3 pages.
PCT/US2018/014257, International Preliminary Report on Patentability, dated Jul. 23, 2019, 9 pages.
PCT/US2018/014257, International Search Report and Written Opinion, dated May 14, 2018, 13 pages.
PCT/US2018/014257, Invitation to Pay Additional Fees, dated Mar. 22, 2018, 2 pages.
PCT/US2018/050480, International Preliminary Reporton Patentability dated Mar. 17, 2020, 7 pages.
PCT/US2018/050480, International Search Report and Written Opinion, dated Jan. 29, 2019, 13 pages.
PCT/US2018/050480, Invitation to Pay Additional Fees, dated Nov. 6, 2018, 3 pages.
PCT/US2019/017192, International Search Report and Written Opinion, dated Jun. 11, 2019, 13 pages.
PCT/US2019/017192, International Preliminary Reporton Patentability, dated Aug. 11, 2020, 7 pages.
PCT/US2019/017192, Invitation to Pay Additional Fees, dated Apr. 16, 2019, 2 pages.
PCT/US2019/041665, Invitation to Pay Additional Fees, dated Oct. 22, 2019, 3 pages.
PCT/US2019/041665, International Search Report and Written Opinion dated Dec. 19, 2019, 16 pages.
Pelton, J.T. et al., "Somatostatin Analogs with Affinity for Opiate Receptors in Rat Brain Binding Assay", Peptides, 6(Suppl 1): 159-163 (1985).
Preza, G., et al., "Minihepcidins are rationally designed small peptides that mimic hepcidin activity in mice and may be useful for the treatment of iron overload", J Clin Invest (2011); 121(12): 4880-4888.
Quiniou, et al., "Specific targeting of the IL-23 receptor, using a novel small peptide noncompetitive antagonist, decreases the inflammatory response". Am J Physiol Regul Integr Comp Physiol. (Nov. 15, 2014); 307(10): R1216-R1230. Epub Aug. 20, 2014.
Ramos, E., et al., "Minihepcidins prevent iron overload in a hepcidin-deficient mouse model of severe hemochromatosis." Blood (Nov. 2012); 120(18): 3829-3836. Epub Sep. 18, 2012.
Rivera, Seth, et al. "Synthetic hepcidin causes rapid dose-dependent hypoferremia and is concentrated in ferroportin-containing organs." Blood (2005); 106.6: 2196-2199.
Rostovtsev, et al., "A Stepwise Huisgen Cycloaddition Process: Copper(I)-Catalyzed Regioselective "Ligation" of Azides and Terminal Alkynes". Angewandte Chemie Int. Ed. (Jul. 2, 2002); 41(14): 2596-2599.

(56) References Cited

OTHER PUBLICATIONS

Sasaki, et al., "D-Arg2-dermorphin tetrapeptide analogs: a potent and long-lasting analgesic activity after subcutaneous administration." Biochem Biophys Res Commun. (1984); 120 (1): 214-218.
Search Report and Written Opinion in Singaporean Application No. 112016096140, dated Mar. 12, 2018, 9 pages.
Search Report and Written Opinion in Singaporean Application No. 11201610799W, dated May 31, 2018, 4 pages.
Search Report and Written Opinion in Singaporean Application No. 11201700327W, dated Mar. 16, 2018, 10 pages.
Shahidi, Neal, et al. "Vedolizumab for the treatment of ulcerative colitis." Expert Opinion on Biological Therapy (2016); 16.1 : 129-135.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
Soler-Ferran and Briskin, "Integrin $\alpha_4\beta_7$ Antagonists: Activities, Mechanisms of Action and Therapeutic Prospects", Current Immunology Reviews (2012), 8(2): 118-134.
Speers, et al., "Activity-Based Protein Profiling in Vivo Using a Copper(I)-Catalyzed Azide-Alkyne [3+2] Cycloaddition". J. Am. Chem. Soc. (Mar. 28, 2003); 125(16): 4686-4687.
Tandara, Leida, and Salamunic, Ilza . "Iron metabolism: current facts and future directions." Biochemia Medica (2012); 22.3: 311-328.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
Tornøe, et al., "Peptidotriazoles on solid phase: [1,2,3]-triazoles by regiospecific copper(i)-catalyzed 1,3-dipolar cycloadditions of terminal alkynes to azides." J Org Chem. (May 3, 2002); 67(9): 3057-3064.
Tuvia, et al., "A Novel Suspension Formulation Enhances Intestinal Absorption of Macromolecules Via Transient and Reversible Transport Mechanisms". Pharm Res. (Feb. 21, 2014); 31(8): 2010-2021.
U.S. Appl. No. 14/050,349, Final Office Action dated Sep. 9, 2015, 17 pages.
U.S. Appl. No. 14/050,349, Non-Final Office Action dated Feb. 27, 2015, 14 pages.
U.S. Appl. No. 14/050,349, Notice of Allowance dated Jan. 12, 2016, 9 pages.
U.S. Appl. No. 14/229,784, Non-Final Office Action dated Aug. 13, 2015, 16 pages.
U.S. Appl. No. 14/229,784, Office Action dated Mar. 8, 2016, 6 pages.
U.S. Appl. No. 14/229,799, Non-Final Office Action dated Jul. 24, 2015, 19 pages.
U.S. Appl. No. 14/229,799, Office Action dated Mar. 4, 2016, 18 pages.
U.S. Appl. No. 14/714,198, Notice of Allowance dated Mar. 17, 2017, 3 pages.
U.S. Appl. No. 14/714,198, Office Action dated Nov. 7, 2016, 6 pages.
U.S. Appl. No. 14/775,469, Notice of Allowance dated Aug. 10, 2017, 11 pages.
U.S. Appl. No. 14/775,469 , Notice of Allowance dated Sep. 5, 2017, 9 pages.
U.S. Appl. No. 14/775,469 , Office Action dated Apr. 11, 2017, 22 pages.
U.S. Appl. No. 14/800,627, Notice of Allowance dated Feb. 15, 2017, 9 pages.
U.S. Appl. No. 14/800,627, Office Action dated Aug. 25, 2016, 11 pages.
U.S. Appl. No. 14/872,975, Notice of Allowance dated Aug. 16, 2017, 9 pages.
U.S. Appl. No. 14/872,975, Office Action dated Dec. 27, 2016, 14 pages.
U.S. Appl. No. 15/046,325, Office Action dated Aug. 1, 2016, 13 pages.
U.S. Appl. No. 15/442,229, Notice of Allowance dated Sep. 12, 2018, 9 pages.
U.S. Appl. No. 15/442,229, Office Action dated Apr. 20, 2018, 12 pages.
U.S. Appl. No. 15/514,983, Office Action dated Nov. 2, 2018, 8 pages.
U.S. Appl. No. 15/614,047, Notice of Allowance dated Jun. 7, 2018, 8 pages.
U.S. Appl. No. 15/698,407, Office Action dated Apr. 25, 2019, 15 pages.
U.S. Appl. No. 15/720,333, Office Action dated Aug. 28, 2018, 24 pages.
U.S. Appl. No. 15/828,214, Notice of Allowance dated Jun. 11, 2018, 9 pages.
U.S. Appl. No. 15/828,214, Office Action dated May 15, 2018, 12 pages.
U.S. Appl. No. 15/831,087, Notice of Allowance dated May 11, 2018, 8 pages.
U.S. Appl. No. 15/831,087, Office Action dated Apr. 12, 2018, 10 pages.
U.S. Appl. No. 15/831,100, Notice of Allowance dated May 8, 2018, 8 pages.
U.S. Appl. No. 15/831,100, Office Action dated Apr. 12, 2018, 11 pages.
U.S. Appl. No. 15/836,648, Office Action dated Nov. 6, 2018, 7 pages.
U.S. Appl. No. 15/514,983, Notice of Allowance dated Jan. 7, 2019, 6 pages.
U.S. Appl. No. 16/128,352, Notice of Allowability dated Feb. 21, 2019, 2 pages.
U.S. Appl. No. 16/128,352, Notice of Allowance dated Feb. 6, 2019, 5 pages.
U.S. Appl. No. 16/289,451, Office Action dated Mar. 21, 2019, 21 pages.
U.S. Appl. No. 16/037,982, Office Action dated Mar. 22, 2019, 29 pages.
U.S. Appl. No. 16/039,813, Office Action dated Apr. 19, 2019, 11 pages.
U.S. Appl. No. 15/698,407, Office Action dated Aug. 5, 2019, 10 pages.
U.S. Appl. No. 16/039,813, Office Action dated Aug. 22, 2019, 11 pages.
U.S. Appl. No. 16/039,813, Notice of Allowance dated Nov. 7, 2019, 10 pages.
U.S. Appl. No. 15/745,371, Office Action dated Dec. 19, 2019, 22 pages.
U.S. Appl. No. 16/039,813, Corrected Notice of Allowability dated Jan. 31, 2020, 5 pages.
U.S. Appl. No. 16/067,568, Office Action dated Apr. 2, 2020, 15 pages.
U.S. Appl. No. 16/478,733, Office Action dated Sep. 9, 2020, 24 pages.
U.S. Appl. No. 16/510,118, Office Action dated Sep. 4, 2020, 16 pages.
Waitemata District Health Board, "Crushing Guide for Oral Medication in Residential Aged Care", 2 pages (2011).
Wang, et al., "Bioconjugation by Copper(I)-Catalyzed Azide-Alkyne [3+2] Cycloaddition". J Am Chem Soc. (Mar. 19, 2003); 125(11): 3192-3193.
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yampolsky and Stoltzfus, "The Exchangeability of Amino Acids in Proteins", Genetics (Aug. 2005); 170(4): 1459-1472. Epub Jun. 8, 2005.

(56) References Cited

OTHER PUBLICATIONS

Yu and Gallagher, "A Naturally Occurring, Soluble Antagonist of Human IL-23 Inhibits the Development and In Vitro Function of Human Th17 Cells", The Journal of Immunology, 185: 7302-7308 (2010).
Annis, et al., "[10] Disulfide bond formation in peptides". Methods Enzymol. (1997); 289: 198-221.
Cheng et al., "The Biomarker Profile of PTG-200, an Oral Peptide Antagonist of IL-23 Receptor, Tracks with Efficacy in a Preclinical Model of IBD". Gastroenterology, AGA Abstracts, vol. 152, Issue 5, Supplement 1, S31, Apr. 1, 2017.
Chermahini et al., "Cyclic peptide nanocapsule as ion carrier for halides: a theoretical survey," Structural Chemistry, 2018, vol. 29, pp. 1351-1357.
Delgado et al., "The uses and properties of PEG-linked proteins". Critical Reviews in Therapeutic Drug Carrier Systems (Jan. 1, 1992); 9(3-4): 249-304.
European Application No. 19750312.1, Extended European Search Report dated Mar. 3, 2022, 11 pages.
Hruby, et al., "Recent Developments in the Design of Receptor Specific Opioid Peptides." Medicinal Research Reviews (1989); 9(3): 343-401.
Hu, et al., "Synthesis and biological evaluations of novel endomorphin analogues containing α-hydroxy-β-phenylalanine (AHPBA) displaying mixed μ/σ opioid receptor agonist and σ opioid receptor antagonist activities". European Journal of Medicinal Chemistry (Mar. 6, 2015); 92: 270-281. Epub Dec. 29, 2014.
Hudecz, et al., "Synthesis, conformation, biodistribution and in vitro cytotoxicity of daunomycin-branched polypeptide conjugates". Bioconjugate Chem. (Jan. 1, 1992); 3(1): 49-57.
Jagasia et al., "Peptide Cyclization and Cyclodimerization by Cu-Mediated Azide-Alkyne Cycloaddition", Journal of Organic Chemistry (Apr. 17, 2009); 74(8): 2964-2974.
Liu and Wang, "Endomorphins: potential roles and therapeutic indications in the development of opioid peptide analgesic drugs". Med Res Rev. (May 2012); 32(3): 536-580. Epub Feb. 1, 2011.
Longobardo, et al., "β-Casomorphins: substitution of phenylalanine with β-homo-phenylalanine increases the μ-type opioid receptor affinity." Bioorganic & Medicinal Chemistry Letters (2000); 10(11): 1185-1188.
Longobardo, et al., "Incorporation of β-amino acids in bioactive peptides: a β-casomorphin case study." Peptides 2002, Abstract P A97, Proceedings of the European Peptide Symposium, 27th, Sorrento, Italy, Aug. 31-Sep. 6, 2002 (2002), 198-199.
Maeda, et al., "Conjugates of anticancer agents and polymers: advantages of macromolecular therapeutics in vivo". Bioconjugate Chem. (Sep./Oct. 1992); 3(5): 3511-362.
Makharia, Govind K., "Current and emerging therapy for celiac disease", Frontiers in Medicine (Mar. 2014); vol. 1, Article 6, pp. 1-11.
Simmerling et. al., "Hydrophobic "Collapse" in a Cyclic Hexapeptide: Computer Simulations of CHDLFC and CAAAAC in Water" Journal of American Chemical Society. 1994. 116. 2534-2547.
Witt, Dariusz, "Recent developments in disulfide bond formation". Synthesis (2008); 16: 2491-2509.
Zalipsky, Samuel, "Functionalized Poly(ethylene glycols) for Preparation of Biologically Relevant Conjugates". Bioconjugate Chem. (1995); 6(2): 150-165.
Co-pending U.S. Appl. No. 17/149,509, inventor Sun, filed Jan. 14, 2021.
Co-pending U.S. Appl. No. 17/149,544, inventor Sun, filed Jan. 14, 2021.
Co-pending U.S. Appl. No. 17/531,538, inventor Sun, et al., filed Nov. 19, 2021.
Co-pending U.S. Appl. No. 17/792,594, inventors Bhandari; Ashok et al., filed Jul. 13, 2022.
Angelucci, et al., "Myelodysplastic Syndromes and Iron Chelation Therapy". Mediterr J Hematol Infect Dis. (Mar. 1, 2017); 9(1): e2017021. eCollection 2017.
Arber, Daniel A., et al., "The 2016 revision to the World Health Organization classification of myeloid neoplasms and acute leukemia", Blood, The Journal of the American Society of Hematology (May 19, 2016); 127(20): 2391-2405.
[Author Unknown] "FDA Grants Orphan Drug Designation For Protagonist Therapeutics' PTG-300 for the Treatment of Beta-Thalassemia", Protagonist Therapeutics, Cision PR Newswire (Mar. 6, 2018); [Press release] http://www.prnewswire.com/news-releases/fda-grants-orphan-drug-designation-for-protagonist-therapeuticsptg-300-for-the-treatment-of-beta-thalassemia-300609386.html, 2 pages.
[Author Unknown] "Protagonist Announces Phase 1 and Preclinical Data on Hepcidin Mimetic PTG-300 Presented at European Hematology Association Annual Meeting", Protagonist Therapeutics, Cision PR Newswire (Jun. 18, 2018); [Press release] https://www.prnewswire.com/news-releases/protagonist-announces-phase-1-and-pre-clinical-data-on-hepcidin-mimetic-ptg-300-presented-at-european-hematology-association-annual-meeting-300667520.html, 2 pages.
[Author Unknown] "Protagonist Therapeutics Announces Fast Track Designation Granted by U.S. FDA to Hepcidin Mimetic PTG-300", Protagonist Therapeutics, Cision PR Newswire (Sep. 27, 2018); [Press release] https://www.prnewswire.com/news-releases/protagonist-therapeutics-announces-fast-track-designation-granted-by-us-fda-to-hepcidin-mimetic-ptg-300-300720035.html, 2 pages.
[Author Unknown] "Protagonist Therapeutics Expands Intellectual Property Portfolio", Protagonist Therapeutics, Cision PR Newswire (Sep. 6, 2018); [Press release] https://www.prnewswire.com/news-releases/protagonist-therapeutics-expands-intellectual-property-portfolio-300707765.html, 1 page.
[Author Unknown] "Protagonist Therapeutics Initiates Phase 2 Study of Novel Hepcidin Mimetic PTG-300 in the Treatment of Patients with Polycythemia Vera", Protagonist Therapeutics, Cision PR Newswire (Oct. 30, 2019); [Press release] https://www.prnewswire.com/news-releases/protagonist-therapeutics-initiates-phase-2-study-of-novel-hepcidin-mimetic-ptg-300-in-the-treatment-of-patients-with-polycythemia-vera-300948611.html, 2 pages.
[Author Unknown] "Protagonist Therapeutics Initiates Phase 2 Trial of Novel Hepcidin Mimetic PTG-300 for the Treatment of Patients with Beta Thalassemia", Protagonist Therapeutics, Cision PR Newswire (Jan. 9, 2019); [Press release] https://www.prnewswire.com/news-releases/protagonist-therapeutics-initiates-phase-2-trial-of-novel-hepcidin-mimetic-ptg-300-for-the-treatment-of-patients-with-beta-thalassemia-300775348.html, 2 pages.
[Author Unknown] "Protagonist Therapeutics Reports Second Quarter 2019 Financial Results", Protagonist Therapeutics, Cision PR Newswire (Aug. 7, 2019); [Press release] https://www.prnewswire.com/news-releases/protagonist-therapeutics-reports-second-quarter-2019-financial-results-300897892.html, 3 pages.
Balwani, Manisha, "Erythropoietic Protoporphyria and X-Linked Protoporphyria: pathophysiology, genetics, clinical manifestations, and management". Mol Genet Metab (Nov. 2019); 128(3): 298-303. Epub Jan. 24, 2019.
Barman-Aksözen, et al., "Delta-aminolevulinic acid synthase 2 expression in combination with iron as modifiers of disease severity in erythropoietic protoporphyria". Molecular Genetics and Metabolism (Nov. 2019); 128(3): 304-308.
Boccia, Ralph V., et al., "Examining the frequency of phlebotomy in patients with polycythemia vera (PV) in the United States: an analysis of data from the REVEAL study", Blood (Dec. 8, 2017); 130(1): 5271.
Burton, et al., "Systemic administration of a pharmacologic iron chelator reduces cartilage lesion development in the Dunkin-Hartley model of primary osteoarthritis". Free Radical Biology and Medicine (Feb. 1, 2022); 179: 47-58.
Carroll, et al., "Hereditary hemochromatosis is characterized by a clinically definable arthropathy that correlates with iron load". Arthritis & Rheumatism (Jan. 2011); 63(1): 286-294.
Casu, Carla, et al., "Minihepcidin peptides as disease modifiers in mice affected by β-thalassemia and polycythemia vera", Blood, The Journal of the American Society of Hematology (2016); 128(2): 265-276.

(56) References Cited

OTHER PUBLICATIONS

Casu, et al., "Hepcidin agonists as therapeutic tools". Blood, The Journal of the American Society of Hematology (Apr. 19, 2018); 131(16): 1790-1794.
Chang, Seung-Gu, et al., "Role of disulfide bonds in the structure and activity of human insulin", Molecules & Cells (Springer Science & Business Media BV) (2003); 16(3): 323-330.
Clark, et al., "The Engineering of an Orally Active Conotoxin for the Treatment of Neuropathic Pain." Angew Chem Int Ed (Sep. 2010); 49: 6545-6548.
Craik, et al., "Potential therapeutic applications of the cyclotides and related cystine knot mini-proteins." Expert Opin Investig Drugs (May 2007); 16(5): 595-604.
Cui, et al., "Serum iron metabolism and erythropoiesis in patients with myelodysplastic syndrome not receiving RBC transfusions". Leuk Res. (2014); 38(5): 545-550.
De Vega, et al., "Modulation of Protein-Protein Interactions by Stabilizing/Mimicking Protein Secondary Structure Elements." Curr Top Med Chem (2007); 7(1): 33-62.
Dutton, et al., "A New Level of Conotoxin Diversity, a Non-native Disulfide Bond Connectivity in—Conotoxin AuIB Reduces Structural Definition but Increases Biological Activity." J Biol Chem (Oct. 2002); 277(50): 48849-48857.
Fass, D., "Disulfide bonding in protein biophysics." Annu Rev Biophys (2012); 41: 63-79. Epub Dec. 20, 2011.
Fosgerau and Hoffman, "Peptide therapeutics: current status and future directions." Drug Discovery Today (2015); 20(1): 122-128.
Foster, Allan B., "Deuterium isotope effects in studies of drug metabolism", Trends in Pharmacological Sciences (1984); 5: 524-527.
Francis, G., et al., "PEGylation of Cytokines and other Therapeutic Proteins and Peptides: the Importance of Biological Optimisation of Coupling Techniques," International Journal of Hematology, Jul. 1998, vol. 68, pp. 1-19.
Fruchtman, Steven M., et al., "From efficacy to safety: a Polycythemia Vera Study group report on hydroxyurea in patients with polycythemia vera", Seminars in hematology (1997); 34(1): 17-23.
Gombotz and Pettit, "Biodegradable Polymers for Protein and Peptide Drug Delivery". Bioconjugate Chem. (Jul. 1, 1995); 6(4): 332-351.
Goptar, I.A., et al., "Properties of Post-Proline Cleaving Enzymes from Tenebrio Molitor," Russian Journal of Bioorganic Chemistry, 2008, vol. 34(3), pp. 280-285.
Guerler and Knapp, "Novel protein folds and their nonsequential structural analogs." Protein Sci (Aug. 2008); 17(8): 1374-1382.
Guharoy and Chakrabarti, "Secondary structure based analysis and classification of biological interfaces: identification of binding motifs in protein-protein interactions." Bioinformatics (2007); 23(15): 1909-1918. Epub May 17, 2007.
Gupta, et al., "A classification of disulfide patterns and its relationship to protein structure and function." Protein Sci (Aug. 2004); 13(8): 2045-2058.
Hartig, et al., "Intramolecular disulphide bond arrangements in nonhomologous proteins." Protein Sci Publ Protein Soc (Feb. 2005); 14(2): 474-482.
Henikoff and Henikoff, "Amino acid substitution matrices from protein blocks." Proc Natl Acad Sci U S A (Nov. 1992); 89(Nov); 10915-10919.
Karim, et al., "The role of disrupted iron homeostasis in the development and progression of arthropathy". Journal of Orthopaedic Research (Jun. 2022); 40(6): 1243-1250.
Kowdley, et al., "An-Open Label Phase 2, Dose-Finding Study of the Safety and Efficacy of Rusfertide (PTG-300), A Hepcidin Mimetic, In Patients with Hereditary Hemochromatosis". AASLD Abstract 649, AASLD Hepatology (2021); 74, No. 1 (Suppl), pp. 25A-25B, 2 pages.
Kowdley, et al., "Monitoring and Management of Nash is an Unmet Need Among Hepatologists and Endocrinologists: An International Mixed-Method Study in Europe and the USA". AASLD Abstract (Poster) 649, AASLD Hepatology (2021); 74, No. 1(Suppl), pp. 394A, 1 page.
Lecha, et al., "Erythropoietic protoporphyria". Orphanet Journal of Rare Diseases (2009); 4: 19, 10 Pages.
List, A.F., "Iron overload in myelodysplastic syndromes: diagnosis and management". Cancer Control (Jan. 2010); 17(1_suppl):2-8, 7 pages.
Martinez, et al., "Hepatic damage and oxidative stress induced by griseofulvin in mice". Cellular and Molecular Biology (Jul. 1, 2009); 55(2): 127-139.
Nguyen, et al., "Bone and joint complications in patients with hereditary hemochromatosis: a cross-sectional study of 93 patients". Therapeutic Advances in Musculoskeletal Disease (Jul. 2020); 12: 1759720X20939405, 14 pages.
Paterson, I.C., et al., "Partial Characterization of Specific Inducers of a Cuticle-Degrading Protease from the Insect Pathogenic Fungus Metarhizium Anisopliae," Microbiology, 1994, vol. 140(11), pp. 3153-3159.
Pearson, T. C. and Wetherley-Mein, G., "Vascular occlusive episodes and venous hæmatocrit IN primary proliferative polycythæmlx", The Lancet (Dec. 9, 1978); 312(8102): 1219-1222.
Pettit, L.D., et al., "Influence of the Proline Residue on the Co-Ordination of Cu(II) to Peptides Containing –Pro- and –Pro –Pro-Subunits," Polyhedron, 1987, vol. 6(1), pp. 45-52.
Rampal, Raajit, et al., "Integrated genomic analysis illustrates the central role of Jak-STAT pathway activation in myeloproliferative neoplasm pathogenesis", e-Blood (May 29, 2014); 123(22): e123-33.
Rector Jr., William G., et al., "Non-hematologic effects of chronic iron deficiency: a study of patients with polycythemia vera treated solely with venesections", Medicine (Nov. 1982); 61(6): 382-389.
Rubinstein and Niv, "Peptidic modulators of protein-protein interactions: Progress and challenges in computational design." Biopolymers (2009); 91(7): 505-513.
Schmidt, et al., "Mild iron deficiency does not ameliorate the phenotype of a murine erythropoietic protoporphyria model". American Journal of Hematology (May 2020); 95(5): 492-496.
Sekeres and Cutler, "How we treat higher-risk myelodysplastic syndromes". Blood (Feb. 6, 2014); 123(6):829-836. Epub Dec. 20, 2013.
Shenoy, et al., "Impact of iron overload and potential benefit from iron chelation in low-risk myelodysplastic syndrome". Blood (Aug. 7, 2014); 124(6): 873-881. Epub Jun. 12, 2014.
Stein, Brady L., et al., "Polycythemia vera: an appraisal of the biology and management 10 years after the discovery of JAK2 V617F", Journal of Clinical Oncology (Nov. 20, 2015); 33(33): 3953-60.
Streiff, Michael B., et al., "The diagnosis and management of polycythemia vera in the era since the Polycythemia Vera Study Group: a survey of American Society of Hematology members' practice patterns", Blood, The Journal of the American Society of Hematology (Feb. 15, 2002); 99(4): 1144-1149.
Taranath, et al., "Regulation of Iron Homeostasis By PTG-300 Improves Disease Parameters in Mouse Models for Beta-Thalassemia and Hereditary Hemochromatosis". Blood (Nov. 13, 2019); 134 (Supplement_1): 3540, 3 pages.
Tefferi, A. et al., Myelodysplastic syndromes. N Engl J Med 361:1872-1885 (2009).
Tefferi, Ayalew and Barbui, Tiziano, "Polycythemia vera and essential thrombocythemia: 2017 update on diagnosis, risk-stratification, and management", American Journal of Hematology (Jan. 1, 2017); 92(1): 94-108.
Temraz, et al., "Iron overload and chelation therapy in myelodysplastic syndromes". Crit Rev Oncol Hematol. (Jul. 2014); 91(1): 64-73. Epub Jan. 24, 2014.
Tsukada, et al., "An Anti-α-Fetoprotein Antibody-Daunorubicin Conjugate With a Novel Poly-L-glutamic Acid Derivative as Intermediate Drug Carrier ". J. Natl. Cancer Inst. (Sep. 1984); 73(3): 721-729.
Whalen, et al., "Association of transferrin saturation with the arthropathy of hereditary hemochromatosis". Clinical Gastroenterology and Hepatology (Oct. 1, 2017); 15(10): 1507-1508.

(56) References Cited

OTHER PUBLICATIONS

White and Yudin, "Contemporary strategies for peptide macrocyclization." Nat Chem (Jun. 2011); 3(7): 509-524.

Wulf, et al., "Inactivation of protoporphyrin IX in erythrocytes in patients with erythropoietic protoporphyria: A new treatment modality". Photodiagnosis and Photodynamic Therapy (Mar. 1, 2020); 29: 101582.

Yoshida, et al., "Erythropoietic protoporphyria-related hepatopathy successfully treated with phlebotomy". Internal Medicine (Sep. 1, 2018); 57(17): 2505-2509.

Garcia, Josep et al., "D-Polyarginine Lipopeptides as Intestinal Permeation Enhancers". ChemMedChem Oct. 8, 2018; 13(19): 2045-2052. Epub Aug. 20, 2018.

Gruschow, et al., "New pacidamycin antibiotics through precursor-directed biosynthesis". Chembiochem. Jan. 26, 2009; 10(2): 355-360.

Maher, Sam et al., "Safety and efficacy of sodium caprate in promoting oral drug absorption: from in vitro to the clinic". Advanced Drug Delivery Reviews Dec. 17, 2009; 61 (15): 1427-1449. Epub Oct. 1, 2009.

Maher, Sam et al., "Application of Permeation Enhancers in Oral Delivery of Macromolecules: An Update". Pharmaceutics Jan. 19, 2019; 11 (1): 41, 23 pages.

Muheem, Abdul et al., "A review on the strategies for oral delivery of proteins and peptides and their clinical perspectives". Saudi Pharmaceutical Journal Jul. 2016; 24(4): 413-428. Epub Jun. 16, 2014.

\* cited by examiner 3-day dosing of Compound ID#105

3-day dosing of Compound ID#105

CONJUGATED HEPCIDIN MIMETICS

CROSS REFERENCE TO RELATED APPLICATIONS

This application is a U.S. national phase application of International application no. PCT/US2019/017192, filed on Feb. 9, 2019, which claims priority to U.S. Provisional Application No. 62/627,948, filed on Feb. 8, 2018, U.S. Provisional Application No. 62/627,952, filed on Feb. 8, 2018, U.S. Provisional Application No. 62/717,390, filed on Aug. 10, 2018, and U.S. Provisional Application No. 62/749,450, filed on Oct. 23, 2018, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is PRTH_031_01WO_ST25.txt. The text file is 116 KB, was created on Feb. 5, 2019, and is being submitted electronically via EFS-Web.

FIELD OF THE INVENTION

The present invention relates, inter alia, to certain hepcidin peptide analogues, including both peptide monomers and peptide dimers, and conjugates and derivatives thereof, as well as compositions comprising the peptide analogues, and to the use of the peptide analogues in the treatment and/or prevention of a variety of diseases, conditions or disorders, including treatment and/or prevention of iron overload diseases such as hereditary hemochromatosis, iron-loading anemias, and other conditions and disorders described herein.

BACKGROUND

Hepcidin (also referred to as LEAP-1), a peptide hormone produced by the liver, is a regulator of iron homeostasis in humans and other mammals. Hepcidin acts by binding to its receptor, the iron export channel ferroportin, causing its internalization and degradation. Human hepcidin is a 25-amino acid peptide (Hep25). See Krause et al. (2000) FEBS Lett 480:147-150, and Park et al. (2001) J Biol Chem 276:7806-7810. The structure of the bioactive 25-amino acid form of hepcidin is a simple hairpin with 8 cysteines that form 4 disulfide bonds as described by Jordan et al. J Biol Chem 284:24155-67. The N terminal region is required for iron-regulatory function, and deletion of 5 N-terminal amino acid residues results in a loss of iron-regulatory function. See Nemeth et al. (2006) Blood 107:328-33.

Abnormal hepcidin activity is associated with iron overload diseases, including hereditary hemochromatosis (HH) and iron-loading anemias. Hereditary hemochromatosis is a genetic iron overload disease that is mainly caused by hepcidin deficiency or in some cases by hepcidin resistance. This allows excessive absorption of iron from the diet and development of iron overload. Clinical manifestations of HH may include liver disease (e.g., hepatic cirrhosis and hepatocellular carcinoma), diabetes, and heart failure. Currently, the only treatment for HH is regular phlebotomy, which is very burdensome for the patients. Iron-loading anemias are hereditary anemias with ineffective erythropoiesis such as β-thalassemia, which are accompanied by severe iron overload. Complications from iron overload are the main cause of morbidity and mortality for these patients. Hepcidin deficiency is the main cause of iron overload in non-transfused patients, and contributes to iron overload in transfused patients. The current treatment for iron overload in these patients is iron chelation which is very burdensome, sometimes ineffective, and accompanied by frequent side effects.

Hepcidin has a number of limitations that restrict its use as a drug, including a difficult synthesis process due in part to aggregation and precipitation of the protein during folding, which in turn leads to high cost of goods. What are needed in the art are compounds having hepcidin activity and also possessing other beneficial physical properties such as improved solubility, stability, and/or potency, so that hepcidin-like biologics might be produced affordably and used to treat hepcidin-related diseases and disorders such as, e.g., those described herein.

The present invention addresses such needs, providing novel peptide analogues, including both peptide monomer analogues and peptide dimer analogues, having hepcidin activity and also having other beneficial properties making the peptides of the present invention suitable alternatives to hepcidin.

BRIEF SUMMARY OF THE INVENTION

The present invention generally relates to peptide analogues, including both monomer and dimers, exhibiting hepcidin activity and methods of using the same.

In one aspect, the present invention includes a hepcidin analogue comprising a peptide of Formula (I):

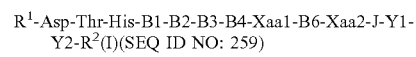

$R^1$-Asp-Thr-His-B1-B2-B3-B4-Xaa1-B6-Xaa2-J-Y1-Y2-$R^2$(I)(SEQ ID NO: 259)

or a peptide dimer comprising two peptides according to Formula I, or a pharmaceutically acceptable salt, or a solvate thereof,
wherein:
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
Xaa1 is B5; and
 i) B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys;
or
 ii) Xaa1 is B5(L1Z); B5 is Lys, D-Lys, Orn, homoSer, Gln, Lys(Ac), Ile, Abu, Leu, or Nleu; and Xaa2 is B7; and B7 is Glu or absent;
each of B1 and B6 is independently
 i) Phe, Dpa, bhPhe, a-MePhe, NMe-Phe, or D-Phe;
 ii) 2-Nal, 1-Nal, D-1-Nal, D-2-Nal, 3,3-diPhenylGly, Tic, Bip, Trp, bhTrp, hPhe, or Tyr(Me); or
 iii) substituted Phe, substituted bhPhe, or substituted Trp, or substituted bhTrp;
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B7 is Dapa, Lys, D-Lys, homoLys, or a-Me-Lys;
L1 is absent, Dapa, D-Dapa, or isoGlu, PEG, Ahx, isoGlu-PEG, PEG-Ahx, isoGlu-Ahx, or isoGlu-PEG-Ahx; Ahx is an aminohexanoic acid moiety;
Z is a half-life extension moiety;

J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;

Y1 is Cys, homoCys, (D)Cys, NMeCys, aMeCys, or Pen; Y2 is an amino acid or absent; Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homoTryptophane, 1-Nal is 1-naphthylalanine, 2-Nal is 2-naphthylalanine, Orn is orinithine, Nleu is norleucine, Abu is 2-aminobutyric acid;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;

wherein i) the peptide of formula I is optionally PEGylated on one or more $R^1$, B1, B2, B3, B4, B5, B6, B7, J, Y1, Y2, or R2; and ii) the peptide is cyclized via a disulfide bond between B3 and Y1.

In one embodiment, the half-life extension moiety is $C_{10}$-$C_{21}$ alkanoyl.

In one embodiment, Xaa1 is B5; B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys; and L1 is attached to $N^\varepsilon$ of Lys, D-Lys, homoLys, or a-Me-Lys; or $N^\beta$ of Dapa;

In another embodiment, Xaa1 is B5(L1Z); B5 is Lys, or D-Lys; and Xaa2 is B7; and B7 is Glu or absent; and L1 is attached to $N^\varepsilon$ of Lys.

In another aspect, the present invention includes a hepcidin analogue comprising a peptide of Formula (A-I):

$R^1$-Asp-Thr-His-B1-B2-B3-B4-B5-B6-B7(L1Z)-J-Y1-Y2-$R^2$ (A-I)     (SEQ ID NO: 260)

or a peptide dimer comprising two peptides according to Formula A-I, or a pharmaceutically acceptable salt, or a solvate thereof, wherein:

$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;

$R^2$ is —$NH_2$ or —OH;

each of B1 and B6 is independently i) Phe, Dpa, bhPhe, a-MePhe, NMe-Phe, or D-Phe ii) 2-Nal, 1-Nal, D-1-Nal, D-2-Nal, 3,3-diPhenylGly, Tic, Bip, Trp, bhTrp, hPhe, or Tyr(Me)

iii) when B6 is Phe, then B5 is other than Lys; or iii) substituted Phe, substituted bhPhe, substituted Trp, or substituted bhTrp;

B2 is Pro, D-Pro, bhPro, D-bhPro, NPC, or D-NPC;

B3 is Cys, homoCys, (D)Cys, a-MeCys, or Pen;

B4 is Ile, Val, Leu, or NLeu;

B5 is absent, Lys, D-Lys, Orn, homoSer, Gln, (D)Gln, Lys(Ac), Ile, Abu, Leu, Ala, D-Ala, bAla, or Nleu;

B7 is a lower or a higher homolog of Lys, a-MeLys, D-Lys, or Dapa; and wherein L1 is attached to $N^\varepsilon$ of Lys, D-Lys, homoLys, or a-Me-Lys; or $N^\beta$ of Dapa;

L1 is absent or isoGlu, PEG, Ahx, isoGlu-PEG, PEG-Ahx, isoGlu-Ahx, or isoGlu-PEG-Ahx; Ahx is an aminohexanoic acid moiety;

Z is a half-life extension moiety;

J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;

Y1 is Cys, homoCys, NMeCys, aMeCys, or Pen; Y2 is an amino acid or absent;

Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homoTryptophane, 1-Nal is 1-naphthylalanine, 2-Nal is 2-naphthylalanine, Orn is orinithine, Nleu is norleucine, Abu is 2-aminobutyric acid;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;

wherein i) the peptide of formula I is optionally PEGylated on one or more $R^1$, B1, B2, B3, B4, B5, B6, J, Y1, Y2, or $R^2$;

ii) the peptide is cyclized via a disulfide bond between B3 and Y1;

iii) when the peptide is a peptide dimer, then B7(L1Z)-J-Y1-Y2 is absent;

iv) when the peptide is a peptide dimer, the peptide dimer is dimerized a) via a linker moiety, b) via an intermolecular disulfide bond between two B3 residues, one in each monomer subunit, or c) via both a linker moiety and an intermolecular disulfide bond between two B3 residues; and d) the linker moiety comprises a half-life extending moiety.

In one embodiment, the half-life extension moiety is $C_{10}$-$C_{21}$ alkanoyl.

In another aspect, the present invention includes a hepcidin analogue comprising a peptide of Formula (B-I):

$R^1$-Asp-Thr-His-B1-B2-B3-B4-B5(L1Z)-B6-B7-J-Y1-Y2-$R^{2(B-I)}$     (SEQ ID NO: 261)

or a peptide dimer comprising two peptides according to Formula B-I, or a pharmaceutically acceptable salt, or a solvate thereof,
wherein:
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —NH$_2$ or —OH;
each of B1 and B6 is independently
  i) Phe, Dpa, bhPhe, a-MePhe, NMe-Phe, or D-Phe;

ii) 2-Nal, 1-Nal, D-1-Nal, D-2-Nal, 3,3-diPhenylGly, Tic, Bip, Trp, bhTrp, hPhe, or Tyr(Me); or iii) substituted Phe, substituted bhPhe, or substituted Trp, or substituted bhTrp;
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B5 is Lys, D-Lys, Orn, homoSer, Gln, Lys(Ac), Ile, Abu, Leu, or Nleu;
B7 is Glu or absent;
L1 is absent or isoGlu, PEG, Ahx, isoGlu-PEG, PEG-Ahx, isoGlu-Ahx, or isoGlu-PEG-Ahx; Ahx is an aminohexanoic acid moiety;
Z is a half-life extension moiety;
J is Pro, Arg, Gly, -Pro-Arg-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys or Pen;
Y2 is an amino acid or absent;
the half-life extension moiety is $C_{10}$-$C_{21}$ alkanoyl;
Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, Npc is L-nipecotic acid, bhomoTrp is L-b-homotryptophan, 1-Nal is 1-naphthylalanine, 2-Nal is 2-naphthylalanine, Orn is ornithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted b-hTrp is N-methyl-L-b-homotryptophan, a-methyl-b-homotryptophan, or b-homotryptophan substituted with F, Cl, OH, or t-Bu;
wherein
  i) the peptide of formula I is optionally PEGylated on one or more $R^1$, B1, B2, B3, B4, B6, B7, J, Y1, Y2, or $R^2$; and
  ii) the peptide is cyclized via a disulfide bond between B3 and Y1; and
  iii) when B6 is Phe, Y1 is Cys, and Y2 is Lys, then J is Pro, Arg, Gly, -Pro-Arg-, -Pro-Lys-,-Pro-(D)Lys-, -Pro-Arg-Ser-, -Pro-Arg-Ser-Lys-(SEQ ID NO:249), or absent.

In particular embodiments of hepcidin analogues disclosed herein, the half-life extending moiety is $C_{10}$-$C_{21}$ alkanoyl.

In one particular embodiment, B7 is Lys, D-Lys, homoLys, or a-Me-Lys.

In particular embodiments of any of the hepcidin analogues or dimers of the present invention, the linker moiety is selected from IsoGlu, Dapa, PEGn where n=1 to 25, PEG11(40 atoms), OEG, IsoGlu-Ahx, IsoGlu-OEG-OEG, IsoGlu-PEG5, IsoGlu-PEGn where n=1 to 25 βAla-PEG2, and βAla-PEG11(40 atoms). In certain embodiments, more than one linker moiety is conjugated to a peptide of the hepcidin analogue or dimer.

In another aspect, the present invention includes a hepcidin analogue comprising a peptide dimer of Formula (A-II):

A-II (SEQ ID NO: 262)

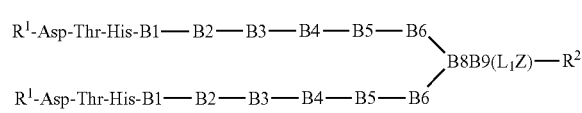

wherein each B8 and B9 is independently Lys, D-Lys, homoLys, or a-Me-Lys; and L1, Z, and $R^2$ are as described for Formula (A-I); and wherein one of the B6s is attached to $N^\varepsilon$ of B8.

In one particular embodiment, B8 is Lys. In another particular embodiment, B8 is D-Lys.

In one particular embodiment, B9 is Lys.

In another aspect, the present invention includes a hepcidin analogue comprising a peptide dimer of Formula (A-III):

A-III (SEQ ID NO: 263)

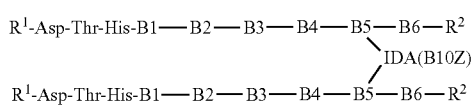

wherein B1, B2, B3, B4, B5, B6, $R^1$, and $R^2$ are as described for Formula (A-I); B10 is a natural or unnatural amino acid; and Z is a half-life extending moiety.

In a particular embodiment, B10 is b-Ala.

In one embodiment, B5 is Lys. In another embodiment, B7 is Lys.

In one embodiment, B5 is D-Lys. In another embodiment, B7 is D-Lys.

In certain embodiments, a hepcidin analogue comprises or consists of a peptide according to the following structure:

Formula Ia (SEQ ID NO: 330)

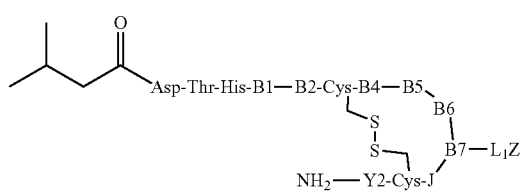

wherein L1, J, Y2, Z, and B1-B7 are as described for Formula (A-I).

In particular embodiments of any of the hepcidin analogues or dimers of the present invention, the half-life extension moiety is selected from $C_{12}$ (Lauric acid), C14 (Mysteric acid), C16(Palmitic acid), C18 (Stearic acid), C20, C12 diacid, C14 diacid, C16 diacid, C18 diacid, C20 diacid, biotin, and isovaleric acid. In certain embodiments, the half-life extension moiety is attached to a linker moiety that is attached to the peptide. In certain embodiments, the half-life extension moiety increases the molecular weight of the hepcidin analogue by about 50 D to about 2 KD. In various embodiments, the half-life extension moiety increases serum half-life, enhances solubility, and/or improves bioavailability of the hepcidin analogue.

In certain embodiments, a peptide analogue or dimer of the present invention comprises an isovaleric acid moiety conjugated to an N-terminal Asp residue.

In certain embodiments, a peptide analogue of the present invention comprises an amidated C-terminal residue.

In certain embodiments, the present invention provides hepcidin analogues, including any hepcidin analogue or peptide disclosed herein or comprising or consisting of a sequence or structure disclosed herein, including but not limited to wherein the hepcidin analogue or peptide comprises a disulfide bond between two Cys residues.

In certain embodiments, a hepcidin analogue or dimer of the present invention comprises the sequence: Asp-Thr-His-Phe-Pro-Cys-Ile-Lys-Phe-Glu-Pro-Arg-Ser-Lys-Gly-Cys-Lys (SEQ ID NO:252), or comprises a sequence having at least 80%, at least 90%, or at least 94% identity to this sequence.

In certain embodiments, a hepcidin analogue or dimer of the present invention comprises the sequence: Asp-Thr-His-Phe-Pro-Cys-Ile-Lys-Phe-Lys-Pro-Arg-Ser-Lys-Gly-Cys-Lys (SEQ ID NO:1), or comprises a sequence having at least 80%, at least 90%, or at least 94% identity to this sequence.

In a related embodiment, the present invention includes a polynucleotide that encodes a peptide of a hepcidin analogue or dimer (or monomer subunit of a dimer) of the present invention.

In a further related embodiment, the present invention includes a vector comprising a polynucleotide of the invention. In particular embodiments, the vector is an expression vector comprising a promoter operably linked to the polynucleotide, e.g., in a manner that promotes expression of the polynucleotide.

In another embodiment, the present invention includes a pharmaceutical composition, comprising a hepcidin analogue, dimer, polynucleotide, or vector of the present invention, and a pharmaceutically acceptable carrier, excipient or vehicle.

In another embodiments, the present invention provides a method of binding a ferroportin or inducing ferroportin internalization and degradation, comprising contacting the ferroportin with at least one hepcidin analogue, dimer or composition of the present invention.

In a further related embodiment, the present invention includes a method for treating a disease of iron metabolism in a subject in need thereof comprising providing to the subject an effective amount of a pharmaceutical composition of the present invention. In certain embodiments, the pharmaceutical composition is provided to the subject by an oral, intravenous, peritoneal, intradermal, subcutaneous, intramuscular, intrathecal, inhalation, vaporization, nebulization, sublingual, buccal, parenteral, rectal, vaginal, or topical route of administration. In certain embodiments, the pharmaceutical composition is provided to the subject by an oral or subcutaneous route of administration. In certain embodiments, the disease of iron metabolism is an iron overload disease. In certain embodiments, the pharmaceutical composition is provided to the subject at most or about twice daily, at most or about once daily, at most or about once every two days, at most or about once a week, or at most or about once a month.

In particular embodiments, the hepcidin analogue is provided to the subject at a dosage of about 1 mg to about 100 mg or about 1 mg to about 5 mg.

In another embodiment, the present invention provides a device comprising pharmaceutical composition of the present invention, for delivery of a hepcidin analogue or dimer of the invention to a subject, optionally orally or subcutaneously.

In yet another embodiment, the present invention includes a kit comprising a pharmaceutical composition of the invention, packaged with a reagent, a device, or an instructional material, or a combination thereof.

DETAILED DESCRIPTION OF THE INVENTION

Figure 1A:
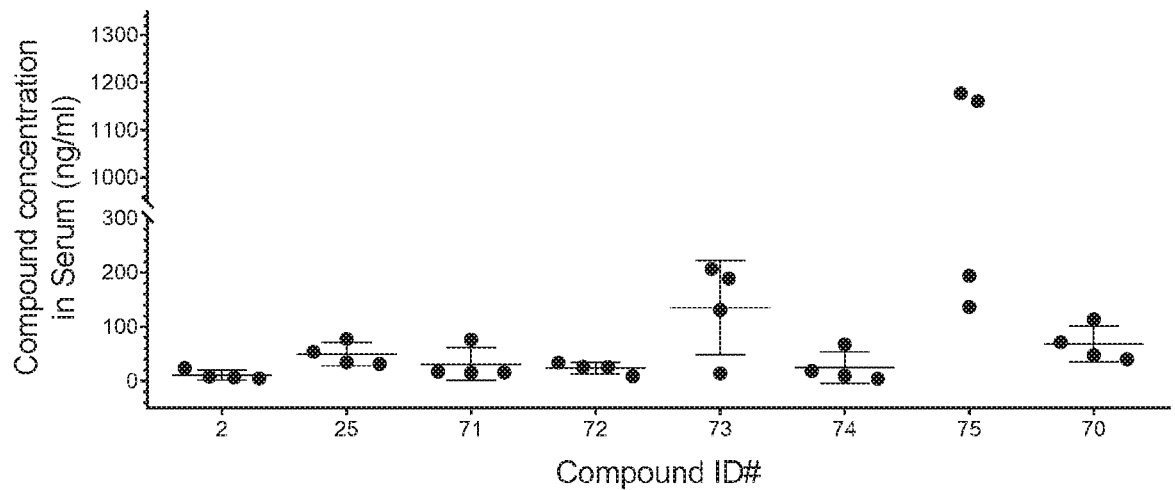
FIGS. 1A and 1B show the reduction of serum iron concentration after dosing of compounds ID 2, 25, 71, 72, 73, 74, 75, and 70 in mice.

The present invention relates generally to hepcidin analogue peptides and methods of making and using the same. In certain embodiments, the hepcidin analogues exhibit one or more hepcidin activity. In certain embodiments, the present invention relates to hepcidin peptide analogues comprising one or more peptide subunit that forms a cyclized structures through an intramolecular bond, e.g., an intramolecular disulfide bond. In particular embodiments, the cyclized structure has increased potency and selectivity as compared to non-cyclized hepcidin peptides and analogies thereof. In particular embodiments, hepcidin analogue peptides of the present invention exhibit increased half-lives, e.g., when delivered orally, as compared to hepcidin or previous hepcidin analogues.

Definitions and Nomenclature

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein, the following terms have the meanings ascribed to them unless specified otherwise.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats). The term "mammal" refers to any mammalian species such as a human, mouse, rat, dog, cat, hamster, guinea pig, rabbit, livestock, and the like.

The term "peptide," as used herein, refers broadly to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring.

The term "peptide analogue" or "hepcidin anloguuue" as used herein, refers broadly to peptide monomers and peptide dimers comprising one or more structural features and/or functional activities in common with hepcidin, or a functional region thereof. In certain embodiments, a peptide analogue includes peptides sharing substantial amino acid sequence identity with hepcidin, e.g., peptides that comprise one or more amino acid insertions, deletions, or substitutions as compared to a wild-type hepcidin, e.g., human hepcidin, amino acid sequence. In certain embodiments, a peptide analogue comprises one or more additional modification, such as, e.g., conjugation to another compound. Encompassed by the term "peptide analogue" is any peptide monomer or peptide dimer of the present invention. In certain instances, a "peptide analog" may also or alternatively be referred to herein as a "hepcidin analogue," "hepcidin peptide analogue," or a "hepcidin analogue peptide."

The recitations "sequence identity", "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997). When utilizing BLAST and Gapped BLAST programs, the default parameters of the respective programs (e.g., XBLAST and NBLAST) can be used.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. In some embodiments of the invention, one or more Met residues are substituted with norleucine (Nle) which is a bioisostere for Met, but which, as opposed to Met, is not readily oxidized. In some embodiments, one or more Trp residues are substituted with Phe, or one or more Phe residues are substituted with Trp, while in some embodiments, one or more Pro residues are substituted with Npc, or one or more Npc residues are substituted with Pro. Another example of a conservative substitution with a residue normally not found in endogenous, mammalian peptides and proteins is the conservative substitution of Arg or Lys with, for example, ornithine, canavanine, aminoethylcysteine or another basic amino acid. In some embodiments, another conservative substitution is the substitution of one or more Pro residues with bhPro or Leu or D-Npc (isonipecotic acid). For further information concerning phenotypically silent substitutions in peptides and proteins, see, for example, Bowie et. al. Science 247, 1306-1310, 1990. In the scheme below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|----|-----|----|---|
| A | N  | H   | M  | F |
| S | D  | R   | L  | Y |
| T | E  | K   | I  | W |
| P | Q  |     | V  |   |
| G |    |     | C  |   |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|----|-----|------|----|---|
| A  | E   | H    | M  | F |
| L  | D   | R    | S  | Y |
| I  |     | K    | T  | W |
| P  |     |      | C  |   |
| G  |     |      | N  |   |
| V  |     |      | Q  |   |

The term "amino acid" or "any amino acid" as used here refers to any and all amino acids, including naturally occurring amino acids (e.g., a-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid.

As is clear to the skilled artisan, the peptide sequences disclosed herein are shown proceeding from left to right, with the left end of the sequence being the N-terminus of the peptide and the right end of the sequence being the C-terminus of the peptide. Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom, corresponding to the presence of a free primary or secondary amino group at the N-terminus, while an "—OH" or an "—NH$_2$" moiety at the C-terminus of the sequence indicates a hydroxy group or an amino group, corresponding to the presence of an amido (CONH$_2$) group at the C-terminus, respectively. In each sequence of the invention, a C-terminal "—OH" moiety may be substituted for a C-terminal "—NH$_2$" moiety, and vice-versa. It is further understood that the moiety at the amino terminus or carboxy terminus may be a bond, e.g., a covalent bond, particularly in situations where the amino terminus or carboxy terminus is bound to a linker or to another chemical moiety, e.g., a PEG moiety.

The term "NH$_2$," as used herein, refers to the free amino group present at the amino terminus of a polypeptide. The term "OH," as used herein, refers to the free carboxy group present at the carboxy terminus of a peptide. Further, the term "Ac," as used herein, refers to Acetyl protection through acylation of the C- or N-terminus of a polypeptide.

The term "carboxy," as used herein, refers to —CO$_2$H.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Abbreviations of Non-Natural Amino Acids and Chemical Moieties

| Abbreviation | Definition |
|---|---|
| bh, b-h, bhomo, or b-homo | β-homo |
| DIG | Diglycolic acid |
| Dapa or Dap | Diaminopropionic acid |

TABLE 1-continued

Abbreviations of Non-Natural Amino Acids and Chemical Moieties

| Abbreviation | Definition |
| --- | --- |
| Daba or Dab | Diaminobutyric acid |
| Pen | Penicillamine |
| Sarc or Sar | Sarcosine |
| Cit | Citroline |
| Cav | Cavanine |
| NMe-Arg | N-Methyl-Arginine |
| NMe-Trp | N-Methyl-Tryptophan |
| NMe-Phe | N-Methyl-Phenylalanine |
| Ac- | Acetyl |
| 2-Nal | 2-Napthylalanine |
| 1-Nal | 1-Napthylalanine |
| Bip | Biphenylalanine |
| βAla or bAla | beta-Alanine |
| Aib | 2-aminoisobutyric acid |
| Azt | azetidine-2-carboxylic acid |
| Tic | L-1,2,3,4-Tetrahydroisoquinoline-3-carboxylic acid |
| Phe(OMe) or Tyr(Me) | Tyrosine (4-Methyl) |
| N-MeLys | N-Methyl-Lysine |
| Dpa or DIP | β,β-diphenylalanine |
| $NH_2$ | Free Amine |
| $CONH_2$ | Amide |
| COOH | Acid |
| Phe(4-F) | 4-Fluoro-Phenylalanine |
| PEG3 | $NH_2CH_2CH_2(OCH_2CH_2)_3CH_2CH_2CO_2H$ |
| m-PEG3 | $CH_3OCH_2CH_2(OCH_2CH_2)_2CH_2CH_2CO_2H$ |
| m-PEG4 | $CH_3OCH_2CH_2(OCH_2CH_2)_3CH_2CH_2CO_2H$ |
| m-PEG8 | $CH_3OCH_2CH_2(OCH_2CH_2)_7CH_2CH_2CO_2H$ |
| PEG11 | O-(2-aminoethyl)-O'-(2-carboxyethyl)-undecaethyleneglycol $NH_2CH_2CH_2(OCH_2CH_2)_{11}CH_2CH_2CO_2H$ |
| PEG13 | Bifunctional PEG linker with 13 PolyEthylene Glycol units |
| PEG25 | Bifunctional PEG linker with 25 PolyEthylene Glycol units |
| PEG1K | Bifunctional PEG linker with PolyEthylene Glycol Mol wt of 1000Da |
| PEG2K | Bifunctional PEG linker with PolyEthylene Glycol Mol wt of 2000Da |
| PEG3.4K | Bifunctional PEG linker with PolyEthylene Glycol Mol wt of 3400Da |
| PEG5K | Bifunctional PEG linker with PolyEthylene Glycol Mol wt of 5000Da |
| IDA or Ida | Iminodiacetic acid |
| IDA-Palm | (Palmityl)-Iminodiacetic acid |
| hPhe | homoPhenylalanine |
| Ahx | Aminohexanoic acid |
| DIG-OH | Glycolic monoacid |
| Triazine | Amino propyl Triazine di-acid |
| Boc-Triazine | Boc-Triazine di-acid |
| Trifluorobutyric acid | 4,4,4-Trifluorobutyric acid |
| 2-Methylltrifluorobutyric acid | 2-methyl-4,4,4-Butyric acid |
| Trifluorpentanoic acid | 5,5,5-Trifluoropentanoic acid |
| 1,4-Phenylenediacetic acid | para-Phenylenediacetic acid |
| 1,3-Phenylenediacetic acid | meta-Phenylenediacetic acid |
| DTT | Dithiothreotol |
| Nle | Norleucine |
| βhTrp or bhTrp | β-homoTryptophane |
| βhPhe or bhPhe | β-homophenylalanine |
| Phe(4-$CF_3$) | 4-TrifluoromethylPhenylalanine |
| βGlu or bGlu | β-Glutamic acid |
| βhGlu or bhGlu | β-homoglutamic acid |
| 2-2-Indane | 2-Aminoindane-2-carboxylic acid |
| 1-1-Indane | 1-Aminoindane-1-carboxylic acid |
| hCha | homocyclohexylalanine |
| Cyclobutyl | Cyclobutylalanine |
| hLeu | Homoleucine |
| Gla | γ-Carboxy-glutamic acid |
| Aep | 3-(2-aminoethoxy)propanoic acid |
| Aea | (2-aminoethoxy)acetic acid |
| IsoGlu-octanoic acid | octanoyl-γ-Glu |
| K-octanoic acid | octanoyl-ε-Lys |
| Dapa(Palm) | Hexadecanoyl-β-Diaminopropionic acid |
| IsoGlu-Palm | hexadecanoyl-γ-Glu |
| C-StBu | S-tert-butylthio-cysteine |
| C-tBu | S-tert-butyl-cysteine |
| N-MeCys or NMeCys | N-methyl-cysteine |
| a-MeCys, aMeCys, or α-MeCys | α-methyl-cysteine |
| hCys | homo-cysteine |

TABLE 1-continued

Abbreviations of Non-Natural Amino Acids and Chemical Moieties

| Abbreviation | Definition |
| --- | --- |
| Dapa(AcBr) | Nγ-(bromoacetyl)-2,3-diaminopropionic acid |
| Tle | tert-Leucine |
| Phg | phenylglycine |
| Oic | octahydroindole-2-carboxylic acid |
| Chg | α-cyclohexylglycine |
| GP-(Hyp) | Gly-Pro-HydroxyPro |
| Inp | isonipecotic acid |
| Amc | 4-(aminomethyl)cyclohexane carboxylic acid |
| Betaine | $(CH_3)_3NCH_2CH_2CO2H$ |
| D-Npc or D-NPC | Isonipecotic acid |
| Npc or NPC | Nipecotic acid |
| (D)Lys, D-Lys, k, or dK | D-Lysine |
| Orn | Orinithine |
| Homoserine | homoserine |
| Nleu or Nle | Norleucine |
| bhPro | b-homoproline |

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). In the case of less common or non-naturally occurring amino acids, unless they are referred to by their full name (e.g., sarcosine, ornithine, etc.), frequently employed three—or four-character codes are employed for residues thereof, including, Sar or Sarc (sarcosine, i.e. N-methylglycine), Aib (α-aminoisobutyric acid), Daba (2,4-diaminobutanoic acid), Dapa (2,3-diaminopropanoic acid), γ-Glu (γ-glutamic acid), pGlu (pyroglutamic acid), Gaba (γ-aminobutanoic acid), β-Pro (pyrrolidine-3-carboxylic acid), 8Ado (8-amino-3,6-dioxaoctanoic acid), Abu (4-aminobutyric acid), bhPro (β-homo-proline), bhPhe (β-homo-L-phenylalanine), bhAsp (β-homo-aspartic acid]), Dpa (β,βdiphenylalanine), Ida (Iminodiacetic acid), hCys (homocysteine), bhDpa (β-homo-β,β-diphenylalanine).

Furthermore, $R^1$ can in all sequences be substituted with isovaleric acid or equivalent. In some embodiments, wherein a peptide of the present invention is conjugated to an acidic compound such as, e.g., isovaleric acid, isobutyric acid, valeric acid, and the like, the presence of such a conjugation is referenced in the acid form. So, for example, but not to be limited in any way, instead of indicating a conjugation of isovaleric acid to a peptide by referencing isovaleroyl, in some embodiments, the present application may reference such a conjugation as isovaleric acid.

The term "L-amino acid," as used herein, refers to the "L" isomeric form of a peptide, and conversely the term "D-amino acid" refers to the "D" isomeric form of a peptide. In certain embodiments, the amino acid residues described herein are in the "L" isomeric form, however, residues in the "D" isomeric form can be substituted for any L-amino acid residue, as long as the desired functional is retained by the peptide.

Unless otherwise indicated, reference is made to the L-isomeric forms of the natural and unnatural amino acids in question possessing a chiral center. Where appropriate, the D-isomeric form of an amino acid is indicated in the conventional manner by the prefix "D" before the conventional three-letter code (e.g. Dasp, (D)Asp or D-Asp; Dphe, (D)Phe or D-Phe).

As used herein, a "lower homolog of Lys" refers to an amino acid having the structure of Lysine but with one or more fewer carbons in its side chain as compared to Lysine.

As used herein, a "higher homolog of Lys" refers to an amino acid having the structure of Lysine but with one or more additional carbon atoms in its side chain as compared to Lysine.

The term "DRP," as used herein, refers to disulfide rich peptides.

The term "dimer," as used herein, refers broadly to a peptide comprising two or more monomer subunits. Certain dimers comprise two DRPs. Dimers of the present invention include homodimers and heterodimers. A monomer subunit of a dimer may be linked at its C—or N-terminus, or it may be linked via internal amino acid residues. Each monomer subunit of a dimer may be linked through the same site, or each may be linked through a different site (e.g., C-terminus, N-terminus, or internal site).

The term "isostere replacement" or "isostere substitution" are used interchangeably herein to refer to any amino acid or other analog moiety having chemical and/or structural properties similar to a specified amino acid. In certain embodiments, an isostere replacement is a conservative substitution with a natural or unnatural amino acid.

The term "cyclized," as used herein, refers to a reaction in which one part of a polypeptide molecule becomes linked to another part of the polypeptide molecule to form a closed ring, such as by forming a disulfide bridge or other similar bond.

The term "subunit," as used herein, refers to one of a pair of polypeptide monomers that are joined to form a dimer peptide composition.

The term "linker moiety," as used herein, refers broadly to a chemical structure that is capable of linking or joining together two peptide monomer subunits to form a dimer.

The term "solvate" in the context of the present invention refers to a complex of defined stoichiometry formed between a solute (e.g., a hepcidin analogue or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

As used herein, a "disease of iron metabolism" includes diseases where aberrant iron metabolism directly causes the disease, or where iron blood levels are dysregulated causing disease, or where iron dysregulation is a consequence of another disease, or where diseases can be treated by modulating iron levels, and the like. More specifically, a disease of iron metabolism according to this disclosure includes iron overload diseases, iron deficiency disorders, disorders of iron biodistribution, other disorders of iron metabolism and other disorders potentially related to iron metabolism, etc. Diseases of iron metabolism include hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia *intermedia*, alpha thalassemia, sideroblastic anemia, *porphyria, porphyria* cutanea *tarda*, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, sickle cell disease, polycythemia vera (primary and secondary), myelodysplasia, pyruvate kinase deficiency, iron-deficiency anemia, iron-refractory iron deficiency anemia, anemia of chronic kidney disease, erythropoietin resistance, iron deficiency of obesity, other anemias, benign or malignant tumors that overproduce hepcidin or induce its overproduction, conditions with hepcidin excess, Friedreich ataxia, *gracile* syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease.

In some embodiments, the disease and disorders are related to iron overload diseases such as iron hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia *intermedia*, alpha thalassemia, sickle cell disease, polycythemia vera (primary and secondary), mylodysplasia, and pyruvate kinase deficiency.

In some embodiments, the hepcidin analogues of the invention are used to treat diseases and disorders that are not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, peptides of the invention may be used to treat these diseases and conditions. Those skilled in the art are readily able to determine whether a given disease can be treated with a peptide according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In certain embodiments of the present invention, the diseases of iron metabolism are iron overload diseases, which include hereditary hemochromatosis, iron-loading anemias, alcoholic liver diseases and chronic hepatitis C.

The term "pharmaceutically acceptable salt," as used herein, represents salts or zwitterionic forms of the peptides or compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see *Handbook of Pharmaceutical Salts: Properties, Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts.

The term "N(alpha)Methylation", as used herein, describes the methylation of the alpha amine of an amino acid, also generally termed as an N-methylation.

The term "sym methylation" or "Arg-Me-sym", as used herein, describes the symmetrical methylation of the two nitrogens of the guanidine group of arginine. Further, the term "asym methylation" or "Arg-Me-asym" describes the methylation of a single nitrogen of the guanidine group of arginine.

The term "acylating organic compounds", as used herein refers to various compounds with carboxylic acid functionality that are used to acylate the N-terminus of an amino acid subunit prior to forming a C-terminal dimer. Non-limiting examples of acylating organic compounds include cyclopropylacetic acid, 4-Fluorobenzoic acid, 4-fluorophenylacetic acid, 3-Phenylpropionic acid, Succinic acid, Glutaric acid, Cyclopentane carboxylic acid, 3,3,3-trifluoropropeonic acid, 3-Fluoromethylbutyric acid, Tetrahedro-2H-Pyran-4-carboxylic acid.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

As used herein, a "therapeutically effective amount" of the peptide agonists of the invention is meant to describe a sufficient amount of the peptide agonist to treat an hepcidin-related disease, including but not limited to any of the diseases and disorders described herein (for example, a disease of iron metabolism). In particular embodiments, the therapeutically effective amount will achieve a desired benefit/risk ratio applicable to any medical treatment.

Peptide Analogues of Hepcidin

The present invention provides peptide analogues of hepcidin, which may be monomers or dimers (collectively "hepcidin analogues").

In some embodiments, a hepcidin analogue of the present invention binds ferroportin, e.g., human ferroportin. In certain embodiments, hepcidin analogues of the present invention specifically bind human ferroportin. As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art. In some embodiments, a hepcidin analogue of the present invention binds ferroportin with greater specificity than a hepcidin reference compound (e.g., any one of the hepcidin reference compounds provided herein). In some embodiments, a hepcidin analogue of the present invention exhibits ferroportin specificity that is at least about 10%, 20%, 30%, 40%, 50%, 60%, 70%, 80%, 90%, 100%, 200%, 300%, 400%, 500%, 700%, 1000%, or 10,000% higher than a hepcidin reference compound (e.g., any one of the hepcidin reference compounds provided herein. In some embodiments, a hepcidin analogue of the present invention exhibits ferroportin specificity that is at least about 5 fold, or at least about 10, 20, 50, or 100 fold higher than a hepcidin reference compound (e.g., any one of the hepcidin reference compounds provided herein.

In certain embodiments, a hepcidin analogue of the present invention exhibits a hepcidin activity. In some embodiments, the activity is an in vitro or an in vivo activity, e.g., an in vivo or an in vitro activity described herein. In some embodiments, a hepcidin analogue of the present invention exhibits at least about 50%, 60%, 70%, 80%, 90%, 95%, 97%, 98%, 99%, or greater than 99% of the activity exhibited by a hepcidin reference compound (e.g., any one of the hepcidin reference compounds provided herein.

In some embodiments, a hepcidin analogue of the present invention exhibits at least about 50%, 60%, 70%, 80%, 90%, 95%, 97%, 98%, 99%, or greater than 99% of the ferroportin binding ability that is exhibited by a hepcidin reference compound. In some embodiments, a hepcidin analogue of the present invention has a lower $IC_{50}$ (i.e., higher binding affinity) for binding to ferroportin, (e.g., human ferroportin) compared to a hepcidin reference compound.

In some embodiments, a hepcidin analogue the present invention has an $IC_{50}$ in a ferroportin competitive binding assay which is at least about 10%, 20%, 30%, 40%, 50%, 60%, 70%, 80%, 90%, 100%, 200%, 300%, 400%, 500%, 700%, or 1000% lower than a hepcidin reference compound.

In certain embodiments, a hepcidin analogue of the present invention exhibits increased hepcidin activity as compared to a hepcidin reference compound. In some embodiments, the activity is an in vitro or an in vivo activity, e.g., an in vivo or an in vitro activity described herein. In certain embodiments, the hepcidin analogue of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater hepcidin activity than a hepcidin reference compound. In certain embodiments, the hepcidin analogue of the present invention exhibits at least about 10%, 20%, 30%, 40%, 50%, 60%, 70%, 80%, 90%, 95%, 97%, 98%, 99% or greater than 99%, 100%, 200% 300%, 400%, 500%, 700%, or 1000% greater activity than a hepcidin reference compound.

In some embodiments, a peptide analogue of the present invention exhibits at least about 50%, 60%, 70%, 80%, 90%, 95%, 97%, 98%, 99%, or greater than 99%, 100%, 200% 300%, 400%, 500%, 700%, or 1000% greater in vitro activity for inducing the degradation of human ferroportin protein as that of a hepcidin reference compound, wherein the activity is measured according to a method described herein.

In some embodiments, a peptide or a peptide dimer of the present invention exhibits at least about 50%, 60%, 70%, 80%, 90%, 95%, 97%, 98%, 99%, or greater than 99%, 100%, 200% 300%, 400%, 500%, 700%, or 1000% greater in vivo activity for inducing the reduction of free plasma iron in an individual as does a hepcidin reference compound, wherein the activity is measured according to a method described herein.

In some embodiments, the activity is an in vitro or an in vivo activity, e.g., an in vivo or an in vitro activity described herein. In certain embodiments, a hepcidin analogue of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, 500%, 700%, or 1000% greater activity than a hepcidin reference compound, wherein the activity is an in vitro activity for inducing the degradation of ferroportin, e.g., as measured according to the Examples herein; or wherein the activity is an in vivo activity for reducing free plasma iron, e.g., as measured according to the Examples herein.

In some embodiments, the hepcidin analogues of the present invention mimic the hepcidin activity of Hep25, the bioactive human 25-amino acid form, are herein referred to as "mini-hepcidins". As used herein, in certain embodiments, a compound (e.g., a hepcidin analogue) having a "hepcidin activity" means that the compound has the ability to lower plasma iron concentrations in subjects (e.g. mice or humans), when administered thereto (e.g. parenterally injected or orally administered), in a dose-dependent and time-dependent manner. See e.g. as demonstrated in Rivera et al. (2005), Blood 106:2196-9. In some embodiments, the peptides of the present invention lower the plasma iron concentration in a subject by at least about 1.2, 1.5, 2, 3, 4, 5, 6, 7, 8, 9, or 10-fold, or at least about 5%, 10%, 20%, 25%, 30%, 40%, 50%, 60%, 70%, 80%, 90%, or about 99%.

In some embodiments, the hepcidin analogues of the present invention have in vitro activity as assayed by the ability to cause the internalization and degradation of ferroportin in a ferroportin-expressing cell line as taught in Nemeth et al. (2006) Blood 107:328-33. In some embodiments, in vitro activity is measured by the dose-dependent loss of fluorescence of cells engineered to display ferroportin fused to green fluorescent protein as in Nemeth et al. (2006) Blood 107:328-33. Aliquots of cells are incubated for 24 hours with graded concentrations of a reference preparation of Hep25 or a mini-hepcidin. As provided herein, the $EC_{50}$ values are provided as the concentration of a given compound (e.g. a hepcidin analogue peptide or peptide dimer of the present invention) that elicits 50% of the maximal loss of fluorescence generated by a reference compound. The $EC_{50}$ of the Hep25 preparations in this assay range from 5 to 15 nM and in certain embodiments, preferred hepcidin analogues of the present invention have $EC_{50}$ values in in vitro activity assays of about 1,000 nM or less. In certain embodiments, a hepcidin analogue of the present invention has an $EC_{50}$ in an in vitro activity assay (e.g., as described in Nemeth et al. (2006) Blood 107:328-33 or the Example herein) of less than about any one of 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, a hepcidin analogue or biotherapeutic composition (e.g., any one of the pharmaceutical compositions described herein) has an $EC_{50}$ value of about 1 nM or less.

Other methods known in the art for calculating the hepcidin activity and in vitro activity of the hepcidin analogues according to the present invention may be used. For example, in certain embodiments, the in vitro activity of the hepcidin analogues or the reference peptides is measured by their ability to internalize cellular ferroportin, which is determined by immunohistochemistry or flow cytometry using antibodies which recognizes extracellular epitopes of ferroportin. Alternatively, in certain embodiments, the in vitro activity of the hepcidin analogues or the reference peptides is measured by their dose-dependent ability to inhibit the efflux of iron from ferroportin-expressing cells that are preloaded with radioisotopes or stable isotopes of iron, as in Nemeth et al. (2006) Blood 107:328-33.

In some embodiments, the hepcidin analogues of the present invention exhibit increased stability (e.g., as measured by half-life, rate of protein degradation) as compared to a hepcidin reference compound. In certain embodiments, the stability of a hepcidin analogue of the present invention is increased at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a hepcidin reference compound. In some embodiments, the stability is a stability that is described herein. In some embodiments, the stability is a plasma stability, e.g., as optionally measured according to the method described herein. In some embodiments, the stability is stability when delivered orally.

In particular embodiments, a hepcidin analogue of the present invention exhibits a longer half-life than a hepcidin reference compound. In particular embodiments, a hepcidin analogue of the present invention has a half-life under a given set of conditions (e.g., temperature, pH) of at least about 5 minutes, at least about 10 minutes, at least about 20 minutes, at least about 30 minutes, at least about 45 minutes, at least about 1 hour, at least about 2 hour, at least about 3 hours, at least about 4 hours, at least about 5 hours, at least about 6 hours, at least about 12 hours, at least about 18 hours, at least about 1 day, at least about 2 days, at least about 4 days, at least about 7 days, at least about 10 days, at least about two weeks, at least about three weeks, at least about 1 month, at least about 2 months, at least about 3 months, or more, or any intervening half-life or range in between, about 5 minutes, about 10 minutes, about 20 minutes, about 30 minutes, about 45 minutes, about 1 hour, about 2 hour, about 3 hours, about 4 hours, about 5 hours, about 6 hours, about 12 hours, about 18 hours, about 1 day, about 2 days, about 4 days, about 7 days, about 10 days, about two weeks, about three weeks, about 1 month, about 2 months, about 3 months, or more, or any intervening half-life or range in between. In some embodiments, the half-life of a hepcidin analogue of the present invention is extended due to its conjugation to one or more lipophilic substituent or half-life extension moiety, e.g., any of the lipophilic substituents or half-life extension moieties disclosed herein. In some embodiments, the half-life of a hepcidin analogue of the present invention is extended due to its conjugation to one or more polymeric moieties, e.g., any of the polymeric moieties or half-life extension moieties disclosed herein. In certain embodiments, a hepcidin analogue of the present invention has a half-life as described above under the given set of conditions wherein the temperature is about 25° C., about 4° C., or about 37° C., and the pH is a physiological pH, or a pH about 7.4.

In certain embodiments, a hepcidin analogue of the present invention, comprising a conjugated half-life extension moiety, has an increased serum half-life following oral, intravenous or subcutaneous administration as compared to the same analogue but lacking the conjugated half-life extension moiety. In particular embodiments, the serum half-life of a hepcidin analogue of the present invention following any of oral, intravenous or subcutaneous administration is at least 12 hours, at least 24 hours, at least 30 hours, at least 36 hours, at least 48 hours, at least 72 hours or at least 168 h. In particular embodiments, it is between 12 and 168 hours, between 24 and 168 hours, between 36 and 168 hours, or between 48 and 168 hours.

In certain embodiments, a hepcidin analogue of the present invention, e.g., a hepcidin analogue comprising a conjugated half-life extension moiety, results in decreased concentration of serum iron following oral, intravenous or subcutaneous administration to a subject. In particular embodiments, the subject's serum iron concentration is decreased to less than 10%, less than 20%, less than 25%, less than 30%, less than 40%, less than 50%, less than 60%, less than 70%, less than 80%, or less than 90% of the serum iron concentration in the absence of administration of the hepcidin analogue to the subject. In particular embodiments, the decreased serum iron concentration remains for a least 1 hour, at least 4 hours, at least 10 hours, at least 12 hours, at least 24 hours, at least 36 hours, at least 48 hours, or at least 72 hours following administration to the subject. In particular embodiments, it remains for between 12 and 168 hours, between 24 and 168 hours, between 36 and 168 hours, or between 48 and 168 hours. In one embodiment, the serum iron concentration of the subject is reduced to less than 20% at about 4 hours or about 10 hours following administration to the subject, e.g., intravenously, orally, or subcutaneously. In one embodiment, the serum iron concentration of the subject is reduced to less than 50% or less than 60% for about 24 to about 30 hours following administration, e.g., intravenously, orally, or subcutaneously.

In some embodiments, the half-life is measured in vitro using any suitable method known in the art, e.g., in some embodiments, the stability of a hepcidin analogue of the present invention is determined by incubating the hepcidin analogue with pre-warmed human serum (Sigma) at 37° C. Samples are taken at various time points, typically up to 24 hours, and the stability of the sample is analyzed by separating the hepcidin analogue from the serum proteins and then analyzing for the presence of the hepcidin analogue of interest using LC-MS.

In some embodiments, the stability of the hepcidin analogue is measured in vivo using any suitable method known in the art, e.g., in some embodiments, the stability of a hepcidin analogue is determined in vivo by administering the peptide or peptide dimer to a subject such as a human or any mammal (e.g., mouse) and then samples are taken from the subject via blood draw at various time points, typically up to 24 hours. Samples are then analyzed as described above in regard to the in vitro method of measuring half-life. In some embodiments, in vivo stability of a hepcidin analogue of the present invention is determined via the method disclosed in the Examples herein.

In some embodiments, the present invention provides a hepcidin analogue as described herein, wherein the hepcidin analogue exhibits improved solubility or improved aggregation characteristics as compared to a hepcidin reference compound. Solubility may be determined via any suitable method known in the art. In some embodiments, suitable methods known in the art for determining solubility include incubating peptides (e.g., a hepcidin analogue of the present invention) in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide (e.g., the hepcidin analogue of the present invention) is more soluble in a given liquid than is a hepcidin reference compound.

In certain embodiments, the present invention provides a hepcidin analogue as described herein, wherein the hepcidin analogue exhibits a solubility that is increased at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a hepcidin reference compound in a particular solution or buffer, e.g., in water or in a buffer known in the art or disclosed herein.

In certain embodiments, the present invention provides a hepcidin analogue as described herein, wherein the hepcidin analogue exhibits decreased aggregation, wherein the aggregation of the peptide in a solution is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold less or at least about 10%, 20%, 30%, 40%, 50%, 60%, 70%, 80%, 90%, 100%, 200%, 300%, 400%, or 500% less than a hepcidin reference compound in a particular solution or buffer, e.g., in water or in a buffer known in the art or disclosed herein.

In some embodiments, the present invention provides a hepcidin analogue, as described herein, wherein the hepcidin analogue exhibits less degradation (i.e., more degradation stability), e.g., greater than or about 10% less, greater than or about 20% less, greater than or about 30% less, greater than or about 40 less, or greater than or about 50% less than a hepcidin reference compound. In some embodiments, degradation stability is determined via any suitable method known in the art. In some embodiments, suitable methods known in the art for determining degradation stability include the method described in Hawe et al J Pharm Sci, VOL. 101, NO. 3, 2012, p 895-913, incorporated herein in its entirety. Such methods are in some embodiments used to select potent sequences with enhanced shelf lives.

In some embodiments, the hepcidin analogue of the present invention is synthetically manufactured. In other embodiments, the hepcidin analogue of the present invention is recombinantly manufactured.

The various hepcidin analogue monomer and dimer peptides of the invention may be constructed solely of natural amino acids. Alternatively, these hepcidin analogues may include unnatural or non-natural amino acids including, but not limited to, modified amino acids. In certain embodiments, modified amino acids include natural amino acids that have been chemically modified to include a group, groups, or chemical moiety not naturally present on the amino acid. The hepcidin analogues of the invention may additionally include D-amino acids. Still further, the hepcidin analogue peptide monomers and dimers of the invention may include amino acid analogs. In particular embodiments, a peptide analogue of the present invention comprises any of those described herein, wherein one or more natural amino acid residues of the peptide analogue is substituted with an unnatural or non-natural amino acid, or a D-amino acid.

In certain embodiments, the hepcidin analogues of the present invention include one or more modified or unnatural amino acids. For example, in certain embodiments, a hepcidin analogue includes one or more of Daba, Dapa, Pen, Sar, Cit, Cav, HLeu, 2-Nal, 1-Nal, d-1-Nal, d-2-Nal, Bip, Phe(4-OMe), Tyr(4-OMe), PhTrp, DhPhe, Phe(4-CF3), 2-2-Indane, 1-1-Indane, Cyclobutyl, PhPhe, hLeu, Gla, Phe(4—NH$_2$), hPhe, 1-Nal, Nle, 3-3-diPhe, cyclobutyl-Ala, Cha, Bip, j-Glu, Phe(4-Guan), homo amino acids, D-amino acids, and various N-methylated amino acids. One having skill in the art will appreciate that other modified or unnatural amino acids, and various other substitutions of natural amino acids with modified or unnatural amino acids, may be made to achieve similar desired results, and that such substitutions are within the teaching and spirit of the present invention.

The present invention includes any of the hepcidin analogues described herein, e.g., in a free or a salt form.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$C$_1$, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements. In particular embodiments, the compounds are isotopically substituted with deuterium. In more particular embodiments, the most labile hydrogens are substituted with deuterium.

The hepcidin analogues of the present invention include any of the peptide monomers or dimers described herein linked to a linker moiety, including any of the specific linker moieties described herein.

The hepcidin analogues of the present invention include peptides, e.g., monomers or dimers, comprising a peptide monomer subunit having at least 85%, at least 90%, at least 92%, at least 94%, at least 95%, at least 98%, or at least 99% amino acid sequence identity to a hepcidin analogue peptide sequence described herein (e.g., any one of the peptides disclosed herein), including but not limited to any of the amino acid sequences shown in Tables 2A, 2B, 3A, 3B, and 4.

In certain embodiments, a peptide analogue of the present invention, or a monomer subunit of a dimer peptide analogue of the present invention, comprises or consists of 7 to 35 amino acid residues, 8 to 35 amino acid residues, 9 to 35 amino acid residues, 10 to 35 amino acid residues, 7 to 25 amino acid residues, 8 to 25 amino acid residues, 9 to 25 amino acid residues, 10 to 25 amino acid residues, 7 to 18 amino acid residues, 8 to 18 amino acid residues, 9 to 18 amino acid residues, or 10 to 18 amino acid residues, and, optionally, one or more additional non-amino acid moieties, such as a conjugated chemical moiety, e.g., a half-life extension moiety, a PEG or linker moiety. In particular embodiments, a monomer subunit of a hepcidin analogue comprises or consists of 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues. In particular embodiments, a monomer subunit of a hepcidin analogue of the present invention comprises or consists of 10 to 18 amino acid residues and, optionally, one or more additional non-amino acid moieties, such as a conjugated chemical moiety, e.g., a PEG or linker moiety. In various embodiments, the monomer subunit comprises or consists of 7 to 35 amino acid residues, 9 to 18 amino acid residues, or 10 to 18 amino acid residues. In particular embodiments of any of the various Formulas described herein, X comprises or consists of 7 to 35 amino acid residues, 8 to 35 amino acid residues, 9 to 35 amino acid residues, 10 to 35 amino acid residues, 7 to 25 amino acid residues, 8 to 25 amino acid residues, 9 to 25 amino acid residues, 10 to 25 amino acid residues, 7 to 18 amino acid residues, 8 to 18 amino acid residues, 9 to 18 amino acid residues, or 10 to 18 amino acid residues.

In particular embodiments, a hepcidin analogue or dimer of the present invention does not include any of the compounds described in PCT/US2014/030352 or PCT/US2015/038370.

Peptide Hepcidin Analogues

In certain embodiments, hepcidin analogues of the present invention comprise a single peptide subunit, optionally conjugated to a half-life extension moiety. In certain embodiments, these hepcidin analogues form cyclized structures through intramolecular disulfide or other bonds.

In one aspect, the present invention includes a hepcidin analogue comprising a peptide of Formula (I):

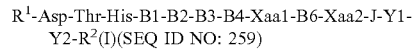

R$^1$-Asp-Thr-His-B1-B2-B3-B4-Xaa1-B6-Xaa2-J-Y1-Y2-R$^2$(I)(SEQ ID NO: 259)

or a peptide dimer comprising two peptides according to Formula I, or a pharmaceutically acceptable salt, or a solvate thereof, wherein:
R$^1$ is hydrogen, C$_1$-C$_6$ alkyl, C$_6$-C$_{12}$ aryl, C$_6$-C$_{12}$ aryl-C$_1$-C$_6$ alkyl, C$_1$-C$_{20}$ alkanoyl, or C$_1$-C$_{20}$ cycloalkanoyl;
R$^2$ is —NH$_2$ or —OH;
Xaa1 is B5; and i) B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys;
or
ii) Xaa1 is B5(L1Z); B5 is Lys, D-Lys, Orn, homoSer, Gln, Lys(Ac), Ile, Abu, Leu, or Nleu; and Xaa2 is B7; and B7 is Glu or absent;

each of B1 and B6 is independently
i) Phe, Dpa, bhPhe, a-MePhe, NMe-Phe, or D-Phe;

ii) 2-Nal, 1-Nal, D-1-Nal, D-2-Nal, 3,3-diPhenylGly, Tic, Bip, Trp, bhTrp, hPhe, or Tyr(Me); or iii) substituted Phe, substituted bhPhe, or substituted Trp, or substituted bhTrp;
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B7 is Dapa, Lys, D-Lys, homoLys, or a-Me-Lys;
L1 is absent, Dapa, D-Dapa, or isoGlu, PEG, Ahx, isoGlu-PEG, PEG-Ahx, isoGlu-Ahx, or isoGlu-PEG-Ahx; Ahx is an aminohexanoic acid moiety;
Z is a half-life extension moiety;
J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys, (D)Cys, NMeCys, aMeCys, or Pen;
Y2 is an amino acid or absent; Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homoTryptophane, 1-Nal is 1-naphthylalanine, 2-Nal is 2-naphthylalanine, Orn is orinithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;
wherein
  i) the peptide of formula I is optionally PEGylated on one or more $R^1$, B1, B2, B3, B4, B5, B6, B7, J, Y1, Y2, or $R^2$; and
  ii) the peptide is cyclized via a disulfide bond between B3 and Y1.

In one embodiment, the half-life extension moiety is $C_{10}$-$C_{21}$ alkanoyl.

In one embodiment, Xaa1 is B5; B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys; and L1 is attached to $N^\varepsilon$ of Lys, D-Lys, homoLys, or a-Me-Lys; or $N^\beta$ of Dapa.

In another embodiment, Xaa1 is B5(L1Z); B5 is Lys, or D-Lys; and Xaa2 is B7; and B7 is Glu or absent; and L1 is attached to $N^\varepsilon$ of Lys.

In one embodiment, the present invention includes a hepcidin analogue comprising a peptide of Formula (A-I):

$R^1$-Asp-Thr-His-B1-B2-B3-B4-B5-B6-B7(L1Z)-J-Y1-Y2-$R^2$(A-I)    (SEQ ID NO: 260)

or a peptide dimer comprising two peptides according to Formula A-I, or a pharmaceutically acceptable salt, or a solvate thereof,
wherein:
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
each of B1 and B6 is independently
  i) Phe, Dpa, bhPhe, a-MePhe, NMe-Phe, or D-Phe;

ii) 2-Nal, 1-Nal, D-1-Nal, D-2-Nal, 3,3-diPhenylGly, Tic, Bip, Trp, bhTrp, hPhe, or Tyr(Me); or iii) substituted Phe, substituted bhPhe, or substituted Trp, or substituted bhTrp;
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B5 is absent, Lys, D-Lys, Orn, homoSer, Gln, (D)Gln, Lys(Ac), Ile, Abu, Leu, Ala, D-Ala, bAla, or Nleu;
B7 is a lower or a higher homolog of Lys, a-MeLys, D-Lys, or Dapa; and wherein L1 is attached to $N^\varepsilon$ of Lys, D-Lys, homoLys, or a-Me-Lys; or $N^\beta$ of Dapa;
L1 is absent or isoGlu, PEG, Ahx, isoGlu-PEG, PEG-Ahx, isoGlu-Ahx, or isoGlu-PEG-Ahx; Ahx is an aminohexanoic acid moiety;
Z is a half-life extension moiety;
J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys, (D)Cys, NMeCys, aMeCys, or Pen;
Y2 is an amino acid or absent; Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydroisoquinoline-3-carboxylic acid, NPC is L-nipecotic acid, bhTrp is b-homoTryptophane, 1-Nal is 1-naphthylalanine, 2-Nal is 2-naphthylalanine, Orn is orinithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted bhTrp is N-methyl-L-b-homotryptophan, a-methyl-b-homotryptophan, or b-homotryptophan substituted with F, Cl, OH, or t-Bu;
and
wherein
  i) the peptide of formula I is optionally PEGylated on one or more $R^1$, B1, B2, B3, B4, B5, B6, J, Y1, Y2, or $R^2$;
  ii) the peptide is cyclized via a disulfide bond between B3 and Y1;
  iii) when B6 is Phe, then B5 is other than Lys;
  iv) when the peptide is a peptide dimer, then B7(L1Z)-J-Y1-Y2 is absent;
  v) when the peptide is a peptide dimer, the peptide dimer is dimerized
    a) via a linker moiety,
    b) via an intermolecular disulfide bond between two B3 residues, one in each monomer subunit, or
    c) via both a linker moiety and an intermolecular disulfide bond between two B3 residues; and
  d) the linker moiety comprises a half-life extending moiety.

In one embodiment, with respect to peptides of Formula (A-I), $R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
  each of B1 and B6 is independently
  i) Phe, Dpa, bhPhe, a-MePhe, NMe-Phe, or D-Phe;

ii) 2-Nal, 1-Nal, D-1-Nal, D-2-Nal, 3,3-diPhenylGly, Tic, Bip, Trp, bhTrp, hPhe, or Tyr(Me); or iii) substituted Phe, substituted bhPhe, or substituted Trp, or substituted bhTrp;
B2 is Pro, D-Pro, bhPro, D-bhPro, NPC, or D-NPC; B3 is Cys, homoCys, or Pen; B4 is Ile, Val, Leu, or NLeu; B5 is Lys, D-Lys, Orn, homoSer, Gln, Lys(Ac), Ile, Abu, Leu, or Nleu; B7 is a lower or a higher homolog of Lys;
$L_1$ is absent or isoGlu, PEG, Ahx, isoGlu-PEG, PEG-Ahx, isoGlu-Ahx, or isoGlu-PEG-Ahx; Ahx is aminohexanoic acid moiety; and wherein $L_1$ is attached to $N^\varepsilon$ of B7; Z is a half-life extension moiety;
J is Pro, -Pro-Arg-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; Y1 is Cys, homoCys or Pen; and Y2 is an amino acid or absent.

In one embodiment, with respect to peptides of Formula (A-I), $R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;

each of B1 and B6 is independently
i) Phe, Dpa, bhPhe, a-MePhe, NMe-Phe, or D-Phe;

ii) 2-Nal, 1-Nal, D-1-Nal, D-2-Nal,
3,3-diPhenylGly, Tic, Bip, Trp, bhTrp, hPhe, or
Tyr(Me); or iii) substituted Phe, substituted bhPhe, substituted Trp, or substituted bhTrp;
B2 is Pro, D-Pro, bhPro, D-bhPro, NPC, or D-NPC; B3 is Cys, homoCys, or Pen; B4 is Ile, Val, Leu, or NLeu; B5 is absent, Lys, D-Lys, Orn, homoSer, Gln, Lys(Ac), Ile, Abu, Leu, Ala, D-Ala, bAla, or Nleu; B7 is a lower or a higher homolog of Lys, a-MeLys, D-Lys, or Dapa; L1 is absent or isoGlu, PEG, Ahx, isoGlu-PEG, PEG-Ahx, isoGlu-Ahx, or isoGlu-PEG-Ahx; Ahx is aminohexanoic acid moiety; and wherein L1 is attached to $N^\varepsilon$ of B7; Z is a half-life extension moiety; J is Pro, -Pro-Arg-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid; Y1 is Cys, homoCys, NMeCys, aMeCys, or Pen; and Y2 is an amino acid or absent.

In a particular embodiment, B5 is D-Lys.

In another embodiment, hepcidin analogue is a peptide dimer according to Formula A-II:

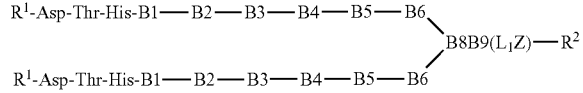

A-II (SEQ ID NO: 262)

wherein L1, Z, B1-B6, $R^1$, and $R^2$ are as described for Formula (A-I); each B8 and B9 is independently Lys, D-Lys, homoLys, or a-Me-Lys; and wherein one of the B6s is attached to $N^\varepsilon$ of B8.

In a particular embodiment, each B8 and B9 is independently Lys, D-Lys, homoLys, or a-Me-Lys. In a more particular embodiment, B9 is Lys. In a particular embodiment, B8 is Lys or D-Lys.

In another embodiment, the hepcidin analogue is a peptide dimer is according to Formula A-III:

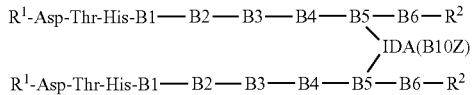

A-III (SEQ ID NO: 263)

wherein B1-B6, $R^1$, and $R^2$ are as described for Formula (A-I); B10 is a natural or unnatural amino acid; and Z is a half-life extending moiety.

In one embodiment, the present invention includes a hepcidin analogue comprising a peptide of Formula (B-I):

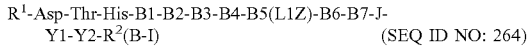

(SEQ ID NO: 264)

or a peptide dimer comprising two peptides according to Formula B-I, or a pharmaceutically acceptable salt, or a solvate thereof, wherein:
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
each of B1 and B6 is independently
i) Phe, Dpa, bhPhe, a-MePhe, NMe-Phe, or D-Phe;
ii) 2-Nal, 1-Nal, D-1-Nal, D-2-Nal, 3,3-diPhenylGly, Tic, Bip, Trp, bhTrp, hPhe, or Tyr(Me); or
iii) substituted Phe, substituted bhPhe, or substituted Trp, or substituted bhTrp;
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B5 is Lys, D-Lys, Orn, homoSer, Gln, Lys(Ac), Ile, Abu, Leu, or Nleu;
B7 is Glu or absent;
$L_1$ is absent or isoGlu, PEG, Ahx, isoGlu-PEG, PEG-Ahx, isoGlu-Ahx, or isoGlu-PEG-Ahx;
Ahx is an aminohexanoic acid moiety;
Z is a half-life extension moiety;
J is Pro, Arg, Gly, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys or Pen;
Y2 is an amino acid or absent;
the half-life extension moiety is $C_{10}$-$C_{21}$ alkanoyl;
Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, Npc is L-nipecotic acid, bhomoTrp is L-b-homotryptophan, 1-Nal is 1-naphthylalanine, 2-Nal is 2-naphthylalanine, Orn is ornithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted b-hTrp is N-methyl-L-b-homotryptophan, a-methyl-b-homotryptophan, or b-homotryptophan substituted with F, Cl, OH, or t-Bu;
wherein
i) the peptide of formula I is optionally PEGylated on one or more $R^1$, B1, B2, B3, B4, B6, B7, J, Y1, Y2, or $R^2$; and
ii) the peptide is cyclized via a disulfide bond between B3 and Y1; and
iii) when B6 is Phe, Y1 is Cys, and Y2 is Lys, then J is Pro, Arg, Gly, -Pro-Arg-, -Pro-Arg-Ser-,-Pro-Arg-Ser-Lys-(SEQ ID NO:249), or absent.

In one embodiment, with respect to peptides of Formula (B-I),
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
each of B1 and B6 is independently
i) Phe, Dpa, bhPhe, a-MePhe, NMe-Phe, or D-Phe;

ii) 2-Nal, 1-Nal, D-1-Nal, D-2-Nal,
3,3-diPhenylGly, Tic, Bip, Trp, bhTrp, hPhe, or
Tyr(Me); or iii) substituted Phe, substituted bhPhe, or substituted Trp, or substituted bhTrp;

B2 is Pro, D-Pro, bhPro, D-bhPro, NPC, or D-NPC;
B3 is Cys, homoCys, or Pen;
B4 is Ile, Val, Leu, or NLeu;
B5 is Lys, D-Lys, Orn, homoSer, Gln, Lys(Ac), Ile, Abu, Leu, or Nleu;
B7 is Glu or absent;
$L_1$ is absent or isoGlu, PEG, Ahx, isoGlu-PEG, PEG-Ahx, isoGlu-Ahx, or isoGlu-PEG-Ahx; Ahx is aminohexanoic acid moiety; and wherein $L_1$ is attached to N of B7;
Z is a half-life extension moiety;
J is Pro, Arg, Gly, -Pro-Arg-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent;
Y1 is Cys, homoCys or Pen;
Y2 is an amino acid or absent;
the half-life extension moiety is $C_{10}$-$C_{21}$ alkanoyl;
Dpa is 3,3-diphenylalanine or b,b-diphenylalanine, bhPhe is b-homophenylalanine, Bip is Biphenylalanine, βhPro is β-homoproline, Tic is L-1,2,3,4,-Tetrahydro-isoquinoline-3-carboxylic acid, Npc is Nipecotic acid, bhTrp is L-β-homoTryptophan, Nal is Naphthylalanine, Orn is ornithine, Nleu is norLeucine, Abu is 2-Aminobutyric acid; substituted Phe is Phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine; substituted β-hPhe is β-homoPhenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted β-hTrp is N-methyl-L-b-homoTyptophan, a-methyl-b-homotryptophan, or b-homotryptophan substituted with F, Cl, OH, or t-Bu;
wherein
 i) the peptide of formula I is optionally PEGylated on $R^1$, B1, B2, B3, B4, B6, B7, J, Y1, Y2, and $R^2$;
 ii) the peptide is cyclized via a disulfide bond between B3 and Y1.

In one particular embodiment, B10 is β-Ala.
In one embodiment, $R^1$ is hydrogen, or $C_1$-$C_{20}$ alkanoyl.
In another embodiment, $R^1$ is hydrogen, isovaleric acid, isobutyric acid or acetyl. In a particular embodiment, $R^1$ is isovaleric acid.
In one embodiment, B2 is Pro, D-Pro, bhPro, D-bhPro, NPC, or D-NPC.
In one embodiment, B3 is Cys. In another embodiment, B3 is homoCys.
In one embodiment, B4 is Ile.
In one embodiment, B5 is absent. In another embodiment, B5 is Ala, D-Ala, or bAla.
In another embodiment, B5 is Lys, D-Lys, Orn, homoSer, Gln, Lys(Ac), Ile, or Nleu.
In another embodiment, the peptide is cyclized via a disulfide bond between B3 and Y1.
In one embodiment, Y1 is Cys or homoCys.
In one embodiment, the half-life extension moiety is $C_{14}$-$C_{20}$ alkanoyl.
In one embodiment, B7 is a lower homolog of Lys. In another embodiment, B7 is a higher homolog of Lys. In a further embodiment, B7 is homoLys, a-MeLys, or abu. In a particular embodiment, B7 is Lys or D-Lys.

In another embodiment, B7 is Dapa.
In one embodiment, the lower homolog of Lys is 2,3-diaminopropanoic acid or 2,4-diaminobutyric acid. In one embodiment, the lower homolog of Lys is L-2,3-diaminopropanoic acid. In another embodiment, the lower homolog of Lys is D-2,3-diaminopropanoic acid. In another embodiment, the lower homolog of Lys is L-2,4-diaminobutyric acid. In another embodiment, the lower homolog of Lys is D-2,4-diaminobutyric acid.
In one embodiment, the higher homolog of Lys is homoLys or L-2,6-diaminohexanoic acid. In another embodiment, the higher homolog of Lys is D-homoLys or D-2,6-diaminohexanoic acid.
In another embodiment, the peptide is according to formula A-IV or B-IV:

$R^1$-Asp-Thr-His-B1-B2-B3-Ile-B5-B6—N(H)C
[CH2CH2CH2CH2N(H)L1Z](H)—C(O)-J-Y1-
Y2-$R^2$(A-IV)                (SEQ ID NO: 265)

$R^1$-Asp-Thr-His-B1-B2-B3-Ile-N(H)C
[CH$_2$CH$_2$CH$_2$CH$_2$N(H)L1Z](H)—C(O)—B6-
B7-J-Y1-Y2-$R^2$(B-IV)

or a peptide dimer comprising two peptides according to Formula (A-IV), or (B-IV), or a pharmaceutically acceptable salt thereof.
In one embodiment, B2 is Pro, D-Pro, or bhPro. In a particular embodiment, B2 is Pro.
In one embodiment, B3 is Cys. In another embodiment, B3 is Pen. In another embodiment, B3 is homoCys.
In another embodiment, the peptide is according to formula A-V or B-V:

$R^1$-Asp-Thr-His-B1-Pro-Cys-Ile-B5-B6—N(H)C
[CH$_2$CH$_2$CH$_2$CH$_2$N(H)L1Z](H)—C(O)-J-Y1-
Y2-$R^2$(A-V)                (SEQ ID NO: 266)

$R^1$-Asp-Thr-His-B1-Pro-Cys-Ile-N(H)C
[CH$_2$CH$_2$CH$_2$CH$_2$N(H)L1Z](H)—C(O)—B6-
B7-J-Y1-Y2-$R^2$(B-V)         (SEQ ID NO: 267)

or a peptide dimer comprising two peptides according to Formula (A-V), or (B-V), or a pharmaceutically acceptable salt thereof;
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
B6 is
 i) Phe, Dpa, bhPhe, a-MePhe, NMe-Phe, or D-Phe;

ii) 2-Nal, 1-Nal, D-1-Nal, D-2-Nal,
  3,3-diPhenylGly, Tic, Bip, Trp, bhTrp, hPhe, or
        Tyr(Me)

iii) when B6 is Phe, then B5 is other than Lys; or
 iv) substituted Phe, substituted bhPhe, substituted Trp, or substituted bhTrp;
B5 is absent, Lys, D-Lys, Orn, homoSer, Gln, (D)Gln, Lys(Ac), Ile, Abu, Leu, Ala, D-Ala, bAla, or Nleu;
L1 is absent or isoGlu, PEG, Ahx, isoGlu-PEG, PEG-Ahx, isoGlu-Ahx, or isoGlu-PEG-Ahx; Ahx is an aminohexanoic acid moiety; and wherein L1 is attached to $N^ε$ of B7;
Z is a half-life extension moiety;
J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys, NMeCys, aMeCys, or Pen;
Y2 is an amino acid or absent;

Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homoTryptophane, 1-Nal is 1-naphthylalanine, 2-Nal is 2-naphthylalanine, Orn is orinithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted bhTrp is N-methyl-L-b-homotryptophan, a-methyl-b-homotryptophan, or b-homotryptophan substituted with F, Cl, OH, or t-Bu;
and B1 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2).

In another embodiment, the peptide is according to formula A-VI or B-VI:

R$^1$-Asp-Thr-His-B1-Pro-Cys-Ile-B5-B6—N(H)C[CH$_2$CH$_2$CH$_2$CH$_2$N(H)L1Z](H)—C(O)-J-Y1-Y2-R$^2$(A-VI)    (SEQ ID NO: 268)

R$^1$-Asp-Thr-His-B1-Pro-Cys-Ile-N(H)C[CH$_2$CH$_2$CH$_2$CH$_2$N(H)L1Z](H)—C(O)—B6-B7-J-Y1-Y2-R$^2$(B-VI)    (SEQ ID NO: 269)

or a peptide dimer comprising two peptides according to Formula Formula (A-VI), or (B-VI), or a pharmaceutically acceptable salt thereof;
wherein
R$^1$ is hydrogen, C$_1$-C$_6$ alkyl, C$_6$-C$_{12}$ aryl, C$_6$-C$_{12}$ aryl-C$_1$-C$_6$ alkyl, C$_1$-C$_{20}$ alkanoyl, or C$_1$-C$_{20}$ cycloalkanoyl;
R$^2$ is —NH$_2$ or —OH;
B5 is absent, Lys, D-Lys, Orn, homoSer, Gln, (D)Gln, Lys(Ac), Ile, Abu, Leu, Ala, D-Ala, bAla, or Nleu;
L1 is absent or isoGlu, PEG, Ahx, isoGlu-PEG, PEG-Ahx, isoGlu-Ahx, or isoGlu-PEG-Ahx; Ahx is an aminohexanoic acid moiety; and wherein L1 is attached to N of B7;
Z is a half-life extension moiety;
J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys, NMeCys, aMeCys, or Pen;
Y2 is an amino acid or absent;
and one of B1 and B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2);

and the other is as described for Formula (A-I).

In one embodiment, B1 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2);

and B6 is as described for Formula (A-I).

In another embodiment, B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2);

and B1 is as described herein.

In a particular embodiment, B6 is Phe.
In a particular embodiment, B1 is Phe.
In another embodiment, the peptide is according to formula A-VII or B-VII:

R$^1$-Asp-Thr-His-B1-Pro-Cys-Ile-B5-Phe-N(H)C[CH$_2$CH$_2$CH$_2$CH$_2$N(H)L1Z](H)—C(O)-J-Y1-Y2-R$^2$(A-VII)    (SEQ ID NO: 270)

R$^1$-Asp-Thr-His-B1-Pro-Cys-Ile-N(H)C[CH$_2$CH$_2$CH$_2$CH$_2$N(H)L1Z](H)—C(O)-Phe-B7-J-Y1-Y2-R$^2$(B-VII)    (SEQ ID NO: 271)

or a peptide dimer comprising two peptides according to Formula A-VII or B-VII, or a pharmaceutically acceptable salt thereof;
wherein R$^1$, R$^2$, B5, B7, L1, Z, J, Y1, and Y2 are as described for Formula (A-I); B7 is as described for Formula (B-I); and B1 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2).

In another embodiment, the peptide is according to formula A-VIII or B-VIII:

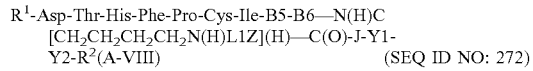
R$^1$-Asp-Thr-His-Phe-Pro-Cys-Ile-B5-B6—N(H)C[CH$_2$CH$_2$CH$_2$CH$_2$N(H)L1Z](H)—C(O)-J-Y1-Y2-R$^2$ (A-VIII) (SEQ ID NO: 272)

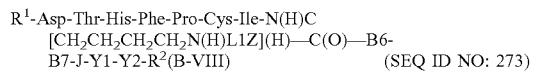
R$^1$-Asp-Thr-His-Phe-Pro-Cys-Ile-N(H)C[CH$_2$CH$_2$CH$_2$CH$_2$N(H)L1Z](H)—C(O)—B6-B7-J-Y1-Y2-R$^2$ (B-VIII) (SEQ ID NO: 273)

or a peptide dimer comprising two peptides according to Formula A-VIII or B-VIII, or a pharmaceutically acceptable salt thereof;
wherein wherein R$^1$, R$^2$, B5, B7, L1, Z, J, Y1, and Y2 are as described for Formula (A-I); B7
is as described for Formula (B-I);
and B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2).

In one embodiment, Y1 is Cys. In another embodiment, Y1 is homoCys. In another embodiment, Y1 is NMeCys. In another embodiment, Y1 is aMeCys.

In another embodiment, the peptide is according to formula A-IXa, A-IXb, B-IXa, or B-IXb:

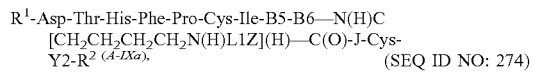
R$^1$-Asp-Thr-His-Phe-Pro-Cys-Ile-B5-B6—N(H)C[CH$_2$CH$_2$CH$_2$CH$_2$N(H)L1Z](H)—C(O)-J-Cys-Y2-R$^2$ (A-IXa), (SEQ ID NO: 274)

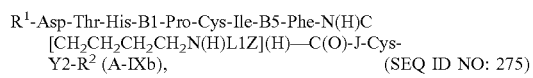
R$^1$-Asp-Thr-His-B1-Pro-Cys-Ile-B5-Phe-N(H)C[CH$_2$CH$_2$CH$_2$CH$_2$N(H)L1Z](H)—C(O)-J-Cys-Y2-R$^2$ (A-IXb), (SEQ ID NO: 275)

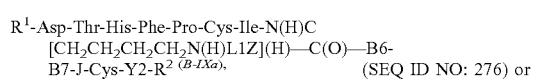
R$^1$-Asp-Thr-His-Phe-Pro-Cys-Ile-N(H)C[CH$_2$CH$_2$CH$_2$CH$_2$N(H)L1Z](H)—C(O)—B6-B7-J-Cys-Y2-R$^2$ (B-IXa), (SEQ ID NO: 276) or

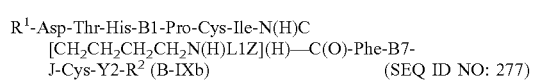
R$^1$-Asp-Thr-His-B1-Pro-Cys-Ile-N(H)C[CH$_2$CH$_2$CH$_2$CH$_2$N(H)L1Z](H)—C(O)-Phe-B7-J-Cys-Y2-R$^2$ (B-IXb) (SEQ ID NO: 277)

or a peptide dimer comprising two peptides according to Formula A-IXa, A-IXb, B-IXa, or B-IXb, or a pharmaceutically acceptable salt thereof;

wherein wherein R$^1$, R$^2$, B5, B7, L1, Z, J, and Y2 are as described for Formula (A-I); B7 is as described for Formula (B-I);
and B1 or B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2).

In one embodiment, Y2 is Lys.
In a particular embodiment, Y2 is absent.
In another embodiment, the peptide is according to formula A-Xa or A-Xb, B-Xa. or B-Xb:

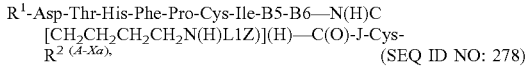
R$^1$-Asp-Thr-His-Phe-Pro-Cys-Ile-B5-B6—N(H)C[CH$_2$CH$_2$CH$_2$CH$_2$N(H)L1Z](H)—C(O)-J-Cys-R$^2$ (A-Xa), (SEQ ID NO: 278)

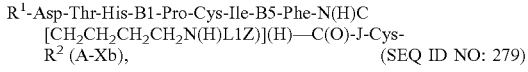
R$^1$-Asp-Thr-His-B1-Pro-Cys-Ile-B5-Phe-N(H)C[CH$_2$CH$_2$CH$_2$CH$_2$N(H)L1Z](H)—C(O)-J-Cys-R$^2$ (A-Xb), (SEQ ID NO: 279)

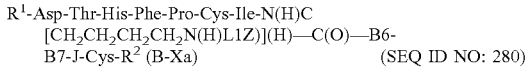
R$^1$-Asp-Thr-His-Phe-Pro-Cys-Ile-N(H)C[CH$_2$CH$_2$CH$_2$CH$_2$N(H)L1Z](H)—C(O)—B6-B7-J-Cys-R$^2$ (B-Xa) (SEQ ID NO: 280)

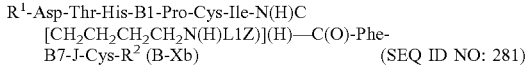
R$^1$-Asp-Thr-His-B1-Pro-Cys-Ile-N(H)C[CH$_2$CH$_2$CH$_2$CH$_2$N(H)L1Z](H)—C(O)-Phe-B7-J-Cys-R$^2$ (B-Xb) (SEQ ID NO: 281)

or a peptide dimer comprising two peptides according to Formula A-Xa or A-Xb, B-Xa. or B-Xb, or a pharmaceutically acceptable salt thereof;
wherein wherein R$^1$, R$^2$, B5, B7, L1, Z, and J are as described for Formula (A-I); B7 is as described for Formula (B-I);
and B1 or B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF$_3$), Phe(4-CH$_3$), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2).

In one embodiment, J is Pro, -Pro-Arg-, -Pro-Lys-, -Pro-(D)Lys-, -Pro-Arg-Ser-,-Pro-Arg-Ser-Lys-(SEQ ID NO:249), -Pro-Arg-Ser-Lys-Sar-(SEQ ID NO:250), or —Pro-Arg-Ser-Lys-Gly-(SEQ ID NO:251).

In another embodiment, J is Pro. In another embodiment, J is —Pro-Arg-. In another embodiment, J is —Pro-Arg-Ser-. In another embodiment, J is —Pro-Arg-Ser-Lys-(SEQ ID NO:249). In another embodiment, J is —Pro-Arg-Ser-Lys-Sar-(SEQ ID NO:250). In another embodiment, J is —Pro-Arg-Ser-Lys-Gly-(SEQ ID NO:251). In a particular embodiment, J is absent.

In another embodiment, J is any amino acid. In a particular embodiment, J is Lys, a lower or higher homolog of Lys, D-Lys, or substituted or unsubstituted Lys.

In another embodiment, the peptide is according to formula A-XIa, A-XIb, B-XIa or B-XIb:

R¹-Asp-Thr-His-Phe-Pro-Cys-Ile-B5-B6—N(H)C
[CH₂CH₂CH₂CH₂N(H)L1Z)](H)—C(O)—Cys-R²
(A-XIa), (SEQ ID NO: 282)

R¹-Asp-Thr-His-B1-Pro-Cys-Ile-B5-Phe-N(H)C
[CH₂CH₂CH₂CH₂N(H)L1Z)](H)—C(O)-Cys-R²
(A-XIb), (SEQ ID NO: 283)

R¹-Asp-Thr-His-Phe-Pro-Cys-Ile-N(H)C
[CH₂CH₂CH₂CH₂N(H)L1Z)](H)—C(O)—B6-
B7-Cys-R² (B-XIa), (SEQ ID NO: 284) or

R¹-Asp-Thr-His-B1-Pro-Cys-Ile-N(H)C
[CH₂CH₂CH₂CH₂N(H)L1Z)](H)—C(O)-Phe-
B7-Cys-R² (B-XIb) (SEQ ID NO: 285)

or a peptide dimer comprising two peptides according to Formula A-XIa, A-XIb, B-XIa or B-XIb, or a pharmaceutically acceptable salt thereof;
wherein wherein R¹, R², B5, B7, L1, and Z are as described for Formula (A-I); B7 is as described for Formula (B-I); and B1 or B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF₃), Phe(4-CH₃), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2).

In another embodiment, B5 is Lys, D-Lys, Orn, homoSer, Gln, Lys(Ac), Ile, or Nleu.

In a particular embodiment, B5 is Lys, or D-Lys.

In one embodiment, B7 is Glu or absent. In another embodiment, B7 is Glu.

In another embodiment, the peptide is according to formula A-XIIa, A-XIIb, A-XIIc, A-XIId, B-XIIa, B-XIIb, B-XIIc, or B-XIId:

R¹-Asp-Thr-His-Phe-Pro-Cys-Ile-Lys-B6—N(H)C
[CH₂CH₂CH₂CH₂N(H)L1Z)](H)—C(O)-Cys-R²
(A-XIIa), (SEQ ID NO: 286)

R¹-Asp-Thr-His-B1-Pro-Cys-Ile-Lys-Phe-N(H)C
[CH₂CH₂CH₂CH₂N(H)L1Z)](H)—C(O)-Cys-R²
(A-XIIb), (SEQ ID NO: 287)

R¹-Asp-Thr-His-Phe-Pro-Cys-Ile-(D)Lys-B6—N(H)C
[CH₂CH₂CH₂CH₂N(H)L1Z)](H)—C(O)-Cys-R²
(A-XIIc), (SEQ ID NO: 288)

R¹-Asp-Thr-His-B1-Pro-Cys-Ile-(D)Lys-Phe-N(H)C
[CH₂CH₂CH₂CH₂N(H)L1Z)](H)—C(O)-Cys-R²
(A-XIId), (SEQ ID NO: 289)

R¹-Asp-Thr-His-Phe-Pro-Cys-Ile-N(H)C
[CH₂CH₂CH₂CH₂N(H)L1Z)](H)—C(O)—B6-
Glu-Cys-R²(B-XIIa), (SEQ ID NO: 290)

R¹-Asp-Thr-His-B1-Pro-Cys-Ile-Lys-Phe-N(H)C
[CH₂CH₂CH₂CH₂N(H)L1Z)](H)—C(O)-Phe-
Glu-Cys-R²(B-XIIb), (SEQ ID NO: 291)

R¹-Asp-Thr-His-Phe-Pro-Cys-Ile-N(H)C
[CH₂CH₂CH₂CH₂N(H)L1Z)](H)—C(O)—B6-
Cys-R²(B-XIIc), (SEQ ID NO: 292) or

R¹-Asp-Thr-His-B1-Pro-Cys-Ile-N(H)C
[CH₂CH₂CH₂CH₂N(H)L1Z)](H)—C(O)-Phe-
Cys-R²(B-XIId) (SEQ ID NO: 293)

or a peptide dimer thereof, or a pharmaceutically acceptable salt thereof, wherein wherein R¹, R², L1, and Z are as described for Formula (A-I); and B1 or B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4-CF₃), Phe(4-CH₃), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4—OH), or β-homoPhe(4-NO2).

In another embodiment, R¹ is isovaleric acid or IVA.

In another embodiment, the peptide is according to formula A-XIIIa, A-XIIIb, A-XIIIc, A-XIIId, B-XIIIa, B-XIIIb, B-XIIIc, or B-XIIId:

IVA-Asp-Thr-His-Phe-Pro-Cys-Ile-Lys-B6—N(H)C
[CH₂CH₂CH₂CH₂N(H)L1Z)](H)—C(O)—Cys-
R²(A-XIIIa), (SEQ ID NO: 294)

IVA-Asp-Thr-His-B1-Pro-Cys-Ile-Lys-Phe-N(H)C
[CH₂CH₂CH₂CH₂N(H)L1Z)](H)—C(O)—Cys-
R²(A-XIIIb), (SEQ ID NO:295)

IVA-Asp-Thr-His-Phe-Pro-Cys-Ile-(D)Lys-B6—N(H)
C[CH₂CH₂CH₂CH₂N(H)L1Z)](H)—C(O)—Cys-
R² (A-XIIIc), (SEQ ID NO: 296)

IVA-Asp-Thr-His-B1-Pro-Cys-Ile-(D)Lys-Phe-N(H)C
[CH₂CH₂CH₂CH₂N(H)L1Z)](H)—C(O)—Cys-
R²(A-XIIId), (SEQ ID NO:297)

IVA-Asp-Thr-His-Phe-Pro-Cys-Ile-N(H)C
[CH₂CH₂CH₂CH₂N(H)L1Z)](H)—C(O)—B6-
Glu-Cys-R²(B-XIIIa), (SEQ ID NO: 298)

IVA-Asp-Thr-His-B1-Pro-Cys-Ile-Lys-Phe-N(H)C
[CH₂CH₂CH₂CH₂N(H)L1Z)](H)—C(O)-Phe-
Glu-Cys-R²(B-XIIIb), (SEQ ID NO: 299)

IVA-Asp-Thr-His-Phe-Pro-Cys-Ile-N(H)C
[CH₂CH₂CH₂CH₂N(H)L1Z)](H)—C(O)—B6-
Cys-R²(B-XIIIc), (SEQ ID NO: 300) or

IVA-Asp-Thr-His-B1-Pro-Cys-Ile-N(H)C
[CH₂CH₂CH₂CH₂N(H)L1Z)](H)—C(O)-Phe-
Cys-R²(B-XIIId) (SEQ ID NO: 301)

or a peptide dimer thereof, or a pharmaceutically acceptable salt thereof, wherein R², L1, and Z, are as described for Formula (A-I); IVA is isovaleric acid; and B1 or B6 is i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me)

ii) Phe(4-F), Phe(4—CF₃), Phe(4—CH₃), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4—CN), β-homoPhe, a substituted β-homoPhe; or iii) β-homoPhe(2-Me), β-homoPhe(3-Me), β-homoPhe (4-Me), β-homoPhe(2-F), β-homoPhe(3-F), β-homoPhe(4-F), β-homoPhe(2-Br), β-homoPhe(3-Br), β-homoPhe(4-Br), β-homoPhe(3—Cl), β-homoPhe(4-I), β-homoPhe(4—OH), or β-homoPhe(4-NO2).

In one embodiment, L1 is a single bond or is absent. In another embodiment, L1 is iso-Glu. In another embodiment, L1 is Ahx. In another embodiment, L1 is iso-Glu-Ahx.

In another embodiment, L1 is PEG. In another embodiment, L1 is iso-Glu-PEG. In another embodiment, L1 is PEG-Ahx. In another embodiment, L1 is iso-Glu-PEG-Ahx. In another embodiment, L1 is Dapa or D-Dapa.

In another embodiment, PEG is PEG1, PEG2, PEG3, PEG4, PEG53, or PEG11.

In one embodiment, Z is Palm. In another embodiment, B1 is Phe. In another embodiment, B6 is Phe. In another embodiment, the peptide is according to formula A-XIVa, A-XIVb, B-XIVa, or B-XIVb:

```
IVA-Asp-Thr-His-Phe-Pro-Cys-Ile-Lys-Phe-N(H)C
   [CH2CH2CH2CH2N(H)L1Z](H)—C(O)—Cys-
   R²(A-XIVa),                         (SEQ ID NO: 302)

IVA-Asp-Thr-His-Phe-Pro-Cys-Ile-(D)Lys-Phe-N(H)
   C[CH2CH2CH2CH2N(H)L1Z](H)—C(O)—Cys-
   R²(A-XIVb),                         (SEQ ID NO: 303)

IVA-Asp-Thr-His-Phe-Pro-Cys-Ile-N(H)C
   [CH2CH2CH2CH2N(H)L1Z](H)—C(O)-Phe-
   Glu-Cys-R²(B-XIVa),                 (SEQ ID NO: 304) or

IVA-Asp-Thr-His-Phe-Pro-Cys-Ile-N(H)C
   [CH2CH2CH2CH2N(H)L1Z](H)—C(O)-Phe-
   Cys-R²(B-XIVb)                      (SEQ ID NO: 305)
``` or a peptide dimer thereof, or a pharmaceutically acceptable salt thereof, wherein R², L1, and Z, are as described for Formula (A-I); and IVA is isovaleric acid.

In one embodiment, J is X and X is an amino acid selected from Lys, D-Lys, Arg, D-Arg, Pro, His, Orn, Daba, Dapa, or homoLys.

In one embodiment, the peptide is according to formula A-XXIa or A-XXIb:

```
R¹-Asp-Thr-His-Phe-Pro-Cys-Ile-B5-B6—N(H)C
   [CH2CH2CH2CH2N(H)L1Z)](H)—C(O)—X-
   Cys-Y2-R²(A-XXIa)                   (SEQ ID NO: 306)

R¹-Asp-Thr-His-B1-Pro-Cys-Ile-B5-Phe-N(H)C
   [CH2CH2CH2CH2N(H)L1Z)](H)—C(O)—X-
   Cys-Y2-R²(A-XXIb)                   (SEQ ID NO: 307)
``` or a peptide dimer thereof, or a pharmaceutically acceptable salt thereof,
wherein R¹, R², B5, L1, Y2, and Z, are as described for Formula (A-I); and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr (Me);
ii) Phe, Phe(4-F), Phe(4—CF₃), Phe(4—CH₃), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4—CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3—Cl), β-homoPhe(4-I), β-homoPhe(4—OH), or β-homoPhe(4-NO2).

In one embodiment, B5 is Lys, D-Lys, Orn, homoSer, Gln, Lys(Ac), Ile, or Nleu. In another embodiment, B5 is Lys, or D-Lys. In another embodiment, B5 is bAla, or D-Ala. In anther embodiment, B5 is Ile. In anther embodiment, B5 is absent.

In another embodiment, the peptide is according to formula A-XXIIa, A-XXIIb, A-XXIIc, or A-XXIId:

```
R¹-Asp-Thr-His-Phe-Pro-Cys-Ile-Lys-B6—N(H)C
   [CH2CH2CH2CH2N(H)L1Z)](H)—C(O)—X-
   Cys-Y2-R² (A-XXIIa)                 (SEQ ID NO: 308)

R¹-Asp-Thr-His-B1-Pro-Cys-Ile-Lys-Phe-N(H)C
   [CH2CH2CH2CH2N(H)L1Z)](H)—C(O)—X-
   Cys-Y2-R² (A-XXIIb)                 (SEQ ID NO: 309)

R¹-Asp-Thr-His-Phe-Pro-Cys-Ile-(D)Lys-B6—N(H)C
   [CH2CH2CH2CH2N(H)L1Z)](H)—C(O)—X-
   Cys-Y2-R² (A-XXIIc)                 (SEQ ID NO: 310)

R¹-Asp-Thr-His-B1-Pro-Cys-Ile-(D)Lys-Phe-N(H)C
   [CH2CH2CH2CH2N(H)L1Z)](H)—C(O)—X-
   Cys-Y2-R² (A-XXIId)                 (SEQ ID NO: 311)
``` or a peptide dimer thereof, or a pharmaceutically acceptable salt thereof,
wherein R¹, R², L1, Y2, and Z, are as described for Formula (A-I); and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr (Me);
ii) Phe, Phe(4-F), Phe(4—CF₃), Phe(4—CH₃), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4—CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3—Cl), β-homoPhe(4-I), β-homoPhe(4—OH), or β-homoPhe(4-NO2).

In a particular embodiment, R¹ is isovaleric acid or IVA.

In one embodiment, the peptide is according to formula A-XXIIIa, A-XXIIIb, A-XXIIIc, or A-XXIIId:

```
IVA-Asp-Thr-His-Phe-Pro-Cys-Ile-Lys-B6—N(H)C
   [CH2CH2CH2CH2N(H)L1Z](H)—C(O)—X-
   Cys-Y2-R² (A-XXIIIa)                (SEQ ID NO: 312)

IVA-Asp-Thr-His-B1-Pro-Cys-Ile-Lys-Phe-N(H)C
   [CH2CH2CH2CH2N(H)L1Z](H)—C(O)—X-
   Cys-Y2-R² (A-XXIIIb)                (SEQ ID NO: 313)

IVA-Asp-Thr-His-Phe-Pro-Cys-Ile-(D)Lys-B6—N(H)
   C[CH2CH2CH2CH2N(H)L1Z](H)—C(O)—X-
   Cys-Y2-R² (A-XXIIIc)                (SEQ ID NO: 314)

IVA-Asp-Thr-His-B1-Pro-Cys-Ile-(D)Lys-Phe-N(H)C
   [CH2CH2CH2CH2N(H)L1Z](H)—C(O)—X-
   Cys-Y2-R² (A-XXIIId)                (SEQ ID NO: 315)
``` or a peptide dimer thereof, or a pharmaceutically acceptable salt thereof,
wherein R², L1, Y2, and Z, are as described for Formula (A-I); IVA is isovaleric acid; and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr (Me);
ii) Phe, Phe(4-F), Phe(4—CF₃), Phe(4—CH₃), Phe(4-tBu), Bip, Phe(4—COOH), Phe(2,4-diCl), Phe(3,4-diCl), Phe(4-carbomyl), Phe(3-carbomyl), Phe(3,4-dimethoxy), Phe(4—CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3—Cl), β-homoPhe(4-I), β-homoPhe(4—OH), or β-homoPhe(4-NO2).

In one embodiment, B1 is Phe. In another embodiment, B6 is Phe.

In one embodiment, B1 is Phe; and B6 is Phe, Dpa, bhPhe, Nap, or hPhe. In another embodiment, B1 is Dpa; and B6 is Phe, Dpa, bhPhe, Nap, or hPhe.

In another embodiment, B6 is Dpa, bhPhe, hPhe, or Nal. In anther embodiment, B6 is Dpa. In another embodiment, B6 is bhPhe. In another embodiment, B6 is hPhe or homoPhe.

In one embodiment, the peptide is according to formula A-XXIVa, or A-XXIVb:

IVA-Asp-Thr-His-Phe-Pro-Cys-Ile-Lys-Phe-N(H)C
[CH$_2$CH$_2$CH$_2$CH$_2$N(H)L1Z](H)—C(O)—X-
Cys-Y2-R$^2$ (A-XXIVa)         (SEQ ID NO: 316)

IVA-Asp-Thr-His-Phe-Pro-Cys-Ile-(D)Lys-Phe-N(H)
C[CH$_2$CH$_2$CH$_2$CH$_2$N(H)L1Z](H)—C(O)—X-
Cys-Y2-R$^2$ (A-XXIVb)         (SEQ ID NO: 317)

or a peptide dimer thereof, or a pharmaceutically acceptable salt thereof,
wherein R$^2$, L1, Y2, and Z, are as described for Formula (A-I); and IVA is isovaleric acid.

In one embodiment, Y2 is absent, Lys, (D)Lys, His, (D)His, Arg, or (D)Arg. In another embodiment, Y2 is Lys, (D)Lys, His, (D)His, Arg, or (D)Arg.

In a particular embodiment, Y2 is absent.

In one embodiment, the peptide is according to formula A-XXVa, or A-XXVb:

IVA-Asp-Thr-His-Phe-Pro-Cys-Ile-Lys-Phe-N(H)C
[CH$_2$CH$_2$CH$_2$CH$_2$N(H)L1Z](H)—C(O)—X-
Cys-R$^2$ (A-XXVa)            (SEQ ID NO: 318)

IVA-Asp-Thr-His-Phe-Pro-Cys-Ile-(D)Lys-Phe-N(H)
C[CH$_2$CH$_2$CH$_2$CH$_2$N(H)L1Z](H)—C(O)—X-
Cys-R$^2$ (A-XXVb)            (SEQ ID NO: 319)

or a peptide dimer thereof, or a pharmaceutically acceptable salt thereof,
wherein R$^2$, L1, and Z, are as described for Formula (A-I); and IVA is isovaleric acid.

In one embodiment, X is His, Pro, Lys, D-Lys, Arg, or D-Arg. In another embodiment, X is Lys, or D-Lys. In another embodiment, X is Lys. In another embodiment, X is D-Lys. In another embodiment, X is Pro. In another embodiment, X is His. In another embodiment, X is Dapa. In another embodiment, X is Orn. In another embodiment, X is Daba. In another embodiment, X is homoLys.

In a particular embodiment, with respect to the peptide according to formula A-I, B1 is F, Dpa, BIP, or bhPhe; B2 is Pro, NCP, (D)Pro, or (D)NCP; B3 is Cys, a-MeCys, or homoCys; B4 is Ile; B5 is D)Lys, bAla, (D)Gln, (D)Ala, Orn, or Ile; B6 is Phe, substituted Phe, or bhPhe; and B7 is Lys, (D)Lys, or Dap.

In a more particular embodiment, with respect to the peptide according to formula A-I, B2 is Pro, B3 is Cys, B4 is Ile, and B6 is Phe or bhPhe.

In a more particular embodiment, with respect to the peptide according to formula A-I, B7(L1Z) is —N(H)C[CH$_2$(CH$_2$CH$_2$)mN(H)L1Z](H)—C(O)—; and wherein m is 0 or 1.

In one embodiment, with respect to the peptide according to formula A-I, B7(L1Z) is —N(H)C[CH$_2$N(H)L1Z](H)—C(O)—.

In a most particular embodiment, with respect to the peptide according to formula A-I, B7(L1Z) is —N(H)C[CH$_2$CH$_2$CH$_2$CH$_2$N(H)L1Z](H)—C(O)—.

In a particular aspect, the present invention provides hepcidin analogue comprising a peptide according to formula C-Ia or C-Ib:

R$^1$-Asp-Thr-His-B1-Pro-Cys-Ile-B5-B6—N(H)C
[CH$_2$N(H)L1Z](H)—C(O)-J-Y1-Y2-R$^2$(C-Ia) (SEQ ID NO: 320)

or

R$^1$-Asp-Thr-His-B1-Pro-Cys-Ile-B5-B6—N(H)C
[CH$_2$CH$_2$CH$_2$CH$_2$N(H)L1Z](H)—C(O)-J-Y1-
Y2-R$^2$(C-Ib)                (SEQ ID NO: 321)

or a peptide dimer thereof, or a pharmaceutically acceptable salt thereof,
wherein R$^1$, R$^2$, L1, Z, J, Y1, and Y2 are as described for for Formula (A-I); and
B1 is F, b-hPhe, or Dpa; B5 is (D)Lys, bAla, (D)Gln, (D)Ala, or Ile; and B6 is Phe, Phe(4-t-Bu), or bhPhe.

In one embodiment, B5 is (D)Lys. In another embodiment, B5 is bAla. In another embodiment, B5 is (D)Ala. In another embodiment, B5 is (D)Gln. In another embodiment, B5 is Ile.

In a more particular embodiment B5 is (D)Lys.

In one embodiment, the peptide is according to formula C-IIa or C-IIb:

R$^1$-Asp-Thr-His-B1-Pro-Cys-Ile-(D)Lys-B6—N(H)C
[CH$_2$N(H)L1Z](H)—C(O)-J-Y1-Y2-R$^2$ (C-IIa),
(SEQ ID NO: 322) or

R$^1$-Asp-Thr-His-B1-Pro-Cys-Ile-(D)Lys-B6—N(H)C
[CH$_2$CH$_2$CH$_2$CH$_2$N(H)L1Z](H)—C(O)-J-Y1-
Y2-R$^2$(C-IIb),              (SEQ ID NO: 323)

or a peptide dimer thereof, or a pharmaceutically acceptable salt thereof,
wherein R$^1$, R$^2$, L1, Z, J, Y1, and Y2 are as described for for Formula (A-I); and
B1 is F, b-hPhe, or Dpa; and B6 is Phe, Phe(4-t-Bu), or bhPhe.

In a more particular embodiment B1 is F. In another embodiment, B1 is Dpa. In another embodiment, B1 is b-hPhe.

In one embodiment, the peptide is according to formula C-IIIa or C-IIIb:

R$^1$-Asp-Thr-His-F-Pro-Cys-Ile-(D)Lys-B6—N(H)C
[CH$_2$CH$_2$CH$_2$CH$_2$N(H)L1Z](H)—C(O)-J-Y1-
Y2-R$^2$(C-IIIa),             (SEQ ID NO: 324)

or

R$^1$-Asp-Thr-His-Dpa-Pro-Cys-Ile-(D)Lys-B6—N(H)
C[CH$_2$CH$_2$CH$_2$CH$_2$N(H)L1Z](H)—C(O)-J-Y1-
Y2-R$^2$(C-IIIb),             (SEQ ID NO: 325)

or a peptide dimer thereof, or a pharmaceutically acceptable salt thereof,
wherein R$^1$, R$^2$, L1, Z, J, Y1, and Y2 are as described for Formula (A-I); and B6 is Phe Phe(4-t-Bu), or bhPhe.

In a more particular embodiment B6 is Phe. In another embodiment, B6 is bhPhe. In another embodiment, B6 is Phe(4-t-Bu).

In one embodiment, the peptide is according to formula C-IVa, C-IVb, C-IVc, or C-IVd:

R$^1$-Asp-Thr-His-F-Pro-Cys-Ile-(D)Lys-Phe-N(H)C
[CH$_2$CH$_2$CH$_2$CH$_2$N(H)L1Z](H)—C(O)-J-Y1-
Y2-R$^2$(C-IVa),              (SEQ ID NO: 326)

R¹-Asp-Thr-His-Dpa-Pro-Cys-Ile-(D)Lys-Phe-N(H)C
[CH₂CH₂CH₂CH₂N(H)L1Z](H)—C(O)-J-Y1-
Y2-R²(C-IVb), (SEQ ID NO: 327)

R¹-Asp-Thr-His-F-Pro-Cys-Ile-(D)Lys-bhPhe-N(H)C
[CH₂CH₂CH₂CH₂N(H)L1Z](H)—C(O)-J-Y1-
Y2-R²(C-IVc), (SEQ ID NO: 328)

R¹-Asp-Thr-His-Dpa-Pro-Cys-Ile-(D)Lys-bhPhe-N
(H)C[CH₂CH₂CH₂CH₂N(H)L1Z](H)—C(O)-J-
Y1-Y2-R²(C-IVd), (SEQ ID NO: 329)

or a peptide dimer thereof, or a pharmaceutically acceptable salt thereof,
wherein R¹, R², L1, Z, J, Y1, and Y2 are as described for Formula (A-I).

In one embodiment, with respective to the peptide of invention, Asp of —Asp-Thr-His-B1— is replaced with dAsp.

In one embodiment, with respective to the peptide of invention, Pro of —Asp-Thr-His-B1-Pro-Cys-Ile-B5-B6— is replaced with dPro, or Npc.

In a particular embodiment, with respective to the peptide of invention, the peptide is cyclized via a disulfide bond between two Cys.

In one embodiment, with respective to the peptide of invention, —N(H)C[CH₂N(H)L1Z](H)—C(O)— is an L-amino acid. In another embodiment, with respective to the peptide of invention, —N(H)C[CH₂N(H)L1Z](H)—C(O)— is an D- amino acid.

In one embodiment, with respective to the peptide of invention, —N(H)C[CH₂CH₂CH₂CH₂N(H)L1Z](H)—C(O)— is an L- amino acid. In another embodiment, with respective to the peptide of invention, —N(H)C[CH₂CH₂CH₂CH₂N(H)L1Z](H)—C(O)— is an D- amino acid.

In one embodiment, -J-Y1-Y2—is —Cys-, -Pro-Cys-, -Lys-Cys-, -(D)Lys-Cys-, -Dap-Cys-, -Cys-(D)Lys-, -Dap-hCys-, -Pro-Arg-Cys-, -Pro-Arg-Ser-Cys-(SEQ ID NO:253), —Pro-Arg-Ser-Lys-Cys-(SEQ ID NO:254), or —Pro-Arg-Ser-Lys-Sar-Cys-(SEQ ID NO:255).

In one embodiment, -J-Y1-Y2—is —Cys-, -Pro-Cys-, -Lys-Cys-, -(D)Lys-Cys-, -Dap-Cys-, -Cys-(D)Lys-, -Dap-hCys-, -Pro-Arg-Cys-, -Pro-Arg-Ser-Cys-(SEQ ID NO:253), or —Pro-Arg-Ser-Lys-Cys-(SEQ ID NO:254).

In one embodiment, -J-Y1-Y2—is —Cys-, -Pro-Cys-, -Pro-Lys-Cys-, -Pro-(D)Lys-Cys-,-Lys-Cys-, -(D)Lys-Cys-, -Dap-Cys-, -Cys-(D)Lys-, -Dap-hCys-, -Pro-Arg-Cys-, or —Pro-Arg-Ser-Cys-(SEQ ID NO:253).

In another embodiment, -J-Y1-Y2—is —(D)Lys-Cys— or —Lys-Cys-.

In another embodiment, -J-Y1-Y2—is —Cys-(D)Lys-.

In another embodiment, -J-Y1-Y2—is —Pro-Arg-Ser-Lys-Cys-(SEQ ID NO:254).

In another embodiment, -J-Y1-Y2—is —Pro-Arg-Ser-Lys-Cys-Lys-(SEQ ID NO:255).

In another embodiment, -J-Y1-Y2—is —Pro-Cys-.

In another embodiment, -J-Y1-Y2—is —Cys-.

In another embodiment, -J-Y1-Y2—is —(D)Lys-Pen-.

In one embodiment, R² is NH₂. In another embodiment, R² is OH.

In one embodiment, L1 is a single bond. In another embodiment, L1 is iso-Glu.

In another embodiment, L1 is Ahx. In another embodiment, L1 is iso-Glu-Ahx. In another embodiment, PEG. In another embodiment, L1 is iso-Glu-PEG. In another embodiment, L1 is PEG-Ahx.

In another embodiment, L1 is iso-Glu-PEG-Ahx. In another embodiment, PEG is PEG1, PEG2, PEG3, PEG4, PEG53, or PEG11. In another embodiment, Z is Palm.

In another embodiment, L1 is Ahx; and Z is Palm.

In another embodiment, L1 is PEG11; and Z is Palm.

In another embodiment, L1 is Dap; and Z is Palm.

In another embodiment, L1 is dDap; and Z is Palm.

In a particular embodiment, the peptide is according to formula (A-I):
R¹-Asp-Thr-His-B1-B2-B3-B4-B5-B6-B7(L1Z)-J-Y1-Y2-R² (A-I) wherein the peptide comprises any of the combinations of B1, B2, B3, B4, B5, B6, B7(L1Z), J, Y1 and Y2 set forth in a row of Table 2A, wherein R¹ is IVA, R² is NH₂, and "abs" indicates "absent". The accompanying sequence identifiers represent the amino acid sequence of peptides according to formula (A-I) having the amino acids indicated for each row Table 2A and indicating the indicated conjugated half-life extension moiety when present.

TABLE 2A

| SEQ ID NO. | B1 | B2 | B3 | B4 | B5 | B6 | B7(L1Z) | J | Y1 | Y2 |
|---|---|---|---|---|---|---|---|---|---|---|
| 3 | F | P | C | I | K | F | K(PEG11-Palm) | PRSKG | C | abs |
| 4 | F | P | C | I | K | F | K(PEG11-Palm) | PRSK | C | abs |
| 5 | F | P | C | I | K | F | K(PEG11-Palm) | PRS | C | abs |
| 6 | F | P | C | I | K | F | K(PEG11-Palm) | PR | C | abs |
| 7 | F | P | C | I | K | F | K(PEG11-Palm) | P | C | abs |
| 8 | F | P | C | I | K | F | K(PEG11-Palm) | abs | C | abs |
| 9 | F | P | C | I | K | F | K(PEG11-Palm) | P | C | K |
| 8 | F | P | C | I | K | F | K(PEG11-Palm) | abs | C | abs |
| 10 | F | P | C | I | (D)Lys | F | K(PEG11-Palm) | abs | C | abs |
| 11 | F | P | C | I | Orn | F | K(PEG11-Palm) | abs | C | abs |
| 12 | F | P | C | I | hSer | F | K(PEG11-Palm) | abs | C | abs |
| 13 | F | P | C | I | Q | F | K(PEG11-Palm) | abs | C | abs |
| 14 | F | P | C | I | K(Ac) | F | K(PEG11-Palm) | abs | C | abs |
| 15 | F | P | C | I | Nleu | F | K(PEG11-Palm) | abs | C | abs |
| 16 | F | P | C | I | I | F | K(PEG11-Palm) | abs | C | abs |
| 17 | F | P | C | I | K | NMePhe | K(PEG11-Palm) | abs | C | abs |
| 18 | F | P | C | I | K | aMePhe | K(PEG11-Palm) | abs | C | abs |
| 19 | F | P | C | I | K | bhPhe | K(PEG11-Palm) | abs | C | abs |
| 20 | F | P | C | I | K | W | K(PEG11-Palm) | abs | C | abs |
| 21 | F | P | C | I | (D)Lys | F | K(Peg8-Palm) | abs | C | abs |
| 22 | F | P | C | I | (D)Lys | F | K(PEG4-Palm) | abs | C | abs |
| 23 | F | P | C | I | (D)Lys | F | K(PEG2-Palm) | abs | C | abs |
| 24 | F | P | C | I | (D)Lys | F | K(PEG1-Palm) | abs | C | abs |
| 25 | F | P | C | I | (D)Lys | F | K(Ahx-Palm) | abs | C | abs |

TABLE 2A-continued

| SEQ ID NO. | B1 | B2 | B3 | B4 | B5 | B6 | B7(L1Z) | J | Y1 | Y2 |
|---|---|---|---|---|---|---|---|---|---|---|
| 26 | F | P | C | I | (D)Lys | F | K(PEG2-IsoGlu-Palm) | abs | C | abs |
| 27 | F | P | C | I | (D)Lys | F | K(IsoGlu-Palm) | abs | C | abs |
| 28 | F | P | C | I | (D)Lys | F | K(IsoGlu-Peg2-Palm) | abs | C | abs |
| 29 | F | P | C | I | (D)Lys | F | K(Peg2-Ahx-Palm) | abs | C | abs |
| 30 | F | P | C | I | (D)Lys | F | K(Palm) | abs | C | abs |
| 33 | F | NPC | C | I | (D)Lys | F | K(PEG11-Palm) | abs | C | abs |
| 34 | F | (D)NPC | C | I | (D)Lys | F | K(PEG11-Palm) | abs | C | abs |
| 35 | F | (D)Pro | C | I | (D)Lys | F | K(PEG11-Palm) | abs | C | abs |
| 36 | F | (D)bhPro | C | I | (D)Lys | F | K(PEG11-Palm) | abs | C | abs |
| 37 | F | bhPro | C | I | (D)Lys | F | K(PEG11-Palm) | abs | C | abs |
| 10 | F | P | C | I | (D)Lys | F | K(PEG11-Palm) | abs | C | abs |
| 38 | BIP | P | C | I | (D)Lys | F | K(PEG11-Palm) | abs | C | abs |
| 135 | Dpa | P | C | I | (D)Lys | F | K(PEG11-Palm) | abs | C | abs |
| 135 | Dpa | P | C | I | (D)Lys | F | K(PEG11-Palm) | abs | C | abs |
| 67 | F | P | C(SH) | I | K | F | K(PEG11-Palm) | P | C(SH) | abs |
| 68 | F | P | C(SH) | I | (D)Lys | F | K(PEG11-Palm) |  | C(SH) | abs |
| 69 | F | P | C(SH) | I | K | F | K(PEG11-Palm) |  | C(SH) | abs |
| 70 | F | P | C | I | (D)Lys | F | K(PEG11-Palm) | P | C | abs |
| 71 | F | P | C | I | (D)Lys | F | K(PEG11-Palm) | PR | C | abs |
| 72 | F | P | C | I | (D)Lys | F | K(PEG11-Palm) | PRS | C | abs |
| 73 | F | P | C | I | (D)Lys | F | K(PEG11-Palm) | PRSK | C | abs |
| 74 | F | P | C | I | (D)Lys | F | K(PEG11-Palm) | PRSKSar | C | abs |
| 75 | F | P | C | I | (D)Lys | F | K(PEG11-Palm) | PRSK | C | K |
| 76 | F | P | C | I | (D)Lys | F | K(PEG11-Palm) | PRS | C | K |
| 77 | F | P | C | I | (D)Lys | F | K(PEG11-Palm) | PR | C | K |
| 78 | F | P | C | I | (D)Lys | F | K(PEG11-Palm) |  | C | K |
| 79 | F | P | C | I | (D)Lys | F | K(PEG11-Palm) | R | C | abs |
| 80 | F | P | C | I | (D)Lys | F | K(PEG11-Palm) | K | C | abs |
| 81 | F | P | C | I | (D)Lys | F | K(PEG11-Palm) | r | C | abs |
| 82 | F | P | C | I | (D)Lys | F | K(PEG11-Palm) | (D)Lys | C | abs |
| 83 | F | P | C | I | (D)Lys | F | K(PEG11-Palm) | K | C | (D)Lys |
| 84 | F | P | C | I | (D)Lys | F | K(PEG11-Palm) | H | C | h |
| 85 | F | P | C | I | (D)Lys | F | K(PEG11-Palm) | R | C | r |
| 86 | F | P | C | I | (D)Lys | F | K(Ahx-Palm) | K | C | abs |
| 87 | F | P | C | I | (D)Lys | F | K(PEG2-Palm) | K | C | abs |
| 88 | F | P | C | I | (D)Lys | F | K(PEG2-PEG2-Palm) | K | C | abs |
| 89 | F | P | C | I | (D)Lys | F | K(PEG2-PEG2-C18 acid) | K | C | abs |
| 90 | F | P | C | I | (D)Lys | F | K(PEG2-PEG2-Ahx-Palm) | K | C | abs |
| 91 | F | P | C | I | (D)Lys | F | K(PEG4-Palm) | K | C | abs |
| 92 | F | P | C | I | (D)Lys | F | K(PEG4-Ahx-Palm) | K | C | abs |
| 93 | F | P | C | I | (D)Lys | F | K(PEG4-PEG4-Palm) | K | C | abs |
| 94 | F | P | C | I | (D)Lys | F | K(PEG4-isoGlu-Palm) | K | C | abs |
| 95 | F | P | C | I | (D)Lys | F | K(PEG8-Palm) | K | C | abs |
| 96 | F | P | C | I | (D)Lys | F | K(Behenic acid) | K | C | abs |
| 97 | F | P | C | I | (D)Lys | F | K(PEG11-Palm) | K | c | abs |
| 98 | F | P | C | I | (D)Lys | F | K(PEG11-Palm) | K | Pen | abs |
| 99 | F | P | C | I | (D)Lys | F | K(PEG11-Palm) | Dap | C | abs |
| 100 | F | P | C | I | (D)Lys | Dpa | K(PEG11-Palm) | K | C | abs |
| 101 | F | P | C | I | (D)Lys | bhPhe | K(PEG11-Palm) | K | C | abs |
| 102 | F | P | C | I | (D)Lys | 2-Nal | K(PEG11-Palm) | K | C | abs |
| 103 | F | P | C | I | (D)Lys | bhPhe | K(PEG11-Palm) | K | C | abs |
| 104 | Dpa | P | C | I | (D)Lys | F | K(PEG11-Palm) | K | C | abs |
| 105 | Dpa | P | C | I | (D)Lys | bhPhe | K(PEG11-Palm) | (D)Lys | C | abs |
| 99 | F | P | C | I | (D)Lys | F | K(PEG11-Palm) | Dap | C | abs |
| 107 | F | P | C | I | (D)Lys | F | k(PEG11-Palm) | (D)Lys | C | abs |
| 110 | Dpa | Npc | C | I | (D)Lys | Phe(4-tBu) | K(PEG11-Palm) | K | C | abs |
| 111 | Dpa | Npc | C | I | (D)Lys | Phe(4-(2-aminoethoxy)) | K(PEG11-Palm) | K | C | abs |
| 112 | Dpa | Npc | C | I | (D)Lys | 2-Nal | K(PEG11-Palm) | K | C | abs |
| 113 | Dpa | Npc | C | I | (D)Lys | Phe(4-COOH) | K(PEG11-Palm) | K | C | abs |
| 114 | F | P | C | I | (D)Lys | F | K(PEG11-Palm) | K | (a-Me)C | abs |
| 115 | F | P | (a-Me)C | I | (D)Lys | F | K(PEG11-Palm) | K | (a-Me)C | abs |
| 116 | F | P | (a-Me)C | I | (D)Lys | F | K(PEG11-Palm) | K | C | abs |

TABLE 2A-continued

| SEQ ID NO. | B1 | B2 | B3 | B4 | B5 | B6 | B7(L1Z) | J | Y1 | Y2 |
|---|---|---|---|---|---|---|---|---|---|---|
| 117 | Dpa | Npc | C | I | (D)Lys | F | K(PEG11-Palm) | (D)Lys | C | abs |
| 118 | F | Npc | C | I | (D)Lys | F | K(PEG11-Palm) | (D)Lys | C | abs |
| 119 | Dpa | bhPhe | C | I | (D)Lys | F | K(PEG11-Palm) | (D)Lys | C | abs |
| 120 | Phe(4-COOH) | P | C | I | (D)Lys | F | K(PEG11-Palm) | (D)Lys | C | abs |
| 121 | bhPhe | P | C | I | (D)Lys | F | K(PEG11-Palm) | (D)Lys | C | abs |
| 122 | Dpa | P | C | I | (D)Lys | bhPhe | K(PEG11-Palm) | (D)Lys | C | abs |
| 125 | Dpa | Npc | C | I | (D)Lys | (a-MePhe) | K(PEG11-Palm) | K | C | abs |
| 126 | Dpa | Npc | C | I | (D)Lys | Phe(4-CN) | K(PEG11-Palm) | K | C | abs |
| 127 | Dpa | Npc | C | I | (D)Lys | Phe(3,4-diF) | K(PEG11-Palm) | K | C | abs |
| 128 | (a-MePhe) | P | C | I | (D)Lys | F | K(PEG11-Palm) | (D)Lys | C | abs |
| 129 | Phe(4-(2-aminoethoxy)) | P | C | I | (D)Lys | F | K(PEG11-Palm) | (D)Lys | C | abs |
| 130 | Dpa | P | C | I | (D)Lys | F | K(PEG11-Palm) | (D)Lys | C | abs |
| 131 | Dpa | P | C | I | (D)Lys | Dpa | K(PEG11-Palm) | (D)Lys | C | abs |
| 132 | Dpa | P | C | I | (D)Lys | F | K(PEG11-Palm) | (D)Lys | Pen | abs |
| 133 | Dpa | P | C | I | (D)Lys | F | K(Peg11-Palm) | K | N-Me-Cys | abs |
| 134 | Dpa | P | C | I | (D)Lys | F | K(Peg11-Palm) | (D)Lys | N-Me-Cys | abs |
| 135 | Dpa | P | C | I | (D)Lys | F | K(Peg11-Palm) | C | | abs |
| 136 | Dpa | P | C | I | (D)Lys | F | K(Peg11-Palm) | Orn | C | abs |
| 137 | Dpa | P | C | I | (D)Lys | F | K(Peg11-Palm) | Dab | C | abs |
| 138 | Dpa | P | C | I | (D)Lys | F | K(Peg11-Palm) | b-hLys | C | abs |
| 139 | Dpa | P | C | I | (D)Lys | F | K(Peg11-Palm) | (D)Lys | C | abs |
| 140 | Dpa | P | C | I | (D)Lys | F | K(Peg11-Palm) | Dap | Pen | abs |
| 141 | Dpa | P | hCys | I | (D)Lys | F | K(Peg11-Palm) | Dap | C | abs |
| 142 | Dpa | P | hCys | I | (D)Lys | F | K(Peg11-Palm) | Dap | C | abs |
| 143 | Dpa | P | C | I | (D)Lys | F | K(Peg11-Palm) | Dap | hCys | abs |
| 144 | F | P | C | I | (D)Lys | F | K(Peg11-Palm) | | C | K |
| 145 | Dpa | P | C | I | bAla | bhPhe | K(Peg11-Palm) | (D)Lys | C | abs |
| 146 | Dpa | P | C | I | (D)Ala | bhPhe | K(Peg11-Palm) | (D)Lys | C | abs |
| 147 | Dpa | P | C | I | I | bhPhe | K(Peg11-Palm) | (D)Lys | C | abs |
| 148 | Dpa | P | C | I | abs | bhPhe | K(Peg11-Palm) | (D)Lys | C | abs |
| 149 | Dpa | Npc | C | I | (D)Lys | Phe(4-tBu) | K(Peg11-Palm) | (D)Lys | C | abs |
| 150 | Dpa | Npc | C | I | (D)Lys | Phe(4-tBu) | K(Peg11-Palm) | abs | C | (D)Lys |
| 182 | Dpa | Npc | C | I | (D)Lys | Phe(4-tBu) | (D)Lys | abs | C | Lys(Peg11-Palm) |
| 151 | Dpa | P | C | I | (D)Lys | bhPhe | K(Ahx-Palm) | Dap | N-Me-Cys | abs |
| 152 | Dpa | P | C | I | (D)Lys | bhPhe | K(Ac) | (D)Lys | C | abs |
| 153 | Dpa | P | C | I | (D)Lys-Peg11* | bhPhe | K(Peg11-Palm) | (D)Lys-Peg11* | C | abs |
| 154 | Dpa | P | C | I | (D)Lys | bhPhe | K(Peg11) | (D)Lys | C | abs |
| 155 | Dpa | P | C | I | (D)Lys | bhPhe | K(Peg11-Octane) | (D)Lys | C | abs |
| 156 | Dpa | P | C | I | (D)Lys | bhPhe | K(Peg11-Lauryl) | (D)Lys | C | abs |
| 157 | Dpa | P | C | I | (D)Lys | bhPhe | K(Peg11*) | (D)Lys | C | abs |
| 158 | Dpa | P | C | I | (D)Lys | bhPhe | K(IsoGlu-Palm) | (D)Lys | C | abs |
| 159 | Dpa | P | C | I | (D)Lys-Ac | bhPhe | K(Peg11-Palm) | (D)Lys-Ac | C | abs |
| 160 | Dpa | P | C | I | (D)Lys | bhPhe | K(Dap-Palm) | abs | C | abs |
| 161 | Dpa | P | C | I | (D)Lys | bhPhe | K(dDap-Palm) | abs | C | abs |
| 162 | Dpa | P | C | I | (D)Lys | bhPhe | Dap(Dap-Palm) | abs | C | abs |
| 163 | Dpa | P | C | I | (D)Lys | bhPhe | Dap(dDap-Palm) | abs | C | abs |
| 164 | Dpa | P | C | I | (D)Lys | bhPhe | Dap(dDap-Palm) | abs | C | abs |
| 165 | Dpa | P | C | I | (D)Lys | bhPhe | K(Ahx-Palm) | (D)Lys | C | abs |
| 166 | Dpa | P | C | I | (D)Lys-Peg11* | bhPhe | K(Ahx-Palm) | (D)Lys-Peg11* | C | abs |
| 167 | Dpa | (D)Pro | C | I | (D)Lys | F | K(Peg11-Palm) | (D)Lys | C | abs |
| 168 | bhPhe | (D)Pro | C | I | (D)Lys | F | K(Peg11-Palm) | (D)Lys | C | abs |
| 169 | Dpa** | P | C | I | (D)Lys | bhPhe | K(Peg11-Palm) | (D)Lys | C | abs |
| 170 | Dpa | P | C | I | (D)Lys | bhPhe | K(Peg11-Palm) | abs | C | (D)Lys |
| 171 | bhPhe | P | C | I | (D)Lys | F | K(Peg11-Palm) | abs | C | (D)Lys |

TABLE 2A-continued

| SEQ ID NO. | B1 | B2 | B3 | B4 | B5 | B6 | B7(L1Z) | J | Y1 | Y2 |
|---|---|---|---|---|---|---|---|---|---|---|
| 172 | bhPhe | Npc | C | I | (D)Lys | F | K(Peg11-Palm) | abs | C | (D)Lys |
| 173 | Dpa | Npc | C | I | (D)Lys | bhPhe | K(Peg11-Palm) | abs | C | (D)Lys |
| 174 | Dpa | P | C | I | dQ | bhPhe | K(Peg11-Palm) | (D)Lys | C | abs |
| 175 | Dpa | P | C | I | (D)Lys | bhPhe | K(Peg11-Palm) | (D)Lys_Ac | C | abs |
| 176 | bhPhe | dP | C | I | (D)Lys | bhPhe | K(Peg11-Palm) | abs | C | (D)Lys |

*PEG11-OMe, **Asp of "R¹-Asp-Thr-His- . . ." is D-aspartic acid instead of L-.
or a peptide dimer thereof; and wherein the peptide is cyclized via a disulfide bond between B3 and Y1.

In a particular embodiment, the peptide is according to formula (B-I):
R¹-Asp-Thr-His-B1-B2-B3-B4-B5(L1Z)-B6-B7-J-Y1-Y2-R² (B-I) (SEQ ID NO: 329) the peptide comprises any of the combinations of B1, B2, B3, B4, B5, B6, B7(L1Z), J, Y1 and Y2 set forth in a row of Table 2B, wherein R¹ is IVA, R² is NH₂, and "abs" indicates "absent."

TABLE 2B

| SEQ ID NO | B1 | B2 | B3 | B4 | B5(L1Z) | B6 | B7 | J | Y1 | Y2 |
|---|---|---|---|---|---|---|---|---|---|---|
| 201 | F | P | C | I | K(isoGlu-Palm) | F | E | PRSKG | C | abs |
| 202 | F | P | C | I | K(isoGlu-Palm) | F | E | PRSK | C | abs |
| 203 | F | P | C | I | K(isoGlu-Palm) | F | E | PRS | C | abs |
| 204 | F | P | C | I | K(isoGlu-Palm) | F | E | PR | C | abs |
| 205 | F | P | C | I | K(isoGlu-Palm) | F | E | P | C | abs |
| 206 | F | P | C | I | K(isoGlu-Palm) | F | E | abs | C | abs |
| 207 | F | P | C | I | K(isoGlu-Palm) | F | abs | abs | C | abs |
| 183 | F | P | C | I | K(isoGlu-Palm) | F | E | PK | C | abs |
| 184 | F | P | C | I | K(isoGlu-Palm) | F | E | (D)Lys | C | abs |
| 210 | F | P | C | I | K(isoGlu-Palm) | F | abs | abs | C | K |
| 211 | F | P | C | I | K(isoGlu-Palm) | F | abs | R | C | K |
| 212 | F | P | C | I | dk[isoGlu-Palm] | NMePhe | abs | G | C | abs |
| 185 | F | P | C | I | dk[isoGlu-Palm] | F | abs | G | C | abs |
| 214 | F | P | C | I | K(isoGlu-Palm) | bhPhe | abs | abs | C | abs |
| 215 | F | P | C | I | K(isoGlu-Palm) | aMePhe | abs | abs | C | abs |
| 216 | DPA | P | C | I | K(isoGlu-Palm) | aMePhe | abs | abs | C | abs |
| 217 | aMePhe | P | C | I | K(isoGlu-Palm) | aMePhe | abs | abs | C | abs |
| 218 | NMePhe | P | C | I | K(isoGlu-Palm) | aMePhe | abs | abs | C | abs |
| 219 | bhPhe | P | C | I | K(isoGlu-Palm) | aMePhe | abs | abs | C | abs |
| 220 | W | P | C | I | K(isoGlu-Palm) | aMePhe | abs | abs | C | abs |
| 221 | F | Npc | C | I | K(isoGlu-Palm) | aMePhe | abs | abs | C | abs |
| 222 | F | P | C | I | K(Peg11-Palm) | F | abs | abs | C | abs |
| 223 | F | P | C | I | K(isoGlu-Palm) | F | abs | abs | C | abs |
| 224 | F | P | C | I | (D)Lys(Peg11-Palm) | F | abs | K | C | abs |
| 225 | F | P | C | I | (D)Lys (Peg11-Palm) | F | abs | (D)Lys | C | abs |
| 226 | F | P | C | I | (D)Lys (Peg11-Palm) | F | (D)Arg | abs | C | Lys |
| 227 | F | P | C | I | K(isoGlu-Palm) | F | abs | K | C | abs |
| 228 | Dpa | P | C | I | K(Peg11-Palm) | bhPhe | abs | (D)Lys | C | abs |
| 229 | Dpa | P | C | I | Lys(Ahx-Palm) | bhPhe | abs | abs | C | abs |
| 230 | Dpa | P | C | I | Lys(Ahx-Palm) | bhPhe | abs | (D)Lys | C | abs | or a dimer thereof; and wherein the peptide is cyclized via a disulfide bond between B3 and Y1.

Particular embodiments of hepcidin analogues comprises a peptide according to the following illustrative structure:

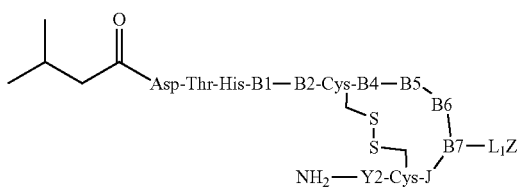

Formula Ia (SEQ ID NO: 330)

In certain embodiments of any of the peptide analogues having any of the various Formulae set forth herein, R¹ is selected from methyl, acetyl, formyl, benzoyl, trifluoroacetyl, isovaleryl, isobutyryl, octanyl, and conjugated amides of lauric acid, hexadecanoic acid, and γ-Glu-hexadecanoic acid.

In certain embodiments, the linker between the peptide and the half-life extension moiety is PEG11, Ahx, or any of the others described herein.

In certain embodiments, the half-life extension moiety is Palm.

In certain embodiment, the present invention includes a polypeptide comprising an amino acid sequence set forth in any of Tables 2A, 2B, 3A, 3B, and 4 (with or without the indicated linker moieties and half-life extension moieties), or having any amino acid sequence with at least 85%, at least 90%, at least 92%, at least 94%, or at least 95% identity to any of these amino acid sequences.

In certain embodiment, the present invention provides a cyclized form of any one of the hepcidin analogues disclosed herein or listed in any of Tables 2A, 2B, 3A, 3B, and 4, comprising a disulfide bond between the two Cys and/or Pen residues. The conjugated half-life extension moiety and the amino acid residue to which it is conjugated are indicated by parentheses and brackets, respectively. Compound ID numbers are indicated by "Compd ID," and reference compounds are indicated by "Ref. Compd."

TABLE 3A

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| Ref. Compd 1 | 1 | Isovaleric acid-DTHFPCIKF-Lys[PEG11-Palm]-PRSKGCK-NH$_2$ | 30 | <15 (1%) | <15 (6%) |
| Ref. Compd. 2 | 2 | Isovaleric acid-DTHFPCIKF-Lys[PEG11-Palm]-PRSK-[SAR]-CK-NH$_2$ | 13 | <15 (1%) | 26 |
| 3 | 3 | Isovaleric acid-DTHFPCIKF-Lys[PEG11-Palm]-PRSKGC-NH$_2$ | 16 | <15 (2%) | <15 (1%) |
| 4 | 4 | Isovaleric acid-DTHFPCIKF-Lys[PEG11-Palm]-PRSKC-NH$_2$ | 32 | <15 (5%) | <15 (10%) |
| 5 | 5 | Isovaleric acid-DTHFPCIKF-Lys[PEG11-Palm]-PRSC-NH$_2$ | 30 | <15 (3%) | <15 (11%) |
| 6 | 6 | Isovaleric acid-DTHFPCIKF-Lys[PEG11-Palm]-PRC-NH$_2$ | 17 | 21 | <15 (10%) |
| 7 | 7 | Isovaleric acid-DTHFPCIKF-Lys[PEG11-Palm]-PC-NH$_2$ | 10 | 29 | 22 |
| 8 | 8 | Isovaleric acid-DTHFPCIKF-Lys[PEG11-Palm]-C-NH$_2$ | 6 | >180 (75%) | 23 |
| 9 | 9 | Isovaleric acid-DTHFPCIKF-Lys[PEG11-Palm]-PCK-NH$_2$ | 15 | <15 min (2%) | 37 |
| 10 | 10 | Isovaleric acid-DTHFPCI-[(D)Lys]-[Phe]-Lys[PEG11-Palm]C-NH$_2$ | 5-60 | >1440 (88%) | <15 (3%) |
| 11 | 11 | Isovaleric acid-DTHFPCI-[Orn]-[Phe]-Lys[PEG11-Palm]-C-NH$_2$ | 4 | 174 | <15 (8%) |
| 12 | 12 | Isovaleric acid-DTHFPCI-[hSer]-[Phe]-Lys[PEG11-Palm]-C-NH$_2$ | 2 | 405 | <15 (10%) |
| 13 | 13 | Isovaleric acid-DTHFPCIQ-[Phe]-Lys[PEG11-Palm]-C-NH$_2$ | 4 | 251 | <15 (7%) |
| 14 | 14 | Isovaleric acid-DTHFPCI-[Lys(Ac)]-[Phe]-Lys[PEG11-Palm]-C-NH$_2$ | 3 | 200 | <15 (7%) |
| 15 | 15 | Isovaleric acid-DTHFPCI-[nLeu]-[Phe]-Lys[PEG11-Palm]-C-NH$_2$ | 2 | 455 | <15 (20%) |
| 16 | 16 | Isovaleric acid-DTHFPCIIF-Lys[PEG11-Palm]-C-NH$_2$ | N.D. | 641 | <15 (41%) |
| 17 | 17 | Isovaleric acid-DTHFPCIK-[NMe-Phe]-Lys[PEG11-Palm]-C-NH$_2$ | N.D. | — | — |
| 18 | 18 | Isovaleric acid-DTHFPCIK-[α-MePhe]-Lys[PEG11-Palm]-C-NH$_2$ | N.D. | — | — |
| 19 | 19 | Isovaleric acid-DTHFPCIK-[β-homoPhe]-Lys[PEG11-Palm]-C-NH$_2$ | N.D. | — | — |
| 20 | 20 | Isovaleric acid-DTHFPCIKW-Lys[PEG11-Palm]-C-NH$_2$ | 4 | — | — |
| 21 | 21 | Isovaleric acid-DTHFPCI-[(D)Lys]-[Phe]-Lys[PEG8-Palm]-C-NH$_2$ | 30 | — | — |
| 22 | 22 | Isovaleric acid-DTHFPCI-[(D)Lys]-[Phe]-Lys[PEG4-Palm]-C-NH$_2$ | 17 | — | — |
| 23 | 23 | Isovaleric acid-DTHFPCI-[(D)Lys]-[Phe]-Lys[PEG2-Palm]-C-NH$_2$ | 40 | — | — |
| 24 | 24 | Isovaleric acid-DTHFPCI-[(D)Lys]-[Phe]-Lys[PEG1-Palm]-C-NH$_2$ | 17 | — | — |
| 25 | 25 | Isovaleric acid-DTHFPCI-[(D)Lys]-[Phe]-Lys[Ahx-Palm]-C-NH$_2$ | 11 | — | — |
| 26 | 26 | Isovaleric acid-DTHFPCI-[(D)Lys]-[Phe]-Lys[PEG2-isoGlu-Palm]-C-NH$_2$ | 13 | — | — |
| 27 | 27 | Isovaleric acid-DTHFPCI-[(D)Lys]-[Phe]-Lys[isoGlu-Palm]-C-NH$_2$ | 35 | — | — |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 28 | 28 | Isovaleric acid-DTHFPCI-[(D)Lys]-[Phe]-Lys[isoGlu-PEG2-Palm]-C-NH$_2$ | 23 | — | — |
| 29 | 29 | Isovaleric acid-DTHFPCI-[(D)Lys]-[Phe]-Lys[PEG2-Ahx-Palm]-C-NH$_2$ | 30 | — | — |
| 30 | 30 | Isovaleric acid-DTHFPCI-[(D)Lys]-[Phe]-Lys[Palm]-C-NH$_2$ | 31 | — | — |
| 31 | 31 | Isovaleric acid-DTHFPCIKF-Lys[PEG11-Palm]-PRSK-[SAR]-[Pen]-K-NH$_2$ | — | — | — |
| 32 | 32 | Isovaleric acid-DTHFPCI-[(D)Lys]-F-Lys[PEG11-Palm]-[Pen]-NH$_2$ | — | — | — |
| 33 | 33 | Isovaleric acid-DTHF-[NPC]-CI-[(D)Lys]-F-Lys[PEG11-Palm]-C-NH$_2$ | — | — | — |
| 34 | 34 | Isovaleric acid-DTHF-[(D)NPC]-CI-[(D)Lys]-F-Lys[PEG11-Palm]-C-NH$_2$ | — | — | — |
| 35 | 35 | Isovaleric acid-DTHF-[(D)Pro]-CI-[(D)Lys]-F-Lys[PEG11-Palm]-C-NH$_2$ | — | — | — |
| 36 | 36 | Isovaleric acid-DTHF-[(d)bhPro]-CI-[(D)Lys]-F-Lys[PEG11-Palm]-C--NH$_2$ | — | — | — |
| 37 | 37 | Isovaleric acid-DTHF-[bhPro]-CI-[(D)Lys]-F-Lys[PEG11-Palm]-C-NH$_2$ | — | — | — |
| 38 | 38 | Isovaleric acid-DTH-[BIP]-PCI-[(D)Lys]-F-Lys[PEG11-Palm]-C-NH$_2$ | — | — | — |
| 39 | 39 | Isovaleric acid-DTH-[BIP]-[NPC]-CI-[(D)Lys]-F-Lys[PEG11-Palm]-C-NH$_2$ | — | — | — |
| 40 | 40 | Isovaleric acid-DTHF-[NPC]-CI-[(D)Lys]-F-Lys[PEG11-Palm]-C-NH$_2$ | — | — | — |
| 41 | 41 | Isovaleric acid-DTHFPCI-[(D)Lys]-F-Lys[(PEG11-Palm)]-PRSK-[SAR]-CK-NH$_2$ | — | — | — |
| 42 | 42 | Isovaleric acid-DTHFPCI-[(D)Lys]-F-Lys[(PEG11-Palm)]-PRSK-[SAR]-C-[(D)Lys]-NH$_2$ | — | — | — |
| 43 | 43 | Isovaleric acid-DTHFPCI-[(D)Lys]-F-Lys[(PEG11-Palm)]-PRS-[(D)Lys]-[SAR]-CK-NH$_2$ | — | — | — |
| 44 | 44 | Isovaleric acid-DTHFPCI-[(D)Lys]-F-Lys[(PEG11-Palm)]-PR-[(D)Ser]-K-[SAR]-CK-NH$_2$ | — | — | — |
| 45 | 45 | Isovaleric acid-DTHFPCI-[(D)Lys]-F-Lys[(PEG11-Palm)]-P-[(D)Arg]-SK-[SAR]-CK-NH$_2$ | — | — | — |
| 46 | 46 | Isovaleric acid-DTHFPCI-[(D)Lys]-F-Lys[(PEG11-Palm)]-PRTK-[SAR]-C-[(D)Lys]-NH$_2$ | — | — | — |
| 47 | 47 | Isovaleric acid-DTHFPCI-[(D)Lys]-F-Lys[(PEG11-Palm)]-PKTR-[SAR]-C-[(D)Lys]-NH$_2$ | — | — | — |
| 48 | 48 | Isovaleric acid-DTHFPCI-[(D)Lys]-F-Lys[(PEG11-Palm)]-P-[N-MeArg]-TK-[SAR]-C-[(D)Lys]-NH$_2$ | — | — | — |
| 49 | 49 | Isovaleric acid-DTHFPCI-[(D)Lys]-F-Lys[(PEG11-Palm)]-P-[(D)Arg]-TK-[SAR]-C-[(D)Lys]-NH$_2$ | — | — | — |
| 50 | 50 | Isovaleric acid-DTHFPCI-[(D)Lys]-F-Lys[(PEG11-Palm)]-PDTH-[SAR]-C-[(D)Lys]-NH$_2$ | — | — | — |
| 51 | 51 | Isovaleric acid-DTHFPCI-[(D)Lys]-F-Lys[(PEG11-Palm)]-P-[(D)Arg]-T-[N-MeLys]-[SAR]-C-[(D)Lys]-NH$_2$ | — | — | — |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 52 | 52 | Isovaleric acid-DTHFPCI-[(D)Lys]-F-Lys[(PEG11-Palm)]-[NPC]-[N-MeArg]-TH-[SAR]-C-[(D)Lys]-NH$_2$ | — | — | — |
| 53 | 53 | Isovaleric acid-DTHFPCIKF-Lys[PEG11-Palm]-PRSK-[SAR]-[Pen]-K-NH$_2$ | — | — | — |
| 54 | 54 | Isovaleric acid-DTHFPCI-[(D)Lys]-F-Lys[PEG11-Palm]-[Pen]-NH$_2$ | — | — | — |
| 55 | 55 | kc-{SAR}-ksrp-k [PEG11-Palm]-fkicpfhtdl-NH$_2$ (Retroinverso of 659 (D)Leu for IVA) | — | — | — |
| 56 | 56 | Isovaleric acid-DTHF-[NPC]-CI-[(D)Lys]-F-Lys[PEG11-Palm]-C-NH$_2$ | — | — | — |
| 57 | 57 | Isovaleric acid-DTHF-[(D)NPC]-CI-[(D)Lys]-F-Lys[PEG11-Palm]-C-NH$_2$ | — | — | — |
| 58 | 58 | Isovaleric acid-DTHF-[(D)Pro]-CI-[(D)Lys]-F-Lys[PEG11-Palm]-C-NH$_2$ | — | — | — |
| 59 | 59 | Isovaleric acid-DTHF-[(D)bhPro]-CI-[(D)Lys]-F-Lys[PEG11-Palm]-C-NH$_2$ | — | — | — |
| 60 | 60 | Isovaleric acid-DTHF-[bhPro]-CI-[(D)Lys]-F-Lys[PEG11-Palm]-C-NH$_2$ | — | — | — |
| 62 | 62 | Isovaleric acid-DTH-[BIP]-PCI-[(D)Lys]-F-Lys[PEG11-Palm]-C-NH$_2$ | — | — | — |
| 63 | 63 | Isovaleric acid-DTH-[BIP]-[NPC]-CI-[(D)Lys]-F-Lys[PEG11-Palm]-C-NH$_2$ | — | — | — |
| 65 | 65 | Isovaleric acid-DTHFPCI-[(D)Lys]-F-C-Lys[PEG11-Palm]-NH$_2$ | — | — | — |
| 66 | 66 | Isovaleric acid-DTHF-[NPC]-CI-[(D)Lys]-F-Lys[PEG11-Palm]-C-NH$_2$ | — | — | — |
| 67 | 67 | Isovaleric acid-DTHFPC(SH)I-[Lys]-[Phe]-Lys[PEG11-Palm]-Pro-C(SH)-NH$_2$ | 13 | — | — |
| 68 | 68 | Isovaleric acid-DTHFPC(SH)I-[(D)Lys]-[Phe]-Lys[PEG11-Palm]-C(SH)-NH$_2$ | 12 | — | — |
| 69 | 69 | Isovaleric acid-DTHFPC(SH)I-[Lys]-[Phe]-Lys[PEG11-Palm]-C(SH)-NH$_2$ | 9 | — | — |
| 70 | 70 | Isovaleric acid-DTHFPCI-[(D)Lys]-[Phe]-Lys[PEG11-Palm]-PC-NH$_2$ | 5 | — | — |
| 71 | 71 | Isovaleric acid-DTHFPCI-[(D)Lys]-[Phe]-Lys[PEG11-Palm]-PRC-NH$_2$ | 8 | — | — |
| 72 | 72 | Isovaleric acid-DTHFPCI-[(D)Lys]-[Phe]-Lys[PEG11-Palm]-PRSC-NH$_2$ | 12 | — | — |
| 73 | 73 | Isovaleric acid-DTHFPCI-[(D)Lys]-[Phe]-Lys[PEG11-Palm]-PRSKC-NH$_2$ | 11 | — | — |
| 74 | 74 | Isovaleric acid-DTHFPCI-[(D)Lys]-[Phe]-Lys[PEG11-Palm]-PRSKSarC-NH$_2$ | 9 | — | — |
| 75 | 75 | Isovaleric acid-DTHFPCI-[(D)Lys]-[Phe]-Lys[PEG11-Palm]-PRSKCK-NH$_2$ | 14 | — | — |
| 76 | 76 | Isovaleric acid-DTHFPCI-[(D)Lys]-[Phe]-Lys[PEG11-Palm]-PPRSCK-NH$_2$ | 16 | — | — |
| 77 | 77 | Isovaleric acid-DTHFPCI-[(D)Lys]-[Phe]-Lys[PEG11-Palm]-PRCK-NH$_2$ | 15 | — | — |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 78 | 78 | Isovaleric acid-DTHFPCI-[(D)Lys]-[Phe]-Lys[PEG11-Palm]-CK-NH$_2$ | 17 | — | — |
| 79 | 79 | Isovaleric acid-DTHFPCI-[(D)Lys]-[Phe]-Lys[PEG11-Palm]-RC-NH$_2$ | 22 | — | — |
| 80 | 80 | Isovaleric acid-DTHFPCI-[(D)Lys]-[Phe]-Lys[PEG11-Palm]-KC-NH$_2$ | 14 | <5 | 7 |
| 81 | 81 | Isovaleric acid-DTHFPCI-[(D)Lys]-[Phe]-Lys[PEG11-Palm]-[(D)Arg]-C-NH$_2$ | 9 | — | — |
| 82 | 82 | Isovaleric acid-DTHFPCI-[(D)Lys]-[Phe]-Lys[PEG11-Palm]-[(D)Lys]-C-NH$_2$ | 13 | 122 | 2 |
| 83 | 83 | Isovaleric acid-DTHFPCI-[(D)Lys]-[Phe]-Lys[PEG11-Palm]-Lys-C-[(D)Lys]-NH$_2$ | 40 | — | — |
| 84 | 84 | Isovaleric acid-DTHFPCI-[(D)Lys]-[Phe]-Lys[PEG11-Palm]-HC-[(D)His]-NH$_2$ | 16 | — | — |
| 85 | 85 | Isovaleric acid-DTHFPCI-[(D)Lys]-[Phe]-Lys[PEG11-Palm]-RC-[(D)Arg]-NH$_2$ | 27 | — | — |
| 86 | 86 | Isovaleric acid-DTHFPCI-[(D)Lys]-[Phe]-Lys-[Ahx-Palm]-KC-NH$_2$ | 9 | — | — |
| 87 | 87 | Isovaleric acid-DTHFPCI-[(D)Lys]-[Phe]-Lys[PEG2-Palm]-KC-NH$_2$ | 15 | — | — |
| 88 | 88 | Isovaleric acid-DTHFPCI-[(D)Lys]-[Phe]-Lys[PEG2-PEG2-Palm]-KC-NH$_2$ | 13 | — | — |
| 89 | 89 | Isovaleric acid-DTHFPCI-[(D)Lys]-[Phe]-Lys[PEG2-PEG2-C18 acid]-KC-NH$_2$ | 27 | — | — |
| 90 | 90 | Isovaleric acid-DTHFPCI-[(D)Lys]-[Phe]-Lys[PEG2-PEG2-Ahx-Palm]-KC-NH$_2$ | 11 | — | — |
| 91 | 91 | Isovaleric acid-DTHFPCI-[(D)Lys]-[Phe]-Lys[PEG4-Palm]-KC-NH$_2$ | 14 | — | — |
| 92 | 92 | Isovaleric acid-DTHFPCI-[(D)Lys]-[Phe]-Lys[PEG4-Ahx-Palm]-KC-NH$_2$ | 21 | — | — |
| 93 | 93 | Isovaleric acid-DTHFPCI-[(D)Lys]-[Phe]-Lys[PEG4-PEG4-Palm]-KC-NH$_2$ | 18 | — | — |
| 94 | 94 | Isovaleric acid-DTHFPCI-[(D)Lys]-[Phe]-Lys[PEG4-isoGlu-Palm]-KC-NH$_2$ | 9 | — | — |
| 95 | 95 | Isovaleric acid-DTHFPCI-[(D)Lys]-[Phe]-Lys[PEG8-Palm]-KC-NH$_2$ | 28 | — | — |
| 96 | 96 | Isovaleric acid-DTHFPCI-[(D)Lys]-[Phe]-Lys-[Behenic acid]-KC-NH$_2$ | 30 | — | — |
| 97 | 97 | Isovaleric acid-DTHFPCI-[(D)Lys]-F-Lys[PEG11-Palm]-K-[(D)Cys]-NH$_2$ | 41 | <15 min (1%) | <15 min (11%) |
| 98 | 98 | Isovaleric acid-DTHFPCI-[(D)Lys]-F-Lys[PEG11-Palm]-K-[Pen]-NH$_2$ | 40 | <15 min (1%) | 30 |
| 99 | 99 | Isovaleric acid-DTHFPCI-[(D)Lys]-F-Lys[PEG11-Palm]-Dap-[Cys]-NH$_2$ | 21 | 68 | <15 min (2%) |
| 100 | 100 | Isovaleric acid-DTHFPCI-[(D)Lys]-[Dpa]-Lys[PEG11-Palm]-K-[Cys]-NH$_2$ | 16 | <5 | <5 |
| 101 | 101 | Isovaleric acid-DTHFPCI-[(D)Lys]-[b-homoPhe]-Lys[PEG11-Palm]-K-[Cys]-NH$_2$ | 24 | <5 | <15% (2%) |
| 102 | 102 | Isovaleric acid-DTHFPCI-[(D)Lys]-[Nal]-Lys[PEG11-Palm]-K-[Cys]-NH$_2$ | 17 | <5 | <15% (4%) |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 103 | 103 | Isovaleric acid-DTHFPCI-[(D)Lys]-[bhomoPhe]-Lys[PEG11-Palm]-K-[Cys]-NH$_2$ | 20 | <5 | <15% (20%) |
| 104 | 104 | Isovaleric acid-D-T-H-[Dpa]-P-C-I-[(D)Lys]-F-Lys[PEG11-Palm]-K-[Cys]-NH$_2$ | 27 | <5 | 145 |
| 105 | 105 | Isovaleric acid-D-T-H-[Dpa]-P-C-I-[(D)Lys]-[b-homoPhe]-Lys[PEG11-Palm]-[(D)Lys]-[Cys]-NH$_2$ | 31 | 99 | 833 |
| 106 | 106 | Isovaleric acid-DTHFPCI-F-Lys[PEG11-Palm]-K-[Cys]-NH$_2$ | 40 | 319 | <5 |
| 107 | 107 | Isovaleric acid-DTHFPCI-[(D)Lys]-F-(D)Lys[PEG11-Palm]-[(D)Lys]-[Cys]-NH$_2$ | 60 | 73 | <5 |
| 109 | 109 | Isovaleric acid-DTH-[Dpa]-[Npc]-C-I-[(D)Lys]-F-[Lys(Peg11-Palm)]-K-C-NH$_2$ | 2 | <5 | 188 |
| 110 | 110 | Isovaleric acid-DTH-[Dpa]-[Npc]-C-I-[(D)Lys]-[Phe(4-tBu)]-[Lys(Peg11-Palm)]-K-C-NH$_2$ | 3 | <5 | 820 |
| 111 | 111 | Isovaleric acid-DTH-[Dpa]-[Npc]-C-I-[(D)Lys]-[Phe[4-(2-aminoethoxy)]-[Lys(Peg11-Palm)]-K-C-NH$_2$ | >3000 | <5 | 1111 |
| 112 | 112 | Isovaleric acid-DTH-[Dpa]-[Npc]-C-I-[(D)Lys]-[2-Nal]-[Lys(Peg11-Palm)]-K-C-NH$_2$ | 4 | <5 | 48 |
| 113 | 113 | Isovaleric acid-DTH-[Dpa]-[Npc]-C-I-[(D)Lys]-[Phe(4-COOH)]-[Lys(Peg11-Palm)]-K-C-NH$_2$ | — | <5 | 311 |
| 114 | 114 | Isovaleric acid-DTH-F-PCI-[(D)Lys]-F-[Lys(Peg11-Palm)]-K-[a-MeCys]-NH$_2$ | 3 | <5 | 2 |
| 115 | 115 | Isovaleric acid-DTHFP-[a-MeCys]-I-[(D)Lys]-F-[Lys(Peg11-Palm)]-K-[a-MeCys]-NH$_2$ | 4 | <5 | 7 |
| 116 | 116 | Isovaleric acid-DTHFP-[a-MeCys]-I-[(D)Lys]-F-[Lys(Peg11-Palm)]-K-C-NH$_2$ | 11 | <5 | 11 |
| 117 | 117 | Isovaleric acid-DTH-[Dpa]-[Npc]-C-I-[(D)Lys]-F-[Lys(Peg11-Palm)]-[(D)Lys]-C-NH$_2$ | 2 | 52 | 1072 |
| 118 | 118 | Isovaleric acid-DTH-F-[Npc]-C-I-[(D)Lys]-F-[Lys(Peg11-Palm)]-[(D)Lys]-C-NH$_2$ | 6 | 63 | 1513 |
| 119 | 119 | Isovaleric acid-DTH-[Dpa]-[β-hPro]-C-I-[(D)Lys]-F-[Lys(Peg11-Palm)]-[(D)Lys]-C-NH$_2$ | — | 107 | 482 |
| 120 | 120 | Isovaleric acid-DTH-[Phe(4-COOH)-PCI-[(D)Lys]-F-[Lys(Peg11-Palm)]-[(D)Lys]-C-NH$_2$ | >1000 | 582 | 18 |
| 121 | 121 | Isovaleric acid-DTH-[b-hPhe]-PCI-[(D)Lys]-F-[Lys(Peg11-Palm)]-[(D)Lys]-C-NH$_2$ | 9 | 95 | >1440 (94%) |
| 122 | 122 | Isovaleric acid-DTH-[Dpa]-PCI-[(D)Lys]-[b-hPhe]-[Lys(Peg11-Palm)]-[(D)Lys]-C-NH$_2$ | 5 | 49 | 794 |
| 125 | 125 | Isovaleric acid-DTH-[Dpa]-[Npc]-C-I-[(D)Lys]-[a-MePhe]-[Lys(Peg11-Palm)]-K-C-NH$_2$ | — | 17 | 840 |
| 126 | 126 | Isovaleric acid-DTH-[Dpa]-[Npc]-C-I-[(D)Lys]-[Phe(4-CN)]-[Lys(Peg11-Palm)]-K-C-NH$_2$ | — | <5 | 128 |
| 127 | 127 | Isovaleric acid-DTH-[Dpa]-[Npc]-C-I-[(D)Lys]-[Phe(3,4-diF)-[Lys(Peg11-Palm)]-K-C-NH$_2$ | 3 | <5 | 26 |
| 128 | 128 | Isovaleric acid-DTH-[a-MePhe]-PCI-[(D)Lys]-F-[Lys(Peg11-Palm)]-[(D)Lys]-C-NH$_2$ | 204 | 583 | >1440 (62%) |
| 129 | 129 | Isovaleric acid-DTH-[Phe[4-(2-aminoethoxy)]-PCI-[(D)Lys]-F-[Lys(Peg11-Palm)]-[(D)Lys]-C-NH$_2$ | >3000 | Fluctuate | >1440 (81%) |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 130 | 130 | Isovaleric acid-DIH-[Dpa]-PCI-[(D)Lys]-F-[Lys(Peg11-Palm)]-[(D)Lys]-C-NH$_2$ | 169 | 14 | 157 |
| 131 | 131 | Isovaleric acid-DTH-[Dpa]-PCI-[(D)Lys]-[Dpa]-[Lys(Peg11-Palm)]-[(D)Lys]-C-NH$_2$ | 14 | 14 | 614 |
| 132 | 132 | Isovaleric acid-DTH-[Dpa]-PCI-[(D)Lys]-F-[Lys(Peg11-Palm)]-[(D)Lys]-Pen-NH$_2$ | 4 | 97 | 934 |
| 133 | 133 | Isovaleric acid-DTH-[Dpa]-PCI-[(D)Lys]-F-[Lys(Peg11-Palm)]-K-[N-Me-Cys]-NH$_2$ | 13.5 | 47 | 543 |
| 134 | 134 | Isovaleric acid-DTH-[Dpa]-PCI-[(D)Lys]-F-[Lys(Peg11-Palm)]-[(D)Lys]-[N-Me-Cys]-NH$_2$ | 22.5 | 44 | 701 |
| 135 | 135 | Isovaleric acid-DTH-[Dpa]-PCI-[(D)Lys]-F-[Lys(Peg11-Palm)]-C-NH$_2$ | 22 | 61 >1440 (78%) | 364 |
| 136 | 136 | Isovaleric acid-DTH-[Dpa]-PCI-[(D)Lys]-F-[Lys(Peg11-Palm)]-[Orn]-C-NH$_2$ | 27 | 53 | 330 |
| 137 | 137 | Isovaleric acid-DTH-[Dpa]-PCI-[(D)Lys]-F-[Lys(Peg11-Palm)]-[Dab]-C-NH$_2$ | 23 | 40 | 525 |
| 138 | 138 | Isovaleric acid-DTH-[Dpa]-PCI-[(D)Lys]-F-[Lys(Peg11-Palm)]-[b-hLys]-C-NH$_2$ | 20.5 | 51 | 569 |
| 139 | 139 | Isovaleric acid-DTH-[Dpa]-PCI-[(D)Lys]-F-[Lys(Peg11-Palm)]-[(D)Lys]-C-NH$_2$ | 19.5 | 67 | 707 |
| 140 | 140 | Isovaleric acid-DTH-[Dpa]-PCI-[(D)Lys]-F-[Lys(Peg11-Palm)]-[Dap]-[Pen]-NH$_2$ | 51 | | 364 |
| 141 | 141 | Isovaleric acid-DTH-[Dpa]-P-[Hcy]-I-[(D)Lys]-F-[Lys(Peg11-Palm)]-[Dap]-C-NH$_2$ | 26.5 | | 896 |
| 142 | 142 | Isovaleric acid-DTH-[Dpa]-P-[Hcy]-I-[(D)Lys]-F-[Lys(Peg11-Palm)]-[Dap]-[Hcy]-NH$_2$ | 12 | 69 | 395 |
| 143 | 143 | Isovaleric acid-DTH-[Dpa]-PCI-[(D)Lys]-F-[Lys(Peg11-Palm)]-[Dap]-[Hcy]-NH$_2$ | 18 | 46 | 377 |
| 144 | 144 | Isovaleric acid-DTHFPCI-[(D)Lys]-F-[Lys(Peg11-Palm)]-CK-NH$_2$ | 32 | | 13 |
| 145 | 145 | Isovaleric acid-DTH-[Dpa]-PCI-[bAla]-[b-hPhe]-[Lys(Peg11-Palm)]-[(D)Lys]-C-NH$_2$ | 18 | | >1440 (59%) |
| 146 | 146 | Isovaleric acid-DTH-[Dpa]-PCI-[(D)Ala]-[b-hPhe]-[Lys(Peg11-Palm)]-[(D)Lys]-C-NH$_2$ | 11 | 1391 | 726 |
| 147 | 147 | Isovaleric acid-DTH-[Dpa]-PCII-[b-hPhe]-[Lys(Peg11-Palm)]-[(D)Lys]-C-NH$_2$ | 24 | 505 | >1440 (49%) |
| 148 | 148 | Isovaleric acid-DTH-[Dpa]-PCI-[b-hPhe]-[Lys(Peg11-Palm)]-[(D)Lys]-C-NH$_2$ | 12 | 635 | 1097 |
| 149 | 149 | Isovaleric acid-DTH-[Dpa]-[Npc]-CI-[(D)Lys]-[Phe(4-tButyl)]-[Lys(Peg11-Palm)]-[(D)Lys]-C-NH$_2$ | 17 | >1440 (54%) | >1440 (77%) |
| 150 | 150 | Isovaleric acid-DTH-[Dpa]-[Npc]-CI-[(D)Lys]-[Phe(4-tButyl)]-[Lys(Peg11-Palm)]-C-[(D)Lys]-NH$_2$ | 22 | >1440 (68%) | >1440 (51%) |
| 151 | 151 | Isovaleric acid-DTH-[Dpa]-PCI-[(D)Lys]-[b-hPhe]-[Lys(Ahx-Palm)]-[Dap]-[N-Me-Cys]-NH$_2$ | 28.5 | fluctuate | 1343 |
| 152 | 152 | Isovaleric acid-DTH-[Dpa]-PCI-[(D)Lys]-[b-hPhe]-[Lys(Ac)]-[(D)Lys]-C-NH$_2$ | 146.5 | >1440 (97%) | >1440 (87%) |
| 153 | 153 | Isovaleric acid-DTH-[Dpa]-PCI-[(D)Lys-Peg11*]-[b-hPhe]-[Lys(Peg11-Palm)]-[(D)Lys-Peg11*]-C-NH$_2$ | 19 | | >1440 (64%) |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 154 | 154 | Isovaleric acid-DTH-[Dpa]-PCI-[(D)Lys]-[b-hPhe]-[Lys-Peg11]-[(D)Lys]-C-NH$_2$ | 404 | | >1440 (108%) |
| 155 | 155 | Isovaleric acid-DTH-[Dpa]-PCI-[(D)Lys]-[b-hPhe]-[Lys(Peg11-Octane)]-[(D)Lys]-C-NH$_2$ | 279 | >1440 | >1440 (102%) |
| 156 | 156 | Isovaleric acid-DTH-[Dpa]-PCI-[(D)Lys]-[b-hPhe]-[Lys(Peg11-Lauryl)]-[(D)Lys]-C-NH$_2$ | 125 | >1440 | >1440 (84%) |
| 157 | 157 | Isovaleric acid-DTH-[Dpa]-PCI-[(D)Lys]-[b-hPhe]-[Lys-Peg11*]-[(D)Lys]-C-NH$_2$ | 347 | >1440 | >1440 (99%) |
| 158 | 158 | Isovaleric acid-DTH-[Dpa]-PCI-[(D)Lys]-[b-hPhe]-[Lys(IsoGlu-Palm)]-[(D)Lys]-C-NH$_2$ | 6 | >1440 | 840 |
| 159 | 159 | Isovaleric acid-DTH-[Dpa]-PCI-[(D)Lys-Ac]-[b-hPhe]-[Lys(Peg11-Palm)]-[(D)Lys-Ac]-C-NH$_2$ | 4 | >1440 | 244 |
| 160 | 160 | Isovaleric acid-DTH-[Dpa]-PCI-[(D)Lys]-[b-hPhe]-[Lys(Dap-Palm)]-C-NH$_2$ | 4 | | 410 |
| 161 | 161 | Isovaleric acid-DTH-[Dpa]-PCI-[(D)Lys]-[b-hPhe]-[Lys(dDap-Palm)]-C-NH$_2$ | 10 | | 810 |
| 162 | 162 | Isovaleric acid-DTH-[Dpa]-PCI-[(D)Lys]-[b-hPhe]-[Dap(Dap-Palm)]-C-NH$_2$ | 8 | | 1153 |
| 163 | 163 | Isovaleric acid-DTH-[Dpa]-PCI-[(D)Lys]-[b-hPhe]-[Dap(dDap-Palm)]-C-NH$_2$ | 7 | | 642 |
| 164 | 164 | Isovaleric acid-DTH-[Dpa]-PCI-[(D)Lys]-[b-hPhe]-[Dap(dDap-Palm)]-C-NH$_2$ | 6 | | 798 |
| 165 | 165 | Isovaleric acid-DTH-[Dpa]-PCI-[(D)Lys]-[b-hPhe]-[Lys(Ahx-Palm)]-[(D)Lys]-C-NH$_2$ | 6 | >1440 | 822 |
| 166 | 166 | Isovaleric acid-DTH-[Dpa]-PCI-[(D)Lys-Peg11*]-[b-hPhe]-[Lys(Ahx-Palm)]-[(D)Lys-Peg11*]-C-NH$_2$ | 6 | >1440 | >1440 (92%) |
| 167 | 167 | Isovaleric Acid-D-T-H-[Dpa]-(D)Pro-C-I-(D)Lys-F-[Lys_Peg11_Palm]-(D)Lys-C-NH$_2$ | 81 | 936 | >1440 |
| 168 | 168 | Isovaleric_Acid-D-T-H-bhPhe-(D)Pro-C-I-(D)Lys-F-[Lys_Peg11_Palm]-(D)Lys-C-NH$_2$ | 54 | >1440 | >1440 |
| 169 | 169 | Isovaleric_Acid-dD-T-H-[Dpa]-P-C-I-(D)Lys-bhPhe-[Lys_Peg11_Palm]-(D)Lys-C-NH$_2$ | 12 | 1182 | >1440 |
| 170 | 170 | Isovaleric_Acid-D-T-H-[Dpa]-P-C-I-(D)Lys-bhPhe-[Lys_Peg11_Palm]-C-(D)Lys-NH$_2$ | 10 | >1440 | 335 |
| 171 | 171 | Isovaleric Acid-D-T-H-bhPhe-P-C-I-(D)Lys-F-[Lys_Peg11_Palm]-C-(D)Lys-NH$_2$ | 47 | >1440 | >1440 |
| 172 | 172 | Isovaleric_Acid-D-T-H-bhPhe-Npc-C-I-(D)Lys-F-[Lys_Peg11_Palm]-C-(D)Lys-NH$_2$ | 39 | >1440 | >1440 |
| 173 | 173 | Isovaleric_Acid-D-T-H-[Dpa]-Npc-C-I-(D)Lys-bhPhe-[Lys_Peg11_Palm]-C-(D)Lys-NH$_2$ | | >1440 | 1314 |
| 174 | 174 | Isovaleric_Acid-D-T-H-[Dpa]-P-C-I-(D)Gln-bhPhe-[Lys_Peg11_Palm]-(D)Lys-C-NH$_2$ | | >1440 | 511 |
| 175 | 175 | Isovaleric_Acid-D-T-H-[Dpa]-P-C-I-(D)Lys-bhPhe-[Lys_Peg11_Palm]-dLys_Ac-C-NH$_2$ | 5 | >1440 | 570 |
| 176 | 176 | Isovaleric_Acid-D-T-H-bhPhe-(D)Pro-C-I-(D)Lys-bhPhe-[Lys_Peg11_Palm]-C-(D)Lys-NH$_2$ | | | |
| 177 | 177 | Isovaleric_Acid-D-T-H--[Dpa]-P-C-I-(D)Lys-bhPhe-[Lys_Ahx_Palm]-R-C-NH$_2$ | | | |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 178 | 178 | Isovaleric_Acid-D-T-H--[Dpa]-P-C-I-(D)Lys-[N-MePhe]-[Lys_Ahx_Palm]-(D)Lys-C-NH$_2$ | | | |
| 179 | 179 | Isovaleric_Acid-D-T-H--[Dpa]-P-[N-MeCys]-I-(D)Lys-bhPhe-[Lys_Ahx_Palm]-(D)Lys-C-NH$_2$ | | | |
| 180 | 180 | Isovaleric_Acid-D-T-H-[N-MePhe-P-C-I-(D)Lys-bhPhe-[Lys_Ahx_Palm]-(D)Lys-C-NH$_2$ | | | |
| 181 | 181 | Isovaleric_Acid-D-T-H--[Dpa]-P-C-I-(D)Lys-bhPhe-[Lys_Ahx_Palm]-(D)Lys-[N-MeCys]-NH$_2$ | | | |

*PEG11-OMe

TABLE 3B

Illustrative Monomer Hepcidin Analogues

| Compd ID | SEQ ID No. | Peptide | FPN IC50 (nM) | SIF Half life (min) | SGF Half life (min) |
|---|---|---|---|---|---|
| 201 | 201 | Isovaleric acid-DTHFPCI-Lys[isoGlu-Palm]-FEPRSKGC-NH$_2$ | 9 | 3 | <15 (4%) |
| 202 | 202 | Isovaleric acid-DTHFPCI-Lys[isoGlu-Palm]-FEPRSKC-NH$_2$ | 11 | 3 | <15 (6%) |
| 203 | 203 | Isovaleric acid-DTHFPCI-Lys[isoGlu-Palm]-FEPRSC-NH$_2$ | 15 | 6 | <15 (7%) |
| 204 | 204 | Isovaleric acid-DTHFPCI-Lys[isoGlu-Palm]-FEPRC-NH$_2$ | 14 | 7 | <15 (12%) |
| 205 | 205 | Isovaleric acid-DTHFPCI-Lys[isoGlu-Palm]-FEPC-NH$_2$ | 64 | 36 | 45 |
| 206 | 206 | Isovaleric acid-DTHFPCI-Lys[isoGlu-Palm]-FEC-NH$_2$ | 267 | 66 | 36 |
| 207 | 207 | Isovaleric acid-DTHFPCI-Lys[isoGlu-Palm]-FC-NH$_2$ | 64 | >300 (86%) | 101 |
| 208 | 183 | Isovaleric acid-DTHFPCI-Lys[isoGlu-Palm]-FEPCK-NH$_2$ | 22 | 16 | 216 |
| 209 | 184 | Isovaleric acid-DTHFPCI-Lys[isoGlu-Palm]-FEPC-[(D)Lys]-NH$_2$ | 47 | 24 | 174 |
| 210 | 210 | Isovaleric acid-DTHFPCI-Lys[isoGlu-Palm]-FCK-NH$_2$ | 60 | 109 | |
| 211 | 211 | Isovaleric acid-DTHFPCI-Lys[isoGlu-Palm]-FRCK-NH$_2$ | 24 | <15 (1%) | |
| 212 | 212 | Isovaleric acid-DTHFPCI-[(D)Lys[isoGlu-Palm]]-[NMe-Phe]-GC-NH$_2$ | 403 | >180 (96%) | |
| 213 | 185 | Isovaleric acid-DTHFPCI-[(D)Lys[isoGlu-Palm]]-FC-NH$_2$ | 1751 | varible | |
| 214 | 214 | Isovaleric acid-DTHFPCI-Lys[isoGlu-Palm]-[β-homoPhe]-C-NH$_2$ | 36 | >180 (70%) | 110 |
| 215 | 215 | Isovaleric acid-DTHFPCI-Lys[isoGlu-Palm]-[α-MePhe]-C-NH$_2$ | 96 | >180 (85%) | <15 (5%) |
| 216 | 216 | Isovaleric acid-DTH-[DIP]-PCI-Lys[isoGlu-Palm]-[α-MePhe]-C-NH$_2$ | 16 | >180 (87%) | 208 |
| 217 | 217 | Isovaleric acid-DTH-[α-MePhe]-PCI-Lys[isoGlu-Palm]-[α-MePhe]-C-NH$_2$ | >3000 | >180 (81%) | 269 |
| 218 | 218 | Isovaleric acid-DTH-[N-MethylPhe]-PCI-Lys[isoGlu-Palm]-[α-MePhe]-C-NH$_2$ | >3000 | >180 (80%) | >300 (79%) |
| 219 | 219 | Isovaleric acid-DTH-[β-homoPhe]-PCI-Lys[isoGlu-Palm]-[α-MePhe]-C-NH$_2$ | 182 | >180 (86%) | >300 (126%) |
| 220 | 220 | Isovaleric acid-DTHWPCI-Lys[isoGlu-Palm]-[α-MePhe]-C-NH$_2$ | 871 | >180 (82%) | 187 |
| 221 | 221 | Isovaleric acid-DTHF-[NPC]-CI-Lys[isoGlu-Palm]-[α-MePhe]-C-NH$_2$ | 79 | >180 (66%) | 189 |
| 222 | 222 | Isovaleric acid-DTHFPCI-Lys[Peg11-Palm]-FC-NH$_2$ | 4 | <5 | <15 |
| 223 | 223 | Isovaleric acid-DTHFPCI-Lys[isoGlu-Palm]-FC-NH$_2$ | 47 | | |
| 224 | 224 | Isovaleric acid-DTHFPCI-(D)Lys[Peg11-Palm]-F-Lys-C-NH$_2$ | 33 | 7 | <15 |
| 225 | 225 | Isovaleric acid-DTHFPCI-(D)Lys[Peg11-Palm]-F-(D)Lys-C-NH$_2$ | 26 | 339 | <15 |

TABLE 3B-continued

Illustrative Monomer Hepcidin Analogues

| Compd ID | SEQ ID No. | Peptide | FPN IC50 (nM) | SIF Half life (min) | SGF Half life (min) |
|---|---|---|---|---|---|
| 226 | 226 | Isovaleric acid-DTHFPCI-(D)Lys[Peg11-Palm]-F-(D)Arg-C-NH$_2$ | 23 | 15 | <15 |
| 227 | 227 | Isovaleric acid-DTHFPCI-Lys[isoGlu-Palm]-F-Lys-C-NH$_2$ | 114 | <5 | 8 |
| 228 | 228 | Isovaleric acid-DTH-Dpa-PCI-Lys[Peg11-Palm]-bhPhe-(D)Lys-C-NH$_2$ | | 462 | 1194 |
| 229 | 229 | Isovaleric acid-DTH-Dpa-PCI-Lys[Ahx-Palm]-bhPhe-C-NH$_2$ | | | |
| 230 | 230 | Isovaleric acid-DTH-Dpa-PCI-Lys[Ahx-Palm]-bhPhe-(D)Lys-C-NH$_2$ | 6 | | >1440 |

In certain embodiment, the present invention includes a hepcidin analogue having a structure or comprising an amino acid sequence set forth below:

(SEQ ID NO: 186)
Isovaleric acid-DTHFPCI-Lys[isoGlu-Palm]-FEPRSKGCK-NH$_2$;

(SEQ ID NO: 201)
Isovaleric acid-DTHFPCI-Lys[isoGlu-Palm]-FEPRSKGC-NH$_2$;

(SEQ ID NO: 202)
Isovaleric acid-DTHFPCI-Lys[isoGlu-Palm]-FEPRSKC-NH$_2$;

(SEQ ID NO: 203)
Isovaleric acid-DTHFPCI-Lys[isoGlu-Palm]-FEPRSC-NH$_2$;

(SEQ ID NO: 204)
Isovaleric acid-DTHFPCI-Lys[isoGlu-Palm]-FEPRC-NH$_2$;

(SEQ ID NO: 205)
Isovaleric acid-DTHFPCI-Lys[isoGlu-Palm]-FEPC-NH$_2$;

(SEQ ID NO: 206)
Isovaleric acid-DTHFPCI-Lys[isoGlu-Palm]-FEC-NH$_2$;

(SEQ ID NO: 207)
Isovaleric acid-DTHFPCI-Lys[isoGlu-Palm]-FC-NH$_2$;

(SEQ ID NO: 208)
Isovaleric acid-DTHFPCI-Lys[isoGlu-Palm]-FEPCK-NH$_2$;

(SEQ ID NO: 209)
Isovaleric acid-DTHFPCI-Lys[isoGlu-Palm]-FEPC-[(D)Lys]-NH$_2$;

(SEQ ID NO: 210)
Isovaleric acid-DTHFPCI-Lys[isoGlu-Palm]-FCK-NH$_2$;

(SEQ ID NO: 211)
Isovaleric acid-DTHFPCI-Lys[isoGlu-Palm]-FRCK-NH$_2$;

(SEQ ID NO: 212)
Isovaleric acid-DTHFPCI-[(D)Lys[isoGlu-Palm]]-[NMe-Phe]-GC-NH$_2$;

(SEQ ID NO: 213)
Isovaleric acid-DTHFPCI-[(D)Lys[isoGlu-Palm]]-FC-NH$_2$;

(SEQ ID NO: 214)
Isovaleric acid-DTHFPCI-Lys[isoGlu-Palm]-[b-homoPhe]-C-NH$_2$;

(SEQ ID NO: 215)
Isovaleric acid-DTHFPCI-Lys[isoGlu-Palm]-[a-MePhe]-C-NH$_2$;

(SEQ ID NO: 216)
Isovaleric acid-DTH-[Dpa]-PCI-Lys[isoGlu-Palm]-[a-MePhe]-C-NH$_2$;

(SEQ ID NO: 217)
Isovaleric acid-DTH-[a-MePhe]-PCI-Lys[isoGlu-Palm]-[a-MePhe]-C-NH$_2$;

(SEQ ID NO: 218)
Isovaleric acid-DTH-[N-MethylPhe]-PCI-Lys[isoGlu-Palm]-[a-MePhe]-C-NH$_2$;

(SEQ ID NO: 219)
Isovaleric acid-DTH-[b-homoPhe]-PCI-Lys[isoGlu-Palm]-[a-MePhe]-C-NH$_2$;

(SEQ ID NO: 220)
Isovaleric acid-DTHWPCI-Lys[isoGlu-Palm]-[a-MePhe]-C-NH$_2$;
or (SEQ ID NO: 221)
Isovaleric acid-DTHF-[NPC]-CI-Lys[isoGlu-Palm-[a-MePhe]-C-NH$_2$;

and wherein the peptide is cyclized via a disulfide bond between two Cys.

In certain embodiment, the present invention includes a hepcidin analogue having a structure or comprising an amino acid sequence set forth below:

(SEQ ID NO: 222)
Isovaleric acid-DTHFPCI-Lys[Peg11-Palm]-

FC-NH$_2$;

(SEQ ID NO: 223)
Isovaleric acid-DTHFPCI-Lys[isoGlu-Palm1]-

FC-NH$_2$;

(SEQ ID NO: 224)
Isovaleric acid-DTHFPCI-(D)Lys[Peg11-Palm]-

F-Lys-C-NH$_2$;

(SEQ ID NO: 225)
Isovaleric acid-DTHFPCI-(D)Lys[Peg11-Palm]-

F-(D)Lys-C-NH$_2$;

(SEQ ID NO: 226)
Isovaleric acid-DTHFPCI-(D)Lys[Peg11-Palm]-

F-(D)Arg-C-NH$_2$;

(SEQ ID NO: 227)
Isovaleric acid-DTHFPCI-Lys[isoGlu-Palm]-F-

Lys-C-NH$_2$;

(SEQ ID NO: 228)
Isovaleric acid-DTH-Dpa-PCI-Lys[Peg11-Palm]- bhPhe-(D)Lys-C-NH$_2$;

(SEQ ID NO: 229)
Isovaleric acid-DTH-Dpa-PCI-Lys[Ahx-Palm]- bhPhe-C-NH$_2$;
or (SEQ ID NO: 230)
Isovaleric acid-DTH-Dpa-PCI-Lys[Ahx-Palm]- bhPhe-(D)Lys-C-NH$_2$;

and wherein the peptide is cyclized via a disulfide bond between two Cys.

In certain embodiment, the present invention provides a peptide or a peptide dimer thereof, wherein the peptide comprises or consists of any one of the peptides disclosed herein or listed in any of Tables 2A, 2B, 3A, 3B and 4. In one embodiment, the peptide comprises a disulfide bond between the two Cys, Cys and N-MeCys, or Cys and Pen residues; or wherein the compound ID is 3-107, 109-122, 125-181 or 201-230. In a particular embodiment, the peptide is any one of peptides wherein the FPN activity is <100 nM. In another particular embodiment, the peptide is any one of peptides wherein the FPN activity is <50 nM. In another particular embodiment, the peptide is any one of peptides wherein the FPN activity is <20 nM. In another particular embodiment, the peptide is any one of peptides wherein the FPN activity is <10 nM. In more particular embodiment, the peptide is any one of peptides wherein the FPN activity is <5 nM.

In certain embodiment, the peptide is selected from a group of peptides listed in Table 2A, 2B, 3A, 3B, and 4, and wherein the SIF half life is >24 h.

In certain embodiment, the peptide is (SEQ ID NO: 10)
Isovaleric acid-DTHFPCI-[(D)Lys]-[Phe]-

Lys[PEG11-Palm]C-NH$_2$;

(SEQ ID NO: 135)
Isovaleric acid-DTH[Dpa]-PCI-[(D)Lys]-

F-[Lys(Peg11-Palm)]-C-NH$_2$;

(SEQ ID NO: 149)
Isovaleric acid-DTH-[Dpa]-[Npc]-CI[(D)Lys]-

[Phe(4-tButyl)-[Lys(Peg11-Palm)]-[(D)Lys]-

C-NH$_2$;

(SEQ ID NO: 150)
Isovaleric acid-DTH-[Dpa]-[Npc]-CI-[(D)Lys]-

[Phe(4-tButyl)-[Lys(Peg11-Palm)]-C-

[(D)Lys]-NH$_2$;

(SEQ ID NO: 152)
Isovaleric acid-DTH-[Dpa]-PCI-[(D)Lys]-[b- hPhe]-[Lys(Ac)]-[(D)Lys]-C-NH$_2$;

(SEQ ID NO: 155)
Isovaleric acid-DTH-[Dpa]-PCI-[(D)Lys]-[b- hPhe]-[Lys(Peg11-Octane)]-[(D)Lys]-C-NH$_2$;

(SEQ ID NO: 156)
Isovaleric acid-DTH-[Dpa]-PCI-[(D)Lys]-[b- hPhe]-[Lys(Peg11-Lauryl)]-[(D)Lys]-C-NH$_2$;

(SEQ ID NO: 157)
Isovaleric acid-DTH-[Dpa]-PCI-[(D)Lys]-[b- hPhe]-[Lys-Peg11*]-[(D)Lys]-C-NH$_2$;

(SEQ ID NO: 158)
Isovaleric acid-DTH-[Dpa]-PCI-[(D)Lys]-[b- hPhe]-[Lys(IsoGlu-Palm)]-[(D)Lys]-C-NH$_2$;

(SEQ ID NO: 159)
Isovaleric acid-DTH-[Dpa]-PCI-[(D)Lys-Ac]-

[b-hPhe]-[Lys(Peg11-Palm)]-[(D)Lys-Ac]-C-NH$_2$;

(SEQ ID NO: 165)
Isovaleric acid-DTH-[Dpa]-PCI-[(D)Lys]-[b- hPhe]-Lys(Ahx-Palm)]-[(D)Lys]-C-NH$_2$;

(SEQ ID NO: 166)
Isovaleric acid-DTH-[Dpa]-PCI-[(D)Lys-

Peg11*]-[b-hPhe]-[Lys(Ahx-Palm)]-

[(D)Lys-Peg11*]-C-NH$_2$;

(SEQ ID NO: 168)
Isovaleric_Acid-D-T-H-bhPhe-(D)Pro-C-I-(D)Lys-

F-[Lys_Peg11_Palm]-(D)Lys-C-NH$_2$;

(SEQ ID NO: 170)
Isovaleric_Acid-D-T-H-[Dpa]-P-C-I-(D)LysbhPhe-[Lys_Peg11_Palm]-C-(D)Lys-NH$_2$;

(SEQ ID NO: 171)
Isovaleric_Acid-D-T-H-bhPhe-P-C-I-(D)Lys-F-

[Lys_Peg11_Palm]-C-(D)Lys-NH$_2$;

(SEQ ID NO: 172)
Isovaleric_Acid-D-T-H-bhPhe-Npc-C-I-(D)Lys-F-

[Lys_Peg11_Palm]-C-(D)Lys-NH$_2$;

-continued

```
                                      (SEQ ID NO: 173)
Isovaleric_Acid-D-T-H-[Dpa]-Npc-C-I-(D)LysbhPhe-[Lys_Peg11_Palm]-C-(D)Lys-NH₂;

(SEQ ID NO: 174)
Isovaleric_Acid-D-T-H-[Dpa]-P-C-I-(D)GlnbhPhe-[Lys_Peg11_Palm]-(D)Lys-C-NH₂;
or (SEQ ID NO: 175)
Isovaleric_Acid-D-T-H-[Dpa]-P-C-I-(D)LysbhPhe-[Lys_Peg11_Palm]-dLys_Ac-C-NH₂;
``` and wherein the peptide is cyclized via a disulfide bond between two Cys.

In certain embodiment, the peptide is selected from a group of peptides listed in Table 3A and wherein the SGF half life is >24 h.

In certain embodiment, the peptide is:

```
                                      (SEQ ID NO: 121)
Isovaleric acid-DTHb-[B-hPhe]-PCI-(D)Lys-F-

Lys(Peg11-Palm)]-[(D)Lys]-C-NH₂;

(SEQ ID NO: 128)
Isovaleric acid-DTH-[a-MePhe]-PCI-[(D)Lys]-F-

Lys(Peg11-Palm)]-[(D)Lys]-C-NH₂;

(SEQ ID NO: 129)
Isovaleric acid-DTH-[Phe[4-(2-aminoethoxy)]-

PCI-[(D)Lys]-F-[Lys(Peg11-Palm)]-[(D)Lys]-
C-NH₂;

(SEQ ID NO: 145)
Isovaleric acid-DTH-[Dpa]-PCI-[BALa]-[b- hPhe]-[Lys(Peg11-Palm)]-[(D)Lys]-C-NH₂;

(SEQ ID NO: 147)
Isovaleric acid-DTH-[Dpa]-PCII-[b-hPhe]-

Lys(Peg11-Palm)]-[(D)Lys]-C-NH₂;

(SEQ ID NO: 149)
Isovaleric acid-DTH-[Dpa]-[Npc]-CI-

[(D)Lys]-[Phe(4-tButyl)]-[Lys(Peg11-Palm)]

[(D)Lys]-C-NH₂;

(SEQ ID NO: 150)
Isovaleric acid-DTH-[Dpa]-[Npc]-CI-

[(D)Lys1-[Phe(4-tButyl)]-[Lys(Peg11-Palm)]-C-

[(D)Lys]-NH₂ ;

(SEQ ID NO: 152)
Isovaleric acid-DTH-[Dpa]-PCI-

[(D)Lys-[b-hPhe]-Lys(Ac)]-[(D)Lys]-C-NH₂;

(SEQ ID NO: 153)
Isovaleric acid-DTH-[Dpa]-PCI-

[(D)Lys-Peg11*]-[b-hPhe]-

Lys(Peg11-Palm)]-[(D)Lys-Peg11*]C-NH₂;

(SEQ ID NO: 154)
Isovaleric acid-DTH-[Dpa]-PCI-[(D)Lys]-[b- hPhe]-[Lys-Peg11]-[(D)Lys]-C-NH₂;

(SEQ ID NO: 155)
Isovaleric acid-DTH-[Dpa]-PCI-[(D)Lys]-[b- hPhe-[Lys-(Peg11-Octane)]-[(D)Lys]-C-NH₂;

(SEQ ID NO: 156)
Isovaleric acid-DTH-[Dpa]-PCI-[(D)Lys]-

[b-hPhe]-Lys(Peg11-Lauryl)]-[(D)Lys]-C-NH₂;

(SEQ ID NO: 157)
Isovaleric acid-DTH-[Dpa]-PCI-[(D)Lys]-

[b-hPhe]-[Lys-Peg11*]-[(D)Lys]-C-NH₂;

(SEQ ID NO: 166)
Isovaleric acid-DTH-[Dpa]-PCI-[(D)Lys-

Peg11*]-[b-hPhe]-[Lys(Ahx-Palm)]-

[(D)Lys-Peg11*]-C-NH₂;

(SEQ ID NO: 167)
Isovaleric_Acid-D-T-H-[Dpa]-(D)Pro-C-I-

(D)Lys-F-[Lys_Peg11_Palm]-(D)Lys-C-NH₂;

(SEQ ID NO:168)
Isovaleric_Acid-D-T-H-bhPhe-(D)Pro-C-I-

(D)Lys-F-[Lys_Peg11_Palm]-(D)Lys-C-NH₂;

(SEQ ID NO: 169)
Isovaleric_Acid-D-T-H-[Dpa]-PCI- (D)Lys-bhPhe-[Lys_Peg11_Palm]-(D)Lys-C-NH₂;

(SEQ ID NO: 171)
Isovaleric_Acid-D-T-H-bhPhe-P-C-I-(D)Lys-F-

[Lys_Peg11_Palm]-C-(D)Lys-NH₂;
 or (SEQ ID NO: 172)
Isovaleric_Acid-D-T-H-bhPhe-Npc-C-I-(D)Lys- F-[Lys_Peg11_Palm]-C-(D)Lys-NH₂;
``` and wherein the peptide is cyclized via a disulfide bond between two Cys.

In certain embodiment, the peptide is selected from a group of peptides listed in Table 3A and wherein the SIF half life is >10 h.

In certain embodiment, the peptide is:

```
                                      (SEQ ID NO: 16)
Isovaleric acid-DTHFPCIIF-Lys[PEG11-Palm]-

C-NH₂;

(SEQ ID NO: 146)
Isovaleric acid-DTH-[Dpa]-PCI-[(D)Ala]-

[b-hPhe]-[Lys(Peg11-Palm)]-[(D)Lys]-C-NH₂;

(SEQ ID NO: 148)
Isovaleric acid-DTH-[Dpa]-PCI-[b-hPhe]-[Lys (Peg11-Palm)]-[(D)Lys]-C-NH₂;
```

(SEQ ID NO: 167)
Isovaleric acid-D-T-H-[Dpa]-(D)Pro-C-I-

(D)Lys-F-[Lys_Peg11_Palm]-(D)Lys-C-NH$_2$;
or (SEQ ID NO: 169)
Isovaleric acid-dD-T-H-[Dpa]-P-C-I-(D)LysbhPhe-[Lys_Peg11_Palm]-(D)Lys-C-NH$_2$;

and wherein the peptide is cyclized via a disulfide bond between two Cys.

In certain embodiment, the peptide is selected from a group of peptides listed in Table 3A and wherein the SGF half life is >10 h.

In certain embodiment, the peptide is:

(SEQ ID NO: 105)
Isovaleric acid-D-T-H-[Dpa]-P-C-I-[(D)Lys]-

[b-homoPhe]-Lys[PEG11-Palm]-[(D)Lvs]-[Cys]-NH$_2$;

(SEQ ID NO: 110)
Isovaleric acid-DTH-[Dpa]-[Npc]-C-I-[(D)Lys]-

[Phe(4-tBu)]-[Lys(Peg11-Palm)]-K-C-NH$_2$;

(SEQ ID NO: 111)
Isovaleric acid-DTH-[Dpa]-[Npc]-C-I-[(D)Lys]-

[Phe[4-(2-aminoethoxy)]-[Lys(Peg11-Palm)]-

K-C-NH$_2$;

(SEQ ID NO: 117)
Isovaleric acid-DTH-[Dpa]-[Npc]-C-I-[(D)Lys]-

F-[Lys(Peg11-Palm)]-[(D)Lys]-C-NH$_2$;

(SEQ ID NO: 118)
Isovaleric acid-DTH-F-[Npc]-C-I-[(D)Lys]-F-

[Lys(Peg11-Palm)]-[(D)Lys]-C-NH$_2$;

(SEQ ID NO: 122)
Isovaleric acid-DTH-[Dpa]-PCI-[(D)Lys]-

[b-hPhe]-[Lys(Peg11-Palm)]-[(D)Lys]-C-NH$_2$;

(SEQ ID NO: 125)
Isovaleric acid-DTH-[Dpa]-[Npc]-C-I-[(D)Lys]-

[a-MePhe]-[Lys(Peg11-Palm)]-K-C-NH$_2$;

(SEQ ID NO: 131)
Isovaleric acid-DTH-[Dpa]-PCI-[(D)Lys]-[Dpa]-

[Lys(Peg11-Palm)]-[(D)Lys]-C-NH$_2$;

(SEQ ID NO: 132)
Isovaleric acid-DTH-[Dpa]-PCI-[(D)Lys]-F-

[Lys(Peg11-Palm)]-[(D)Lys]-Pen-NH$_2$;

(SEQ ID NO: 134)
Isovaleric acid-DTH-[Dpa]-PCI-[(D)Lys]-F-

[Lys(Peg11-Palm)]-[(D)Lys]-[N-Me-Cys]-NH$_2$;

(SEQ ID NO: 139)
Isovaleric acid-DTH-[Dpa]-PCI-[(D)Lys]-F-

[Lys(Peg11-Palm)]-[(D)Lys]-C-NH$_2$;

(SEQ ID NO: 141)
Isovaleric acid-DTH-[Dpa]-P-[Hcy]-I-[(D)Lys]-F-

[Lys(Peg11-Palm)]-|]Dap|-C-NH$_2$;

(SEQ ID NO: 146)
Isovaleric acid-DTH-[Dpa]-PCI-[(D)Ala]-[b-hPhe]-

[Lys(Peg11-Palm)]-[(D)Lys]-C-NH$_2$;

(SEQ ID NO: 148)
Isovaleric acid-DTH-[Dpa]-PCI-[b-hPhe]-

[Lys(Peg11-Palm)]-[(D)Lys]-C-NH$_2$;

(SEQ ID NO: 151)
Isovaleric acid-DTH-[Dpa]-PCI-[(D)Lys]-

[b-hPhe]-[Lys(Ahx-Palm)]-[Dap]-[N-Me-Cys]-NH$_2$;

(SEQ ID NO: 158)
Isovaleric acid-DTH-[Dpa]-PCI-[(D)Lys]-

[b-hPhe]-[Lys(IsoGlu-Palm)]-[(D)Lys]-C-NH$_2$;

(SEQ ID NO: 161)
Isovaleric acid-DTH-[Dpa]-PCI-[(D)Lys]-

[b-hPhe]-[Lys(dDap-Palm)]-C-NH$_2$;

(SEQ ID NO: 162)
Isovaleric acid-DTH-[Dpa]-PCI-[(D)Lys]-

[b-hPhe]-[Dap(Dap-Palm)]-C-NH$_2$;

(SEQ ID NO: 163)
Isovaleric acid-DTH-[Dpa]-PCI-[(D)Lys]-

[b-hPhe]-[Dap(dDap-Palm)]-C-NH$_2$;

(SEQ ID NO: 164)
Isovaleric acid-DTH-[Dpa]-PCI-[(D)Lys]-

[b-hPhe]-[Dap(dDap-Palm)]-C-NH$_2$;

(SEQ ID NO: 165)
Isovaleric acid-DTH-[Dpa]-PCI-[(D)Lys]-

[b-hPhe]-[Lys(Ahx-Palm)]-[(D)Lys]-C-NH$_2$;
or (SEQ ID NO: 173)
lsovaleric_Acid-D-T-H-[Dpa]-Npc-C-I-

(D)Lys-bhPhe-[Lys_Peg11_Palm|-C-(D)Lys-NH$_2$;

and wherein the peptide is cyclized via a disulfide bond between two Cys.

In certain embodiment, the peptide is selected from a group of peptides listed in Table 3A and wherein the SGF half life and SIF half life is >24 h.

In certain embodiment, the peptide is:

(SEQ ID NO: 149)
Isovaleric acid-DTH-[Dpa]-[Npc]-CI-[(D)Lys]-

[Phe(4-tButyl)]-[Lys(Peg11-Palm)]-[(D)Lys]-

C-NH$_2$;

(SEQ ID NO: 150)
Isovaleric acid-DTH-[Dpa]-[Npc]-CI-[(D)Lys]-

[Phe(4-tButyl)]-[Lys(Peg11-Palm)]-C-

[(D)Lys]-NH$_2$;

(SEQ ID NO: 152)
Isovaleric acid-DTH-[Dpa]-PCI-[(D)Lys]-[b-hPhe]-[Lys(Ac)]-[(D)Lys]-C-NH$_2$;

(SEQ ID NO: 155)
Isovaleric acid-DTH-[Dpa]-PCI-[(D)Lys]-[b-hPhe]-Lys(Peg11-Octane)]-[(D)Lys]-C-NH$_2$;

(SEQ ID NO: 156)
Isovaleric acid-DTH-[Dpa]-PCI-[(D)Lys]-[b-hPhe]-[Lys(Peg11-Lauryl)]-[(D)Lys]-C-NH$_2$;

(SEQ ID NO: 157)
Isovaleric acid-DTH-[Dpa]-PCI-[(D)Lys]-[b-hPhe]-[Lys-Peg11*]-[(D)Lys]-C-NH$_2$;

(SEQ ID NO: 166)
Isovaleric acid-DTH-[Dpa]-PCI-[(D)Lys-Peg11*]-[b-hPhe]-[Lys(Ahx-Palm)]-[(D)Lys-Peg11*]-C-NH$_2$;

(SEQ ID NO: 168)
Isovaleric_Acid-D-T-H-bhPhe-(D)Pro-C-I-(D)Lys-F-[Lys_Peg11_Palm]-(D)Lys-C-NH$_2$;

(SEQ ID NO: 171)
Isovaleric_Acid-D-T-H-bhPhe-P-C-I-(D)Lys-F-[Lys_Peg11_Palm]-C-(D)Lys-NH$_2$;

(SEQ ID NO: 172)
Isovaleric_Acid-D-T-H-bhPhe-Npc-C-I-(D)Lys-F-[Lys_Peg11_Palm]-C-(D)Lys-NH$_2$;
or (SEQ ID NO: 173)
Isovaleric_Acid-D-T-H-[Dpa]-Npc-C-I-(D)Lys-bhPhe-[Lys_Peg11_Palm]-C-(D)Lys-NH$_2$;

and wherein the peptide is cyclized via a disulfide bond between two Cys.

In certain embodiments, the peptide is:

(SEQ ID NO: 114)
Isovaleric acid-DTHFPCI-[(D)Lys]-[Phe]-Lys[PEG11-Palm]-K-[a-MeCys]-NH$_2$;

(SEQ ID NO: 187)
Isovaleric acid-DTHFPCI-[(D)Lys]-[Phe]-Lys[PEG11-Palm]-[Orn]-C-NH$_2$;

(SEQ ID NO: 188)
Isovaleric acid-DTHFPCI-[(D)Lys]-[Phe]-Lys[PEG11-Palm]-[Dab]-C-NH$_2$;

(SEQ ID NO: 189)
Isovaleric acid-DTHFPCI-[(D)Lys]-[Phe]-Lys[PEG11-Palm]-[homoLys]-C-NH$_2$;

(SEQ ID NO: 190)
Isovaleric acid-DTHFPCI-[(D)Lys]-[Dab]-Lys[PEG11-Palm]-KC-NH$_2$;

(SEQ ID NO: 191)
Isovaleric acid-DTH[Dpa]PCI-[(D)Lys]-[bhPhe]-Lys[PEG11-Palm]-KC-NH$_2$;

(SEQ ID NO: 192)
Isovaleric acid-DTHFPCI-[(D)Lys]-[Phe]-[(D)Lys]-[PEG11-Palm]-KC-NH$_2$;
or (SEQ ID NO: 107)
Isovaleric acid-DTHFPCI-[(D)Lys]-[Phe]-[(D)Lys]-[PEG11-Palm]-[(D)Lys]-C-NH$_2$;

and wherein the peptide is cyclized via a disulfide bond between two Cys.

In certain embodiments, the peptide is:

(SEQ ID NO: 167)
Isoyaleric_Acid-D-T-H[Dpa]-(D)Pro-C-I-(D)Lys-F-[Lys_Peg11_Palm]-(D)Lys-C-NH$_2$;

(SEQ ID NO: 168)
Isovaleric_Acid-D-T-H-bhPhe-(D)Pro-C-I-(D)Lys-F-[Lys_Peg11_Palm]-(D)Lys-C-NH$_2$;

(SEQ ID NO: 169)
Isoyaleric_Acid-dD-T-H[Dpa]-P-C-I-(D)Lys-bhPhe-[Lys_Peg11_Palm]-(D)Lys-C-NH$_2$;

(SEQ ID NO: 170)
Isovaleric_Acid-D-T-[Dpa]-P-C-I-(D)Lys-bhPhe-[Lys_Peg11_Palm]-C-(D)Lys-NH$_2$;

(SEQ ID NO: 171)
Isovaleric_Acid-D-T-H-bhPhe-P-C-I-(D)Lys-F-[Lys_Peg11_Palm]-C-(D)Lys-NH$_2$;

SEQ ID NO: 172)
Isovaleric_Acid-D-T-H-bhPhe-Npc-C-I-(D)Lys-F-[Lys_Peg11_Palm]-C-(D)Lys-NH$_2$;

(SEQ ID NO: 173)
Isovaleric_Acid-D-T-H-[Dpa]-Npc-C-I-(D)Lys-bhPhe-[Lys_Peg11_Palm]-C-(D)Lys-NH$_2$;

(SEQ ID NO: 174)
Isoyaleric_Acid-D-T-H-[Dpa]-P-C-I-(D)Gln-bhPhe-[Lys_Peg11_Palm]-(D)Lys-C-NH$_2$;

(SEQ ID NO: 175)
Isovaleric_Acid-D-T-H-[Dpa]-P-C-I-(D)Lys-bhPhe-[Lys_Peg11_Palm]-dLys_Ac-C-NH$_2$;
or (SEQ ID NO: 176)
Isoyaleric_Acid-D-T-H-bhPhe-(D)Pro-C-I-(D)Lys-bhPhe-[Lys_Peg11_Pal]-C-(D)Lys-NH$_2$;

and wherein the peptide is cyclized via a disulfide bond between two Cys.

In certain embodiment, the present invention includes a peptide having a structure or comprising an amino acid sequence set forth below:

(SEQ ID NO: 145)
Isovaleric acid-DTH-[Dpa]-PCI[b-Ala]-
[b-hPhe]-[Lys(Peg11-Palm)]-[(D)Lys]-C-NH$_2$;

(SEQ ID NO: 150)
Isovaleric acid-DTH-[Dpa]-[Npc]-CI-[(D)Lys]-
[Phe(4-tButyl)-[Lys(Peg11-Palm)]-C-[(D)Lys]-
NH$_2$;

(SEQ ID NO: 160)
Isovaleric acid-DTH-[Dpa]-PCI-[(D)Lys]-[b-
hPhe]-Lys(Dap-Palm)]-C-NH$_2$;

(SEQ ID NO: 161)
Isovaleric acid-DTH-[Dpa]-PCI-[(D)Lys]-[b-
hPhe]-Lys(dDap-Palm)]-C-NH$_2$;

(SEQ ID NO: 162)
Isovaleric acid-DTH-[Dpa]-PCI-[(D)Lys]-[b-
hPhe]-[Dap(Dap-Palm)]-C-NH$_2$;

(SEQ ID NO: 163)
Isovaleric acid-DTH-[Dpa]-PCI-[(D)Lys]-[b-
hPhe]-[Dap(dDap-Palm)]-C-NH$_2$;

(SEQ ID NO: 164)
Isovaleric acid-DTH-[Dpa]-PCI-[(D)Lys]-[b-
hPhe]-[Dap(dDap-Palm)]-C-NH$_2$;

(SEQ ID NO: 165)
Isovaleric acid-DTH-[Dpa]-PCI-[(D)Lys]-[b-
hPhe]-Lys(Ahx-Palm)]-[(D)Lys]-C-NH$_2$;
or (SEQ ID NO: 168)
Isovaleric_Acid-D-T-H-bhPhe-(D)Pro-C-I-
(D)Lys-F-[Lys_Peg11_Palm]-(D)Lys-C-NH$_2$;

and wherein the peptide is cyclized via a disulfide bond between two Cys.

In certain embodiment, the present invention includes a peptide having a structure or comprising an amino acid sequence set forth below:

(SEQ ID NO:169)
Isovaleric_Acid-dD-T-H-[Dpa]-P-C-I-(D)Lys-bhPhe-
[Lys_Peg11_Palm]-(D)Lys-C-NH$_2$;

SEQ ID NO: 173)
Isovaleric_Acid-D-T-H-[Dpa]-Npc-C-I-(D)Lys-bhPhe-
[Lys_Peg11_Palm]-C-(D)Lys-NH$_2$;
or (SEQ ID NO: 166)
Isovaleric acid-DTH-[Dpa]-PCI-[(D)Lys-Peg11*]-[b-
hPhe]-[Lys(Ahx-Palm)]-[(D)Lys-Peg11*]-C-NH$_2$;

and wherein the peptide is cyclized via a disulfide bond between two Cys.

In certain embodiment, the present invention includes a peptide having a structure or comprising an amino acid sequence set forth below:

(SEQ ID NO: 25)
Isovaleric acid-DTHFPCI-[(D)Lys]-[Phe]-Lys[Ahx-
Palm]-C-NH$_2$;

(SEQ ID NO: 70)
Isovaleric acid-DTHFPCI-[(D)Lys]-[Phe]-Lys[PEG11-
Palm]-PC-NH$_2$;

(SEQ ID NO: 71)
Isovaleric acid-DTHFPCI-[(D)Lys]-[Phe]-Lys[PEG11-
Palm]-PRC-NH$_2$;

(SEQ ID NO: 72)
Isovaleric acid-DTHFPCI-[(D)Lys]-[Phe]-Lys[PEG11-
Palm]-PRSC-NH$_2$;

(SEQ ID NO: 73)
Isovaleric acid-DTHFPCI-[(D)Lys]-[Phe]-Lys[PEG11-
Palm]-PRSKC-NH$_2$;

(SEQ ID NO: 74)
Isovaleric acid-DTHFPCI-[(D)Lys]-[Phe]-Lys[PEG11-
Palm]-PRSKSarC-NH$_2$;
or (SEQ ID NO: 75)
Isovaleric acid-DTHFPCI-[(D)Lys]-[Phe]-Lys[PEG11-
Palm]-PRSKCK-NH$_2$;

and wherein the peptide is cyclized via a disulfide bond between two Cys.

In certain embodiment, the present invention includes a peptide having a structure or comprising an amino acid sequence set forth below:

(SEQ ID NO: 80)
Isovaleric acid-DTHFPCI-[(D)Lys]-[Phe]-Lys[PEG11-
Palm]-KC-NH$_2$;

(SEQ ID NO: 105)
Isovaleric acid-D-T-H-[Dpa]-P-C-I-[(D)Lys]-[b-
homoPhe-Lys[PEG11-Palm]-[(D)Lys]-[Cys]-NH$_2$;

(SEQ ID NO: 145)
Isovaleric acid-DTH-[Dpa]-PCI-[bAla]-[b-hPhe]-[Lys
(Peg11-Palm)]-[(D)Lys]-C-NH$_2$;

(SEQ ID NO: 146)
Isovaleric acid-DTH-[Dpa]-PCI-[(D)Ala]-[b-hPhe]-
[Lys(Peg11-Palm)]-[(D)Lys]-C-NH$_2$;

(SEQ ID NO: 147)
Isovaleric acid-DTH-[Dpa]-PCII-[b-hPhe]-[Lys(Peg11-
Palm)]-[(D)Lys]-C-NH$_2$;

(SEQ ID NO: 148)
Isovaleric acid-DTH-[Dpa]-PCI-[b-hPhe]-[Lys(Peg11-
Palm)]-[(D)Lys]-C-NH$_2$;

```
                                          (SEQ ID NO: 149)
Isovaleric acid-DTH-[Dpa]-[Npc]-CI-[(D)Lys]-[Phe(4- tButyl)]-[Lys(Peg11-Palm)]-[(D)Lys]-C-NH2;

(SEQ ID NO: 150)
Isovaleric acid-DTH-[Dpa]-[Npc]-CI-[(D)Lys]-[Phe(4- tButyl)]-[Lys(Peg11-Palm)]-C-[(D)Lys]-NH2;

(SEQ ID NO: 162)
Isovaleric acid-DTH-[Dpa]-PCI-[(D)Lys]-[b-hPhe]-

[Dap(Dap-Palm)]-C-NH2;

(SEQ ID NO: 163)
Isovaleric acid-DTH-[Dpa]-PCI-[(D)Lys]-[b-hPhe]-

[Dap(dDap-Palm)]-C-NH2;

(SEQ ID NO: 164)
Isovaleric acid-DTH-[Dpa]-PCI-[(D)Lys]-[b-hPhe]-

[Dap(dDap-Palm)]-C-NH2;

(SEQ ID NO: 165)
Isovaleric acid-DTH-[Dpa]-PCI-[(D)Lys]-[b-hPhe]-

[Lys(Ahx-Palm)]-[(D)Lys]-C-NH2;

(SEQ ID NO: 166)
Isovaleric acid-DTH-[Dpa]-PCI-[(D)Lys-Peg11*]-[b- hPhe]-[Lys(Ahx-Palm)]-[(D)Lys-Peg11*]-C-NH2;

(SEQ ID NO: 167)
Isovaleric_Acid-D-T-H-[Dpa]-(D)Pro-C-I-(D)Lys-F-

[Lys_Peg11_Palm]-(D)Lys-C-NH2;

(SEQ ID NO: 168)
Isovaleric_Acid-D-T-H-bhPhe-(D)Pro-C-I-(D)Lys-F-

[Lys_Peg11_Palm]-(D)Lys-C-NH2;

(SEQ ID NO: 169)
Isovaleric_Acid-dD-T-H-[Dpa]-P-C-I-(D)Lys-bhPhe-

[Lys_Peg11_Palm]-(D)Lys-C-NH2;

(SEQ ID NO: 170)
Isovaleric_Acid-D-T-H-[Dpa]-P-C-I-(D)Lys-bhPhe-

[Lys_Peg11_Palm]-C-(D)Lys-NH2;

(SEQ ID NO: 171)
Isovaleric_Acid-D-T-H-bhPhe-P-C-I-(D)Lys-F-[Lys_

Peg11_Palm]-C-(D)Lys-NH2;

(SEQ ID NO: 172)
Isovaleric_Acid-D-T-H-bhPhe-Npc-C-I-(D)Lys-F-[Lys_

Peg11_Palm]-C-(D)Lys-NH2;

(SEQ ID NO: 173)
Isovaleric_Acid-D-T-H-[Dpa]-Npc-C-I-(D)Lys-bhPhe-

[Lys_Peg11_Palm]-C-(D)Lys-NH2;

(SEQ ID NO: 174)
Isovaleric_Acid-D-T-H-[Dpa]-P-C-I-(D)Gln-bhPhe-

[Lys_Peg11_Palm]-(D)Lys-C-NH2;
or (SEQ ID NO: 175)
Isovaleric_Acid-D-T-H-[Dpa]-P-C-I-(D)Lys-bhPhe-

[Lys_Peg11_Palm]-dLys_Ac-C-NH2;
``` and wherein the peptide is cyclized via a disulfide bond between two Cys.

In certain embodiment, the present invention includes a peptide having a structure or comprising an amino acid sequence of

```
                                          (SEQ ID NO: 165)
Isovaleric acid-DTH-[Dpa]-PCI-[(D)Lys]-[b-hPhe]-

[Lys(Ahx-Palm)]-[(D)Lys]-C-NH2;
``` and wherein the peptide is cyclized via a disulfide bond between two Cys.

In certain embodiment, the present invention includes a peptide having a structure or comprising an amino acid sequence of

```
                                          (SEQ ID NO: 105)
Isovaleric acid-D-T-H-[Dpa]-P-C-I-[(D)Lys]-[b- homoPhe]-Lys[PEG11-Palm]-[(D)Lys]-[Cys]-NH2;
``` and wherein the peptide is cyclized via a disulfide bond between two Cys.

In certain embodiment, the present invention provides a cyclized form of any one of the hepcidin analogues listed in any of Tables 2A, 2B, 3A, 3B and 4, comprising a disulfide bond between the two Cys and/or Pen residues; and wherein the compound ID is 3-107, 109-122, 125-181 or 201-230. In a particular embodiment, the ID is 80, 105, 145, 146, 147, 148, 149, 150, 162, 163, 164, 165, 166, 167, 168, 169, 170, 171, 172, 173, 174, 175, 10, 71, 73, 75, 86, 118, 121, 122, 130, 131, 132, 136, 137, 138, 139, 144, 151, 154, 158, 159, 160, 161, or 176. In a more particular embodiment, the ID is 80, 105, 145, 146, 147, 148, 149, 150, 162, 163, 164, 165, 166, 167, 168, 169, 170, 171, 172, 173, 174, or 175. The conjugated half-life extension moiety and the amino acid residue to which it is conjugated are indicated by parentheses and brackets, respectively.

Peptide Dimer Hepcidin Analogues

In certain embodiments, the present invention includes dimer hepcidin analogues, which include dimers of any of the monomer hepcidin analogues described herein, including dimers comprising any of the monomer peptides sequences or structures set forth in the formulaes described herein, e.g., various embodiments of Formulas I, I', (A-I)-(A-XXIVb), and (B-I)-(B-XIVb), and certain dimers of sequences or structures set forth in Table 2A, Table 2B, Table 3A and Table 3B. These dimers fall within the scope of the general term "hepcidin analogues" as used herein. The term "dimers," as in peptide dimers, refers to compounds in which two peptide monomer subunits are linked. A peptide dimer of the present invention may comprise two identical monomer subunits, resulting in a homodimer, or two non-identical monomer subunits, resulting in a heterodimer. A cysteine dimer comprises two peptide monomer subunits linked through a disulfide bond between a cysteine residue in one monomer subunit and a cysteine residue in the other monomer subunit.

In certain embodiments, a dimer hepcidin analogue comprises two polypeptide sequences of Formula (I'):

$$R^1\text{-Asp-Thr-His-B1-B2-B3-B4-B5-B6} \quad (I')$$

or a pharmaceutically acceptable salt or solvate thereof, wherein:

$R^1$, B1, B2, B3, B4, B5, and B6 are as described for Formula (A-I); the dimers are linked via a linker moiety and through a disulfide bond between two B3s; and wherein the dimer hepcidin analogue comprises a conjugated half-life extension moiety.

In one embodiment, the monomers are linked via B8B9 (L1Z)R2 and wherein each B8 and B9 is independently Lys, D-Lys, homoLys, or a-Me-Lys; L1, Z, and R2 are as described herein; and wherein one of the B6s is attached to $N^\varepsilon$ of B8.

In one embodiment, the peptide dimer is according to formula A-II:

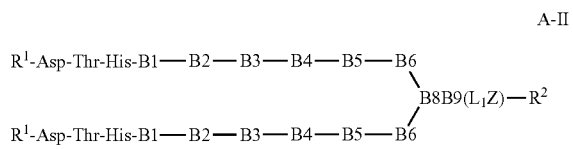

and wherein each B8 and B9 is independently Lys, D-Lys, homoLys, or a-Me-Lys; B1-B6, L1, Z, and $R^2$ are as described for Formula (A-I); and wherein one of the B6s is attached to $N^\varepsilon$ of B8.

In one embodiment, B9 is Lys. In another embodiment, B8 is Lys or D-Lys.

In certain embodiments, the hepcidin analogue comprises two polypeptide sequences of Formula (I"):

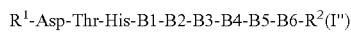

or a pharmaceutically acceptable salt or solvate thereof, wherein:
$R^1$, B1, B2, B3, B4, B5, and B6 are as described for Formula (A-I); the dimers are linked via a linker moiety and through a disulfide bond between two B3s; and wherein the dimer hepcidin analogue comprises a conjugated half-life extension moiety.

In one embodiment, the peptide dimer is according to formula A-III:

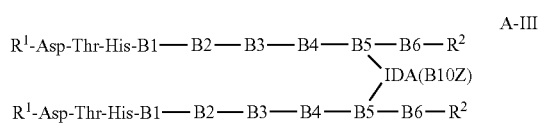

$R^1$, B1, B2, B3, B4, B5, and B6 are as described for Formula (A-I); the dimers are linked via a linker moiety and through a disulfide bond between two B3s; B10 is a natural or unnatural amino acid; and Z is a half-life extending moiety.

In certain embodiments, the peptide dimer is according to Formula A-I or III, and B1 is Phe.

In certain embodiments, the peptide dimer is according to Formula A-I or III, and B2 is Pro.

In certain embodiments, the peptide dimer is according to Formula A-I or III, and B3 is Cys.

In certain embodiments, the peptide dimer is according to Formula A-I or III, and B4 is Ile.

In certain embodiments, the peptide dimer is according to Formula A-I or III, and B6 is Phe.

In one embodiment, the peptide dimer is according to Formula A-I, and each B8 and B9 is independently lower or higher homolog of Lys.

In one embodiment, the peptide dimer is according to Formula A-I, and one of the B6s is attached to $N^\varepsilon$ of B8.

In one embodiment, the peptide dimer is according to Formula A-II, and B10 is b-Ala.

In one embodiment, the peptide dimer is according to Formula A-II, and B10 is b-Ala.

In one embodiment, the peptide dimer is according to Formula A-II, and one of the carboxy of IDA is attached to B5 of a first monomer; and the other carboxy of IDA is attached to B5 of a second monomer.

In particular embodiments, the linker moiety is bound to the C-terminus of each hepcidin analogue. In particular embodiments, the linker moiety is bound to the N-terminus of each hepcidin analogue. In particular embodiments, the linker moiety is bound to the N-terminus of one hepcidin analogue and the C-terminus of the other hepcidin analogue present in the dimer.

In certain embodiments, the half-life extension moiety is conjugated to the linker moiety.

In some embodiments, the hepcidin analogues of the present invention are active in a dimer conformation, in particular when free cysteine residues are present in the peptide. In certain embodiments, this occurs either as a synthesized dimer or, in particular, when a free cysteine monomer peptide is present and under oxidizing conditions, dimerizes.

In some embodiments, the dimer is a homodimer. In other embodiments, the dimer is a heterodimer.

In certain embodiments, a hepcidin analogue dimer of the present invention is a peptide dimer comprising two hepcidin analogue peptide monomers of the invention.

In certain embodiment, the present invention includes a polypeptide comprising an amino acid sequence set forth in any of Tables 2A, 2B, 3A, 3B, or 4 (with or without the indicated linker moieties and half-life extension moieties), or having any amino acid sequence with at least 85%, at least 90%, at least 92%, at least 94%, or at least 95% identity to any of these amino acid sequences. In related embodiments, the present invention includes a dimer comprising two polypeptides, each comprising an amino acid sequence set forth in any of Tables 2A, 2B, 3A, or 3B (with or without the indicated linker moieties and half-life extension moieties), or having any amino acid sequence with at least 85%, at least 90%, at least 92%, at least 94%, or at least 95% identity to any of these amino acid sequences. In particular embodiments, a peptide dimer hepcidin analogue comprises one or more, e.g., two, peptide monomer subunits shown in any of Tables 2A, 2B, 3A or 3B. The conjugated half-life extension moiety and the amino acid residue to which it is conjugated may be indicated by parentheses and/or brackets. Table 4 shows dimer hepcidin analogues, each comprising a dimer of the sequences in parentheses followed by a subscript "2", which are linked by the indicated one or more linkers, e.g., Lys or IDA, and conjugated to the indicated half-life extension moiety, e.g., octanoic acid or Palm.

TABLE 4

Illustrative Dimer Hepcidin Analogues

| Compd ID | SEQ ID No. | Peptide | FPN IC50 | SIF Half life (min) | SGF Half life (min) |
|---|---|---|---|---|---|
| 501 | 231 | (Isovaleric acid-DTHFPCIKF)2K-Lys[isoGlu-Palm]-NH$_2$ | 28 nM | 50 | 49 |
| 502 | 232 | (Isovaleric acid-DTHFPCIKF)$_2$-[D-Lys]-Lys[isoGlu-Palm]-NH$_2$ | 33 nM | 43 | 173 |
| 503 | 233 | (Isovaleric acid-DTHFPCI-[D-Lys]-F)$_2$-Lys[isoGlu-Palm]-NH$_2$ | 21 nM | >1440 (65%) | 52 |
| 504 | 234 | (Isovaleric acid-DTHFPCIK-[Phe(4-OCH2CH2NH$_2$)])$_2$K-Lys[isoGlu-Palm]-NH$_2$ | 20 nM | 13 | 16 |
| 505 | 235 | (Isovaleric acid-DTHFPCIK-[a-MePhe])$_2$K-Lys[isoGlu-Palm]-NH$_2$ | 18 nM | 596 | 192 |
| 506 | 236 | (Isovaleric acid-DTHFPCI-[D-Lys]-F)$_2$-IDA-[(b-Ala)-Palm]-NH$_2$ | 4 nM | >1290 (100%) | >1290 (57%) |
| 507 | 237 | (Isovaleric acid-DTHFPCIK-[NMe-Phe])$_2$-IDA-[(b-Ala)-Palm]-NH$_2$ | 10 nM | >1290 (100%) | 26 |
| 508 | 238 | (Isovaleric acid-DTHFPCIK-[a-MePhe])$_2$-IDA-[(b-Ala)-Palm]-NH$_2$ | 9 nM | >1290 (80%) | 35 |
| 509 | 239 | (Isovaleric acid-DTHFPCIIF-[D-Lys])$_2$-IDA-[(b-Ala)-Palm]-NH$_2$ | 433 nM | >1290 (54%) | variable |
| 510 | 240 | (Isovaleric acid-DTHFPCI-[D-Lys]-[a-MePhe])$_2$-K-Lys[isoGlu-Palm]-NH$_2$ | 8 nM | 1441 | 187 |
| 511 | 241 | (Isovaleric acid-DTH-[BIP]-PCI-[D-Lys]-F)$_2$-K-Lys[isoGlu-Palm]-NH$_2$ | TBC | 449 | >1440 (89%) |
| 512 | 242 | (Isovaleric acid-DTHFPCIK-[b-homoPhe])$_2$K-Lys[isoGlu-Palm]-NH$_2$ | 5 nM | >1440 (93%) | 283 |
| 513 | 243 | (Isovaleric acid-DTHFPCIK-[b-homoPhe])$_2$K-Lys[isoGlu-Palm]-NH$_2$ | 5 nM | >1440 (71%) | 109 |
| 514 | 244 | (Isovaleric acid-DTHFPCI-[D-Lys]-[NMe-Phe])$_2$-IDA-[(b-Ala)-Palm]-NH$_2$ | 4 nM | >1440 (80%) | 117 |
| 515 | 245 | (Isovaleric acid-DTH-[BIP]-PCI-[D-Lys]-[NMe-Phe])$_2$-IDA-[(b-Ala)-Palm]-NH$_2$ | 26 nM | variable | 345 |
| 516 | 246 | (Isovaleric acid-DTHFPCIK-[b-homoPhe])$_2$-IDA-[(b-Ala)-Palm]-NH$_2$ | 6 nM | variable | 1249 |
| 517 | 247 | (Isovaleric acid-DTHFPCI-[D-Lys]-[b-homoPhe])$_2$-IDA-[(b-Ala)-Palm]-NH$_2$ | 5 nM | >240 (86%) | >1440 (51%) |
| 518 | 248 | (Isovaleric acid-DTHF-[Npc]-CI-[D-Lys]-[NMe-Phe])$_2$-IDA-[(b-Ala)-Palm]-NH$_2$ | 8 nM | variable | 1241 |

In particular embodiments, the monomer subunits may be dimerized by a disulfide bridge between two cysteine residues, one in each peptide monomer subunit, or they may be dimerized by another suitable linker moiety, including those described herein. Some of the monomer subunits are shown having C- and/or N-termini that both comprise free amine.

Thus, to produce a peptide dimer inhibitor, the monomer subunit may be modified to eliminate either the C- or N-terminal free amine, thereby permitting dimerization at the remaining free amine. Further, in some instances, a terminal end of one or more monomer subunits is acylated with an acylating organic compound selected from the group consisting of: 2-me-Trifluorobutyl, Trifluoropentyl, Acetyl, Octonyl, Butyl, Pentyl, Hexyl, Palmityl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, monomer subunits comprise both a free carboxy terminal and a free amino terminal, whereby a user may selectively modify the subunit to achieve dimerization at a desired terminus. One having skill in the art will, therefore, appreciate that the monomer subunits of the instant invention may be selectively modified to achieve a single, specific amine for a desired dimerization.

It is further understood that the C-terminal residues of the monomer subunits disclosed herein may be amides, unless otherwise indicated. Further, it is understood that, in certain embodiments, dimerization at the C-terminus is facilitated by using a suitable amino acid with a side chain having amine functionality, as is generally understood in the art. Regarding the N-terminal residues, it is generally understood that dimerization may be achieved through the free amine of the terminal residue, or may be achieved by using a suitable amino acid side chain having a free amine, as is generally understood in the art.

Moreover, it is understood that the side chains of one or more internal residue comprised in the hepcidin analogue peptide monomers of the present invention can be utilized for the purpose of dimerization. In such embodiments, the side chain is in some embodiments a suitable natural amino acid (e.g., Lys), or alternatively it is an unnatural amino acid comprising a side chain suitable for conjugation, e.g., to a suitable linker moiety, as defined herein.

The linker moieties connecting monomer subunits may include any structure, length, and/or size that is compatible with the teachings herein. In at least one embodiment, a linker moiety is selected from the non-limiting group consisting of: cysteine, lysine, DIG, PEG4, PEG4-biotin, PEG13, PEG25, PEG1K, PEG2K, PEG3.4K, PEG4K, PEG5K, IDA, IDA-Palm, ADA, Boc-IDA, Glutaric acid, Isophthalic acid, 1,3-phenylenediacetic acid, 1,4-phenylenediacetic acid, 1,2-phenylenediacetic acid, Triazine, Boc- Triazine, IDA-biotin, PEG4-Biotin, AADA, suitable aliphatics, aromatics, heteroaromatics, and polyethylene glycol based linkers having a molecular weight from approximately 400 Da to approximately 40,000 Da. Non-limiting examples of suitable linker moieties are provided in Table 5. In particular embodiment, any of these linker moieties may alternatively link a half-life extension moiety to a hepcidin analogue.

TABLE 5

| Abbreviation | Description | Structure |
|---|---|---|
| DIG | DIGlycolic acid | |
| PEG4 | Bifunctional PEG linker with 4 PolyEthylene Glycol units | 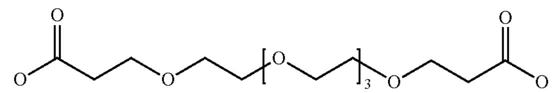 |
| PEG13 | Bifunctional PEG linker with 13 PolyEthylene Glycol units | 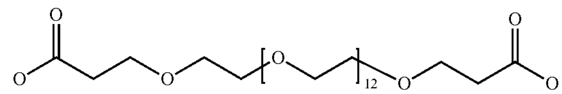 |
| PEG25 | Bifunctional PEG linker with 25 PolyEthylene Glycol units | 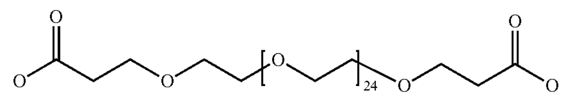 |
| PEG1K | Bifunctional PEG linker with PolyEthylene Glycol Mol wt of 1000 Da | |
| PEG2K | Bifunctional PEG linker with PolyEthylene Glycol Mol wt of 2000 Da | |
| PEG3.4K | Bifunctional PEG linker with PolyEthylene Glycol Mol wt of 3400 Da | |
| PEG5K | Bifunctional PEG linker with PolyEthylene Glycol Mol wt of 5000 Da | |
| DIG | Diglycolic acid | |
| β-Ala-IDA | β-Ala-Iminodiacetic acid | 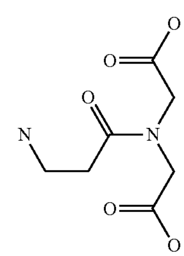 |
| Boc-β-Ala-IDA | Boc-β-Ala-Iminodiacetic acid | 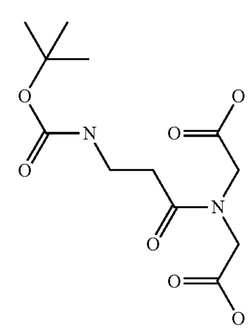 [SMILES: CC(C)(C)OC(=O)NCCC(=O)N(CC(=O)O)CC(=O)O] |

TABLE 5-continued

Illustrative Linker Moieties

| Abbreviation | Description | Structure |
|---|---|---|
| Ac-β-Ala-IDA | Ac-β-Ala-Iminodiacetic acid | 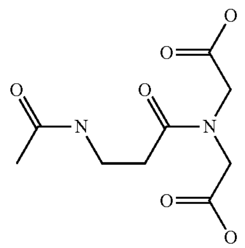 [SMILES: CC(=O)NCCC(=O)N(CC(=O)O)CC(=O)O] |
| Palm-β-Ala-IDA- | Palmityl-β-Ala-Iminodiacetic acid | 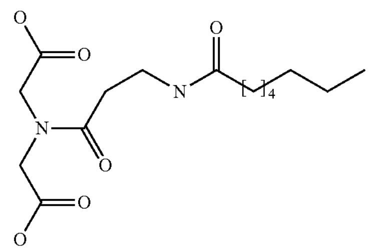 |
| GTA | Glutaric acid | 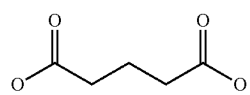 |
| PMA | Pemilic acid | 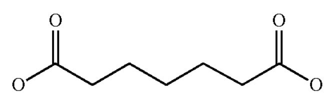 [SMILES: O=C(O)CCCCCC(=O)O] |
| AZA | Azelaic acid | 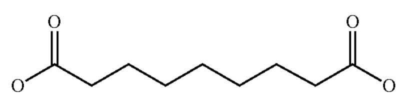 [SMILES: O=C(O)CCCCCCCC(=O)O] |
| DDA | Dodecanedioic acid | 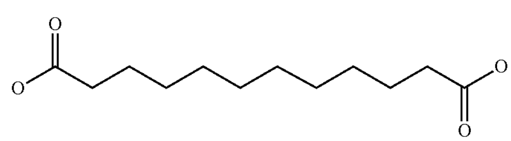 [SMILES: O=C(O)CCCCCCCCCCC(=O)O] |
| IPA | Isopthalic acid | 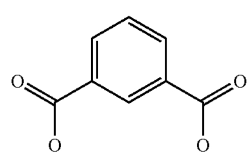 [SMILES: O=C(O)c1cccc(C(=O)O)c1] |
| 1,3-PDA | 1,3-Phenylenediacetic acid | 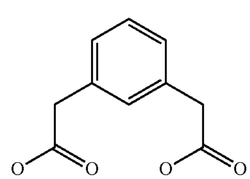 [SMILES: O=C(O)Cc1cccc(CC(=O)O)c1] |
| 1,4-PDA | 1,4-Phenylenediacetic acid | 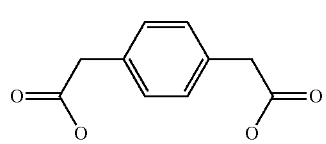 [SMILES: O=C(O)Cc1ccc(CC(=O)O)cc1] |

TABLE 5-continued

Illustrative Linker Moieties

| Abbreviation | Description | Structure |
|---|---|---|
| 1,2-PDA | 1,2-Phenylenediacetic acid | 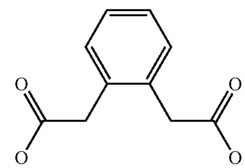 [SMILES: O=C(O)Cc1ccccc1CC(=O)O] |
| Triazine | Amino propyl Triazine di-acid | 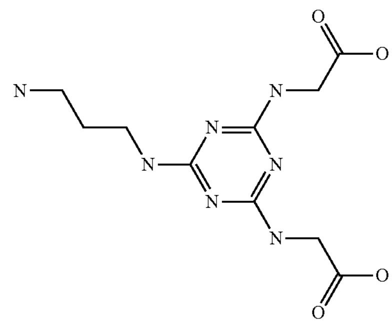 [SMILES: NCCCNc1nc(NCC(=O)O)nc(NCC(=O)O)n1] |
| Boc-Triazine | Boc-Triazine di-acid | 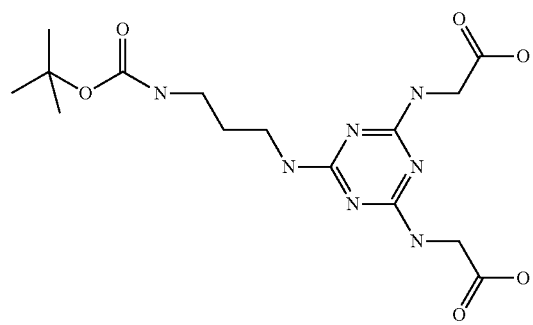 [SMILES: CC(C)(C)OC(=O)NCCCNc1nc(NCC(=O)O)nc(NCC(=O)O)n1] |
| IDA | Iminodiacetic acid | 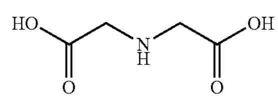 |
| AIDA | n-Acetyl imino acetic acid | 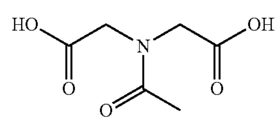 |
| Biotin-β-ala-IDA- | N-Biotin-β-Ala-Iminodiacetic acid | 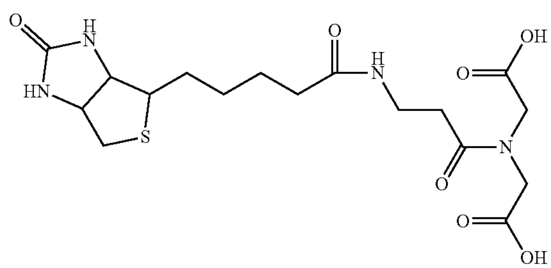 [SMILES: O=C(O)CN(CC(=O)O)C(=O)CCNC(=O)CCCCC1SCC2NC(=O)NC21] |
| Lys | Lysine | 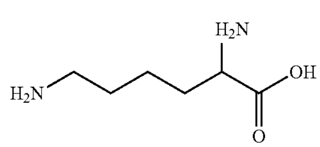 |

One having skill in the art will appreciate that the C- and N-terminal and internal linker moieties disclosed herein are non-limiting examples of suitable linker moieties, and that the present invention may include any suitable linker moiety.

In certain embodiments of any of the hepcidin analogue peptide dimers, the N-terminus of each peptide monomer subunit is connected by a linker moiety.

In certain embodiments of any of the hepcidin analogue peptide dimers, the C— terminus of each peptide monomer subunit is connected by a linker moiety.

In certain embodiments, the side chains of one or more internal amino acid residues (e.g., Lys residues) comprised in each peptide monomer subunit of a hepcidin analogue peptide dimer are connected by a linker moiety.

In certain embodiments of any of the hepcidin analogue peptide dimers, the C— terminus, the N terminus, or an internal amino acid (e.g., a lysine sidechain) of each peptide monomer subunit is connected by a linker moiety and at least two cysteine or Pen residues of the hepcidin analogue peptide dimers are linked by a disulfide bridge. In some embodiments, a peptide dimer has a general structure shown below. Non-limiting schematic examples of such hepcidin analogues are shown in the following illustration:

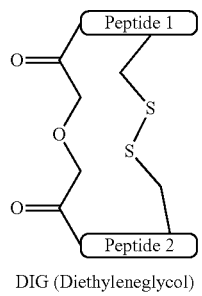
DIG (Diethyleneglycol)

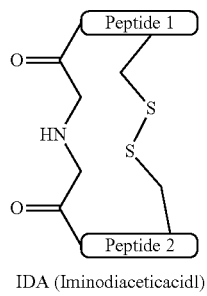
IDA (Iminodiaceticacidl)

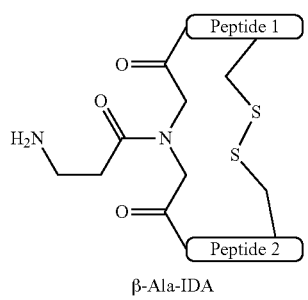
β-Ala-IDA

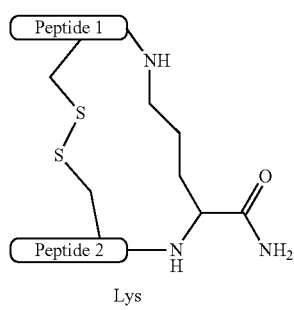
Lys

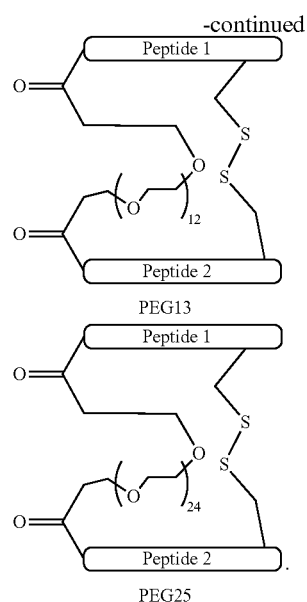
PEG13

PEG25

Peptide Analogue Conjugates

In certain embodiments, hepcidin analogues of the present invention, including both monomers and dimers, comprise one or more conjugated chemical substituents, such as lipophilic substituents and polymeric moieties, collectively referred to herein as half-life extension moieties. Without wishing to be bound by any particular theory, it is believed that the lipophilic substituent binds to albumin in the bloodstream, thereby shielding the hepcidin analogue from enzymatic degradation, and thus enhancing its half-life. In addition, it is believed that polymeric moieties enhance half-life and reduce clearance in the bloodstream, and in some cases enhance permeability through the epithelium and retention in the lamina propria. Moreover, it is also surmised that these substituents in some cases may enhance permeability through the epithelium and retention in the lamina propria. The skilled person will be well aware of suitable techniques for preparing the compounds employed in the context of the invention. For examples of non-limiting suitable chemistry, see, e.g., WO98/08871, WO00/55184, WO00/55119, Madsen et al (J. Med. Chem. 2007, 50, 6126-32), and Knudsen et al. 2000 (J. Med Chem. 43, 1664-1669).

In one embodiment, the side chains of one or more amino acid residues (e.g., Lys residues) in a hepcidin analogue of the invention is further conjugated (e.g., covalently attached) to a lipophilic substituent or other half-life extension moiety. The lipophilic substituent may be covalently bonded to an atom in the amino acid side chain, or alternatively may be conjugated to the amino acid side chain via one or more spacers or linker moieties. The spacer or linker moiety, when present, may provide spacing between the hepcidin analogue and the lipophilic substituent. In particular embodiments, the half-life extension moiety is conjugated to the hepcidin analogue via a linker moiety, which in certain embodiments is a linker moiety shown in Table 5 or Table 7, or depicted in any of the illustrative compounds shown in Table 2A, 2B, 3A, 3B, and 4.

In certain embodiments, the lipophilic substituent or half-life extension moiety comprises a hydrocarbon chain having from 4 to 30 C atoms, for example at least 8 or 12 C atoms, and preferably 24 C atoms or fewer, or 20 C atoms or fewer. The hydrocarbon chain may be linear or branched and may be saturated or unsaturated. In certain embodiments, the hydrocarbon chain is substituted with a moiety which forms part of the attachment to the amino acid side chain or the spacer, for example an acyl group, a sulfonyl group, an N atom, an O atom or an S atom. In some embodiments, the hydrocarbon chain is substituted with an acyl group, and accordingly the hydrocarbon chain may form part of an alkanoyl group, for example palmitoyl, caproyl, lauroyl, myristoyl or stearoyl.

A lipophilic substituent may be conjugated to any amino acid side chain in a hepcidin analogue of the invention. In certain embodiment, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. In certain embodiments, the lipophilic substituent is conjugated to Lys. An amino acid shown as Lys in any of the formula provided herein may be replaced by, e.g., Dbu, Dpr or Orn where a lipophilic substituent is added.

In further embodiments of the present invention, alternatively or additionally, the side-chains of one or more amino acid residues in a hepcidin analogue of the invention may be conjugated to a polymeric moiety or other half-life extension moiety, for example, in order to increase solubility and/or half-life in vivo (e.g., in plasma) and/or bioavailability. Such modifications are also known to reduce clearance (e.g. renal clearance) of therapeutic proteins and peptides.

As used herein, "Polyethylene glycol" or "PEG" is a polyether compound of general formula H—(O—CH$_2$—CH$_2$)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g., viscosity) due to chain length effects, their chemical properties are nearly identical. The polymeric moiety is preferably water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Also encompassed are PEGs that are prepared for purpose of half-life extension, for example, mono-activated, alkoxy-terminated polyalkylene oxides (POA's) such as mono-methoxy-terminated polyethyelene glycols (mPEG's); bis activated polyethylene oxides (glycols) or other PEG derivatives are also contemplated. Suitable polymers will vary substantially by weights ranging from about 200 to about 40,000 are usually selected for the purposes of the present invention. In certain embodiments, PEGs having molecular weights from 200 to 2,000 daltons or from 200 to 500 daltons are used. Different forms of PEG may also be used, depending on the initiator used for the polymerization process, e.g., a common initiator is a monofunctional methyl ether PEG, or methoxypoly(ethylene glycol), abbreviated mPEG. Other suitable initiators are known in the art and are suitable for use in the present invention.

Lower-molecular-weight PEGs are also available as pure oligomers, referred to as monodisperse, uniform, or discrete. These are used in certain embodiments of the present invention.

PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear. The numbers that are often included in the names of PEGs indicate their average molecular weights (e.g. a PEG with n=9 would have an average molecular weight of approximately 400 daltons, and would be labeled PEG 400.

As used herein, "PEGylation" is the act of coupling (e.g., covalently) a PEG structure to the hepcidin analogue of the invention, which is in certain embodiments referred to as a "PEGylated hepcidin analogue". In certain embodiments, the PEG of the PEGylated side chain is a PEG with a molecular weight from about 200 to about 40,000. In certain embodiments, the PEG portion of the conjugated half-life extension moiety is PEG3, PEG4, PEG5, PEG6, PEG7, PEG8, PEG9, PEG10, or PEG11. In particular embodiments, it is PEG11.

In certain embodiments, the PEG of a PEGylated spacer is PEG3 or PEG8. In some embodiments, a spacer is PEGylated. In certain embodiments, the PEG of a PEGylated spacer is PEG3, PEG4, PEG5, PEG6, PEG7, PEG8, PEG9, PEG10, or PEG11. In certain embodiments, the PEG of a PEGylated spacer is PEG3 or PEG8.

In some embodiments, the present invention includes a hepcidin analogue peptide (or a dimer thereof) conjugated with a PEG that is attached covalently, e.g., through an amide, a thiol, via click chemistry, or via any other suitable means known in the art. In particular embodiments PEG is attached through an amide bond and, as such, certain PEG derivatives used will be appropriately functionalized. For example, in certain embodiments, PEG11, which is O-(2-aminoethyl)-O'-(2-carboxyethyl)-undecaethyleneglycol, has both an amine and carboxylic acid for attachment to a peptide of the present invention. In certain embodiments, PEG25 contains a diacid and 25 glycol moieties.

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57 and Tsukada, et al. (1984), J. Natl. Cancer Inst., vol. 73: 721-729. The polymeric moiety may be straight-chain or branched. In some embodiments, it has a molecular weight of 500-40,000 Da, for example 500-10,000 Da, 1000-5000 Da, 10,000-20,000 Da, or 20,000-40,000 Da.

In some embodiments, a hepcidin analogue of the invention may comprise two or more such polymeric moieties, in which case the total molecular weight of all such moieties will generally fall within the ranges provided above.

In some embodiments, the polymeric moiety may be coupled (by covalent linkage) to an amino, carboxyl or thiol group of an amino acid side chain. Certain examples are the thiol group of Cys residues and the epsilon amino group of Lys residues, and the carboxyl groups of Asp and Glu residues may also be involved.

The skilled worker will be well aware of suitable techniques which can be used to perform the coupling reaction. For example, a PEG moiety bearing a methoxy group can be coupled to a Cys thiol group by a maleimido linkage using reagents commercially available from Nektar Therapeutics AL. See also WO 2008/101017, and the references cited above, for details of suitable chemistry. A maleimide-functionalised PEG may also be conjugated to the side-chain sulfhydryl group of a Cys residue.

As used herein, disulfide bond oxidation can occur within a single step or is a two-step process. As used herein, for a single oxidation step, the trityl protecting group is often employed during assembly, allowing deprotection during cleavage, followed by solution oxidation. When a second disulfide bond is required, one has the option of native or selective oxidation. For selective oxidation requiring orthogonal protecting groups, Acm and Trityl is used as the protecting groups for cysteine. Cleavage results in the removal of one protecting pair of cysteine allowing oxidation of this pair. The second oxidative deprotection step of the cysteine protected Acm group is then performed. For native oxidation, the trityl protecting group is used for all cysteines, allowing for natural folding of the peptide.

A skilled worker will be well aware of suitable techniques which can be used to perform the oxidation step.

In particular embodiments, a hepcidin analogue of the present invention comprises a half-life extension moiety, which may be selected from but is not limited to the following: Ahx-Palm, PEG2-Palm, PEG11-Palm, isoGlu-Palm, dapa-Palm, isoGlu-Lauric acid, isoGlu-Mysteric acid, and isoGlu-Isovaleric acid.

In particular embodiments, a hepcidin analogue comprises a half-life extension moiety having the structure shown below, wherein n=0 to 24 or n=14 to 24:

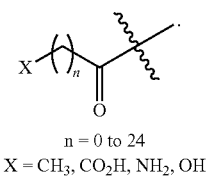

n = 0 to 24
X = CH$_3$, CO$_2$H, NH$_2$, OH

In certain embodiments, a hepcidin analogue of the present invention comprises a conjugated half-life extension moiety shown in Table 6.

TABLE 6

Illustrative Half-Life Extension Moieties

| # | Conjugates |
|---|---|
| C1 | C12 (Lauric acid) |
| C2 | C14 (Mysteric acid) |
| C3 | C16 (Palm or Palmitic acid) |
| C4 | C18 (Stearic acid) |
| C5 | C20 |

TABLE 6-continued

Illustrative Half-Life Extension Moieties

| # | Conjugates |
|---|---|
| C6 | 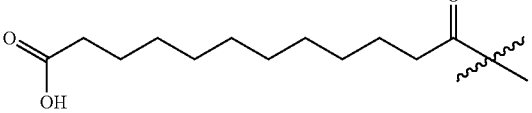<br>C12 diacid |
| C7 | 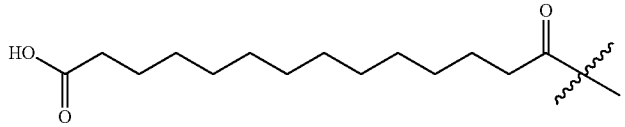<br>C14 diacid |
| C8 | 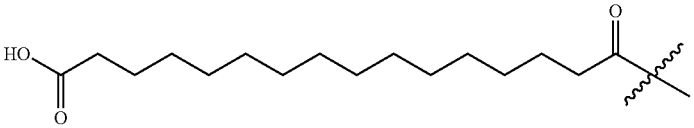<br>C16 diacid |
| C9 | 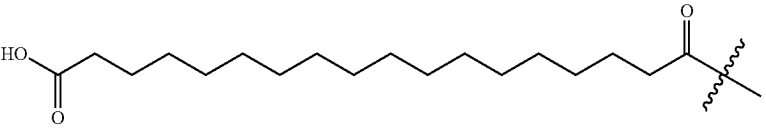<br>C18 diacid |
| C10 | 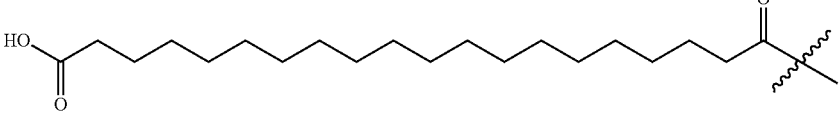<br>C20 diacid |
| C11 | 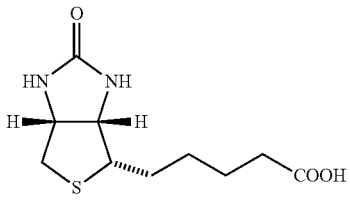<br>Biotin |
| C12 | 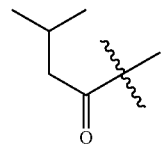<br>Isovaleric acid |

In certain embodiments, a half-life extension moiety is conjugated directly to a hepcidin analogue, while in other embodiments, a half-life extension moiety is conjugated to a hepcidin analogue peptide via a linker moiety, e.g., any of those depicted in Tables 5 or 7.

TABLE 7

Illustrative Linker Moieties

| # | Linker Moiety |
|---|---|
| L1 | IsoGlu |
| L2 | Dapa |
| L3 | Ahx |
| L4 | Lipdic based linkers: n = 1 to 24 |
| L5 | PEG1 |
| L6 | PEG2 |
| L7 | PEG11 (40 atoms) n = 11 |
| L8 | PEG based linkers n = 1 to 25 |

TABLE 7-continued

Illustrative Linker Moieties

| # | Linker Moiety |
|---|---|
| L9 | OEG |
| L10 | IsoGlu-Ahx |
| L11 | IsoGlu-OEG-OEG |
| L12 | IsoGlu-PEG5 |
| L13 | IsoGlu-PEGn (n = 1-25) |
| L14 | βAla-PEG2 |
| L15 | βAla-PEG11 (40 atoms) |

With reference to linker structures shown in Table 7, reference to n=1 to 24 or n=1 to 25, or the like, (e.g., in L4, L8 or L13) indicates that n may be any integer within the recited range. For example, for L4 shown in Table 7, n could be 1, 2, 3, etc., wherein when n=5, L4 has the structure shown in L3 (Ahx).

In particular embodiments, a hepcidin analogue of the present invention comprises any of the linker moieties shown in Table 7 and any of the half-life extension moieties shown in Table 6, including any of the following combinations shown in Table 8.

TABLE 8

Illustrative Combinations of Linkers and Half-Life Extension Moieties in Hepcidin Analogues

| Linker | Half-Life Extension Moiety |
|---|---|
| L1 | C1 |
| L2 | C1 |
| L3 | C1 |
| L4 | C1 |

TABLE 8-continued

Illustrative Combinations of Linkers and Half-Life Extension Moieties in Hepcidin Analogues

| Linker | Half-Life Extension Moiety |
|---|---|
| L5 | C1 |
| L6 | C1 |
| L7 | C1 |
| L8 | C1 |
| L9 | C1 |
| L10 | C1 |
| L11 | C1 |
| L12 | C1 |
| L13 | C1 |
| L14 | C1 |
| L15 | C1 |
| L1 | C2 |
| L2 | C2 |
| L3 | C2 |
| L4 | C2 |
| L5 | C2 |
| L6 | C2 |
| L7 | C2 |
| L8 | C2 |
| L9 | C2 |
| L10 | C2 |
| L11 | C2 |
| L12 | C2 |
| L13 | C2 |
| L14 | C2 |
| L15 | C2 |
| L1 | C3 |
| L2 | C3 |
| L3 | C3 |
| L4 | C3 |
| L5 | C3 |
| L6 | C3 |
| L7 | C3 |
| L8 | C3 |
| L9 | C3 |
| L10 | C3 |
| L11 | C3 |
| L12 | C3 |
| L13 | C3 |
| L14 | C3 |
| L15 | C3 |
| L1 | C4 |
| L2 | C4 |
| L3 | C4 |
| L4 | C4 |
| L5 | C4 |
| L6 | C4 |
| L7 | C4 |
| L8 | C4 |
| L9 | C4 |
| L10 | C4 |
| L11 | C4 |
| L12 | C4 |
| L13 | C4 |
| L14 | C4 |
| L15 | C4 |
| L1 | C5 |
| L2 | C5 |
| L3 | C5 |
| L4 | C5 |
| L5 | C5 |
| L6 | C5 |
| L7 | C5 |
| L8 | C5 |
| L9 | C5 |
| L10 | C5 |
| L11 | C5 |
| L12 | C5 |
| L13 | C5 |
| L14 | C5 |
| L15 | C5 |
| L1 | C6 |
| L2 | C6 |
| L3 | C6 |
| L4 | C6 |
| L5 | C6 |
| L6 | C6 |
| L7 | C6 |
| L8 | C6 |
| L9 | C6 |
| L10 | C6 |
| L11 | C6 |
| L12 | C6 |
| L13 | C6 |
| L14 | C6 |
| L15 | C6 |
| L1 | C7 |
| L2 | C7 |
| L3 | C7 |
| L4 | C7 |
| L5 | C7 |
| L6 | C7 |
| L7 | C7 |
| L8 | C7 |
| L9 | C7 |
| L10 | C7 |
| L11 | C7 |
| L12 | C7 |
| L13 | C7 |
| L14 | C7 |
| L15 | C7 |
| L1 | C8 |
| L2 | C8 |
| L3 | C8 |
| L4 | C8 |
| L5 | C8 |
| L6 | C8 |
| L7 | C8 |
| L8 | C8 |
| L9 | C8 |
| L10 | C8 |
| L11 | C8 |
| L12 | C8 |
| L13 | C8 |
| L14 | C8 |
| L15 | C8 |
| L1 | C9 |
| L2 | C9 |
| L3 | C9 |
| L4 | C9 |
| L5 | C9 |
| L6 | C9 |
| L7 | C9 |
| L8 | C9 |
| L9 | C9 |
| L10 | C9 |
| L11 | C9 |
| L12 | C9 |
| L13 | C9 |
| L14 | C9 |
| L15 | C9 |
| L1 | C10 |
| L2 | C10 |
| L3 | C10 |
| L4 | C10 |
| L5 | C10 |
| L6 | C10 |
| L7 | C10 |
| L8 | C10 |
| L9 | C10 |
| L10 | C10 |
| L11 | C10 |
| L12 | C10 |
| L13 | C10 |
| L14 | C10 |
| L15 | C10 |
| L1 | C11 |
| L2 | C11 |
| L3 | C11 |
| L4 | C11 |

TABLE 8-continued

Illustrative Combinations of Linkers and Half-Life Extension Moieties in Hepcidin Analogues

| Linker | Half-Life Extension Moiety |
|---|---|
| L5 | C11 |
| L6 | C11 |
| L7 | C11 |
| L8 | C11 |
| L9 | C11 |
| L10 | C11 |
| L11 | C11 |
| L12 | C11 |
| L13 | C11 |
| L14 | C11 |
| L15 | C11 |
| L1 | C12 |
| L2 | C12 |
| L3 | C12 |
| L4 | C12 |
| L5 | C12 |
| L6 | C12 |
| L7 | C12 |
| L8 | C12 |
| L9 | C12 |
| L10 | C12 |
| L11 | C12 |
| L12 | C12 |
| L13 | C12 |
| L14 | C12 |
| L15 | C12 |

In certain embodiments, a hepcidin analogue comprises two or more linkers. In particular embodiments, the two or more linkers are concatamerized, i.e., bound to each other.

In related embodiments, the present invention includes polynucleotides that encode a polypeptide having a peptide sequence present in any of the hepcidin analogues described herein.

In addition, the present invention includes vectors, e.g., expression vectors, comprising a polynucleotide of the present invention.

Methods of Treatment

In some embodiments, the present invention provides methods for treating a subject afflicted with a disease or disorder associated with dysregulated hepcidin signaling, wherein the method comprises administering to the subject a hepcidin analogue of the present invention. In some embodiments, the hepcidin analogue that is administered to the subject is present in a composition (e.g., a pharmaceutical composition). In one embodiment, a method is provided for treating a subject afflicted with a disease or disorder characterized by increased activity or expression of ferroportin, wherein the method comprises administering to the individual a hepcidin analogue or composition of the present invention in an amount sufficient to (partially or fully) bind to and agonize ferroportin in the subject. In one embodiment, a method is provided for treating a subject afflicted with a disease or disorder characterized by dysregulated iron metabolism, wherein the method comprises administering to the subject a hepcidin analogue or composition of the present invention.

In some embodiments, methods of the present invention comprise providing a hepcidin analogue or a composition of the present invention to a subject in need thereof. In particular embodiments, the subject in need thereof has been diagnosed with or has been determined to be at risk of developing a disease or disorder characterized by dysregulated iron levels (e.g., diseases or disorders of iron metabolism; diseases or disorders related to iron overload; and diseases or disorders related to abnormal hepcidin activity or expression). In particular embodiments, the subject is a mammal (e.g., a human).

In certain embodiments, the disease or disorder is a disease of iron metabolism, such as, e.g., an iron overload disease, iron deficiency disorder, disorder of iron biodistribution, or another disorder of iron metabolism and other disorder potentially related to iron metabolism, etc. In particular embodiments, the disease of iron metabolism is hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia *intermedia*, alpha thalassemia, beta thalassemia, sideroblastic anemia, *porphyria, porphyria* cutanea *tarda*, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, transfusion-dependent anemia, hemolytic anemia, erythropoietin resistance, iron deficiency of obesity, other anemias, benign or malignant tumors that overproduce hepcidin or induce its overproduction, conditions with hepcidin excess, Friedreich ataxia, *gracile* syndrome, Hallervorden-Spatz disease, Wilson's disease, pulmonary hemosiderosis, hepatocellular carcinoma, cancer (e.g., liver cancer), hepatitis, cirrhosis of liver, pica, chronic renal failure, insulin resistance, diabetes, atherosclerosis, neurodegenerative disorders, dementia, multiple sclerosis, Parkinson's disease, Huntington's disease, or Alzheimer's disease.

In certain embodiments, the disease or disorder is related to iron overload diseases such as iron hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia *intermedia*, alpha thalassemia.

In certain embodiments, the disease or disorder is one that is not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, peptides of the invention may be used to treat these diseases and conditions. Those skilled in the art are readily able to determine whether a given disease can be treated with a peptide according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In certain embodiments, the disease or disorder is postmenopausal osteoporosis.

In certain embodiments of the present invention, the diseases of iron metabolism are iron overload diseases, which include hereditary hemochromatosis, iron-loading anemias, alcoholic liver diseases, heart disease and/or failure, cardiomyopathy, and chronic hepatitis C.

In particular embodiments, any of these diseases, disorders, or indications are caused by or associated with a deficiency of hepcidin or iron overload.

In some embodiments, methods of the present invention comprise providing a hepcidin analogue of the present invention (i.e., a first therapeutic agent) to a subject in need thereof in combination with a second therapeutic agent. In certain embodiments, the second therapeutic agent is provided to the subject before and/or simultaneously with and/or after the pharmaceutical composition is administered to the subject. In particular embodiments, the second therapeutic agent is iron chelator. In certain embodiments, the second therapeutic agent is selected from the iron chelators Deferoxamine and Deferasirox (Exjade™). In another embodiment, the method comprises administering to the subject a third therapeutic agent.

The present invention provides compositions (for example pharmaceutical compositions) comprising one or more hepcidin analogues of the present invention and a pharmaceutically acceptable carrier, excipient or diluent. A pharmaceutically acceptable carrier, diluent or excipient refers to a non-toxic solid, semi-solid or liquid filler, diluent, encapsulating material or formulation auxiliary of any type. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, Pa., USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

In certain embodiments, the compositions comprise two or more hepcidin analogues disclosed herein. In certain embodiments, the combination is selected from one of the following: (i) any two or more of the hepcidin analogue peptide monomers shown therein; (ii) any two or more of the hepcidin analogue peptide dimers disclosed herein; (iii) any one or more of the hepcidin analogue peptide monomers disclosed herein, and any one or more of the hepcidin analogue peptide dimers disclosed herein.

It is to be understood that the inclusion of a hepcidin analogue of the invention (i.e., one or more hepcidin analogue peptide monomers of the invention or one or more hepcidin analogue peptide dimers of the present invention) in a pharmaceutical composition also encompasses inclusion of a pharmaceutically acceptable salt or solvate of a hepcidin analogue of the invention. In particular embodiments, the pharmaceutical compositions further comprise one or more pharmaceutically acceptable carrier, excipient, or vehicle.

In certain embodiments, the invention provides a pharmaceutical composition comprising a hepcidin analogue, or a pharmaceutically acceptable salt or solvate thereof, for treating a variety of conditions, diseases, or disorders as disclosed herein or elsewhere (see, e.g., Methods of Treatment, herein). In particular embodiments, the invention provides a pharmaceutical composition comprising a hepcidin analogue peptide monomer, or a pharmaceutically acceptable salt or solvate thereof, for treating a variety of conditions, diseases, or disorders as disclosed herein elsewhere (see, e.g., Methods of Treatment, herein).

In particular embodiments, the invention provides a pharmaceutical composition comprising a hepcidin analogue peptide dimer, or a pharmaceutically acceptable salt or solvate thereof, for treating a variety of conditions, diseases, or disorders as disclosed herein.

The hepcidin analogues of the present invention may be formulated as pharmaceutical compositions which are suited for administration with or without storage, and which typically comprise a therapeutically effective amount of at least one hepcidin analogue of the invention, together with a pharmaceutically acceptable carrier, excipient or vehicle.

In some embodiments, the hepcidin analogue pharmaceutical compositions of the invention are in unit dosage form. In such forms, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration, e.g., any one of the routes and means of administration disclosed herein.

In particular embodiments, the hepcidin analogue, or the pharmaceutical composition comprising a hepcidin analogue, is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. One embodiment of a biodegradable matrix is a matrix of one of either polylactide, polyglycolide, or polylactide co-glycolide (co-polymers of lactic acid and glycolic acid).

In certain embodiments, the compositions are administered parenterally, subcutaneously or orally. In particular embodiments, the compositions are administered orally, intracisternally, intravaginally, intraperitoneally, intrarectally, topically (as by powders, ointments, drops, suppository, or transdermal patch, including delivery intravitreally, intranasally, and via inhalation) or buccally. The term "parenteral" as used herein refers to modes of administration which include intravenous, intramuscular, intraperitoneal, intrasternal, subcutaneous, intradermal and intra-articular injection and infusion. Accordingly, in certain embodiments, the compositions are formulated for delivery by any of these routes of administration.

In certain embodiments, pharmaceutical compositions for parenteral injection comprise pharmaceutically acceptable sterile aqueous or nonaqueous solutions, dispersions, suspensions or emulsions, or sterile powders, for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, beta-cyclodextrin, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants. These compositions may also contain adjuvants such as preservative, wetting agents, emulsifying agents, and dispersing agents. Prolonged absorption of an injectable pharmaceutical form may be brought about by the inclusion of agents which delay absorption, such as aluminum monostearate and gelatin.

Injectable depot forms include those made by forming microencapsule matrices of the hepcidin analogue in one or more biodegradable polymers such as polylactide-polyglycolide, poly(orthoesters), poly(anhydrides), and (poly)glycols, such as PEG.

Depending upon the ratio of peptide to polymer and the nature of the particular polymer employed, the rate of release of the hepcidin analogue can be controlled. Depot injectable formulations are also prepared by entrapping the hepcidin analogue in liposomes or microemulsions compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Hepcidin analogues of the present invention may also be administered in liposomes or other lipid-based carriers. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a hepcidin analogue of the present invention, stabilizers, preservatives, excipients, and the like. In certain embodiments, the lipids comprise phospholipids, including the phosphatidyl cholines (lecithins) and serines, both natural and synthetic. Methods to form liposomes are known in the art.

Pharmaceutical compositions to be used in the invention suitable for parenteral administration may comprise sterile aqueous solutions and/or suspensions of the peptide inhibitors made isotonic with the blood of the recipient, generally using sodium chloride, glycerin, glucose, mannitol, sorbitol, and the like.

In some aspects, the invention provides a pharmaceutical composition for oral delivery. Compositions and hepcidin analogues of the instant invention may be prepared for oral administration according to any of the methods, techniques, and/or delivery vehicles described herein. Further, one having skill in the art will appreciate that the hepcidin analogues of the instant invention may be modified or integrated into a system or delivery vehicle that is not disclosed herein, yet is well known in the art and compatible for use in oral delivery of peptides.

In certain embodiments, formulations for oral administration may comprise adjuvants (e.g. resorcinols and/or nonionic surfactants such as polyoxyethylene oleyl ether and n-hexadecylpolyethylene ether) to artificially increase the permeability of the intestinal walls, and/or enzymatic inhibitors (e.g. pancreatic trypsin inhibitors, diisopropylfluorophosphate (DFF) or trasylol) to inhibit enzymatic degradation. In certain embodiments, the hepcidin analogue of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

In particular embodiments, oral dosage forms or unit doses compatible for use with the hepcidin analogues of the present invention may include a mixture of hepcidin analogue and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of hepcidin analogue, wherein the dosage form comprises at least one of a pill, a tablet, a capsule, a gel, a paste, a drink, a syrup, ointment, and suppository. In some instances, an oral dosage form is provided that is designed and configured to achieve delayed release of the hepcidin analogue in the subject's small intestine and/or colon.

In one embodiment, an oral pharmaceutical composition comprising a hepcidin analogue of the present invention comprises an enteric coating that is designed to delay release of the hepcidin analogue in the small intestine. In at least some embodiments, a pharmaceutical composition is provided which comprises a hepcidin analogue of the present invention and a protease inhibitor, such as aprotinin, in a delayed release pharmaceutical formulation. In some instances, pharmaceutical compositions of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In one embodiment, a pharmaceutical composition comprising a hepcidin analogue of the present invention is provided in an enteric coating, the enteric coating being designed to protect and release the pharmaceutical composition in a controlled manner within the subject's lower gastrointestinal system, and to avoid systemic side effects. In addition to enteric coatings, the hepcidin analogues of the instant invention may be encapsulated, coated, engaged or otherwise associated within any compatible oral drug delivery system or component. For example, in some embodiments a hepcidin analogue of the present invention is provided in a lipid carrier system comprising at least one of polymeric hydrogels, nanoparticles, microspheres, micelles, and other lipid systems.

To overcome peptide degradation in the small intestine, some embodiments of the present invention comprise a hydrogel polymer carrier system in which a hepcidin analogue of the present invention is contained, whereby the hydrogel polymer protects the hepcidin analogue from proteolysis in the small intestine and/or colon. The hepcidin analogues of the present invention may further be formulated for compatible use with a carrier system that is designed to increase the dissolution kinetics and enhance intestinal absorption of the peptide. These methods include the use of liposomes, micelles and nanoparticles to increase GI tract permeation of peptides.

Various bioresponsive systems may also be combined with one or more hepcidin analogue of the present invention to provide a pharmaceutical agent for oral delivery.

In some embodiments, a hepcidin analogue of the instant invention is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for a hepcidin analogue disclosed herein, wherein the surface of the hepcidin analogue surface is modified to comprise mucoadhesive properties through hydrogen bonds, polymers with linked mucins or/and hydrophobic interactions. These modified peptide molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the hepcidin analogue.

Other embodiments comprise a method for oral delivery of a hepcidin analogue of the present invention, wherein the hepcidin analogue is provided to a subject in combination with permeation enhancers that promote the transport of the peptides across the intestinal mucosa by increasing paracellular or transcellular permeation. For example, in one embodiment, a permeation enhancer is combined with a hepcidin analogue, wherein the permeation enhancer comprises at least one of a long-chain fatty acid, a bile salt, an amphiphilic surfactant, and a chelating agent. In one embodiment, a permeation enhancer comprising sodium N-[hydroxybenzoyl)amino] caprylate is used to form a weak noncovalent association with the hepcidin analogue of the instant invention, wherein the permeation enhancer favors membrane transport and further dissociation once reaching the blood circulation. In another embodiment, a hepcidin analogue of the present invention is conjugated to oligoarginine, thereby increasing cellular penetration of the peptide into various cell types. Further, in at least one embodiment a noncovalent bond is provided between a peptide inhibitor of the present invention and a permeation enhancer selected from the group consisting of a cyclodextrin (CD) and a dendrimers, wherein the permeation enhancer reduces peptide aggregation and increasing stability and solubility for the hepcidin analogue molecule.

Other embodiments of the invention provide a method for treating a subject with a hepcidin analogue of the present invention having an increased half-life. In one aspect, the present invention provides a hepcidin analogue having a half-life of at least several hours to one day in vitro or in vivo (e.g., when administered to a human subject) sufficient for daily (q.d.) or twice daily (b.i.d.) dosing of a therapeutically effective amount. In another embodiment, the hepcidin analogue has a half-life of three days or longer sufficient for weekly (q.w.) dosing of a therapeutically effective amount. Further, in another embodiment, the hepcidin analogue has a half-life of eight days or longer sufficient for bi-weekly (b.i.w.) or monthly dosing of a therapeutically effective amount. In another embodiment, the hepcidin analogue is derivatized or modified such that is has a longer half-life as compared to the underivatized or unmodified hepcidin analogue. In another embodiment, the hepcidin analogue contains one or more chemical modifications to increase serum half-life.

When used in at least one of the treatments or delivery systems described herein, a hepcidin analogue of the present invention may be employed in pure form or, where such forms exist, in pharmaceutically acceptable salt form.

Dosages

The total daily usage of the hepcidin analogues and compositions of the present invention can be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, the age, body weight, general health, sex and diet of the patient; d) the time of administration, route of administration, and rate of excretion of the specific hepcidin analogue employed; e) the duration of the treatment; f) drugs used in combination or coincidental with the specific hepcidin analogue employed, and like factors well known in the medical arts.

In particular embodiments, the total daily dose of the hepcidin analogues of the invention to be administered to a human or other mammal host in single or divided doses may be in amounts, for example, from 0.0001 to 300 mg/kg body weight daily or 1 to 300 mg/kg body weight daily. In certain embodiments, a dosage of a hepcidin analogue of the present invention is in the range from about 0.0001 to about 100 mg/kg body weight per day, such as from about 0.0005 to about 50 mg/kg body weight per day, such as from about 0.001 to about 10 mg/kg body weight per day, e.g. from about 0.01 to about 1 mg/kg body weight per day, administered in one or more doses, such as from one to three doses. In particular embodiments, a total dosage is about 1 mg, about 2 mg, about 3 mg, about 4 mg, about 5 mg, about 6 mg, about 7 mg, about 8 mg, about 9 mg, or about 10 mg about once or twice weekly, e.g., for a human patient. In particular embodiments, the total dosage is in the range of about 1 mg to about 5 mg, or about 1 mg to about 3 mg, or about 2 mg to about 3 mg per human patient, e.g., about once weekly.

In various embodiments, a hepcidin analogue of the invention may be administered continuously (e.g. by intravenous administration or another continuous drug administration method), or may be administered to a subject at intervals, typically at regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like.

Such regular hepcidin analogue administration regimens of the invention may, in certain circumstances such as, e.g., during chronic long-term administration, be advantageously interrupted for a period of time so that the medicated subject reduces the level of or stops taking the medication, often referred to as taking a "drug holiday." Drug holidays are useful for, e.g., maintaining or regaining sensitivity to a drug especially during long-term chronic treatment, or to reduce unwanted side-effects of long-term chronic treatment of the subject with the drug. The timing of a drug holiday depends on the timing of the regular dosing regimen and the purpose for taking the drug holiday (e.g., to regain drug sensitivity and/or to reduce unwanted side effects of continuous, long-term administration). In some embodiments, the drug holiday may be a reduction in the dosage of the drug (e.g. to below the therapeutically effective amount for a certain interval of time). In other embodiments, administration of the drug is stopped for a certain interval of time before administration is started again using the same or a different dosing regimen (e.g. at a lower or higher dose and/or frequency of administration). A drug holiday of the invention may thus be selected from a wide range of time-periods and dosage regimens. An exemplary drug holiday is two or more days, one or more weeks, or one or more months, up to about 24 months of drug holiday. So, for example, a regular daily dosing regimen with a peptide, a peptide analogue, or a dimer of the invention may, for example, be interrupted by a drug holiday of a week, or two weeks, or four weeks, after which time the preceding, regular dosage regimen (e.g. a daily or a weekly dosing regimen) is resumed. A variety of other drug holiday regimens are envisioned to be useful for administering the hepcidin analogues of the invention.

Thus, the hepcidin analogues may be delivered via an administration regime which comprises two or more administration phases separated by respective drug holiday phases.

During each administration phase, the hepcidin analogue is administered to the recipient subject in a therapeutically effective amount according to a pre-determined administration pattern. The administration pattern may comprise continuous administration of the drug to the recipient subject over the duration of the administration phase. Alternatively, the administration pattern may comprise administration of a plurality of doses of the hepcidin analogue to the recipient subject, wherein said doses are spaced by dosing intervals.

A dosing pattern may comprise at least two doses per administration phase, at least five doses per administration phase, at least 10 doses per administration phase, at least 20 doses per administration phase, at least 30 doses per administration phase, or more.

Said dosing intervals may be regular dosing intervals, which may be as set out above, including once daily, twice daily, once every two, three, four, five or six days, once or twice weekly, once or twice monthly, or a regular and even less frequent dosing interval, depending on the particular dosage formulation, bioavailability, and pharmacokinetic profile of the hepcidin analogue of the present invention.

An administration phase may have a duration of at least two days, at least a week, at least 2 weeks, at least 4 weeks, at least a month, at least 2 months, at least 3 months, at least 6 months, or more.

Where an administration pattern comprises a plurality of doses, the duration of the following drug holiday phase is longer than the dosing interval used in that administration pattern. Where the dosing interval is irregular, the duration of the drug holiday phase may be greater than the mean interval between doses over the course of the administration phase. Alternatively the duration of the drug holiday may be longer than the longest interval between consecutive doses during the administration phase.

The duration of the drug holiday phase may be at least twice that of the relevant dosing interval (or mean thereof), at least 3 times, at least 4 times, at least 5 times, at least 10 times, or at least 20 times that of the relevant dosing interval or mean thereof.

Within these constraints, a drug holiday phase may have a duration of at least two days, at least a week, at least 2 weeks, at least 4 weeks, at least a month, at least 2 months, at least 3 months, at least 6 months, or more, depending on the administration pattern during the previous administration phase.

An administration regime comprises at least 2 administration phases.

Consecutive administration phases are separated by respective drug holiday phases. Thus the administration regime may comprise at least 3, at least 4, at least 5, at least 10, at least 15, at least 20, at least 25, or at least 30 administration phases, or more, each separated by respective drug holiday phases.

Consecutive administration phases may utilise the same administration pattern, although this may not always be desirable or necessary. However, if other drugs or active agents are administered in combination with a hepcidin analogue of the invention, then typically the same combination of drugs or active agents is given in consecutive administration phases. In certain embodiments, the recipient subject is human.

In some embodiments, the present invention provides compositions and medicaments comprising at least one hepcidin analogue as disclosed herein. In some embodiments, the present invention provides a method of manufacturing medicaments comprising at least one hepcidin analogue as disclosed herein for the treatment of diseases of iron metabolism, such as iron overload diseases. In some embodiments, the present invention provides a method of manufacturing medicaments comprising at least one hepcidin analogue as disclosed herein for the treatment of diabetes (Type I or Type II), insulin resistance, or glucose intolerance. Also provided are methods of treating a disease of iron metabolism in a subject, such as a mammalian subject, and preferably a human subject, comprising administering at least one hepcidin analogue, or composition as disclosed herein to the subject.

In some embodiments, the hepcidin analogue or the composition is administered in a therapeutically effective amount. Also provided are methods of treating diabetes (Type I or Type II), insulin resistance, or glucose intolerance in a subject, such as a mammalian subject, and preferably a human subject, comprising administering at least one hepcidin analogue or composition as disclosed herein to the subject. In some embodiments, the hepcidin analogue or composition is administered in a therapeutically effective amount.

In some embodiments, the invention provides a process for manufacturing a hepcidin analogue or a hepcidin analogue composition (e.g., a pharmaceutical composition), as disclosed herein.

In some embodiments, the invention provides a device comprising at least one hepcidin analogue of the present invention, or pharmaceutically acceptable salt or solvate thereof for delivery of the hepcidin analogue to a subject.

In some embodiments, the present invention provides methods of binding a ferroportin or inducing ferroportin internalization and degradation which comprises contacting the ferroportin with at least one hepcidin analogue, or hepcidin analogue composition as disclosed herein.

In some embodiments, the present invention provides kits comprising at least one hepcidin analogue, or hepcidin analogue composition (e.g., pharmaceutical composition) as disclosed herein packaged together with a reagent, a device, instructional material, or a combination thereof.

In some embodiments, the present invention provides a method of administering a hepcidin analogue or hepcidin analogue composition (e.g., pharmaceutical composition) of the present invention to a subject via implant or osmotic pump, by cartridge or micro pump, or by other means appreciated by the skilled artisan, as well-known in the art. In some embodiments, the present invention provides complexes which comprise at least one hepcidin analogue as disclosed herein bound to a ferroportin, preferably a human ferroportin, or an antibody, such as an antibody which specifically binds a hepcidin analogue as disclosed herein, Hep25, or a combination thereof.

In some embodiments, the hepcidin analogue of the present invention has a measurement (e.g., an $EC_{50}$) of less than 500 nM within the FPN internalization assay. As a skilled person will realize, the function of the hepcidin analogue is dependent on the tertiary structure of the hepcidin analogue and the binding surface presented. It is therefore possible to make minor changes to the sequence encoding the hepcidin analogue that do not affect the fold or are not on the binding surface and maintain function. In other embodiments, the present invention provides a hepcidin analogue having 85% or higher (e.g., 85%, 90%, 91%, 92%, 93%, 94%, 95%, 96%, 97%, 98%, 99%, or 99.5%) identity or homology to an amino acid sequence of any hepcidin analogue described herein that exhibits an activity (e.g., hepcidin activity), or lessens a symptom of a disease or indication for which hepcidin is involved.

In other embodiments, the present invention provides a hepcidin analogue having 85% or higher (e.g., 85%, 90%, 91%, 92%, 93%, 94%, 95%, 96%, 97%, 98%, 99%, or 99.5%) identity or homology to an amino acid sequence of any hepcidin analogue presented herein, or a peptide according to any one of the formulae or hepcidin analogues described herein.

In some embodiments, a hepcidin analogue of the present invention may comprise functional fragments or variants thereof that have at most 10, 9, 8, 7, 6, 5, 4, 3, 2, or 1 amino acid substitutions compared to one or more of the specific peptide analogue sequences recited herein.

In addition to the methods described in the Examples herein, the hepcidin analogues of the present invention may be produced using methods known in the art including chemical synthesis, biosynthesis or in vitro synthesis using recombinant DNA methods, and solid phase synthesis. See e.g. Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, Ill., which are herein incorporated by reference. The hepcidin analogues of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and Scopes (1982) Protein Purification, Springer- Verlag, NY, which are herein incorporated by reference. Alternatively, the hepcidin analogues of the present invention may be made by recombinant DNA techniques known in the art. Thus, polynucleotides that encode the polypeptides of the present invention are contemplated herein. In certain preferred embodiments, the polynucleotides are isolated. As used herein "isolated polynucleotides" refers to polynucleotides that are in an environment different from that in which the polynucleotide naturally occurs.

EXAMPLES

The following examples demonstrate certain specific embodiments of the present invention. The following examples were carried out using standard techniques that are well known and routine to those of skill in the art, except where otherwise described in detail. It is to be understood that these examples are for illustrative purposes only and do not purport to be wholly definitive as to conditions or scope of the invention. As such, they should not be construed in any way as limiting the scope of the present invention.

ABBREVIATIONS

DCM: dichloromethane
DMF: N,N-dimethylformamide
NMP: N-methylpyrolidone
HBTU: O-(Benzotriazol-1-yl)-N,N,N',N'-tetramethyluronium hexafluorophosphate
HATU: 2-(7-aza-1H-benzotriazole-1-yl)-1,1,3,3-tetramethyluronium hexafluorophosphate
DCC: Dicyclohexylcarbodiimide
NHS: N-hydroxysuccinimide
DIPEA: diisopropylethylamine
EtOH: ethanol
Et2O: diethyl ether
Hy: hydrogen
TFA: trifluoroacetic acid
TIS: triisopropylsilane
ACN: acetonitrile
HPLC: high performance liquid chromatography
ESI-MS: electron spray ionization mass spectrometry
PBS: phosphate-buffered saline
Boc: t-butoxycarbonyl
Fmoc: Fluorenylmethyloxycarbonyl
Acm: acetamidomethyl
IVA: Isovaleric acid (or Isovaleryl)

K( ): In the peptide sequences provided herein, wherein a compound or chemical group is presented in parentheses directly after a Lysine residue, it is to be understood that the compound or chemical group in the parentheses is a side chain conjugated to the Lysine residue. So, e.g., but not to be limited in any way, K-[(PEG8)]- indicates that a PEG8 moiety is conjugated to a side chain of this Lysine.

Palm: Indicates conjugation of a palmitic acid (palmitoyl).

As used herein "C( )" refers to a cysteine residue involved in a particular disulfide bridge. For example, in Hepcidin, there are four disulfide bridges: the first between the two C(1) residues; the second between the two C(2) residues; the third between the two C(3) residues; and the fourth between the two C(4) residues. Accordingly, in some embodiments, the sequence for Hepcidin is written as follows:

(SEQ ID NO: 156)
Hy-DTHFPIC(1)IFC(2)C(3)GC(2)C(4)HRSKC(3)GMC(4)C(1)

KT-OH;

Example 1

Synthesis of Peptide Analogues

Unless otherwise specified, reagents and solvents employed in the following were available commercially in standard laboratory reagent or analytical grade, and were used without further purification.

Procedure for Solid-Phase Synthesis of Peptides Method A

Peptide analogues of the invention were chemically synthesized using optimized 9-fluorenylmethoxy carbonyl (Fmoc) solid phase peptide synthesis protocols. For C-terminal amides, rink-amide resin was used, although wang and trityl resins were also used to produce C-terminal acids. The side chain protecting groups were as follows: Glu, Thr and Tyr: O-tButyl; Trp and Lys: t-Boc (t-butyloxycarbonyl); Arg: N-gamma-2,2,4,6,7-pentamethyldihydrobenzofuran-5-sulfonyl; His, Gln, Asn, Cys: Trityl. For selective disulfide bridge formation, Acm (acetamidomethyl) was also used as a Cys protecting group. For coupling, a four to ten-fold excess of a solution containing Fmoc amino acid, HBTU and DpaEA (1:1:1.1) in DMF was added to swelled resin [HBTU: O-(Benzotriazol-1-yl)-N,N,N',N'-tetramethyluronium hexafluorophosphate; DpaEA: diisopropylethylamine; DMF: dimethylformamide]. HATU (O-(7-azabenzotriazol-1-yl)-1,1,3,3,-tetramethyluronium hexafluorophosphate) was used instead of HBTU to improve coupling efficiency in difficult regions. Fmoc protecting group removal was achieved by treatment with a DMF, piperidine (2:1) solution.

Method B

Alternatively, peptides were synthesized utilizing the CEM liberty Blue Microwave assisted peptide synthesizer. Using the Liberty Blue, FMOC deprotection was carried out by addition of 20% 4-methylpiperdine in DMF with 0.1M Oxyma in DMF and then heating to 900° C. using microwave irradiation for 4 min. After DMF washes the FMOC-amino acids were coupled by addition of 0.2M amino acid (4-6 eq), 0.5M DIC (4-6 eq) and 1M Oxyma (with 0.1M DIEA) 4-6 eq (all in DMF). The coupling solution is heated using microwave radiation to 90° C. for 4 min. A second coupling is employed when coupling Arg or other sterically hindered amino acids. When coupling with histidine, the reaction is heated to 50° C. for 10 min. The cycles are repeated until the full length peptide is obtained.

Procedure for Cleavage of Peptides Off Resin

Side chain deprotection and cleavage of the peptide analogues of the invention (e.g., Compound No. 2) was achieved by stirring dry resin in a solution containing trifluoroacetic acid, water, ethanedithiol and tri-isopropylsilane (90:5:2.5:2.5) for 2 to 4 hours. Following TFA removal, peptide was precipitated using ice-cold diethyl ether. The solution was centrifuged and the ether was decanted, followed by a second diethyl ether wash. The peptide was dissolved in an acetonitrile, water solution (1:1) containing 0.1% TFA (trifluoroacetic acid) and the resulting solution was filtered. The linear peptide quality was assessed using electrospray ionization mass spectrometry (ESI-MS).

Procedure for Purification of Peptides

Purification of the peptides of the invention (e.g., Compound No. 2) was achieved using reverse-phase high performance liquid chromatography (RP-HPLC). Analysis was performed using a C18 column (3 μm, 50×2 mm) with a flow rate of 1 mL/min. Purification of the linear peptides was achieved using preparative RP-HPLC with a C18 column (5 μm, 250×21.2 mm) with a flow rate of 20 mL/min. Separation was achieved using linear gradients of buffer B in A (Buffer A: Aqueous 0.05% TFA; Buffer B: 0.043% TFA, 90% acetonitrile in water).

Procedure for Oxidation of Peptides

Method A (Single disulfide oxidation). Oxidation of the unprotected peptides of the invention was achieved by adding drop-wise iodine in MeOH (1 mg per 1 mL) to the peptide in a solution (ACN: $H_2O$, 7: 3, 0.5% TFA). After stirring for 2 min, ascorbic acid portion wise was added until the solution was clear and the sample was immediately loaded onto the HPLC for purification.

Method B (Selective oxidation of two disulfides). When more than one disulfide was present, selective oxidation was often performed. Oxidation of the free cysteines was achieved at pH 7.6 $NH_4CO_3$ solution at 1 mg/10 mL of peptide. After 24 h stirring and prior to purification the solution was acidified to pH 3 with TFA followed by lyophilization. The resulting single oxidized peptides (with ACM protected cysteines) were then oxidized/selective deprotection using iodine solution. The peptide (1 mg per 2 mL) was dissolved in $MeOH/H_2O$, 80:20 iodine dissolved in the reaction solvent was added to the reaction (final concentration: 5 mg/mL) at room temperature. The solution was stirred for 7 minutes before ascorbic acid was added portion wise until the solution is clear. The solution was then loaded directly onto the HPLC.

Method C (Native oxidation). When more than one disulfide was present and when not performing selective oxidations, native oxidation was performed. Native oxidation was achieved with 100 mM $NH_4CO_3$ (pH7.4) solution in the presence of oxidized and reduced glutathione (peptide/GSH/GSSG, 1:100:10 molar ratio) of (peptide: GSSG: GSH, 1:10, 100). After 24 h stirring and prior to RP-HPLC purification the solution was acidified to pH 3 with TFA followed by lyophilization.

Procedure of Cysteine Oxidation to Produce Dimers.

Oxidation of the unprotected peptides of the invention was achieved by adding drop-wise iodine in MeOH (1 mg per 1 mL) to the peptide in a solution (ACN: $H_2O$, 7: 3, 0.5% TFA). After stirring for 2 min, ascorbic acid portion wise was added until the solution was clear and the sample was immediately loaded onto the HPLC for purification.

Procedure for Dimerization.

Glyoxylic acid (DIG), IDA, or Fmoc-β-Ala-IDA was pre-activated as the N-hydoxysuccinimide ester by treating 1 equivalent (abbreviated "eq") of the acid with 2.2 eq of both N-hydoxysuccinimide (NHS) and dicyclohexyl carbodiimide (DCC) in NMP (N-methyl pyrolidone) at a 0.1 M final concentration. For the PEG13 and PEG25 linkers, these chemical entities were purchased pre-formed as the activated succinimide ester. The activated ester ~ 0.4 eq was added slowly to the peptide in NMP (1 mg/mL) portionwise. The solution was left stirring for 10 min before 2-3 additional aliquots of the linker ~0.05 eq were slowly added. The solution was left stirring for a further 3 h before the solvent was removed under vaccuo and the residue was purified by reverse phase HPLC. An additional step of stirring the peptide in 20% piperidine in DMF (2×10 min) before an additional reverse phase HPLC purification was performed.

One of skill in the art will appreciate that standard methods of peptide synthesis may be used to generate the compounds of the invention.

Linker Activation and Dimerization

Peptide monomer subunits were linked to form hepcidin analogue peptide dimers as described below.

Small Scale DIG Linker Activation Procedure: 5 mL of NMP was added to a glass vial containing IDA diacid (304.2 mg, 1 mmol), N-hydroxysuccinimide (NHS, 253.2 mg, 2.2 eq. 2.2 mmol) and a stirring bar. The mixture was stirred at room temperature to completely dissolve the solid starting materials. N, N'-Dicyclohexylcarbodiimide (DCC, 453.9 mg, 2.2 eq., 2.2 mmol) was then added to the mixture. Precipitation appeared within 10 min and the reaction mixture was further stirred at room temperature overnight. The reaction mixture was then filtered to remove the precipitated dicyclohexylurea (DCU). The activated linker was kept in a closed vial prior to use for dimerization. The nominal concentration of the activated linker was approximately 0.20 M.

For dimerization using PEG linkers, there was no pre-activation step involved. Commercially available pre-activated bi-functional PEG linkers were used.

Dimerization Procedure: 2 mL of anhydrous DMF was added to a vial containing peptide monomer (0.1 mmol). The pH of the peptide was the adjusted to 8-9 with DIEA. Activated linker (IDA or PEG13, PEG 25) (0.48eq relative to monomer, 0.048 mmol) was then added to the monomer solution. The reaction mixture was stirred at room temperature for one hour. Completion of the dimerization reaction was monitored using analytical HPLC. The time for completion of dimerization reaction varied depending upon the linker. After completion of reaction, the peptide was precipitated in cold ether and centrifuged. The supernatant ether layer was discarded. The precipitation step was repeated twice. The crude dimer was then purified using reverse phase HPLC (Luna C18 support, 10u, 100A, Mobile phase A: water containing 0.1% TFA, mobile phase B: Acetonitrile (ACN) containing 0.1% TFA, gradient of 15% B and change to 45% B over 60 min, flow rate 15 ml/min). Fractions containing pure product were then freeze-dried on a lyophilizer.

Conjugation of Half-Life Extension Moieties

Conjugation of peptides were performed on resin. Lys (ivDde) was used as the key amino acid. After assembly of the peptide on resin, selective deprotection of the ivDde group occurred using 3×5 min 2% hydrazine in DMF for 5 min. Activation and acylation of the linker using HBTU, DIEA 1-2 equivalents for 3 h, and Fmoc removal followed by a second acylation with the lipidic acid gave the conjugated peptide.

Example 2

Activity of Peptide Analogues

Peptide analogues were tested in vitro for induction of internalization of the human ferroportin protein. Following internalization, the ferroporin protein is degraded. The assay used (FPN activity assay) measures a decrease in fluorescence of the receptor.

The cDNA encoding the human ferroportin (SLC40A1) was cloned from a cDNA clone from Origene (NM_014585). The DNA encoding the ferroportin was amplified by PCR using primers also encoding terminal restriction sites for subcloning, but without the termination codon. The ferroportin receptor was subcloned into a mammalian GFP expression vector containing a neomycin (G418) resistance marker in such that the reading frame of the ferroportin was fused in frame with the GFP protein. The fidelity of the DNA encoding the protein was confirmed by DNA sequencing. HEK293 cells were used for transfection of the ferroportin-GFP receptor expression plasmid. The cells were grown according to standard protocol in growth medium and transfected with the plasmids using Lipofectamine (manufacturer's protocol, Invitrogen). The cells stably expressing ferroportin-GFP were selected using G418 in the growth medium (in that only cells that have taken up and incorporated the cDNA expression plasmid survive) and sorted several times on a Cytomation MoFlo™ cell sorter to obtain the GFP-positive cells (488 nm/530 nm). The cells were propagated and frozen in aliquots.

To determine activity of the hepcidin analogues (compounds) on the human ferroportin, the cells were incubated in 96 well plates in standard media, without phenol red. Compound was added to desired final concentration for at least 18 hours in the incubator. Following incubation, the remaining GFP-fluorescence was determined either by whole cell GFP fluorescence (Envision plate reader, 485/535 filter pair), or by Beckman Coulter Quanta™ flow cytometer (express as Geometric mean of fluorescence intensity at 485 nm/525 nm). Compound was added to desired final concentration for at least 18 hours but no more than 24 hours in the incubator.

In certain experiments, reference compounds included native Hepcidin, Mini-Hepcidin, and $R^1$-Mini-Hepcidin, which is an analog of mini-hepcidin. The "RI" in RI-Mini-Hepcidin refers to Retro Inverse. A retro inverse peptide is a peptide with a reversed sequence in all D amino acids. An example is that Hy-Glu-Thr-His-$NH_2$ becomes Hy-DHis-DThr-DGlu-$NH_2$. The $EC_{50}$ of these reference compounds for ferroportin internalization/degradation was determined according to the FPN activity assay described above. These peptides served as control standards.

TABLE 9

| | Reference compounds | |
|---|---|---|
| Name | Sequence | Potency EC50 (nM) |
| Hepcidin | Hy-DTHFPIC(1)IFC(2)C(3)GC(2)C(4)HRSKC(3)GMC(4)C(1)KT-OH (SEQ ID NO: 256) | 34 |
| Mini-Hepcidin 1-9 | Hy-DTHFPICIF-$NH_2$ (SEQ ID NO: 257) | 712 |
| RI-Mini Hepcidin | Hy-DPhe-DIle-DCys-DIle-DPro-DPhe-DHis-DThr-DAsp-$NH_2$ (SEQ ID NO: 258) | >10 μM |
| Ref. Compd 1 | Isovaleric acid-DTHFPCIKF-Lys[PEG11-Palm]-PRSKGCK-$NH_2$ (SEQ ID NO: 1) | 30 |
| Ref. Compd. 2 | Isovaleric acid-DTHFPCIKF-Lys[PEG11-Palm]-PRSK-[SAR]-CK-$NH_2$ (SEQ ID NO: 2) | 13 |

The potency $EC_{50}$ values (nM) determined for various peptide analogues of the present invention are provided in Tables 3A, 3B, and 4. These values were determined as described herein.

Example 3

In Vivo Validation of Peptide Analogues

Hepcidin analogues of the present invention were tested for in vivo activity, to determine their ability to decrease free $Fe^{2+}$ in serum.

A hepcidin analogue or vehicle control were administered to mice (n=3/group) at 1000 nmol/kg either intravenously or subcutaneously. Serum samples were taken from groups of mice administered with the hepcidin analog at 30 min, 1 h, 2 h, 4 h, 10 h, 24 h, 30 h, 36 h, and 48 h post-administration. Iron content in plasma/serum was measured using a colorimetric assay on the Cobas c 111 according to instructions from the manufacturer of the assay (assay: IRON2: ACN 661).

In another experiment, various hepcidin analogues or vehicle control were administered to mice (n=3/group) at 1000 nmol/kg subcutaneously. Serum samples were taken from groups of mice administered with vehicle or hepcidin analog at 30 h and 36 h post-administration. Iron content in plasma/serum was measured using a colorimetric assay on the Cobas c 111 according to instructions from the manufacturer of the assay (assay: IRON2: ACN 661).

These studies demonstrate that hepcidin analogues of the present invention reduce serum iron levels for at least 30 hours, thus demonstrating their increased serum stability.

Example 4

In Vitro Validation of Peptide Analogues

Based in part on the structure activity relationships (SAR) determined from the results of the experiments described herein, a variety of Hepcidin-like peptides of the present invention were synthesized using the method described in Example 1, and in vitro activity was tested as described in Example 2. Reference compounds included native Hepcidin, Mini-Hepcidin, $R^1$-Mini-Hepcidin, Reference Compound 1 and Reference Compound 2. $EC_{50}$ values of the peptides are shown in summary Table 3A and Table 3B.

Example 5

Plasma Stability

Plasma stability experiments were undertaken to complement the in vivo results and assist in the design of potent, stable Ferroportin agonists. In order to predict the stability in rat and mouse plasma, ex vivo stability studies were initially performed in these matrices.

Peptides of interest (20 μM) were incubated with pre-warmed plasma (BioreclamationIVT) at 37° C. Aliquots were taken at various time points up to 24 hours (e.g. 0, 0.25, 1, 3, 6 and 24 hr), and immediately quenched with 4 volumes of organic solvent (acetonitrile/methanol (1:1) and 0.1% formic acid, containing 1 μM internal standard). Quenched samples were stored at 4° C. until the end of the experiment and centrifuged at 17,000 g for 15 minutes. The supernatant were diluted 1:1 with deionized water and analyzed using LC-MS. Percentage remaining at each time point was calculated based on the peak area ratio (analyte over internal standard) relative to the initial level at time zero. Half-lives were calculated by fitting to a first-order exponential decay equation using GraphPad. Table 9 shows the results of this study.

TABLE 9

Plasma Stability of Representative Compounds

| Compound ID# | Stability in Mouse Plasma (hr) | Stability in Rat Plasma (hr) |
|---|---|---|
| 10 | | 3.83 |
| 27 | | 24 |
| 80 | 11 | 3.5 |
| 86 | 15.8 | |
| 105 | 17.3 | 4.34 |
| 117 | | 3.7 |
| 118 | | 3.05 |
| 121 | | 3.3 |
| 122 | | 3.63 |
| 131 | | 3 |
| 132 | | 3.9 |
| 152 | | 24 |
| 154 | | 24 |
| 155 | | 1 |
| 156 | | 4.23 |
| 157 | | 24 |
| 158 | | 24 |
| 165 | | 14.8 |

Example 6

Reduction of Serum Iron in Mice

Figure 1B:
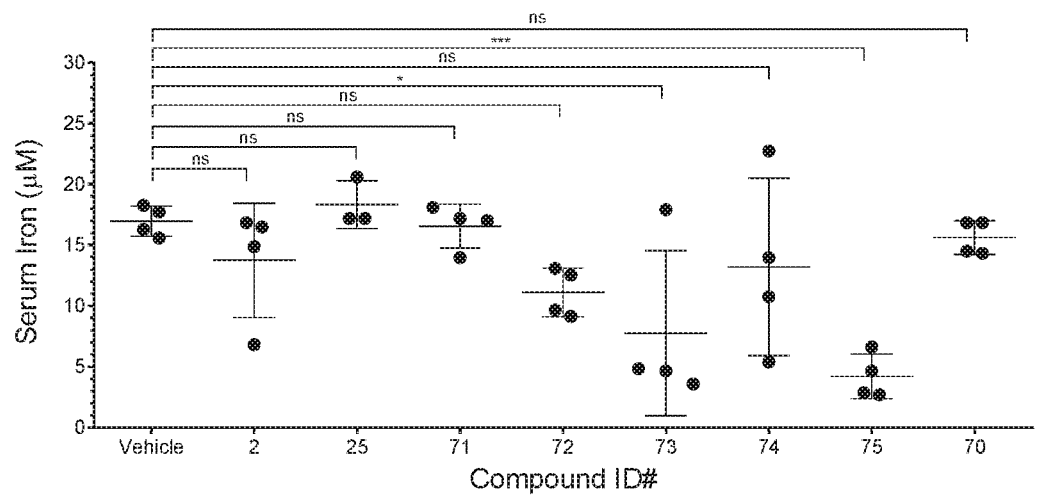

Hepcidin mimetic compounds, designed for oral stability, were tested for systemic absorption by PO dosing in a wild type mouse model C57BL/6. The animals were acclimatized in normal rodent diet for 4-5 days prior to study start and fasted overnight prior to study start. Groups of 4 animals each received either Vehicle or the Compounds as shown in FIGS. 1A & 1B. The compounds were formulated in Saline at a concentration of 5 mg/mL. The mice received dosing solution via oral gavage at volume of 200 μl per animal of body weight 20 g. Each group received 1 dose of compounds at 50 mg/kg/dose. The group marked for vehicle received only the formulation. Blood was drawn at 4 hours post-dose and serum was prepared for PK and PD measurements. The compound concentration was measured by mass spectrometry method and iron concentration in the samples was measured using the colorimetric method on Roche cobas c system.

In this triage experiment, multiple compounds were tested (Compound ID #2, 25, 71, 72, 73, 74, 75, 70) for systemic serum iron reduction with oral dosing of the compounds. The compound ID #73 and 75 showed significant reduction in serum iron, FIG. 1B, and also greater than 100 ng/mL serum concentration (except for one animal dosed with Cmpd #73) as shown in FIG. 1A. There was a good correlation between the observed serum concentration of compounds #73 & #75 and the serum iron reduction in the animals.

Example 7

Reduction of Serum Iron in Mice

In another experiment, a new set of compounds were tested for systemic absorption by PO dosing in a wild type mouse model C57BL/6. The animals were acclimatized in normal rodent diet for 4-5 days prior to study start. Overnight prior to the first dose, the mice were switched to a low iron diet (with 2 ppm iron) and this diet was maintained during the rest of the study. Groups of 5 animals each received either Vehicle or the Compounds as shown in FIG. 1. The concentration of compounds was at 30 mg/mL, formulated in 0.7% NaCl+10 mM NaAcetate buffer. Food was withdrawn around 2 hours prior to each dose to ensure that the stomach was clear of any food particles prior to PO dosing. The mice received dosing solution via oral gavage at volume of 200 µl per animal of body weight 20 g. Each group received 2 doses of compound at 300 mg/kg/dose, on successive days. The group marked for vehicle received only the formulation. Blood was drawn at 4.5 hours post-last-dose and serum was prepared for PD measurements. Serum iron concentration was measured using the colorimetric method on Roche cobas c system.

Figure 2:
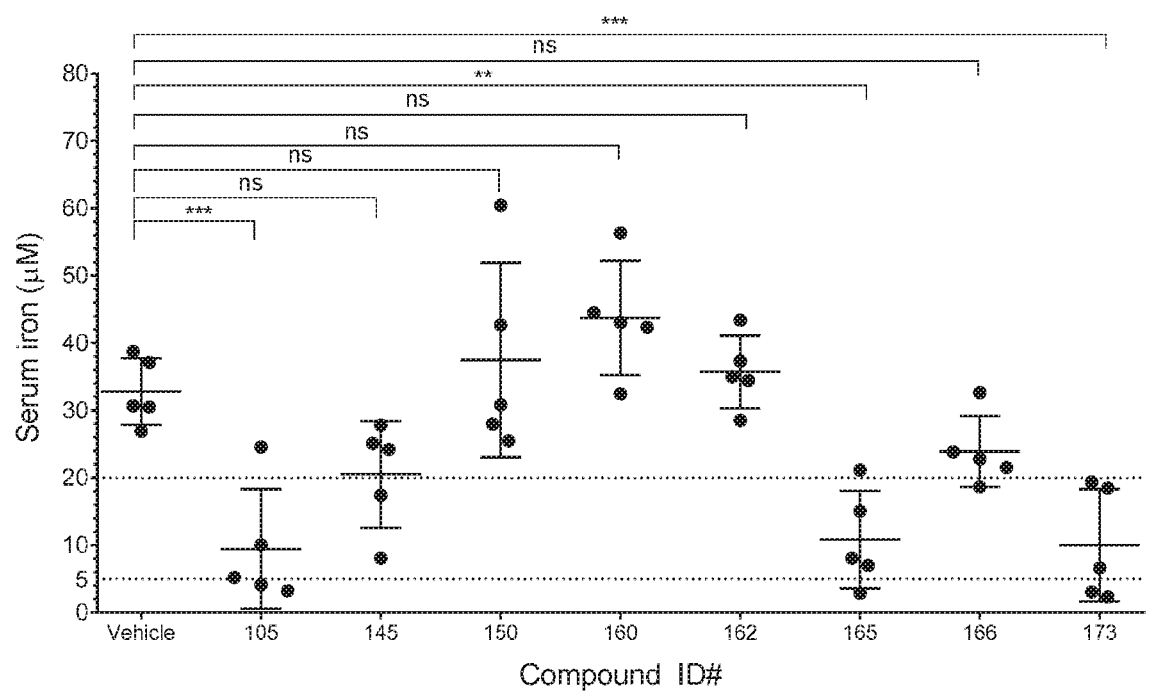
FIG. 2 shows the reduction of serum iron concentration after dosing of compounds ID 105, 145, 150, 160, 162, 165, 166, and 173 in mice.

In this triage experiment, multiple compounds were tested (Compound ID #105, 145, 150, 160, 162, 165, 166, 173) for systemic serum iron reduction with oral dosing of the compounds. The compound ID #105, 165 and 173 showed significant reduction in serum iron, FIG. 2.

Example 8

Figure 3:
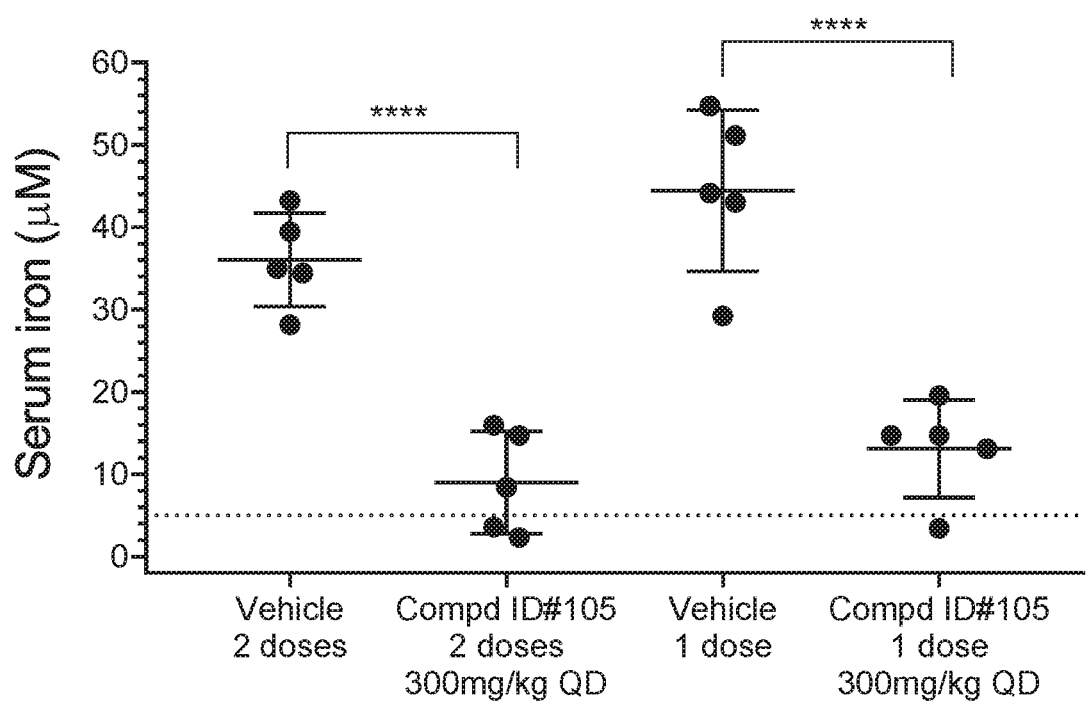
FIG. 3 shows PD effects for in vivo serum iron reducing abilities of Compound ID 105 in mice.

Pharmacodynamic Effects for the Serum Iron Reducing Abilities of Compound #105 in Mice In a second in vivo study, the Compound ID #105 was tested for pharmacodynamic effect with a single dose of 300 mg/kg/dose vs. 2 doses of 300 mg/kg over two days QD (once per day). C57BL/6 mice were acclimatized in normal rodent diet for 4-5 days prior to study start. Over the night prior to the first dose, the mice were switched to a low iron diet (with 2 ppm iron) and this diet was maintained during the rest of the study. Groups of 5 animals each received either Vehicle or the Compounds as shown in FIG. 3. The compound was formulated in 0.7% NaCl+10 mM NaAcetate buffer at 30 mg/mL concentration. Food was withdrawn around 2 hours prior to each dose to ensure that the stomach was clear of any food particles prior to PO dosing. The mice received dosing solution via oral gavage at volume of 200 µl per animal of body weight 20 g. As shown in the FIG. 3, both groups that were treated with Compound ID #105 showed significant reductions in serum iron concentration as compared to their respective vehicle groups.

Example 9

PK/PD Effects of Oral Dosing of Compound #105 in Mice

In another in vivo study with healthy Wild Type mouse model C57/BL6, Compound ID #105 was tested for PK and PD effect with multiple dosing over three days. The mice were maintained under normal rodent feed during the acclimatization and switched to iron-deficient diet (with ~2 ppm iron) one night prior to the first dose. Groups of 5 mice each received a total of 6 doses of either vehicle or CompoundID #105 at different dose strengths, in a BID format over three days. Mice were dosed via. oral gavage with Compound ID #105 formulated in 0.7% saline and 10 mM Sodium Acetate. The different groups received either vehicle, 150 mg/kg/dose BID, 75 mg/kg/dose BID, 37.5 mg/kg/dose BID, or 18.75 mg/kg/dose BID. An additional group received 100 mg/kg/dose BID in addition to a total of 100 mg/kg/day of compound in drinking water (DW), thereby receiving a total dose of 300 g/kg/day. At 3 hours post-last-dose the vehicle group marked for iron-challenge and all the CmpdID #105 dosed groups received iron solution via. oral gavage at 4 mg/kg iron per animal. Blood was collected at 90 min post-iron-challenge to prepare serum for PK and PD measurements. The compound concentration was measured by mass spectrometry method and iron concentration in the samples was measured using the colorimetric method on Roche cobas c system.

Figure 4A:
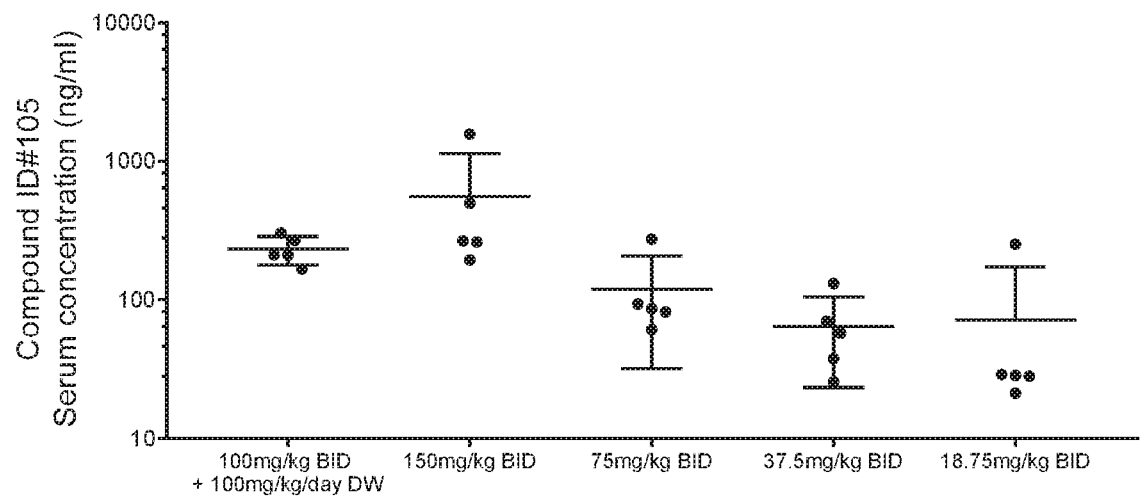
FIGS. 4A and 4B show PK and PD effect of serum iron reduction of Compound ID 105 in wild type mice.
Figure 4B:
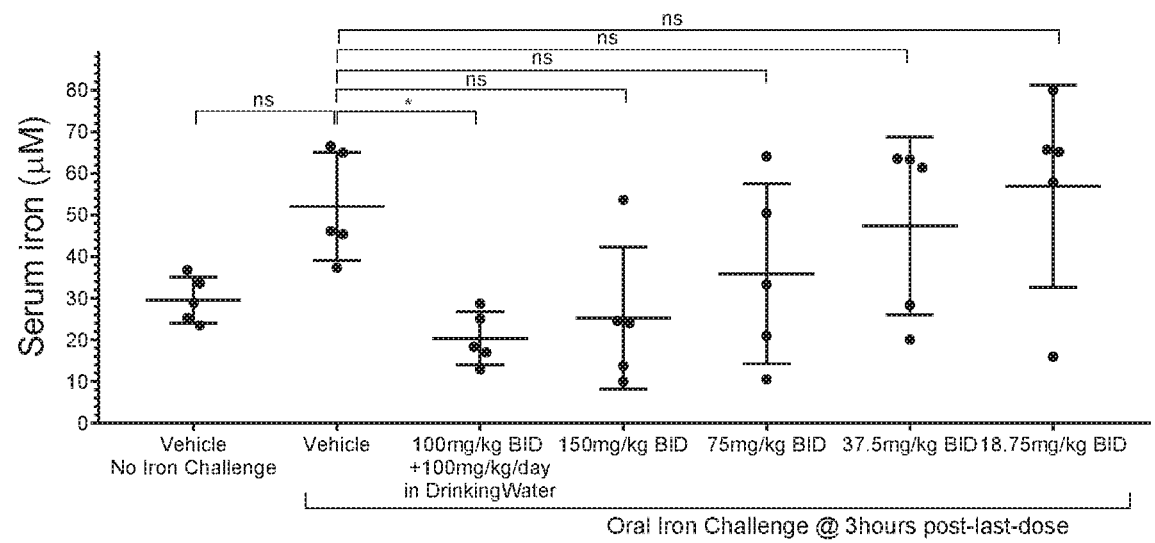

As shown in FIG. 4A, there was an increased absorption of the orally dosed Cmpd #105, when the dose was higher at 300 mg/kg/day (in groups receiving 150 mg/kg BID or 100 mg/kg BID+compound in drinking water). Also, there was a dose dependent decrease in this absorption, at 75 mg/kg BID and lower doses. In correlation, the PD effect of reduced absorption of orally provided iron solution was maximum in groups that received 300 mg/kg/day; i.e. groups dosed either 150 mg/kg BID or 100 mg/kg BID+100 mg/kg in DW, FIG. 4B. At lower doses, the PD effect was lower, in correlation with the observed serum iron concentration.

Example 10

Reduction of Serum Iron in Mice

In a separate triage, a new set of compounds were tested for their pharmacodynamic effect when dosed orally in the wild type mouse model C57BL/6. The animals were acclimatized in normal rodent diet for 4-5 days prior to study start. The group of 5 animals designated to receive two doses of Compound ID #105 received an iron-deficient diet (with 2-ppm iron) on the night prior to the first dose and all the other groups designated for single dose of different compounds were treated with iron-deficient diet for two nights prior to the compound dosing. The concentration of compounds in the dosing solution was at 30 mg/mL, formulated in 0.7% NaCl+10 mM NaAcetate buffer. Food was withdrawn around 2 hours prior to any dosing to ensure that the stomach was clear of any food particles prior to PO dosing. The mice received dosing solution via oral gavage at volume of 200 µl per animal of body weight 20 g. The group marked for vehicle received only the formulation. Blood was drawn at 4.5 hours post-last-dose and serum was prepared for PD measurements. Serum iron concentration was measured using the colorimetric method on Roche cobas c system.

Figure 5:
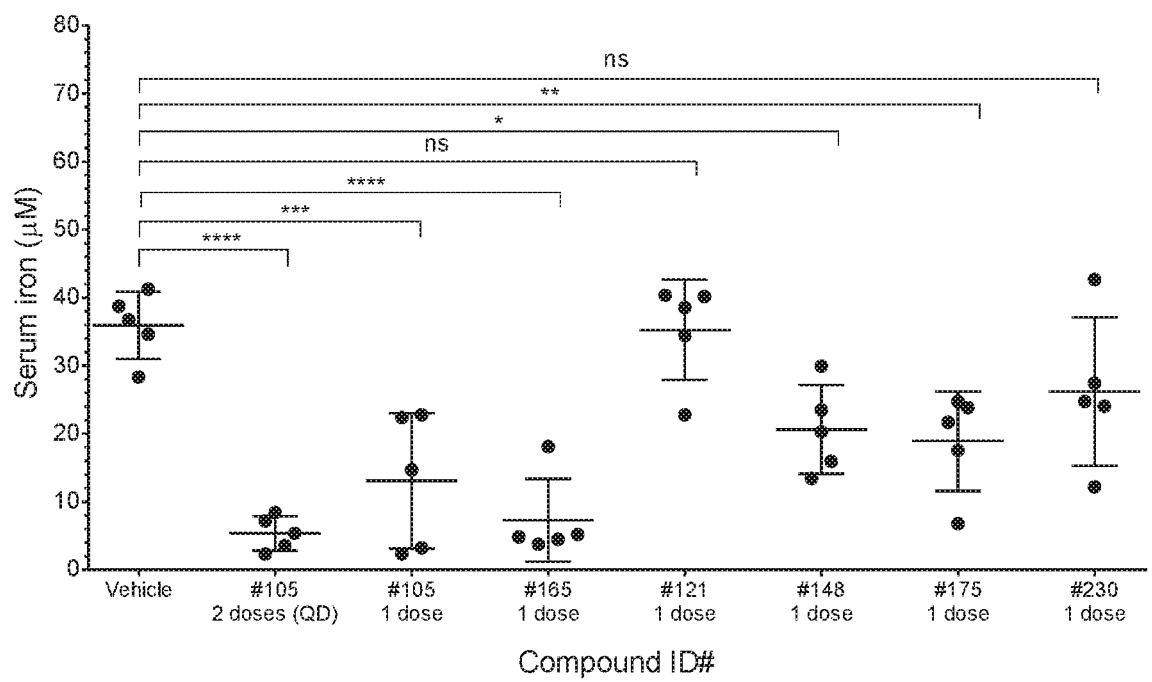
FIG. 5 shows the reduction of serum iron concentration with oral dosing of compounds ID 105, 165, 148, and 175 in mice.

In this triage experiment, multiple compounds were tested (Compound ID #105, 165, 121, 148, 175 and 230) for systemic serum iron reduction with oral dosing of the compounds. The compounds ID #105 (both single dose and 2-doses), 165, 148 and 175 showed significant reduction in serum iron, as shown in FIG. 5.

Example 11

Stability in Simulated Gastric Fluid

Blank SGF was prepared by adding 2 g sodium chloride, 7 mL hydrochloric acid (37%) in a final volume of 1 L water, and adjusted pH to 1.2.

SGF was prepared by dissolving 320 mg Pepsin (Sigma®, P6887, from Porcine Stomach Mucosa) in 100 mL Blank SGF and stirred at room temperature for 30 minutes. The solution was filtered through 0.45 µm membrane and aliquot and stored at −20° C.

Experimental compounds of interest (at a concentration of 20 µM) were incubated with pre-warmed SGF at 37° C. Aliquots were taken at various time points up to 24 hours (e.g., 0, 0.25, 1, 3, 6 and 24 hr), and immediately quenched with 4 volumes of organic solvent (acetonitrile/methanol (1:1) and 0.1% formic acid, containing 1 µM internal standard). Quenched samples were stored at 4° C. until the end of the experiment and centrifuged at 4,000 rpm for 10 minutes. The supernatant were diluted 1:1 with deionized water and analyzed using LC-MS. Percentage remaining at each time point was calculated based on the peak area ratio (analyte over internal standard) relative to the initial level at time zero. Half-lives were calculated by fitting to a first-order exponential decay equation using GraphPad.

Example 12

Stability in Simulated Intestinal Fluids

Blank FaSSIF was prepared by dissolving 0.348 g NaOH, 3.954 g sodium phosphate monobasic monohydrate and 6.186 g NaCl in a final volume of 1 liter water (pH adjusted to 6.5).

FaSSIF was prepared by dissolving 1.2 g porcine pancreatin (Chem-supply, PL378) in 100 mL Blank FaSSIF and stirred at room temperature for 30 minutes. The solution was filtered through 0.45 µm membrane and aliquot and stored at −20° C.

Experimental compounds of interest (20 µM) were incubated with pre-warmed FaSSIF (1% pancreatin in final incubation mixture) at 37° C. Aliquots were taken at various time points up to 24 hours (e.g. 0, 0.25, 1, 3, 6 and 24 hr), and immediately quenched with 4 volumes of organic solvent (acetonitrile/methanol (1:1) and 0.1% formic acid, containing 1 µM internal standard). Quenched samples were stored at 4° C. until the end of the experiment and centrifuged at 4,000 rpm for 10 minutes. The supernatant were diluted 1:1 with deionized water and analyzed using LC-MS. Percentage remaining at each time point was calculated based on the peak area ratio (analyte over internal standard) relative to the initial level at time zero. Half-lives were calculated by fitting to a first-order exponential decay equation using GraphPad. Results are shown in Tables 3A, 3B, and 4.

Example 13

Modified Experimental for Peptides Prone to "Non-Specific Binding"

Compounds of interest (at concentration of 20 µM) were mixed with pre-warmed FaSSIF (1% pancreatin in final working solution). The solution mixture was aliquoted and incubated at 37° C. The number of aliquots required was equivalent to the number of time points (e.g. 0, 0.25, 1, 3, 6 and 24 hr). At each time point, one aliquot was taken and immediately quenched with 4 volumes of organic solvent (acetonitrile/methanol (1:1) and 0.10% formic acid, containing 1 µM internal standard). The remaining steps were the same as the generic experimental.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. A hepcidin analogue comprising:

(a) a peptide according to Formula I:

$R^1$-Asp-Thr-His-B1-B2-B3-B4-Xaa1-B6-Xaa2-J-Y1-Y2-$R^2$(I)

or (b) a peptide dimer comprising two peptides according to Formula I, or a pharmaceutically acceptable salt thereof, wherein:

$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;

$R^2$ is —$NH_2$ or —OH;

Xaa1 is B5; and
  i) B5 is absent, Lys, D-Lys, Orn, homoSer, Gln, (D)Gln, Lys(Ac), Ile, Abu, Leu, Ala, D-Ala, bAla, or Nleu; and
  ii) Xaa2 is B7(L1Z);

or

Xaa1 is B5(L1Z); and
  i) B5 is Lys, D-Lys, Orn, homoSer, Gln, Lys(Ac), Ile, Abu, Leu, or Nleu; and
  ii) Xaa2 is absent or B7;

each of B1 and B6 is independently a-MePhe, NMe-Phe, 2-Nal, 1-Nal, D-1-Nal, D-2-Nal, 3,3-diPhenylGly, Tic, Bip, Trp, bhTrp, hPhe, substituted Phe, substituted bhPhe, substituted Trp, or substituted bhTrp;

B2 is Pro, D-Pro, bhPro, D-bhPro, NPC, or D-NPC;

B3 is Cys, homoCys, (D)Cys, a-MeCys, or Pen;

B4 is Ile, Val, Leu, or NLeu;

B7 is Glu, Dapa, Lys, D-Lys, homoLys, or a-Me-Lys;

L1 is absent, Dapa, D-Dapa, isoGlu, PEG, Ahx, isoGlu-PEG, PEG-Ahx, isoGlu-Ahx, or isoGlu-PEG-Ahx;

Z is a half-life extension moiety;

J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent;

Y1 is Cys, homoCys, (D)Cys, NMeCys, aMeCys, or Pen;

Y2 is an amino acid or absent;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;

Peg1 is —C(O)—$CH_2$—$CH_2$—O—$CH_2$—$CH_2$—NH—;

Peg2 is —C(O)—$CH_2$—$CH_2$—O—$CH_2$—$CH_2$—O—$CH_2$—$CH_2$—NH—;

Peg4 is —C(O)—$CH_2$—$CH_2$—(O—$CH_2$—$CH_2$)$_4$—NH—;

Peg8 is —C(O)—$CH_2$—$CH_2$—(O—$CH_2$—$CH_2$)$_8$—NH—; and

Peg11 is —C(O)—$CH_2$—$CH_2$—(O—$CH_2$—$CH_2$)$_{11}$—O—$CH_2$—$CH_2$—NH—;

wherein i) the peptide of formula I is optionally PEGylated with Peg1, Peg2, Peg4, Peg8, or Peg11 on one or more $R^1$, B1, B2, B3, B4, B5, B6, B7, J, Y1, Y2, or $R^2$; and ii) the peptide is cyclized via a disulfide bond between B3 and Y1.

2. The hepcidin analogue according to claim 1, comprising a peptide according to Formula A-I:

$R^1$-Asp-Thr-His-B1-B2-B3-B4-B5-B6-B7(L1Z)-J-Y1-Y2-$R^2$(A-I)

or a pharmaceutically acceptable salt thereof, wherein:

$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;

$R^2$ is —$NH_2$ or —OH;

each of B1 and B6 is independently
a-MePhe, NMe-Phe,
2-Nal, 1-Nal, D-1-Nal, D-2-Nal, 3,3-diPhenylGly, Tic, Bip, Trp, bhTrp, hPhe, Tyr(Me), substituted Phe, substituted bhPhe, substituted Trp, or substituted bhTrp;

B2 is Pro, D-Pro, bhPro, D-bhPro, NPC, or D-NPC;

B3 is Cys, homoCys, (D)Cys, a-MeCys, or Pen;

B4 is Ile, Val, Leu, or NLeu;

B5 is absent, Lys, D-Lys, Orn, homoSer, Gln, (D)Gln, Lys(Ac), Ile, Abu, Leu, Ala, D-Ala, bAla, or Nleu;

B7 is Dapa, Lys, D-Lys, homoLys, or a-Me-Lys; and wherein L1 is attached to $N^\varepsilon$ of Lys, D-Lys, homoLys, or a-Me-Lys; or $N^\beta$ of Dapa;

L1 is absent, Dapa, D-Dapa, or isoGlu, PEG, Ahx, isoGlu-PEG, PEG-Ahx, isoGlu-Ahx, or isoGlu-PEG-Ahx;

Z is a half-life extension moiety, wherein the half-life extension moiety is $C_{10}$-$C_{21}$ alkanoyl;

J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-

Ser-Lys-Sar-(SEQ ID NO:250), -Pro-Arg-Ser-Lys-Gly-(SEQ ID NO:251), or absent;

Y1 is Cys, homoCys, (D)Cys, NMeCys, aMeCys, or Pen;

Y2 is an amino acid or absent;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu; and PEG is as described in claim 1;

wherein i) the peptide of formula I is optionally PEGylated on one or more $R^1$, B1, B2, B3, B4, B5, B6, J, Y1, Y2, or $R^2$;

ii) the peptide is cyclized via a disulfide bond between B3 and Y1; and iii) when B6 is Phe, then B5 is other than Lys.

3. The hepcidin analogue according to claim 1, comprising a peptide according to Formula B-I:

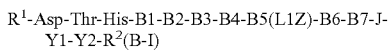

or a pharmaceutically acceptable salt thereof, wherein:

$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;

$R^2$ is —$NH_2$ or —OH;

each of B1 and B6 is independently
NMe-Phe,
2-Nal, 1-Nal, D-1-Nal, D-2-Nal, 3,3-diPhenylGly, Tic, Bip, Trp, bhTrp, hPhe, Tyr(Me), substituted Phe, substituted bhPhe, substituted Trp, or substituted bhTrp;

B2 is Pro, D-Pro, bhPro, D-bhPro, NPC, or D-NPC;

B3 is Cys, homoCys, (D)Cys, a-MeCys, or Pen;

B4 is Ile, Val, Leu, or NLeu;

B5 is Lys, D-Lys, Orn, homoSer, Gln, Lys(Ac), Ile, Abu, Leu, or Nleu;

B7 is Glu or absent;

$L_1$ is absent or isoGlu, PEG, Ahx, isoGlu-PEG, PEG-Ahx, isoGlu-Ahx, or isoGlu-PEG-Ahx;

Z is a half-life extension moiety, wherein the half-life extension moiety is $C_{10}$-$C_{21}$ alkanoyl;

J is Pro, Arg, Gly, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent;

Y1 is Cys, homoCys or Pen;

Y2 is an amino acid or absent;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted b-hTrp is N-methyl-L-b-homotryptophan, a-methyl-b-homotryptophan, or b-homotryptophan substituted with F, Cl, OH, or t-Bu; and PEG is as described in claim 1;

wherein i) the peptide of formula I is optionally PEGylated on one or more $R^1$, B1, B2, B3, B4, B6, B7, J, Y1, Y2, or $R^2$; and ii) the peptide is cyclized via a disulfide bond between B3 and Y1; and iii) when Y1 is Cys, and Y2 is Lys, then J is Pro, Arg, Gly, -Pro-Arg-, -Pro-Arg-Ser-,-Pro-Arg-Ser-Lys-(SEQ ID NO:249), or absent.

4. The hepcidin analogue or pharmaceutically acceptable salt thereof according to claim 1, wherein —J-Y1-Y2— is —Cys-, -Pro-Cys-, -Lys-Cys-, -(D)Lys-Cys-,-(D)Lys-Pen-,-Dap-Cys-, -Cys-(D)Lys-, -Dap-hCys-, -Pro-Arg-Cys-, -Pro-Arg-Ser-Cys-(SEQ ID NO:253), -Pro-Arg-Ser-Lys-Cys-(SEQ ID NO:254), or —Pro-Arg-Ser-Lys-Sar-Cys-(SEQ ID NO:255).

5. The hepcidin analogue or pharmaceutically acceptable salt thereof according to claim 1, wherein L1 is a single bond, iso-Glu, Ahx, iso-Glu-Ahx, PEG, PEG-Ahx, iso-Glu-PEG-Ahx; and wherein PEG is PEG1, PEG2, PEG3, PEG4, or PEG11.

6. The hepcidin analogue or pharmaceutically acceptable salt thereof according to claim 1, wherein Z is Palm.

7. The hepcidin analogue or pharmaceutically acceptable salt thereof according to claim 1, wherein $R^2$ is $NH_2$.

8. The hepcidin analogue or pharmaceutically acceptable salt thereof according to claim 1, wherein $R^2$ is OH.

9. A pharmaceutical composition comprising the hepcidin analogue or pharmaceutically acceptable salt thereof of claim 1 and a pharmaceutically acceptable carrier, excipient, or vehicle.

10. A method for treating a disease of iron metabolism in a subject in need thereof comprising providing to the subject an effective amount of the pharmaceutical composition of claim 9.

* * * * *

UNITED STATES PATENT AND TRADEMARK OFFICE
CERTIFICATE OF CORRECTION

| | | |
|---|---|---|
| PATENT NO. | : 11,753,443 B2 | |
| APPLICATION NO. | : 16/964708 | |
| DATED | : September 12, 2023 | |
| INVENTOR(S) | : Gregory Thomas Bourne et al. | |

It is certified that error appears in the above-identified patent and that said Letters Patent is hereby corrected as shown below:

In the Claims

At Claim 3, Column 293, Line 40, please replace "NMe-Phe," with --a-MePhe, NMe-Phe,--

Signed and Sealed this
Ninth Day of July, 2024

Katherine Kelly Vidal
*Director of the United States Patent and Trademark Office*

SEQUENCE LISTING

```
<160> NUMBER OF SEQ ID NOS: 258

<210> SEQ ID NO 1
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 1

Asp Thr His Phe Pro Cys Ile Lys Phe Lys Pro Arg Ser Lys Gly Cys
1               5                   10                  15

Lys

<210> SEQ ID NO 2
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine

<400> SEQUENCE: 2
```

```
Asp Thr His Phe Pro Cys Ile Lys Phe Lys Pro Arg Ser Lys Xaa Cys
1               5                   10                  15

Lys

<210> SEQ ID NO 3
<211> LENGTH: 16
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 3

Asp Thr His Phe Pro Cys Ile Lys Phe Lys Pro Arg Ser Lys Gly Cys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 4

Asp Thr His Phe Pro Cys Ile Lys Phe Lys Pro Arg Ser Lys Cys
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 5

Asp Thr His Phe Pro Cys Ile Lys Phe Lys Pro Arg Ser Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 6

Asp Thr His Phe Pro Cys Ile Lys Phe Lys Pro Arg Cys
1               5                   10

<210> SEQ ID NO 7
```

```
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 7

Asp Thr His Phe Pro Cys Ile Lys Phe Lys Pro Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 8

Asp Thr His Phe Pro Cys Ile Lys Phe Lys Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 9

Asp Thr His Phe Pro Cys Ile Lys Phe Lys Pro Cys Lys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 10

Asp Thr His Phe Pro Cys Ile Lys Phe Lys Cys
1               5                   10

<210> SEQ ID NO 11
<211> LENGTH: 11
<212> TYPE: PRT
<213> ORGANISM: Artificial Sequence
```

```
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: Ornithine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 11

Asp Thr His Phe Pro Cys Ile Xaa Phe Lys Cys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: Homoserine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 12

Asp Thr His Phe Pro Cys Ile Xaa Phe Lys Cys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 13

Asp Thr His Phe Pro Cys Ile Gln Phe Lys Cys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 14

Asp Thr His Phe Pro Cys Ile Lys Phe Lys Cys
1               5                   10
```

```
<210> SEQ ID NO 15
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: Nle
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 15

Asp Thr His Phe Pro Cys Ile Xaa Phe Lys Cys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 16

Asp Thr His Phe Pro Cys Ile Ile Phe Lys Cys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (9)..(9)
<223> OTHER INFORMATION: N-Methyl-Phenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 17

Asp Thr His Phe Pro Cys Ile Lys Xaa Lys Cys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (9)..(9)
<223> OTHER INFORMATION: Alpha-Methyl-Phenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
```

<400> SEQUENCE: 18

Asp Thr His Phe Pro Cys Ile Lys Xaa Lys Cys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (9)..(9)
<223> OTHER INFORMATION: Beta homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 19

Asp Thr His Phe Pro Cys Ile Lys Xaa Lys Cys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 20

Asp Thr His Phe Pro Cys Ile Lys Trp Lys Cys
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG8-Palm conjugated half-life extension moiety

<400> SEQUENCE: 21

Asp Thr His Phe Pro Cys Ile Lys Phe Lys Cys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE

```
<222> LOCATION: (10)..(10)
<223> OTHER INFORMATION: PEG4-Palm conjugated half-life extension moiety

<400> SEQUENCE: 22

Asp Thr His Phe Pro Cys Ile Lys Phe Lys Cys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG2-Palm conjugated half-life extension moiety

<400> SEQUENCE: 23

Asp Thr His Phe Pro Cys Ile Lys Phe Lys Cys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG1-Palm conjugated half-life extension moiety

<400> SEQUENCE: 24

Asp Thr His Phe Pro Cys Ile Lys Phe Lys Cys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: Aminohexanoic acid-palmityl conjugated half-
      life extension moiety

<400> SEQUENCE: 25

Asp Thr His Phe Pro Cys Ile Lys Phe Lys Cys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Made in Lab - hepcidin analogue
```

```
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG2-hexadecanoyl-gamma-Glu conjugated half-
      life extension moiety

<400> SEQUENCE: 26

Asp Thr His Phe Pro Cys Ile Lys Phe Lys Cys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: Hexadecanoyl-gamma-Glu conjugated half-life
      extension moiety

<400> SEQUENCE: 27

Asp Thr His Phe Pro Cys Ile Lys Phe Lys Cys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: IsoGlu-PEG2-Palm conjugated half-life extension
      moiety

<400> SEQUENCE: 28

Asp Thr His Phe Pro Cys Ile Lys Phe Lys Cys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG2-Ahx-Palm conjugated half-life extension
      moiety

<400> SEQUENCE: 29

Asp Thr His Phe Pro Cys Ile Lys Phe Lys Cys
```

```
                1               5                  10
```

```
<210> SEQ ID NO 30
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: Palm conjugated half-life extension moiety

<400> SEQUENCE: 30

Asp Thr His Phe Pro Cys Ile Lys Phe Lys Cys
1               5                  10

<210> SEQ ID NO 31
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (16)..(16)
<223> OTHER INFORMATION: Penicillamine

<400> SEQUENCE: 31

Asp Thr His Phe Pro Cys Ile Lys Phe Lys Pro Arg Ser Lys Xaa Xaa
1               5                  10                  15

Lys

<210> SEQ ID NO 32
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Penicillamine

<400> SEQUENCE: 32

Asp Thr His Phe Pro Cys Ile Lys Phe Lys Xaa
1               5                  10

<210> SEQ ID NO 33
```

```
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 33

Asp Thr His Phe Xaa Cys Ile Lys Phe Lys Cys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: D-form Nipecotic acid
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 34

Asp Thr His Phe Xaa Cys Ile Lys Phe Lys Cys
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: D-form proline
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 35

Asp Thr His Phe Pro Cys Ile Lys Phe Lys Cys
1               5                   10

<210> SEQ ID NO 36
<211> LENGTH: 11
```

```
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: D-form beta homoproline
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 36

Asp Thr His Phe Xaa Cys Ile Lys Phe Lys Cys
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: beta homoproline
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 37

Asp Thr His Phe Xaa Cys Ile Lys Phe Lys Cys
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: biphenylalanine
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 38

Asp Thr His Xaa Pro Cys Ile Lys Phe Lys Cys
1               5                   10

<210> SEQ ID NO 39
<211> LENGTH: 11
<212> TYPE: PRT
```

```
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: biphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 39

Asp Thr His Xaa Xaa Cys Ile Lys Phe Lys Cys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form Lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 40

Asp Thr His Phe Xaa Cys Ile Lys Phe Lys Cys
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine

<400> SEQUENCE: 41

Asp Thr His Phe Pro Cys Ile Lys Phe Lys Pro Arg Ser Lys Xaa Cys
1               5                   10                  15

Lys
```

```
<210> SEQ ID NO 42
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 42

Asp Thr His Phe Pro Cys Ile Lys Phe Lys Pro Arg Ser Lys Xaa Cys
1               5                   10                  15

Lys

<210> SEQ ID NO 43
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (14)..(14)
<223> OTHER INFORMATION: D-form lysine
<220> FEATURE:
<221> NAME/KEY: MOD_RES
<222> LOCATION: (15)..(15)
<223> OTHER INFORMATION: Sarcosine

<400> SEQUENCE: 43

Asp Thr His Phe Pro Cys Ile Lys Phe Lys Pro Arg Ser Lys Xaa Cys
1               5                   10                  15

Lys

<210> SEQ ID NO 44
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
```

```
<223> OTHER INFORMATION: PEG11-Palm conjugated half-life extension
      moiety
<220> FEATURE:
<221> NAME/KEY: MOD_RES
<222> LOCATION: (13)..(13)
<223> OTHER INFORMATION: D-form serine
<220> FEATURE:
<221> NAME/KEY: MOD_RES
<222> LOCATION: (15)..(15)
<223> OTHER INFORMATION: Sarcosine

<400> SEQUENCE: 44

Asp Thr His Phe Pro Cys Ile Lys Phe Lys Pro Arg Ser Lys Xaa Cys
1               5                   10                  15

Lys

<210> SEQ ID NO 45
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: D-form arginine
<220> FEATURE:
<221> NAME/KEY: MOD_RES
<222> LOCATION: (15)..(15)
<223> OTHER INFORMATION: Sarcosine

<400> SEQUENCE: 45

Asp Thr His Phe Pro Cys Ile Lys Phe Lys Pro Arg Ser Lys Xaa Cys
1               5                   10                  15

Lys

<210> SEQ ID NO 46
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 46

Asp Thr His Phe Pro Cys Ile Lys Phe Lys Pro Arg Thr Lys Xaa Cys
1               5                   10                  15
```

Lys

<210> SEQ ID NO 47
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 47

Asp Thr His Phe Pro Cys Ile Lys Phe Lys Pro Arg Thr Arg Xaa Cys
1               5                   10                  15

Lys

<210> SEQ ID NO 48
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: N-methylarginine
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 48

Asp Thr His Phe Pro Cys Ile Lys Phe Lys Pro Xaa Thr Lys Xaa Cys
1               5                   10                  15

Lys

<210> SEQ ID NO 49
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:

```
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: D-form arginine
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 49

Asp Thr His Phe Pro Cys Ile Lys Phe Lys Pro Arg Thr Lys Xaa Cys
1               5                   10                  15

Lys

<210> SEQ ID NO 50
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 50

Asp Thr His Phe Pro Cys Ile Lys Phe Lys Pro Asp Thr His Xaa Cys
1               5                   10                  15

Lys

<210> SEQ ID NO 51
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
```

```
<223> OTHER INFORMATION: D-form arginine
<220> FEATURE:
<221> NAME/KEY: MOD_RES
<222> LOCATION: (14)..(14)
<223> OTHER INFORMATION: N-methyllysine
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 51

Asp Thr His Phe Pro Cys Ile Lys Phe Lys Pro Arg Thr Xaa Xaa Cys
1               5                   10                  15

Lys

<210> SEQ ID NO 52
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: nipecotic acid
<220> FEATURE:
<221> NAME/KEY: MOD_RES
<222> LOCATION: (12)..(12)
<223> OTHER INFORMATION: N-methylarginine
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: D-form lysine

<400> SEQUENCE: 52

Asp Thr His Phe Pro Cys Ile Lys Phe Lys Xaa Xaa Thr His Xaa Cys
1               5                   10                  15

Lys

<210> SEQ ID NO 53
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MOD_RES
```

```
<222> LOCATION: (16)..(16)
<223> OTHER INFORMATION: Penicillamine

<400> SEQUENCE: 53

Asp Thr His Phe Pro Cys Ile Lys Phe Lys Pro Arg Ser Lys Xaa Xaa
1               5                   10                  15

Lys

<210> SEQ ID NO 54
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Penicillamine

<400> SEQUENCE: 54

Asp Thr His Phe Pro Cys Ile Lys Phe Lys Xaa
1               5                   10

<210> SEQ ID NO 55
<211> LENGTH: 18
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (1)..(1)
<223> OTHER INFORMATION: D-form lysine
<220> FEATURE:
<221> NAME/KEY: MOD_RES
<222> LOCATION: (2)..(2)
<223> OTHER INFORMATION: D-form cysteine
<220> FEATURE:
<221> NAME/KEY: MOD_RES
<222> LOCATION: (3)..(3)
<223> OTHER INFORMATION: Sarcosine
<220> FEATURE:
<221> NAME/KEY: MOD_RES
<222> LOCATION: (4)..(4)
<223> OTHER INFORMATION: D-form lysine
<220> FEATURE:
<221> NAME/KEY: MOD_RES
<222> LOCATION: (5)..(5)
<223> OTHER INFORMATION: D-form serine
<220> FEATURE:
<221> NAME/KEY: MOD_RES
<222> LOCATION: (6)..(6)
<223> OTHER INFORMATION: D-form arginine
<220> FEATURE:
<221> NAME/KEY: MOD_RES
<222> LOCATION: (7)..(7)
<223> OTHER INFORMATION: D-form proline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: PEG11-Palm conjugated half-life extension
```

```
              moiety
<220> FEATURE:
<221> NAME/KEY: MOD_RES
<222> LOCATION: (9)..(9)
<223> OTHER INFORMATION: D-form phenylalanine
<220> FEATURE:
<221> NAME/KEY: MOD_RES
<222> LOCATION: (10)..(10)
<223> OTHER INFORMATION: D-form lysine
<220> FEATURE:
<221> NAME/KEY: MOD_RES
<222> LOCATION: (11)..(11)
<223> OTHER INFORMATION: D-form isoleucine
<220> FEATURE:
<221> NAME/KEY: MOD_RES
<222> LOCATION: (12)..(12)
<223> OTHER INFORMATION: D-form cysteine
<220> FEATURE:
<221> NAME/KEY: MOD_RES
<222> LOCATION: (13)..(13)
<223> OTHER INFORMATION: D-form proline
<220> FEATURE:
<221> NAME/KEY: MOD_RES
<222> LOCATION: (14)..(14)
<223> OTHER INFORMATION: D-form phenylalanine
<220> FEATURE:
<221> NAME/KEY: MOD_RES
<222> LOCATION: (15)..(15)
<223> OTHER INFORMATION: D-form histidine
<220> FEATURE:
<221> NAME/KEY: MOD_RES
<222> LOCATION: (16)..(16)
<223> OTHER INFORMATION: D-form threonine
<220> FEATURE:
<221> NAME/KEY: MOD_RES
<222> LOCATION: (17)..(17)
<223> OTHER INFORMATION: D-form aspartic acid
<220> FEATURE:
<221> NAME/KEY: MOD_RES
<222> LOCATION: (18)..(18)
<223> OTHER INFORMATION: D-form leucine

<400> SEQUENCE: 55

Lys Cys Xaa Lys Ser Arg Pro Lys Phe Lys Ile Cys Pro Phe His Thr
1               5                   10                  15

Asp Leu

<210> SEQ ID NO 56
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 56

Asp Thr His Phe Xaa Cys Ile Lys Phe Lys Cys
1               5                   10

<210> SEQ ID NO 57
<211> LENGTH: 11
<212> TYPE: PRT
```

```
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: isoipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 57

Asp Thr His Phe Xaa Cys Ile Lys Phe Lys Cys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: D-form proline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 58

Asp Thr His Phe Pro Cys Ile Lys Phe Lys Cys
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: D-form beta homoproline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 59

Asp Thr His Phe Xaa Cys Ile Lys Phe Lys Cys
1               5                   10

<210> SEQ ID NO 60
<211> LENGTH: 11
<212> TYPE: PRT
<213> ORGANISM: Artificial Sequence
```

```
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: Beta homoproline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 60

Asp Thr His Phe Xaa Cys Ile Lys Phe Lys Cys
1               5                   10

<210> SEQ ID NO 61

<400> SEQUENCE: 61

000

<210> SEQ ID NO 62
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Biphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 62

Asp Thr His Xaa Pro Cys Ile Lys Phe Lys Cys
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Biphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
```

<400> SEQUENCE: 63

Asp Thr His Xaa Xaa Cys Ile Lys Phe Lys Cys
1               5                   10

<210> SEQ ID NO 64

<400> SEQUENCE: 64

000

<210> SEQ ID NO 65
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (11)..(11)
<223> OTHER INFORMATION: PEG11-Palm conjugated half-life extension
      moiety

<400> SEQUENCE: 65

Asp Thr His Phe Pro Cys Ile Lys Phe Cys Lys
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 66

Asp Thr His Phe Xaa Cys Ile Lys Phe Lys Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (6)..(6)
<223> OTHER INFORMATION: Sulfhydryl (-SH) modification
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)

<223> OTHER INFORMATION: Sulfhydryl (-SH) modification

<400> SEQUENCE: 67

Asp Thr His Phe Pro Cys Ile Lys Phe Lys Pro Cys
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (6)..(6)
<223> OTHER INFORMATION: Sulfhydryl (-SH) modification
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Sulfhydryl (-SH) modification

<400> SEQUENCE: 68

Asp Thr His Phe Pro Cys Ile Lys Phe Lys Cys
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (6)..(6)
<223> OTHER INFORMATION: Sulfhydryl (-SH) modification
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Sulfhydryl (-SH) modification

<400> SEQUENCE: 69

Asp Thr His Phe Pro Cys Ile Lys Phe Lys Cys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

```
<400> SEQUENCE: 70

Asp Thr His Phe Pro Cys Ile Lys Phe Lys Pro Cys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 71

Asp Thr His Phe Pro Cys Ile Lys Phe Lys Pro Arg Cys
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 72

Asp Thr His Phe Pro Cys Ile Lys Phe Lys Pro Arg Ser Cys
1               5                   10

<210> SEQ ID NO 73
<211> LENGTH: 15
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 73

Asp Thr His Phe Pro Cys Ile Lys Phe Lys Pro Arg Ser Lys Cys
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Made in Lab - hepcidin analogue
```

```
-continued

<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (15)..(15)
<223> OTHER INFORMATION: Sarcosine

<400> SEQUENCE: 74

Asp Thr His Phe Pro Cys Ile Lys Phe Lys Pro Arg Ser Lys Xaa Cys
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 75

Asp Thr His Phe Pro Cys Ile Lys Phe Lys Pro Arg Ser Lys Cys Lys
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 76

Asp Thr His Phe Pro Cys Ile Lys Phe Lys Pro Pro Arg Ser Cys Lys
1               5                   10                  15

<210> SEQ ID NO 77
<211> LENGTH: 14
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
```

```
<400> SEQUENCE: 77

Asp Thr His Phe Pro Cys Ile Lys Phe Lys Pro Arg Cys Lys
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 78

Asp Thr His Phe Pro Cys Ile Lys Phe Lys Cys Lys
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 79

Asp Thr His Phe Pro Cys Ile Lys Phe Lys Arg Cys
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 80

Asp Thr His Phe Pro Cys Ile Lys Phe Lys Lys Cys
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Made in Lab - hepcidin analogue
```

```
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form arginine

<400> SEQUENCE: 81

Asp Thr His Phe Pro Cys Ile Lys Phe Lys Arg Cys
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 82

Asp Thr His Phe Pro Cys Ile Lys Phe Lys Lys Cys
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (13)..(13)
<223> OTHER INFORMATION: D-form lysine

<400> SEQUENCE: 83

Asp Thr His Phe Pro Cys Ile Lys Phe Lys Lys Cys Lys
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
```

```
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (13)..(13)
<223> OTHER INFORMATION: D-form histidine

<400> SEQUENCE: 84

Asp Thr His Phe Pro Cys Ile Lys Phe Lys His Cys His
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (13)..(13)
<223> OTHER INFORMATION: D-form arginine

<400> SEQUENCE: 85

Asp Thr His Phe Pro Cys Ile Lys Phe Lys Arg Cys Arg
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: Ahx-Palm conjugated half-life extension moiety

<400> SEQUENCE: 86

Asp Thr His Phe Pro Cys Ile Lys Phe Lys Lys Cys
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
```

```
<223> OTHER INFORMATION: PEG2-Palm conjugated half-life extension moiety

<400> SEQUENCE: 87

Asp Thr His Phe Pro Cys Ile Lys Phe Lys Lys Cys
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG2-PEG2-Palm conjugated half-life extension
      moiety

<400> SEQUENCE: 88

Asp Thr His Phe Pro Cys Ile Lys Phe Lys Lys Cys
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG2-PEG2-C18 acid conjugated half-life
      extension moiety

<400> SEQUENCE: 89

Asp Thr His Phe Pro Cys Ile Lys Phe Lys Lys Cys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG2-PEG2-Ahx-Palm conjugated half-life
      extension moiety

<400> SEQUENCE: 90

Asp Thr His Phe Pro Cys Ile Lys Phe Lys Lys Cys
1               5                   10

<210> SEQ ID NO 91
<211> LENGTH: 12
<212> TYPE: PRT
<213> ORGANISM: Artificial Sequence
<220> FEATURE:
```

```
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG4-Palm acid conjugated half-life extension
      moiety

<400> SEQUENCE: 91

Asp Thr His Phe Pro Cys Ile Lys Phe Lys Lys Cys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG4-Ahx-Palm conjugated half-life extension
      moiety

<400> SEQUENCE: 92

Asp Thr His Phe Pro Cys Ile Lys Phe Lys Lys Cys
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG4-PEG4-Palm conjugated half-life extension
      moiety

<400> SEQUENCE: 93

Asp Thr His Phe Pro Cys Ile Lys Phe Lys Lys Cys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG4-isoGlu-Palm conjugated half-life extension
      moiety

<400> SEQUENCE: 94
```

```
Asp Thr His Phe Pro Cys Ile Lys Phe Lys Lys Cys
1               5                   10
```

<210> SEQ ID NO 95
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG8-Palm conjugated half-life extension moiety

<400> SEQUENCE: 95

```
Asp Thr His Phe Pro Cys Ile Lys Phe Lys Lys Cys
1               5                   10
```

<210> SEQ ID NO 96
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: Behenic acid conjugated half-life extension
      moiety

<400> SEQUENCE: 96

```
Asp Thr His Phe Pro Cys Ile Lys Phe Lys Lys Cys
1               5                   10
```

<210> SEQ ID NO 97
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: D-form cysteine

<400> SEQUENCE: 97

```
Asp Thr His Phe Pro Cys Ile Lys Phe Lys Lys Cys
1               5                   10
```

<210> SEQ ID NO 98
<211> LENGTH: 12
<212> TYPE: PRT
<213> ORGANISM: Artificial Sequence
<220> FEATURE:
<223> OTHER INFORMATION: Made in Lab - hepcidin analogue

```
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: Penicillamine

<400> SEQUENCE: 98

Asp Thr His Phe Pro Cys Ile Lys Phe Lys Lys Cys
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Diaminopropionic acid

<400> SEQUENCE: 99

Asp Thr His Phe Pro Cys Ile Lys Phe Lys Xaa Cys
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: beta,beta-diphenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 100

Asp Thr His Phe Pro Cys Ile Lys Xaa Lys Lys Cys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
```

<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 101

Asp Thr His Phe Pro Cys Ile Lys Xaa Lys Lys Cys
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Napthylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 102

Asp Thr His Phe Pro Cys Ile Lys Xaa Lys Lys Cys
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 103

Asp Thr His Phe Pro Cys Ile Lys Xaa Lys Lys Cys
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES

```
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 104

Asp Thr His Xaa Pro Cys Ile Lys Phe Lys Lys Cys
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 105

Asp Thr His Xaa Pro Cys Ile Lys Xaa Lys Lys Cys
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (9)..(9)
<223> OTHER INFORMATION: PEG11-Palm conjugated half-life extension
      moiety

<400> SEQUENCE: 106

Asp Thr His Phe Pro Cys Ile Phe Lys Lys Cys
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
```

```
<223> OTHER INFORMATION: D-form lysine
<220> FEATURE:
<221> NAME/KEY: MOD_RES
<222> LOCATION: (10)..(10)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 107

Asp Thr His Phe Pro Cys Ile Lys Phe Lys Lys Cys
1               5                   10

<210> SEQ ID NO 108

<400> SEQUENCE: 108

000

<210> SEQ ID NO 109
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 109

Asp Thr His Xaa Xaa Cys Ile Lys Phe Lys Lys Cys
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
```

```
<223> OTHER INFORMATION: Phenylalanine (4-tBu)
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 110

Asp Thr His Xaa Xaa Cys Ile Lys Xaa Lys Lys Cys
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Phenylalanine (4-(2-aminoethoxy))
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 111

Asp Thr His Xaa Xaa Cys Ile Lys Xaa Lys Lys Cys
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: 2-Napthylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 112

Asp Thr His Xaa Xaa Cys Ile Lys Xaa Lys Lys Cys
1               5                   10
```

```
<210> SEQ ID NO 113
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Phenylalanine (4-COOOH)
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 113

Asp Thr His Xaa Xaa Cys Ile Lys Xaa Lys Lys Cys
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: Alpha-methylcysteine

<400> SEQUENCE: 114

Asp Thr His Phe Pro Cys Ile Lys Phe Lys Lys Xaa
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (6)..(6)
<223> OTHER INFORMATION: Alpha-methylcysteine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
```

```
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: Alpha-methylcysteine

<400> SEQUENCE: 115

Asp Thr His Phe Pro Xaa Ile Lys Phe Lys Lys Xaa
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (6)..(6)
<223> OTHER INFORMATION: Alpha-methylcysteine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 116

Asp Thr His Phe Pro Xaa Ile Lys Phe Lys Lys Cys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 117

Asp Thr His Xaa Xaa Cys Ile Lys Phe Lys Lys Cys
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Made in Lab - hepcidin analogue
```

```
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 118

Asp Thr His Phe Xaa Cys Ile Lys Phe Lys Lys Cys
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Beta-homoproline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 119

Asp Thr His Xaa Xaa Cys Ile Lys Phe Lys Lys Cys
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Phenylalanine (4-COOH)
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
```

```
<222> LOCATION: (11)..(11)
<223> OTHER INFORMATION: D-form lysine

<400> SEQUENCE: 120

Asp Thr His Xaa Pro Cys Ile Lys Phe Lys Lys Cys
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta-homophenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 121

Asp Thr His Xaa Pro Cys Ile Lys Phe Lys Lys Cys
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 122

Asp Thr His Xaa Pro Cys Ile Lys Xaa Lys Lys Cys
1               5                   10

<210> SEQ ID NO 123

<400> SEQUENCE: 123

000
```

<210> SEQ ID NO 124

<400> SEQUENCE: 124

000

<210> SEQ ID NO 125
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Alpha-methylphenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 125

Asp Thr His Xaa Xaa Cys Ile Lys Xaa Lys Lys Cys
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Phenylalanine (4-CN)
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 126

Asp Thr His Xaa Xaa Cys Ile Lys Xaa Lys Lys Cys
1               5                   10

<210> SEQ ID NO 127
<211> LENGTH: 12
<212> TYPE: PRT

```
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Phenylalanine (3,4-diF)
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 127

Asp Thr His Xaa Xaa Cys Ile Lys Xaa Lys Lys Cys
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Alpha-methylphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 128

Asp Thr His Xaa Pro Cys Ile Lys Phe Lys Lys Cys
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Phenylalanine (4-(2-aminoethoxy))
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
```

```
      moiety
<220> FEATURE:
<221> NAME/KEY: MOD_RES
<222> LOCATION: (11)..(11)
<223> OTHER INFORMATION: D-form lysine

<400> SEQUENCE: 129

Asp Thr His Xaa Pro Cys Ile Lys Phe Lys Lys Cys
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 130

Asp Ile His Xaa Pro Cys Ile Lys Phe Lys Lys Cys
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: beta,beta-diphenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 131

Asp Thr His Xaa Pro Cys Ile Lys Xaa Lys Lys Cys
1               5                   10

<210> SEQ ID NO 132
<211> LENGTH: 12
<212> TYPE: PRT
```

```
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine
<220> FEATURE:
<221> NAME/KEY: MOD_RES
<222> LOCATION: (12)..(12)
<223> OTHER INFORMATION: Penicillamine

<400> SEQUENCE: 132

Asp Thr His Xaa Pro Cys Ile Lys Phe Lys Lys Xaa
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: N-methyl-cysteine

<400> SEQUENCE: 133

Asp Thr His Xaa Pro Cys Ile Lys Phe Lys Lys Xaa
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
```

```
       moiety
<220> FEATURE:
<221> NAME/KEY: MOD_RES
<222> LOCATION: (11)..(11)
<223> OTHER INFORMATION: D-form lysine
<220> FEATURE:
<221> NAME/KEY: MOD_RES
<222> LOCATION: (12)..(12)
<223> OTHER INFORMATION: N-methyl-cysteine

<400> SEQUENCE: 134

Asp Thr His Xaa Pro Cys Ile Lys Phe Lys Lys Xaa
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
       moiety

<400> SEQUENCE: 135

Asp Thr His Xaa Pro Cys Ile Lys Phe Lys Cys
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
       moiety
<220> FEATURE:
<221> NAME/KEY: MOD_RES
<222> LOCATION: (11)..(11)
<223> OTHER INFORMATION: Orn

<400> SEQUENCE: 136

Asp Thr His Xaa Pro Cys Ile Lys Phe Lys Xaa Cys
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
```

```
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Diaminobutyric acid

<400> SEQUENCE: 137

Asp Thr His Xaa Pro Cys Ile Lys Phe Lys Xaa Cys
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Beta-homolysine

<400> SEQUENCE: 138

Asp Thr His Xaa Pro Cys Ile Lys Phe Lys Xaa Cys
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 139
```

```
Asp Thr His Xaa Pro Cys Ile Lys Phe Lys Lys Cys
1               5                   10
```

<210> SEQ ID NO 140
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Diaminopropionic acid
<220> FEATURE:
<221> NAME/KEY: MOD_RES
<222> LOCATION: (12)..(12)
<223> OTHER INFORMATION: Penicillamine

<400> SEQUENCE: 140

```
Asp Thr His Xaa Pro Cys Ile Lys Phe Lys Xaa Xaa
1               5                   10
```

<210> SEQ ID NO 141
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (6)..(6)
<223> OTHER INFORMATION: Homocysteine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Diaminopropionic acid

<400> SEQUENCE: 141

```
Asp Thr His Xaa Pro Xaa Ile Lys Phe Lys Xaa Cys
1               5                   10
```

<210> SEQ ID NO 142
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:

```
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (6)..(6)
<223> OTHER INFORMATION: Homocysteine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Diaminopropionic acid
<220> FEATURE:
<221> NAME/KEY: MOD_RES
<222> LOCATION: (12)..(12)
<223> OTHER INFORMATION: Homocystein

<400> SEQUENCE: 142

Asp Thr His Xaa Pro Xaa Ile Lys Phe Lys Xaa Xaa
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: Diaminopropionic acid
<220> FEATURE:
<221> NAME/KEY: MOD_RES
<222> LOCATION: (12)..(12)
<223> OTHER INFORMATION: Homocystein

<400> SEQUENCE: 143

Asp Thr His Xaa Pro Cys Ile Lys Phe Lys Xaa Xaa
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
``` moiety

<400> SEQUENCE: 144

Asp Thr His Phe Pro Cys Ile Lys Phe Lys Cys Lys
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: Beta-alanine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 145

Asp Thr His Xaa Pro Cys Ile Xaa Xaa Lys Lys Cys
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form alanine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 146

Asp Thr His Xaa Pro Cys Ile Ala Xaa Lys Lys Cys
1               5                   10

<210> SEQ ID NO 147
<211> LENGTH: 12
<212> TYPE: PRT

```
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 147

Asp Thr His Xaa Pro Cys Ile Ile Xaa Lys Lys Cys
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: Beta-homophenylalanine
<220> FEATURE:
<221> NAME/KEY: MISC_FEATURE
<222> LOCATION: (9)..(9)
<223> OTHER INFORMATION: PEG11-Palm conjugated half-life extension
      moiety
<220> FEATURE:
<221> NAME/KEY: MOD_RES
<222> LOCATION: (10)..(10)
<223> OTHER INFORMATION: D-form lysine

<400> SEQUENCE: 148

Asp Thr His Xaa Pro Cys Ile Xaa Lys Lys Cys
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Phenylalanine (4-tButyl)
```

```
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 149

Asp Thr His Xaa Xaa Cys Ile Lys Xaa Lys Lys Cys
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Phenylalanine (4-tButyl)
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: D-form lysine

<400> SEQUENCE: 150

Asp Thr His Xaa Xaa Cys Ile Lys Xaa Lys Cys Lys
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: Ahx-Palm conjugated half-life extension moiety
<220> FEATURE:
<221> NAME/KEY: MOD_RES
<222> LOCATION: (11)..(11)
```

```
<223> OTHER INFORMATION: Diaminopropionic acid
<220> FEATURE:
<221> NAME/KEY: MOD_RES
<222> LOCATION: (12)..(12)
<223> OTHER INFORMATION: N-methyl-cysteine

<400> SEQUENCE: 151

Asp Thr His Xaa Pro Cys Ile Lys Xaa Lys Xaa Xaa
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MOD_RES
<222> LOCATION: (10)..(10)
<223> OTHER INFORMATION: ACETYLATION
<220> FEATURE:
<221> NAME/KEY: MOD_RES
<222> LOCATION: (11)..(11)
<223> OTHER INFORMATION: D-form lysine

<400> SEQUENCE: 152

Asp Thr His Xaa Pro Cys Ile Lys Xaa Lys Lys Cys
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: PEG11-OMe conjugated half-life extension moiety
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine
<220> FEATURE:
<221> NAME/KEY: MISC_FEATURE
<222> LOCATION: (11)..(11)
```

<223> OTHER INFORMATION: PEG11-OMe conjugated half-life extension moiety

<400> SEQUENCE: 153

Asp Thr His Xaa Pro Cys Ile Lys Xaa Lys Lys Cys
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11 conjugated half-life extension moiety
<220> FEATURE:
<221> NAME/KEY: MOD_RES
<222> LOCATION: (11)..(11)
<223> OTHER INFORMATION: D-form lysine

<400> SEQUENCE: 154

Asp Thr His Xaa Pro Cys Ile Lys Xaa Lys Lys Cys
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-octane conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 155

Asp Thr His Xaa Pro Cys Ile Lys Xaa Lys Lys Cys
1               5                   10

<210> SEQ ID NO 156
<211> LENGTH: 12
<212> TYPE: PRT
<213> ORGANISM: Artificial Sequence

```
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Lauryl conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 156

Asp Thr His Xaa Pro Cys Ile Lys Xaa Lys Lys Cys
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-OMe conjugated half-life extension moiety
<220> FEATURE:
<221> NAME/KEY: MOD_RES
<222> LOCATION: (11)..(11)
<223> OTHER INFORMATION: D-form lysine

<400> SEQUENCE: 157

Asp Thr His Xaa Pro Cys Ile Lys Xaa Lys Lys Cys
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
```

```
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: IsoGlu-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 158

Asp Thr His Xaa Pro Cys Ile Lys Xaa Lys Lys Cys
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 159

Asp Thr His Xaa Pro Cys Ile Lys Xaa Lys Lys Cys
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: Dap-Palm conjugated half-life extension moiety
```

```
<400> SEQUENCE: 160

Asp Thr His Xaa Pro Cys Ile Lys Xaa Lys Cys
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: D-form Dap-Palm conjugated half-life extension
      moiety

<400> SEQUENCE: 161

Asp Thr His Xaa Pro Cys Ile Lys Xaa Lys Cys
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MOD_RES
<222> LOCATION: (10)..(10)
<223> OTHER INFORMATION: Diaminopropionic acid
<220> FEATURE:
<221> NAME/KEY: MISC_FEATURE
<222> LOCATION: (10)..(10)
<223> OTHER INFORMATION: Dap-Palm conjugated half-life extension moiety

<400> SEQUENCE: 162

Asp Thr His Xaa Pro Cys Ile Lys Xaa Xaa Cys
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
```

```
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MOD_RES
<222> LOCATION: (10)..(10)
<223> OTHER INFORMATION: Diaminopropionic acid
<220> FEATURE:
<221> NAME/KEY: MISC_FEATURE
<222> LOCATION: (10)..(10)
<223> OTHER INFORMATION: D-form Dap-Palm conjugated half-life extension
      moiety

<400> SEQUENCE: 163

Asp Thr His Xaa Pro Cys Ile Lys Xaa Xaa Cys
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MOD_RES
<222> LOCATION: (10)..(10)
<223> OTHER INFORMATION: Diaminopropionic acid
<220> FEATURE:
<221> NAME/KEY: MISC_FEATURE
<222> LOCATION: (10)..(10)
<223> OTHER INFORMATION: D-form Dap-Palm conjugated half-life extension
      moiety

<400> SEQUENCE: 164

Asp Thr His Xaa Pro Cys Ile Lys Xaa Xaa Cys
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
```

```
<223> OTHER INFORMATION: Ahx-Palm conjugated half-life extension moiety
<220> FEATURE:
<221> NAME/KEY: MOD_RES
<222> LOCATION: (11)..(11)
<223> OTHER INFORMATION: D-form lysine

<400> SEQUENCE: 165

Asp Thr His Xaa Pro Cys Ile Lys Xaa Lys Lys Cys
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: PEG11-OMe conjugated half-life extension moiety
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: Ahx-Palm conjugated half-life extension moiety
<220> FEATURE:
<221> NAME/KEY: MOD_RES
<222> LOCATION: (11)..(11)
<223> OTHER INFORMATION: D-form lysine
<220> FEATURE:
<221> NAME/KEY: MISC_FEATURE
<222> LOCATION: (11)..(11)
<223> OTHER INFORMATION: PEG11-OMe conjugated half-life extension moiety

<400> SEQUENCE: 166

Asp Thr His Xaa Pro Cys Ile Lys Xaa Lys Lys Cys
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: D-form proline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
```

<223> OTHER INFORMATION: D-form lysine

<400> SEQUENCE: 167

Asp Thr His Xaa Pro Cys Ile Lys Phe Lys Lys Cys
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta-homophenylalanine
<220> FEATURE:
<221> NAME/KEY: MOD_RES
<222> LOCATION: (5)..(5)
<223> OTHER INFORMATION: D-form proline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 168

Asp Thr His Xaa Pro Cys Ile Lys Phe Lys Lys Cys
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (1)..(1)
<223> OTHER INFORMATION: D-form aspartic acid
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 169

Asp Thr His Xaa Pro Cys Ile Lys Xaa Lys Lys Cys
1               5                   10

```
<210> SEQ ID NO 170
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
     moiety
<220> FEATURE:
<221> NAME/KEY: MOD_RES
<222> LOCATION: (12)..(12)
<223> OTHER INFORMATION: D-form lysine

<400> SEQUENCE: 170

Asp Thr His Xaa Pro Cys Ile Lys Xaa Lys Cys Lys
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta-homophenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
     moiety
<220> FEATURE:
<221> NAME/KEY: MOD_RES
<222> LOCATION: (12)..(12)
<223> OTHER INFORMATION: D-form lysine

<400> SEQUENCE: 171

Asp Thr His Xaa Pro Cys Ile Lys Phe Lys Cys Lys
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta-homophenylalanine
<220> FEATURE:
<221> NAME/KEY: MOD_RES
<222> LOCATION: (5)..(5)
<223> OTHER INFORMATION: Nipecotic acid
```

```
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: D-form lysine

<400> SEQUENCE: 172

Asp Thr His Xaa Xaa Cys Ile Lys Phe Lys Cys Lys
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (12)..(12)
<223> OTHER INFORMATION: D-form lysine

<400> SEQUENCE: 173

Asp Thr His Xaa Xaa Cys Ile Lys Xaa Lys Cys Lys
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form glutamine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
```

```
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 174

Asp Thr His Xaa Pro Cys Ile Gln Xaa Lys Lys Cys
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: D-form lysine
<220> FEATURE:
<221> NAME/KEY: MOD_RES
<222> LOCATION: (11)..(11)
<223> OTHER INFORMATION: ACETYLATION

<400> SEQUENCE: 175

Asp Thr His Xaa Pro Cys Ile Lys Xaa Lys Lys Cys
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta-homophenylalanine
<220> FEATURE:
<221> NAME/KEY: MOD_RES
<222> LOCATION: (5)..(5)
<223> OTHER INFORMATION: D-form proline
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
```

```
<221> NAME/KEY: MOD_RES
<222> LOCATION: (12)..(12)
<223> OTHER INFORMATION: D-form lysine

<400> SEQUENCE: 176

Asp Thr His Xaa Pro Cys Ile Lys Xaa Lys Cys Lys
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: Ahx-Palm conjugated half-life extension moiety

<400> SEQUENCE: 177

Asp Thr His Xaa Pro Cys Ile Lys Xaa Lys Arg Cys
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: N-Methylphenylalanine
<220> FEATURE:
<221> NAME/KEY: MISC_FEATURE
<222> LOCATION: (10)..(10)
<223> OTHER INFORMATION: Ahx-Palm conjugated half-life extension moiety
<220> FEATURE:
<221> NAME/KEY: MOD_RES
<222> LOCATION: (11)..(11)
<223> OTHER INFORMATION: D-form lysine

<400> SEQUENCE: 178

Asp Thr His Xaa Pro Cys Ile Lys Xaa Lys Lys Cys
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
```

```
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (6)..(6)
<223> OTHER INFORMATION: N-Methycysteine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-Homophenylalanine
<220> FEATURE:
<221> NAME/KEY: MISC_FEATURE
<222> LOCATION: (10)..(10)
<223> OTHER INFORMATION: Ahx-Palm conjugated half-life extension moiety
<220> FEATURE:
<221> NAME/KEY: MOD_RES
<222> LOCATION: (11)..(11)
<223> OTHER INFORMATION: D-form lysine

<400> SEQUENCE: 179

Asp Thr His Xaa Pro Xaa Ile Lys Xaa Lys Lys Cys
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: N-Methylphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: Ahx-Palm conjugated half-life extension moiety
<220> FEATURE:
<221> NAME/KEY: MOD_RES
<222> LOCATION: (11)..(11)
<223> OTHER INFORMATION: D-form lysine

<400> SEQUENCE: 180

Asp Thr His Xaa Pro Cys Ile Lys Xaa Lys Lys Cys
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
```

```
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: Ahx-Palm conjugated half-life extension moiety
<220> FEATURE:
<221> NAME/KEY: MOD_RES
<222> LOCATION: (11)..(11)
<223> OTHER INFORMATION: D-form lysine
<220> FEATURE:
<221> NAME/KEY: MOD_RES
<222> LOCATION: (12)..(12)
<223> OTHER INFORMATION: N-Methylcysteine

<400> SEQUENCE: 181

Asp Thr His Xaa Pro Cys Ile Lys Xaa Lys Lys Xaa
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
<221> NAME/KEY: MOD_RES
<222> LOCATION: (5)..(5)
<223> OTHER INFORMATION: Nipecotic aCID
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Phenylalanine (4-tBu)
<220> FEATURE:
<221> NAME/KEY: MOD_RES
<222> LOCATION: (10)..(10)
<223> OTHER INFORMATION: D-form lysine
<220> FEATURE:
<221> NAME/KEY: MISC_FEATURE
<222> LOCATION: (12)..(12)
<223> OTHER INFORMATION: PEG11-Palm conjugated half-life extension
      moiety

<400> SEQUENCE: 182

Asp Thr His Xaa Xaa Cys Ile Lys Xaa Lys Cys Lys
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: isoGlu-Palm conjugated half-life extension
      moiety

<400> SEQUENCE: 183

Asp Thr His Phe Pro Cys Ile Lys Phe Glu Pro Lys Cys
1               5                   10

<210> SEQ ID NO 184
<211> LENGTH: 12
```

```
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: isoGlu-Palm conjugated half-life extension
      moiety
<220> FEATURE:
<221> NAME/KEY: MOD_RES
<222> LOCATION: (11)..(11)
<223> OTHER INFORMATION: D-form lysine

<400> SEQUENCE: 184

Asp Thr His Phe Pro Cys Ile Lys Phe Glu Lys Cys
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: isoGlu-Palm conjugated half-life extension
      moiety

<400> SEQUENCE: 185

Asp Thr His Phe Pro Cys Ile Lys Phe Gly Cys
1               5                   10

<210> SEQ ID NO 186
<211> LENGTH: 17
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: isoGlu-Palm conjugated half-life extension
      moiety

<400> SEQUENCE: 186

Asp Thr His Phe Pro Cys Ile Lys Phe Glu Pro Arg Ser Lys Gly Cys
1               5                   10                  15

Lys

<210> SEQ ID NO 187
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
```

```
<222> LOCATION: (11)..(11)
<223> OTHER INFORMATION: Ornithine

<400> SEQUENCE: 187

Asp Thr His Phe Pro Cys Ile Lys Phe Lys Xaa Cys
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: diaminobutyric acid

<400> SEQUENCE: 188

Asp Thr His Phe Pro Cys Ile Lys Phe Lys Xaa Cys
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety
<220> FEATURE:
<221> NAME/KEY: MOD_RES
<222> LOCATION: (11)..(11)
<223> OTHER INFORMATION: homolysine

<400> SEQUENCE: 189

Asp Thr His Phe Pro Cys Ile Lys Phe Lys Xaa Cys
1               5                   10

<210> SEQ ID NO 190

<400> SEQUENCE: 190

000

<210> SEQ ID NO 191
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: beta,beta-diphenylalanine
<220> FEATURE:
```

```
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 191

Asp Thr His Xaa Pro Cys Ile Lys Xaa Lys Lys Cys
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (10)..(10)
<223> OTHER INFORMATION: D-form lysine
<220> FEATURE:
<221> NAME/KEY: MISC_FEATURE
<222> LOCATION: (10)..(10)
<223> OTHER INFORMATION: PEG11-Palm conjugated half-life extension
      moiety

<400> SEQUENCE: 192

Asp Thr His Phe Pro Cys Ile Lys Phe Lys Lys Cys
1               5                   10

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000
```

-continued

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 16
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 201

Asp Thr His Phe Pro Cys Ile Lys Phe Glu Pro Arg Ser Lys Gly Cys
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 202

Asp Thr His Phe Pro Cys Ile Lys Phe Glu Pro Arg Ser Lys Cys
1               5                   10                  15

<210> SEQ ID NO 203
<211> LENGTH: 14
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 203

Asp Thr His Phe Pro Cys Ile Lys Phe Glu Pro Arg Ser Cys
1               5                   10

<210> SEQ ID NO 204
<211> LENGTH: 13
<212> TYPE: PRT

```
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 204

Asp Thr His Phe Pro Cys Ile Lys Phe Glu Pro Arg Cys
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 205

Asp Thr His Phe Pro Cys Ile Lys Phe Glu Pro Cys
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 206

Asp Thr His Phe Pro Cys Ile Lys Phe Glu Cys
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 207

Asp Thr His Phe Pro Cys Ile Lys Phe Cys
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
``` moiety

<400> SEQUENCE: 208

Asp Thr His Phe Pro Cys Ile Lys Phe Glu Pro Cys Lys
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (13)..(13)
<223> OTHER INFORMATION: D-form lysine

<400> SEQUENCE: 209

Asp Thr His Phe Pro Cys Ile Lys Phe Glu Pro Cys Lys
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 210

Asp Thr His Phe Pro Cys Ile Lys Phe Cys Lys
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 211

Asp Thr His Phe Pro Cys Ile Lys Phe Cys Arg Lys
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)

```
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: N-Methyl-Phenylalanine

<400> SEQUENCE: 212

Asp Thr His Phe Pro Cys Ile Lys Xaa Gly Cys
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: IsoGlu-Palm conjugated half-life extension
      moiety

<400> SEQUENCE: 213

Asp Thr His Phe Pro Cys Ile Lys Phe Cys
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Beta-homophenylalanine

<400> SEQUENCE: 214

Asp Thr His Phe Pro Cys Ile Lys Xaa Cys
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Alpha- Methylphenylalanine

<400> SEQUENCE: 215

Asp Thr His Phe Pro Cys Ile Lys Xaa Cys
1               5                   10
```

```
<210> SEQ ID NO 216
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta,Beta-diphenylalanine
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Alpha- Methylphenylalanine

<400> SEQUENCE: 216

Asp Thr His Xaa Pro Cys Ile Lys Xaa Cys
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Alpha-Methyl Phenylalanine
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Alpha- Methylphenylalanine

<400> SEQUENCE: 217

Asp Thr His Xaa Pro Cys Ile Lys Xaa Cys
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: N-Methyl Phenylalanine
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Alpha- Methylphenylalanine

<400> SEQUENCE: 218

Asp Thr His Xaa Pro Cys Ile Lys Xaa Cys
1               5                   10

<210> SEQ ID NO 219
```

```
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta-homophenylalanine
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Alpha- Methylphenylalanine

<400> SEQUENCE: 219

Asp Thr His Xaa Pro Cys Ile Lys Xaa Cys
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Alpha- Methylphenylalanine

<400> SEQUENCE: 220

Asp Thr His Trp Pro Cys Ile Lys Xaa Cys
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MISC_FEATURE
<222> LOCATION: (8)..(8)
<223> OTHER INFORMATION: IsoGlu-Palm conjugated half-life extension
      moiety
<220> FEATURE:
<221> NAME/KEY: MOD_RES
<222> LOCATION: (9)..(9)
<223> OTHER INFORMATION: Alpha- Methylphenylalanine

<400> SEQUENCE: 221

Asp Thr His Phe Xaa Cys Ile Lys Xaa Cys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Made in Lab - hepcidin analogue
```

```
<220> FEATURE:
<221> NAME/KEY: MISC_FEATURE
<222> LOCATION: (8)..(8)
<223> OTHER INFORMATION: PEG11-Palm conjugated half-life extension
      moiety

<400> SEQUENCE: 222

Asp Thr His Phe Pro Cys Ile Lys Phe Cys
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: isoGlu-Palm conjugated half-life extension
      moiety

<400> SEQUENCE: 223

Asp Thr His Phe Pro Cys Ile Lys Phe Cys
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: PEG11-Palm conjugated half-life extension
      moiety

<400> SEQUENCE: 224

Asp Thr His Phe Pro Cys Ile Lys Phe Lys Cys
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: PEG11-Palm conjugated half-life extension
      moiety
<220> FEATURE:
<221> NAME/KEY: MOD_RES
<222> LOCATION: (10)..(10)
<223> OTHER INFORMATION: D-form lysine

<400> SEQUENCE: 225

Asp Thr His Phe Pro Cys Ile Lys Phe Lys Cys
1               5                   10

<210> SEQ ID NO 226
```

```
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (8)..(8)
<223> OTHER INFORMATION: D-form lysine
<220> FEATURE:
<221> NAME/KEY: MISC_FEATURE
<222> LOCATION: (8)..(8)
<223> OTHER INFORMATION: PEG11-Palm conjugated half-life extension
      moiety
<220> FEATURE:
<221> NAME/KEY: MOD_RES
<222> LOCATION: (10)..(10)
<223> OTHER INFORMATION: D-form arginine

<400> SEQUENCE: 226

Asp Thr His Phe Pro Cys Ile Lys Phe Arg Cys
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MISC_FEATURE
<222> LOCATION: (8)..(8)
<223> OTHER INFORMATION: isoGlu-Palm conjugated half-life extension
      moiety

<400> SEQUENCE: 227

Asp Thr His Phe Pro Cys Ile Lys Phe Lys Cys
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta,Beta-diphenylalanine
<220> FEATURE:
<221> NAME/KEY: MISC_FEATURE
<222> LOCATION: (8)..(8)
<223> OTHER INFORMATION: PEG11-Palm conjugated half-life extension
      moiety
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MOD_RES
<222> LOCATION: (10)..(10)
<223> OTHER INFORMATION: D-form lysine

<400> SEQUENCE: 228

Asp Thr His Xaa Pro Cys Ile Lys Xaa Lys Cys
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Made in Lab - hepcidin analogue
```

```
<220> FEATURE:
<221> NAME/KEY: MOD_RES
<222> LOCATION: (4)..(4)
<223> OTHER INFORMATION: Beta,Beta-diphenylalanine
<220> FEATURE:
<221> NAME/KEY: MISC_FEATURE
<222> LOCATION: (8)..(8)
<223> OTHER INFORMATION: Ahx-Palm conjugated half-life extension moiety
<220> FEATURE:
<221> NAME/KEY: MOD_RES
<222> LOCATION: (9)..(9)
<223> OTHER INFORMATION: Beta-homophenylalanine

<400> SEQUENCE: 229

Asp Thr His Xaa Pro Cys Ile Lys Xaa Cys
1               5                   10

<210> SEQ ID NO 230
<211> LENGTH: 11
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (4)..(4)
<223> OTHER INFORMATION: Beta,Beta-diphenylalanine
<220> FEATURE:
<221> NAME/KEY: MISC_FEATURE
<222> LOCATION: (8)..(8)
<223> OTHER INFORMATION: Ahx-Palm conjugated half-life extension moiety
<220> FEATURE:
<221> NAME/KEY: MOD_RES
<222> LOCATION: (9)..(9)
<223> OTHER INFORMATION: Beta-homophenylalanine
<220> FEATURE:
<221> NAME/KEY: MOD_RES
<222> LOCATION: (11)..(11)
<223> OTHER INFORMATION: D-form lysine

<400> SEQUENCE: 230

Asp Thr His Xaa Pro Cys Ile Lys Xaa Cys Lys
1               5                   10

<210> SEQ ID NO 231
<211> LENGTH: 9
<212> TYPE: PRT
<213> ORGANISM: Artificial Sequence
<220> FEATURE:
<223> OTHER INFORMATION: Sythetic Construct - Dimer linked by K-K-
      isoGlu-Palm conjugated half-life meoiety

<400> SEQUENCE: 231

Asp Thr His Phe Pro Cys Ile Lys Phe
1               5

<210> SEQ ID NO 232
<211> LENGTH: 9
<212> TYPE: PRT
<213> ORGANISM: Artificial Sequence
<220> FEATURE:
<223> OTHER INFORMATION: Sythetic Construct - Dimer linked by dK-K-
      isoGlu-Palm conjugated half-life meoiety

<400> SEQUENCE: 232

Asp Thr His Phe Pro Cys Ile Lys Phe
1               5

<210> SEQ ID NO 233
<211> LENGTH: 9
<212> TYPE: PRT
```

```
<213> ORGANISM: Artificial Sequence
<220> FEATURE:
<223> OTHER INFORMATION: Sythetic Construct - Dimer linked by K-isoGlu-
      Palm conjugated half-life meoiety
<220> FEATURE:
<221> NAME/KEY: MOD_RES
<222> LOCATION: (8)..(8)
<223> OTHER INFORMATION: D-form lysine

<400> SEQUENCE: 233

Asp Thr His Phe Pro Cys Ile Lys Phe
1               5

<210> SEQ ID NO 234
<211> LENGTH: 9
<212> TYPE: PRT
<213> ORGANISM: Artificial Sequence
<220> FEATURE:
<223> OTHER INFORMATION: Sythetic Construct - Dimer linked by K-K-
      isoGlu-Palm conjugated half-life moiety
<220> FEATURE:
<221> NAME/KEY: MOD_RES
<222> LOCATION: (9)..(9)
<223> OTHER INFORMATION: Phe (4-OCH2CH2NH2)

<400> SEQUENCE: 234

Asp Thr His Phe Pro Cys Ile Lys Xaa
1               5

<210> SEQ ID NO 235
<211> LENGTH: 9
<212> TYPE: PRT
<213> ORGANISM: Artificial Sequence
<220> FEATURE:
<223> OTHER INFORMATION: Sythetic Construct - Dimer linked by K-K-
      isoGlu-Palm conjugated half-life meoiety
<220> FEATURE:
<221> NAME/KEY: MOD_RES
<222> LOCATION: (9)..(9)
<223> OTHER INFORMATION: Alpha-Methylphenylalanine

<400> SEQUENCE: 235

Asp Thr His Phe Pro Cys Ile Lys Xaa
1               5

<210> SEQ ID NO 236
<211> LENGTH: 9
<212> TYPE: PRT
<213> ORGANISM: Artificial Sequence
<220> FEATURE:
<223> OTHER INFORMATION: Sythetic Construct - Dimer linked by IDA
      [(beta-alanine)-Palm] conjugated half-life meoiety
<220> FEATURE:
<221> NAME/KEY: MOD_RES
<222> LOCATION: (8)..(8)
<223> OTHER INFORMATION: D-form lysine

<400> SEQUENCE: 236

Asp Thr His Phe Pro Cys Ile Lys Phe
1               5

<210> SEQ ID NO 237
<211> LENGTH: 9
<212> TYPE: PRT
<213> ORGANISM: Artificial Sequence
<220> FEATURE:
<223> OTHER INFORMATION: Sythetic Construct - Dimer linked by IDA
      [(beta-alanine)-Palm] conjugated half-life meoiety
<220> FEATURE:
<221> NAME/KEY: MOD_RES
<222> LOCATION: (9)..(9)
```

<223> OTHER INFORMATION: N-Methylphenylalanine

<400> SEQUENCE: 237

Asp Thr His Phe Pro Cys Ile Lys Xaa
1               5

<210> SEQ ID NO 238
<211> LENGTH: 9
<212> TYPE: PRT
<213> ORGANISM: Artificial Sequence
<220> FEATURE:
<223> OTHER INFORMATION: Sythetic Construct - Dimer linked by IDA
      [(beta-alanine)-Palm] conjugated half-life meoiety
<220> FEATURE:
<221> NAME/KEY: MOD_RES
<222> LOCATION: (9)..(9)
<223> OTHER INFORMATION: Alpha-Methylphenylalanine

<400> SEQUENCE: 238

Asp Thr His Phe Pro Cys Ile Lys Xaa
1               5

<210> SEQ ID NO 239
<211> LENGTH: 10
<212> TYPE: PRT
<213> ORGANISM: Artificial Sequence
<220> FEATURE:
<223> OTHER INFORMATION: Sythetic Construct - Dimer linked by IDA
      [(beta-alanine)-Palm] conjugated half-life meoiety
<220> FEATURE:
<221> NAME/KEY: MOD_RES
<222> LOCATION: (10)..(10)
<223> OTHER INFORMATION: D-form lysine

<400> SEQUENCE: 239

Asp Thr His Phe Pro Cys Ile Ile Phe Lys
1               5                   10

<210> SEQ ID NO 240
<211> LENGTH: 9
<212> TYPE: PRT
<213> ORGANISM: Artificial Sequence
<220> FEATURE:
<223> OTHER INFORMATION: Sythetic Construct - Dimer linked by K-K-
      isoGlu-Palm conjugated half-life moiety
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Alpha-Methylphenylalanine

<400> SEQUENCE: 240

Asp Thr His Phe Pro Cys Ile Lys Xaa
1               5

<210> SEQ ID NO 241
<211> LENGTH: 9
<212> TYPE: PRT
<213> ORGANISM: Artificial Sequence
<220> FEATURE:
<223> OTHER INFORMATION: Sythetic Construct - Dimer linked by K-K-
      isoGlu-Palm conjugated half-life moiety
<220> FEATURE:
<221> NAME/KEY: MOD_RES
<222> LOCATION: (4)..(4)
<223> OTHER INFORMATION: Biphenylalanine
<220> FEATURE:
<221> NAME/KEY: MOD_RES

```
<222> LOCATION: (8)..(8)
<223> OTHER INFORMATION: D-form lysine

<400> SEQUENCE: 241

Asp Thr His Xaa Pro Cys Ile Lys Phe
1               5

<210> SEQ ID NO 242
<211> LENGTH: 9
<212> TYPE: PRT
<213> ORGANISM: Artificial Sequence
<220> FEATURE:
<223> OTHER INFORMATION: Sythetic Construct - Dimer linked by K-K-
      isoGlu-Palm conjugated half-life moiety
<220> FEATURE:
<221> NAME/KEY: MOD_RES
<222> LOCATION: (9)..(9)
<223> OTHER INFORMATION: Beta-homophenylalanine

<400> SEQUENCE: 242

Asp Thr His Phe Pro Cys Ile Lys Xaa
1               5

<210> SEQ ID NO 243
<211> LENGTH: 9
<212> TYPE: PRT
<213> ORGANISM: Artificial Sequence
<220> FEATURE:
<223> OTHER INFORMATION: Sythetic Construct - Dimer linked by K-K-
      isoGlu-Palm conjugated half-life moiety
<220> FEATURE:
<221> NAME/KEY: MOD_RES
<222> LOCATION: (9)..(9)
<223> OTHER INFORMATION: Beta-homophenylalanine

<400> SEQUENCE: 243

Asp Thr His Phe Pro Cys Ile Lys Xaa
1               5

<210> SEQ ID NO 244
<211> LENGTH: 9
<212> TYPE: PRT
<213> ORGANISM: Artificial Sequence
<220> FEATURE:
<223> OTHER INFORMATION: Sythetic Construct - Dimer linked by  IDA
      [(beta-alanine)-Palm] conjugated half-life meoiety
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: N-Methylphenylalanine

<400> SEQUENCE: 244

Asp Thr His Phe Pro Cys Ile Lys Xaa
1               5

<210> SEQ ID NO 245
<211> LENGTH: 9
<212> TYPE: PRT
<213> ORGANISM: Artificial Sequence
<220> FEATURE:
<223> OTHER INFORMATION: Sythetic Construct - Dimer linked by  IDA
      [(beta-alanine)-Palm] conjugated half-life meoiety
<220> FEATURE:
<221> NAME/KEY: MOD_RES
<222> LOCATION: (4)..(4)
<223> OTHER INFORMATION: Biphenylalanine
<220> FEATURE:
```

```
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: N-Methylphenylalanine

<400> SEQUENCE: 245

Asp Thr His Xaa Pro Cys Ile Lys Xaa
1               5

<210> SEQ ID NO 246
<211> LENGTH: 9
<212> TYPE: PRT
<213> ORGANISM: Artificial Sequence
<220> FEATURE:
<223> OTHER INFORMATION: Sythetic Construct - Dimer linked by  IDA
      [(beta-alanine)-Palm] conjugated half-life meoiety
<220> FEATURE:
<221> NAME/KEY: MOD_RES
<222> LOCATION: (9)..(9)
<223> OTHER INFORMATION: Beta-homophenylalanine

<400> SEQUENCE: 246

Asp Thr His Phe Pro Cys Ile Lys Xaa
1               5

<210> SEQ ID NO 247
<211> LENGTH: 9
<212> TYPE: PRT
<213> ORGANISM: Artificial Sequence
<220> FEATURE:
<223> OTHER INFORMATION: Sythetic Construct - Dimer linked by  IDA
      [(beta-alanine)-Palm] conjugated half-life meoiety
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: Beta-homophenylalanine

<400> SEQUENCE: 247

Asp Thr His Phe Pro Cys Ile Lys Xaa
1               5

<210> SEQ ID NO 248
<211> LENGTH: 9
<212> TYPE: PRT
<213> ORGANISM: Artificial Sequence
<220> FEATURE:
<223> OTHER INFORMATION: Sythetic Construct - Dimer linked by  IDA
      [(beta-alanine)-Palm] conjugated half-life meoiety
<220> FEATURE:
<221> NAME/KEY: MOD_RES
<222> LOCATION: (5)..(5)
<223> OTHER INFORMATION: Nipecotic acid
<220> FEATURE:
<221> NAME/KEY: MOD_RES
<222> LOCATION: (8)..(8)
<223> OTHER INFORMATION: D-form lysine
<220> FEATURE:
<221> NAME/KEY: MOD_RES
<222> LOCATION: (9)..(9)
<223> OTHER INFORMATION: N-Methylphenylalanine

<400> SEQUENCE: 248

Asp Thr His Phe Xaa Cys Ile Lys Xaa
1               5
```

<210> SEQ ID NO 249
<211> LENGTH: 4
<212> TYPE: PRT
<213> ORGANISM: Artificial Sequence
<220> FEATURE:
<223> OTHER INFORMATION: Made in Lab - peptide insert

<400> SEQUENCE: 249

Pro Arg Ser Lys
1

<210> SEQ ID NO 250
<211> LENGTH: 5
<212> TYPE: PRT
<213> ORGANISM: Artificial Sequence
<220> FEATURE:
<223> OTHER INFORMATION: Made in Lab - peptide insert
<220> FEATURE:
<221> NAME/KEY: MOD_RES
<222> LOCATION: (5)..(5)
<223> OTHER INFORMATION: sarcosine

<400> SEQUENCE: 250

Pro Arg Ser Lys Xaa
1               5

<210> SEQ ID NO 251
<211> LENGTH: 5
<212> TYPE: PRT
<213> ORGANISM: Artificial Sequence
<220> FEATURE:
<223> OTHER INFORMATION: Made in Lab - peptide insert

<400> SEQUENCE: 251

Pro Arg Ser Lys Gly
1               5

<210> SEQ ID NO 252
<211> LENGTH: 17
<212> TYPE: PRT
<213> ORGANISM: Artificial Sequence
<220> FEATURE:
<223> OTHER INFORMATION: Made in Lab - hepcidin analogue

<400> SEQUENCE: 252

Asp Thr His Phe Pro Cys Ile Lys Phe Glu Pro Arg Ser Lys Gly Cys
1               5                   10                  15

Lys

<210> SEQ ID NO 253
<211> LENGTH: 4
<212> TYPE: PRT
<213> ORGANISM: Artificial Sequence
<220> FEATURE:
<223> OTHER INFORMATION: Made in Lab - peptide insert

<400> SEQUENCE: 253

Pro Arg Ser Cys
1

<210> SEQ ID NO 254
<211> LENGTH: 5
<212> TYPE: PRT
<213> ORGANISM: Artificial Sequence
<220> FEATURE:
<223> OTHER INFORMATION: Made in Lab - peptide insert

```
<400> SEQUENCE: 254

Pro Arg Ser Lys Cys
1               5

<210> SEQ ID NO 255
<211> LENGTH: 6
<212> TYPE: PRT
<213> ORGANISM: Artificial Sequence
<220> FEATURE:
<223> OTHER INFORMATION: Made in Lab - peptide insert

<400> SEQUENCE: 255

Pro Arg Ser Lys Cys Lys
1               5

<210> SEQ ID NO 256
<211> LENGTH: 25
<212> TYPE: PRT
<213> ORGANISM: Homo sapiens

<400> SEQUENCE: 256

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 257
<211> LENGTH: 9
<212> TYPE: PRT
<213> ORGANISM: Homo sapiens

<400> SEQUENCE: 257

Asp Thr His Phe Pro Ile Cys Ile Phe
1               5

<210> SEQ ID NO 258
<211> LENGTH: 9
<212> TYPE: PRT
<213> ORGANISM: Artificial Sequence
<220> FEATURE:
<223> OTHER INFORMATION: Made in Lab - hepcidin analogue
<220> FEATURE:
<221> NAME/KEY: MOD_RES
<222> LOCATION: (1)..(1)
<223> OTHER INFORMATION: D-form phenylalanine
<220> FEATURE:
<221> NAME/KEY: MOD_RES
<222> LOCATION: (2)..(2)
<223> OTHER INFORMATION: D-form isoleucine
<220> FEATURE:
<221> NAME/KEY: MOD_RES
<222> LOCATION: (3)..(3)
<223> OTHER INFORMATION: D-form cysteine
<220> FEATURE:
<221> NAME/KEY: MOD_RES
<222> LOCATION: (4)..(4)
<223> OTHER INFORMATION: D-form isoleucine
<220> FEATURE:
<221> NAME/KEY: MOD_RES
<222> LOCATION: (5)..(5)
<223> OTHER INFORMATION: D-form proline
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (7)..(7)
<223> OTHER INFORMATION: D-form histidine
<220> FEATURE:
```

```
<221> NAME/KEY: MOD_RES
<222> LOCATION: (8)..(8)
<223> OTHER INFORMATION: D-form threonine
<220> FEATURE:
<221> NAME/KEY: MOD_RES
<222> LOCATION: (9)..(9)
<223> OTHER INFORMATION: D-form aspartic acid

<400> SEQUENCE: 258

Phe Ile Cys Ile Pro Phe His Thr Asp
1               5
```